(12) United States Patent
Kim et al.

(10) Patent No.: US 12,045,978 B2
(45) Date of Patent: Jul. 23, 2024

(54) MEDICAL IMAGE ANALYSIS METHOD, MEDICAL IMAGE ANALYSIS DEVICE, AND MEDICAL IMAGE ANALYSIS SYSTEM

(71) Applicant: NEUROPHET INC., Seoul (KR)

(72) Inventors: Dong Hyeon Kim, Seoul (KR); Zun Hyan Rieu, Seongnam-si (KR); Eun Young Kim, Ansan-si (KR)

(73) Assignee: NEUROPHET INC., Seoul (KR)

( * ) Notice: Subject to any disclaimer, the term of this patent is extended or adjusted under 35 U.S.C. 154(b) by 357 days.

(21) Appl. No.: 17/515,466

(22) Filed: Oct. 30, 2021

(65) Prior Publication Data
US 2022/0207722 A1 Jun. 30, 2022

Related U.S. Application Data

(63) Continuation of application No. PCT/KR2020/019412, filed on Dec. 30, 2020.

(51) Int. Cl.
*G06T 7/00* (2017.01)
*G06T 7/11* (2017.01)
*A61B 6/00* (2006.01)

(52) U.S. Cl.
CPC ............ *G06T 7/0012* (2013.01); *G06T 7/11* (2017.01); *A61B 6/5217* (2013.01);
(Continued)

(58) Field of Classification Search
CPC . G06T 7/11; G06T 7/0012; G06T 7/00; G06T 2207/20036; G06T 2207/20084;
(Continued)

(56) References Cited

U.S. PATENT DOCUMENTS 7,324,673 B1 1/2008 Yamanaka et al.
10,444,317 B2 * 10/2019 Tamada ............. G01R 33/4824
(Continued)

FOREIGN PATENT DOCUMENTS

JP 2001-209785 8/2001
JP 2016-209267 12/2016
(Continued)

OTHER PUBLICATIONS

Korean Office Action dated Mar. 8, 2021 as received in application No. 10-2020-0187934.
(Continued)

*Primary Examiner* — Tuan H Nguyen
(74) *Attorney, Agent, or Firm* — Maschoff Brennan

(57) ABSTRACT

A method of analyzing a medical image includes acquiring a correction parameter computed based on a correlation between a first morphological value that is acquired from a first medical image acquired under a first scan condition and is related to a target element, and a second morphological value that is acquired from a second medical image acquired under a second scan condition and is related to the target element. A target medical image is acquired under the second scan condition. A target region related to the target element is acquired by segmenting the target medical image into regions corresponding to elements including the target element. A target morphological value related to the target element is based on voxel data corresponding to the target region. A corrected morphological value is based on the target morphological value and the correction parameter. A morphological index is outputted based on the corrected morphological value.

17 Claims, 81 Drawing Sheets

(52) U.S. Cl.
CPC ............... *G06T 2207/10081* (2013.01); *G06T 2207/10088* (2013.01); *G06T 2207/20036* (2013.01); *G06T 2207/20084* (2013.01); *G06T 2207/30016* (2013.01); *G06T 2207/30168* (2013.01)

(58) Field of Classification Search
CPC . G06T 2207/10081; G06T 2207/10088; G06T 2207/30016; G06T 2207/30168; G06T 7/155; A61B 6/5217; A61B 2576/00
See application file for complete search history.

(56) References Cited

U.S. PATENT DOCUMENTS

| | | | |
|---|---|---|---|
| 2006/0227929 A1* | 10/2006 | Takanezawa | G01N 33/03 378/5 |
| 2014/0363062 A1 | 12/2014 | Han | |
| 2016/0278733 A1 | 9/2016 | Ogura | |
| 2018/0284212 A1 | 10/2018 | Tamada | |
| 2020/0175652 A1 | 6/2020 | Agarwal | |
| 2020/0327663 A1 | 10/2020 | Namgoong | |

FOREIGN PATENT DOCUMENTS

| | | |
|---|---|---|
| JP | 2018-167025 | 11/2018 |
| JP | 2019-000628 | 1/2019 |
| JP | 2019-005557 | 1/2019 |
| JP | 2019-171019 | 10/2019 |
| JP | 2020-531074 | 6/2020 |
| KR | 2014-0144065 | 12/2014 |
| KR | 2019-0105452 | 1/2019 |
| KR | 10-2058884 | 12/2019 |
| KR | 2020-0005408 | 1/2020 |
| KR | 10-2099415 | 4/2020 |
| KR | 2020-0106602 | 9/2020 |
| WO | 2014-167935 | 10/2014 |

OTHER PUBLICATIONS

Korean Office Action dated Mar. 9, 2021 as received in application No. 10-2020-0187931.
Korean Office Action dated Mar. 9, 2021 as received in application No. 10-2020-0187932.
Korean Office Action dated Mar. 11, 2021 as received in application No. 10-2020-0187930.
Korean Notice of Allowance dated Jul. 13, 2021 as received in application No. 10-2020-0187930.
International Search report dated Sep. 28, 2021 as received in application No. PCT/KR2020/019412.
Written Opinion dated Sep. 28, 2021 as received in application No. PCT/KR2020/019412.
Rondina et al. "Selecting the most relevant brain regions to discriminate Alzheimer's disease patients from healthy controls using multiple kernel learning: A comparison across functional and structural imaging modalities and atlases" NeuroImage: Clinical 17 (2018).

* cited by examiner

FIG. 29
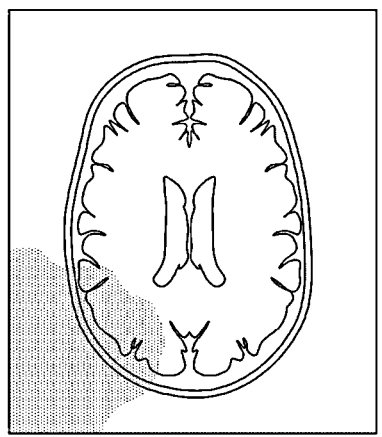 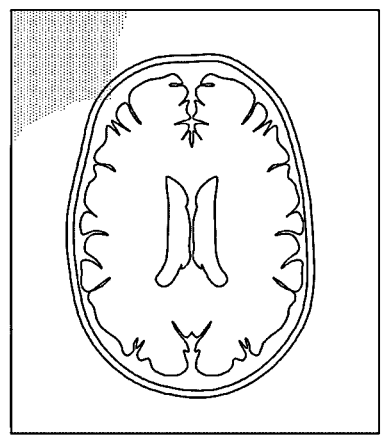
(a) (b)

FIG. 74

|  | AD | Vad | FTLD |
|---|---|---|---|
| FRONTAL LOBE ATROPHY | - | + | +++ |
| TEMPORAL LOBE ATROPHY | ++ | + | +++ |
| PARIETAL LOBE ATROPHY | ++ | + | - |
| HIPPOCAMPAL ATROPHY | +++ | ++ | ++ |
| WHITE MATTER LESION | - | +++ | - |
| CINGULATE GYRUS ATROPHY | - | + | - |

MEDICAL IMAGE ANALYSIS METHOD, MEDICAL IMAGE ANALYSIS DEVICE, AND MEDICAL IMAGE ANALYSIS SYSTEM

TECHNICAL FIELD

The present application relates to a medical image analysis method, a medical image analysis device, and a medical image analysis system capable of analyzing a medical image.

BACKGROUND ART

Due to the improvement of image segmentation technology, it is possible to segment a medical image to calculate an auxiliary diagnostic index related to a disease, and thus recently, the field of medical image analysis has been attracting attention.

In particular, medical image analysis technology is being used in various fields to provide an auxiliary diagnostic index for dementia, and in order to provide objective dementia-specific auxiliary diagnostic information, it is essential to more accurately compute a morphological character of a specific region from a medical image.

However, conventional medical image analysis technology has several restrictions due to the presence of errors in a medical image itself, such as artifacts that are not suitable for image segmentation in the medical image, and has a limitation in that auxiliary diagnostic information for the same target subject may be different according to a scan condition in which the medical image is acquired. Also, conventional medical image analysis technology uses a method of performing image segmentation after standardizing a brain included in a medical image with respect to a standard brain model. Thus, the conventional medical image analysis technology has a problem in that it is not possible to provide completely "personalized" auxiliary diagnostic information for a target subject, so there are limitations in situations where high accuracy is required.

Accordingly, there is a need to develop an image analysis method and device capable of providing identifiable diagnosis information to a user even when noise is included in an image. There is a need to develop an image analysis method and device for acquiring auxiliary diagnostic information in consideration of a scan condition in which a medical image is captured and for acquiring personalized diagnostic auxiliary information for a target subject.

DISCLOSURE

Technical Problem

The present invention is directed to providing a medical image analysis method, a medical image analysis device, and a medical image analysis system capable of providing information regarding a medical image.

The objects of the present invention are not limited to the aforementioned object, and other objects which are not described herein should be clearly understood by those skilled in the art from the following description and the accompanying drawings.

Technical Solution

According to a method for analyzing a medical image disclosed in the present application, the method comprises: obtaining a calibrating parameter calculated based on a correlation between a first morphological value related to a target element obtained from a first medical image acquired under a first scan condition and a second morphological value related to the target element obtained from a second medical image acquired under a second scan condition; obtaining a target medical image acquired under the second scan condition; obtaining a target area related to the target element from the target medical image by performing a segmentation of the target medical image into a plurality of areas corresponding a plurality of elements including the target element; obtaining a target morphological value related to the target element based on a voxel data corresponding to the target area; obtaining a calibrated morphological value based on the target morphological value and the calibrating parameter; and outputting a morphological index based on the calibrated morphological value.

According to a device for analyzing a medical image disclosed in the present application, the device comprises: an image acquisition unit for obtaining a target medical image; and a controller for providing analysis information of a medical image based on the target medical image, and wherein the controller configured to: obtain a calibrating parameter calculated based on a correlation between a first morphological value related to a target element obtained from a first medical image acquired under a first scan condition and a second morphological value related to the target element obtained from a second medical image acquired under a second scan condition; obtain a target medical image acquired under the second scan condition; obtain a target area related to the target element from the target medical image by performing a segmentation of the target medical image into a plurality of areas corresponding a plurality of elements including the target element; obtain a target morphological value related to the target element based on a voxel data corresponding to the target area; obtain a calibrated morphological value based on the target morphological value and the calibrating parameter; and output a morphological index based on the calibrated morphological value.

According to a method for analyzing a medical image disclosed in the present application, the method comprises: obtaining a target medical image; obtaining a target scan condition related to the target medical image; obtaining a target morphological value related to a target element based on a voxel data of a target area corresponding to the target element included in the target medical image; determining a target calibrating parameter, based on the target scan condition, among one or more calibrating parameters; and outputting a morphological index based on the determined target calibrating parameter and the target morphological value, and wherein the determining the target calibrating parameter comprises: when the target scan condition is corresponded to a first scan condition, the target calibrating parameter is determined to a first calibrating parameter for calibrating a first morphological value which is obtained under the first scan condition and which is related the target element; and when the target scan condition is corresponded to a second scan condition, the target calibrating parameter is determined to a second calibrating parameter for calibrating a second morphological value which is obtained under the second scan condition different to the first scan condition and which is related the target element.

According to a device for analyzing a medical image disclosed in the present application, the device comprises: an image acquisition unit for obtaining a target medical image; and a controller for providing analysis information of a medical image based on the target medical image, and wherein the controller configured to: obtain a target scan condition related to the target medical image; obtain a target morphological value related to a target element based on a voxel data of a target area corresponding to the target element included in the target medical image; determine a target calibrating parameter, based on the target scan condition, among one or more calibrating parameters; and output a morphological index based on the determined target calibrating parameter and the target morphological value, and wherein the determining the target calibrating parameter comprises: when the target scan condition is corresponded to a first scan condition, the target calibrating parameter is determined to a first calibrating parameter for calibrating a first morphological value which is obtained under the first scan condition and which is related the target element; and when the target scan condition is corresponded to a second scan condition, the target calibrating parameter is determined to a second calibrating parameter for calibrating a second morphological value which is obtained under the second scan condition different to the first scan condition and which is related the target element.

Advantageous Effects

According to an embodiment of the present application, it is possible to increase the reliability of a medical image analysis result by performing quality analysis on a target medical image and providing a user with information on the analysis result.

According to an embodiment of the present application, it is possible to more accurately calculate a morphological index by calculating a morphological index on the basis of a medical image of a target subject and appropriately applying a correction parameter in consideration of a scan condition in which the medical image is acquired or the location of a target element.

According to an embodiment of the present application, it is possible to improve user convenience by selectively providing index information necessary for a user among various pieces of index information acquired through the analysis of a target medical image.

Advantageous effects of the present invention are not limited to the aforementioned effects, and other advantageous effects that are not described herein will be clearly understood by those skilled in the art from the following description and the accompanying drawings.

DESCRIPTION OF DRAWINGS

FIG. 29 is a diagram illustrating an image in which an artifact is generated.

FIG. 74 is a diagram illustrating indices related to some target diseases.

BEST MODES

Figure 1:
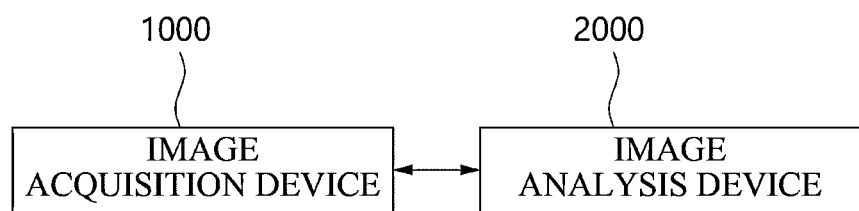
FIG. 1 is a schematic diagram of a medical image analysis system according to an embodiment of the present application.

According to a method for analyzing a medical image disclosed in the present application, the method comprises: obtaining a target medical image including at least one artifact; obtaining artifact information related to the artifact based on the target medical image, wherein the artifact information includes an artifact region in which the artifact is distributed; obtaining a plurality of regions corresponding to one or more anatomically distinguished elements based on the target medical image by using a first neural network model, wherein the first neural network model is trained to obtain the plurality of regions based on the medical image, wherein the plurality of regions includes a first region corresponding to a first element, a second region corresponding to a second element and a third region corresponding to a third element; obtaining a degree of overlap between the artifact region and a region of interest, wherein the region of interest includes at least a portion of the first region; determining a first quality of the target medical image based on the degree of overlap; outputting information related to the quality of the target medical image based on a result of the first quality determination.

According to a method for analyzing a medical image disclosed in the present application, wherein the first element is a skull, wherein the first region includes a region corresponding to the skull, and wherein the region of interest is a cranial region or an internal region of the skull.

According to a method for analyzing a medical image disclosed in the present application, wherein the second element is related to a target disease being diagnosed, and wherein the region of interest includes at least a portion of the second region.

According to a method for analyzing a medical image disclosed in the present application, wherein the artifact region is obtained using a second neural network model trained to determine whether the artifact is present in the medical image, and wherein the artifact region is a region on a feature map that has a relevance to the target artifact greater than a reference value, and wherein the feature map is obtained from the second neural network model and is related to the target artifact included in the target medical image.

According to a method for analyzing a medical image disclosed in the present application, wherein the artifact region includes a first region and a second region located inside the first region, wherein the first region is a region on the feature map that has a relevance to the target artifact greater than a first reference value, wherein the second region is a region on the feature map that has a relevance to the target artifact greater than a second reference value, wherein the second reference value is greater than the first reference value.

According to a method for analyzing a medical image disclosed in the present application, wherein the artifact region is obtained using a second neural network model trained to segment a region corresponding to the artifact included in the medical image.

According to a method for analyzing a medical image disclosed in the present application, the determining of the degree of overlap comprises: obtaining an outer line of the artifact region and an outer line of the region of interest from the target medical image; and determining whether the artifact and the region of interest are overlapped to each other, based on whether the outer line of the artifact and the outer line of the region of the interest overlap on the medical image.

According to a method for analyzing a medical image disclosed in the present application, the determining the first quality comprises: determining that the quality of the target medical image is normal when there are less than two intersection points between the outer line of the artifact area and the outer line of the region of interest on the target medical image; and determining that the quality of the target medical image is abnormal when there are two or more intersection points between the outer line of the artifact area and the outer line of the region of interest on the target medical image.

According to a method for analyzing a medical image disclosed in the present application, the obtaining the degree of overlap comprises: obtaining a count number of pixels included in both the artifact region and the region of interest on the target medical image; and determining the degree of overlap between the artifact and the region of interest based on the number of pixels.

According to a method for analyzing a medical image disclosed in the present application, the determining the first quality comprises: determining that the quality of the target medical image is abnormal when the number of pixels included in both the artifact region and the region of interest exceeds a predetermined reference value; and determining that the quality of the target medical image is normal when the number of pixels included in both the artifact region and the region of interest is less than or equal to a predetermined reference value.

According to a method for analyzing a medical image disclosed in the present application, the method further comprises: determining a second quality of the target medical image based on the third region, wherein the determining the second quality comprises obtaining a morphological index based on the third region and determining whether the morphological index satisfies a quantitative criteria.

The morphological index may be obtained based on the first region and the third region.

The morphological index may be obtained based on a ratio of a volume of the first region to a volume of the third region.

The third region may be a region corresponding to an element located at the bottom of the target medical image.

The third region may be a region corresponding to an element related to diagnosis of a target disease.

According to a method for analyzing a medical image disclosed in the present application, the outputting information related to the quality of the target medical image comprises: displaying error information generated based on a result of the first quality determination and a selection window related to the error information, wherein the error information includes the artifact information and information about the plurality of regions.

According to a method for analyzing a medical image disclosed in the present application, wherein the selection window includes a first object, and the method further comprises: performing a subsequent operation according to a user selection on the first object included in the selection window, wherein the subsequent operation includes one of an operation of analyzing the target medical image, an operation of correcting the target medical image, and an operation of re-photographing the target medical image.

According to a device for analyzing a medical image disclosed in the present application, the device comprises: an acquisition unit obtaining the medical image, a processing unit for obtaining image quality information based on the medical image, and an output unit for outputting the image quality information;

wherein the processing unit is configured to:
obtain a target medical image including at least one artifact; obtain artifact information related to the artifact based on the target medical image, wherein the artifact information includes an artifact region in which the artifact is distributed; obtain a plurality of regions corresponding to one or more anatomically distinguished elements based on the target medical image by using a first neural network model, wherein the first neural network model is trained to obtain the plurality of regions based on the medical image, wherein the plurality of regions includes a first region corresponding to a first element, a second region corresponding to a second element and a third region corresponding to a third element; obtain a degree of overlap between the artifact region and a region of interest, wherein the region of interest includes at least a portion of the first region; determine a first quality of the target medical image based on the degree of overlap; output information related to the quality of the target medical image based on a result of the first quality determination.

According to a device for analyzing a medical image disclosed in the present application, wherein the first element is a skull, wherein the first region includes a region corresponding to the skull, and wherein the region of interest is a cranial region or an internal region of the skull.

According to a device for analyzing a medical image disclosed in the present application, wherein the second element is related to a target disease being diagnosed, and wherein the region of interest includes at least a portion of the second region.

According to a device for analyzing a medical image disclosed in the present application, wherein the artifact region is obtained using a second neural network model trained to determine whether the artifact is present in the medical image, and wherein the artifact region is a region on a feature map that has a relevance to the target artifact greater than a reference value, and wherein the feature map is obtained from the second neural network model and is related to the target artifact included in the target medical image.

According to a device for analyzing a medical image disclosed in the present application, wherein the artifact region includes a first region and a second region located inside the first region, wherein the first region is a region on the feature map that has a relevance to the target artifact greater than a first reference value, wherein the second region is a region on the feature map that has a relevance to the target artifact greater than a second reference value, wherein the second reference value is greater than the first reference value.

According to a device for analyzing a medical image disclosed in the present application, wherein the artifact region is obtained using a second neural network model trained to segment a region corresponding to the artifact included in the medical image.

According to a device for analyzing a medical image disclosed in the present application, wherein the processing unit is configured to determine of the degree of overlap, by obtaining an outer line of the artifact region and an outer line of the region of interest from the target medical image; and determining whether the artifact and the region of interest are overlapped each other, based on whether the outer line of the artifact and the outer line of the region of the interest overlap on the medical image.

According to a device for analyzing a medical image disclosed in the present application, wherein the processing unit is configured to determine that the quality of the target medical image is normal when there are less than two intersection points between the outer line of the artifact area and the outer line of the region of interest on the target medical image, and determine that the quality of the target medical image is abnormal when there are two or more intersection points.

According to a device for analyzing a medical image disclosed in the present application, wherein the processing unit is configured to obtain the degree of overlap by obtaining a count number of pixels included in both the artifact region and the region of interest on the target medical image; and determining the degree of overlap between the artifact and the region of interest based on the number of pixels.

According to a device for analyzing a medical image disclosed in the present application, wherein the processing unit is configured to determine that the quality of the target medical image is abnormal when the number of pixels included in both the artifact region and the region of interest exceeds a predetermined reference value, and determine that the quality of the target medical image is normal when the number of pixels included in both the artifact region and the region of interest is less than or equal to a predetermined reference value.

According to a device for analyzing a medical image disclosed in the present application, wherein the processing unit is configured to obtain a morphological index based on the third region, and determine a second quality based on whether the morphological index satisfies a quantitative criteria.

The morphological index may be obtained based on the first region and the third region.

The morphological index may be obtained based on a ratio of a volume of the first region to a volume of the third region.

The third region may be a region corresponding to an element located at the bottom of the target medical image.

The third region may be a region corresponding to an element related to diagnosis of a target disease.

According to a method for analyzing a brain image disclosed in the present application, the method comprises: obtaining a brain image including a voxel data; obtaining a first boundary defining a first inner region which is an inner region of a skull region, and a reference region by segmenting the brain image into a plurality of regions including the skull region and the reference region; obtaining a second inner region having a second boundary by modifying at least a part of the first boundary related to the first inner region based on the reference region, wherein a part of the second region is included in the first inner region and includes a target element; obtaining a first volumetric value related to the target element based on the voxel data corresponding to the target element; obtaining a second volumetric value related to the second inner region based on the voxel data included to the second boundary; and calculating a volumetric index based on the first volumetric value and the second volumetric value.

According to a method for analyzing a brain image disclosed in the present application, the method further comprises: aligning the brain image for obtaining the second inner region.

According to a method for analyzing a brain image disclosed in the present application, the aligning the brain image comprises: obtaining a first feature region and a second feature region from the brain image; calculating a first feature point based on the first feature region and a second feature point based on the second feature region; obtaining photographing direction of the brain image based on the first feature point and the second feature point; and aligning the brain image such that the photographing direction is parallel to reference direction.

According to a method for analyzing a brain image disclosed in the present application, wherein the first feature region is a region corresponding to an anterior commissure, the second feature region is a region corresponding to a posterior commissure, the first feature point is included in a boundary defining the region corresponding to the anterior commissure, and the second feature point is included in a boundary defining the region corresponding to the posterior commissure.

According to a method for analyzing a brain image disclosed in the present application, the aligning the brain image comprises: obtaining a data related to direction of the brain image included in the brain image; obtaining photographing direction of the brain image based on the data related to the direction of the brain image; and aligning the brain image such that the photographing direction is parallel to reference direction.

According to a method for analyzing a brain image disclosed in the present application, the obtaining the second inner region comprises: obtaining a reference plane adjacent to the reference region from the brain image; and obtaining the second inner region having the second boundary by modifying a part of the first boundary of the first inner region based on the reference plane.

According to a method for analyzing a brain image disclosed in the present application, wherein the reference plane is a plane parallel to a transverse plane of the brain image, and the obtaining the second inner region comprises: modifying a part of the first boundary located on a lower side of the reference plane, based on the first inner region located on an upper side of the reference plane; and obtaining the second inner region having the second boundary based on the modified first boundary.

According to a method for analyzing a brain image disclosed in the present application, wherein the reference region is a region corresponding to a cerebellum, and the reference plane is adjacent to an inferior edge of a boundary defining the region corresponding to the cerebellum.

According to a method for analyzing a brain image disclosed in the present application, wherein the reference region is a region corresponding to a cerebellum, and the reference plane is adjacent to an inferior edge of a boundary defining the region corresponding to the cerebellum.

According to a method for analyzing a brain image disclosed in the present application, the obtaining the second inner region comprises: obtaining a first feature region and a second region from the brain image; calculating a first feature point based on the first feature region and a second feature point based on the second feature region; obtaining reference direction connecting the first feature point and the second feature point base on the first feature point and the second feature point; obtaining a reference plane parallel to the reference direction; and obtaining the second inner region having the second boundary by modifying a part of the first boundary of the first inner region based on the reference plane.

According to a method for analyzing a brain image disclosed in the present application, wherein the reference region is a region corresponding to a cervical vertebra, the reference plane is adjacent to the region corresponding to the cervical vertebra and is vertical to a sagittal plane.

According to a method for analyzing a brain image disclosed in the present application, the obtaining the second inner region comprises: modifying a part of the first boundary located on a lower side of the reference plane, based on the first inner region located on an upper side of the reference plane; and obtaining the second inner region having the second boundary based on the modified first boundary.

According to a method for analyzing a brain image disclosed in the present application, wherein the volumetric index is defined as a ratio of the first volumetric value to the second volumetric value.

According to a method for analyzing a medical image disclosed in the present application, the calculating the volumetric index of the target element further comprises: obtaining a first calibrating parameter for calibrating the first volumetric value, wherein the first calibrating parameter is obtained based on a position of the target element or a scan condition in which the brain image is acquired; calculating the first calibrated volumetric value based on the first calibrating parameter and the first volumetric value; obtaining a second calibrating parameter for calibrating the second volumetric value, wherein the second calibrating parameter is obtained based on a position of the target element or a scan condition in which the brain image is acquired; calculating the second calibrated volumetric value based on the second calibrating parameter and the second volumetric value; and calculating the volumetric index based on the first calibrated volumetric value and the second calibrated volumetric value.

According to a method for analyzing a medical image disclosed in the present application, wherein a scan condition in which the brain image is acquired is related to at least one of a magnetic field strength related to a resolution of the medical image of a medical image device, a manufacturer of the medical image device, and a setting parameter related to a magnetic field generated by the medical image device.

According to a device for analyzing a brain image disclosed in the present application, the device comprises: an image acquisition unit obtaining a brain image; and a controller providing a brain image analysis information based on the brain image;

wherein the controller is configured to:
obtain the brain image including a voxel data; obtain a first boundary defining a first inner region which is an inner region of a skull region, and a reference region by segmenting the brain image into a plurality of regions including the skull region and the reference region; obtain a second inner region having a second boundary by modifying at least a part of the first boundary related to the first inner region based on the reference region, wherein a part of the second region is included in the first inner region and includes a target element; obtain a first volumetric value related to the target element based on the voxel data corresponding to the target element; obtain a second volumetric value related to the second inner region based on the voxel data included to the second boundary; and calculate a volumetric index based on the first volumetric value and the second volumetric value.

According to a device for analyzing a brain image disclosed in the present application, wherein the controller is configured to align the brain image for obtaining the second inner region.

According to a device for analyzing a brain image disclosed in the present application, wherein the controller is configured to align the brain image, by obtaining a first feature region and a second feature region from the brain image; calculating a first feature point based on the first feature region and a second feature point based on the second feature region; obtaining photographing direction of the brain image based on the first feature point and the second feature point; and aligning the brain image such that the photographing direction is parallel to reference direction.

According to a device for analyzing a brain image disclosed in the present application, wherein the first feature region is a region corresponding to an anterior commissure, the second feature region is a region corresponding to a posterior commissure, the first feature point is included in a boundary defining the region corresponding to the anterior commissure, and the second feature point is included in a boundary defining the region corresponding to the posterior commissure.

According to a device for analyzing a brain image disclosed in the present application, wherein the controller is configured to align the brain image, by obtaining a data related to direction of the brain image included in the brain image; obtaining photographing direction of the brain image based on the data related to the direction of the brain image; and aligning the brain image such that the photographing direction is parallel to reference direction.

According to a device for analyzing a brain image disclosed in the present application, wherein the controller is configured to obtain the second inner region by obtaining a reference plane adjacent to the reference region from the brain image; and obtaining the second inner region having the second boundary by modifying a part of the first boundary of the first inner region based on the reference plane.

According to a device for analyzing a brain image disclosed in the present application, wherein the reference plane is a plane parallel to a transverse plane of the brain image, and the controller is configured to obtain the second inner region by modifying a part of the first boundary located on a lower side of the reference plane, based on the first inner region located on an upper side of the reference plane; and obtaining the second inner region having the second boundary based on the modified first boundary.

According to a device for analyzing a brain image disclosed in the present application, wherein the reference region is a region corresponding to a cerebellum, and the reference plane is adjacent to an inferior edge of a boundary defining the region corresponding to the cerebellum.

According to a device for analyzing a brain image disclosed in the present application, wherein the controller is configured to obtain the second inner region by obtaining a first feature region and a second region from the brain image; calculating a first feature point based on the first feature region and a second feature point based on the second feature region; obtaining reference direction connecting the first feature point and the second feature point base on the first feature point and the second feature point; obtaining a reference plane parallel to the reference direction; and obtaining the second inner region having the second boundary by modifying a part of the first boundary of the first inner region based on the reference plane.

According to a device for analyzing a brain image disclosed in the present application, wherein the reference region is a region corresponding to a cervical vertebra, the reference plane is adjacent to the region corresponding to the cervical vertebra and is vertical to a sagittal plane.

According to a device for analyzing a brain image disclosed in the present application, wherein the controller is configured to modify a part of the first boundary located on a lower side of the reference plane, based on the first inner region located on an upper side of the reference plane; and obtain the second inner region having the second boundary based on the modified first boundary.

According to a device for analyzing a brain image disclosed in the present application, wherein the controller is configured to define the volumetric index as a ratio of the first volumetric value to the second volumetric value.

According to a device for analyzing a medical image disclosed in the present application, wherein the controller is configured to calculating the volumetric index of the target element by: obtaining a first calibrating parameter for calibrating the first volumetric value, wherein the first calibrating parameter is obtained based on a position of the target element or a scan condition in which the brain image is acquired; calculating the first calibrated volumetric value based on the first calibrating parameter and the first volumetric value; obtaining a second calibrating parameter for calibrating the second volumetric value, wherein the second calibrating parameter is obtained based on a position of the target element or a scan condition in which the brain image is acquired; calculating the second calibrated volumetric value based on the second calibrating parameter and the second volumetric value; and calculating the volumetric index based on the first calibrated volumetric value and the second calibrated volumetric value.

According to a device for analyzing a medical image disclosed in the present application, wherein a scan condition in which the brain image is acquired is related to at least one of a magnetic field strength related to a resolution of the medical image of a medical image device, a manufacturer of the medical image device, and a setting parameter related to a magnetic field generated by the medical image device.

According to a method for analyzing a medical image disclosed in the present application, the method comprises: obtaining a calibrating parameter calculated based on a correlation between a first morphological value related to a target element obtained from a first medical image acquired under a first scan condition and a second morphological value related to the target element obtained from a second medical image acquired under a second scan condition; obtaining a target medical image acquired under the second scan condition; obtaining a target area related to the target element from the target medical image by performing a segmentation of the target medical image into a plurality of areas corresponding a plurality of elements including the target element; obtaining a target morphological value related to the target element based on a voxel data corresponding to the target area; obtaining a calibrated morphological value based on the target morphological value and the calibrating parameter; and outputting a morphological index based on the calibrated morphological value.

According to a method for analyzing a medical image disclosed in the present application, wherein the calibrating parameter includes a parameter calculating the first morphological value based on the second morphological value, and the obtaining the calibrated morphological value comprises, based on the target morphological value and the calibrating parameter, obtaining the calibrated morphological value which is an estimated morphological value of the target element under the first scan condition.

According to a method for analyzing a medical image disclosed in the present application, wherein the calibrating parameter includes a parameter related to a linear function for calculating the first morphological value based on the second morphological value, and the obtaining the calibrated morphological value comprises: obtaining the calibrated morphological value based on the target morphological value and the linear function including the parameter.

According to a method for analyzing a medical image disclosed in the present application, wherein each of the first scan condition and the second scan condition is related to at least one of a magnetic field strength related to a resolution of the medical image of a medical image device, a manufacturer of the medical image device, and a setting parameter related to a magnetic field generated by the medical image device.

According to a method for analyzing a medical image disclosed in the present application, wherein the target medical image is obtained from a first object having a first feature, wherein the calibrating parameter is obtained from the first medical image and the second medical image obtained from a second object having the first feature, and wherein the first feature is related to an age or a sex of object.

According to a method for analyzing a medical image disclosed in the present application, wherein the segmentation is performed using a neural network for obtaining the plurality of areas corresponding to the plurality of elements based on the target medical image.

According to a method for analyzing a medical image disclosed in the present application, the method further comprises: converting the target medical image acquired under the second scan condition to medical image corresponding to image acquired under the first scan condition, and wherein the segmentation is performed based on the converted medical image.

According to a method for analyzing a medical image disclosed in the present application, wherein when the first scan condition and the second scan condition are related to the magnetic field strength, the calibrating parameter includes a parameter set for converting the second morphological value which is related to target element and is obtained from the second medical image acquired under the second magnetic field into the first morphological value which is related to target element and is obtained from the first medical image acquired under the first magnetic field, and wherein when the target medical image is acquired under the second magnetic field, the calibrated morphological value is obtained based on the target morphological value and the parameter set.

According to a device for analyzing a medical image disclosed in the present application, the device comprises: an image acquisition unit for obtaining a target medical image; and a controller for providing analysis information of a medical image based on the target medical image, and wherein the controller configured to: obtain a calibrating parameter calculated based on a correlation between a first morphological value related to a target element obtained from a first medical image acquired under a first scan condition and a second morphological value related to the target element obtained from a second medical image acquired under a second scan condition; obtain a target medical image acquired under the second scan condition; obtain a target area related to the target element from the target medical image by performing a segmentation of the target medical image into a plurality of areas corresponding a plurality of elements including the target element; obtain a target morphological value related to the target element based on a voxel data corresponding to the target area; obtain a calibrated morphological value based on the target morphological value and the calibrating parameter; and output a morphological index based on the calibrated morphological value.

According to a device for analyzing a medical image disclosed in the present application, wherein the calibrating parameter includes a parameter calculating the first morphological value based on the second morphological value, and the controller is configured to obtain the calibrated morphological value which is an estimated morphological value of the target element under the first scan condition based on the target morphological value and the calibrating parameter.

According to a device for analyzing a medical image disclosed in the present application, wherein the calibrating parameter includes a parameter related to a linear function for calculating the first morphological value based on the second morphological value, and the controller is configured to obtain the calibrated morphological value based on the target morphological value and the linear function including the parameter.

According to a device for analyzing a medical image disclosed in the present application, wherein each of the first scan condition and the second scan condition is related to at least one of a magnetic field strength related to a resolution of the medical image of a medical image device, a manufacturer of the medical image device, and a setting parameter related to a magnetic field generated by the medical image device.

According to a device for analyzing a medical image disclosed in the present application, wherein the target medical image is obtained from a first object having a first feature, wherein the calibrating parameter is obtained from the first medical image and the second medical image obtained from a second object having the first feature, and wherein the first feature is related to an age or a sex of object.

According to a device for analyzing a medical image disclosed in the present application, wherein the segmentation is performed using a neural network for obtaining the plurality of areas corresponding to the plurality of elements based on the target medical image.

According to a device for analyzing a medical image disclosed in the present application, wherein the controller is configured to convert the target medical image acquired under the second scan condition to medical image corresponding to image acquired under the first scan condition, and wherein the segmentation is performed based on the converted medical image.

According to a device for analyzing a medical image disclosed in the present application, the device further comprises: an output module for outputting a morphological information obtained based on the morphological index and a morphological index database, and wherein the morphological information includes a percentile information on the morphological index database of the morphological index related to the object of the target medical image, and wherein the output module is configured to output the morphological information reflecting the percentile information.

According to a device for analyzing a medical image disclosed in the present application, wherein, when the first scan condition and the second scan condition are related to the magnetic field strength, the calibrating parameter includes a parameter set for converting the second morphological value which is related to target element and is obtained from the second medical image acquired under the second magnetic field into the first morphological value which is related to target element and is obtained from the first medical image acquired under the first magnetic field, and wherein when the target medical image is acquired under the second magnetic field, the calibrated morphological value is obtained based on the target morphological value and the parameter set.

According to a method for analyzing a medical image disclosed in the present application, the method comprises: obtaining a target medical image; obtaining a target scan condition related to the target medical image; obtaining a target morphological value related to a target element based on a voxel data of a target area corresponding to the target element included in the target medical image; determining a target calibrating parameter, based on the target scan condition, among one or more calibrating parameters; and outputting a morphological index based on the determined target calibrating parameter and the target morphological value, and wherein the determining the target calibrating parameter comprises: when the target scan condition is corresponded to a first scan condition, the target calibrating parameter is determined to a first calibrating parameter for calibrating a first morphological value which is obtained under the first scan condition and which is related the target element; and when the target scan condition is corresponded to a second scan condition, the target calibrating parameter is determined to a second calibrating parameter for calibrating a second morphological value which is obtained under the second scan condition different to the first scan condition and which is related the target element.

According to a method for analyzing a medical image disclosed in the present application, the outputting the morphological index comprises: when the target scan condition is corresponded to the first scan condition, calculating a first calibrated morphological index based on the target morphological value and the first calibrating parameter, and when the target scan condition is corresponded to the second scan condition, calculating a second calibrated morphological index based on the target morphological value and the second calibrating parameter; and when the target scan condition is corresponded to the first scan condition, outputting the first calibrated morphological index, and when the target scan condition is corresponded to the second scan condition, outputting the second calibrated morphological index.

According to a method for analyzing a medical image disclosed in the present application, the method further comprises: obtaining a reference scan condition serving as a reference for determining the target calibrating parameter.

According to a method for analyzing a medical image disclosed in the present application, wherein the first calibrating parameter includes a parameter for calculating an estimated morphological value under a third scan condition from a morphological value obtained under the first scan condition, and wherein the second calibrating parameter includes a parameter for calculating an estimated morphological value under the third scan condition from a morphological value obtained under the second scan condition, and the calculating the first calibrated morphological index comprises: obtaining a first calibrated morphological value which is an estimated morphological value of the target element under the second scan condition based on the target morphological value and the first calibrating parameter, the calculating the second calibrated morphological index comprises: obtaining a second calibrated morphological value which is an estimated morphological value of the target element under the third scan condition based on the target morphological value and the second calibrating parameter.

According to a method for analyzing a medical image disclosed in the present application, wherein the first calibrating parameter includes a first parameter set related to a first linear function for calculating an estimated morphological value under a third scan condition from a morphological value obtained under the first scan condition, and wherein the second calibrating parameter includes a second parameter set related to a second linear function for calculating an estimated morphological value under the third scan condition from a morphological value obtained under the second scan condition, and the calculating the first calibrated morphological index comprises: obtaining a first calibrated morphological value based on the target morphological value and the first linear function including the first calibrating parameter, the calculating the second calibrated morphological index comprises: obtaining a second calibrated morphological value based on the target morphological value and the second linear function including the second calibrating parameter.

According to a method for analyzing a medical image disclosed in the present application, wherein each of the first scan condition, the second scan condition and the target scan condition is related to at least one of a magnetic field strength related to a resolution of the medical image of a medical image device, a manufacturer of the medical image device, and a setting parameter related to a magnetic field generated by the medical image device.

According to a method for analyzing a medical image disclosed in the present application, wherein the target medical image is obtained from an object having a first feature, wherein the first calibrating parameter or the second calibrating parameter are obtained from the first medical image and wherein the second medical image obtained from an object having the first feature, and the first feature is related to an age or a sex of an object.

According to a method for analyzing a medical image disclosed in the present application, the obtaining the target morphological value comprises: obtaining a target area related to the target element from the target medical image by performing a segmentation of the target medical image into a plurality of areas corresponding a plurality of elements including the target element; and obtaining a target morphological value related to the target element based on a voxel data corresponding to the target area, wherein the segmentation is performed using a neural network for obtaining the plurality of areas corresponding to the plurality of elements based on the target medical image.

According to a method for analyzing a medical image disclosed in the present application, the method further comprises: converting the target medical image acquired under the target scan condition to medical image corresponding to image acquired under a scan condition other than the target scan condition, and wherein the segmentation is performed based on the converted medical image.

According to a method for analyzing a medical image disclosed in the present application, wherein when the first scan condition, the second scan condition and the target scan condition are related to the magnetic field strength, the first calibrating parameter includes a first parameter set for calibrating the first morphological value related to the target element obtained under the first magnetic field strength, and the second calibrating parameter includes a second parameter set for calibrating the second morphological value related to the target element obtained under the second magnetic field strength, and the determining the target calibrating parameter comprises: when the target scan condition is corresponded to the first scan condition, the target calibrating parameter is determined to the first parameter set; and when the target scan condition is corresponded to the second scan condition, the target calibrating parameter is determined to the second parameter set.

According to a device for analyzing a medical image disclosed in the present application, the device comprises: an image acquisition unit for obtaining a target medical image; and a controller for providing analysis information of a medical image based on the target medical image, and wherein the controller configured to: obtain a target scan condition related to the target medical image; obtain a target morphological value related to a target element based on a voxel data of a target area corresponding to the target element included in the target medical image; determine a target calibrating parameter, based on the target scan condition, among one or more calibrating parameters; and output a morphological index based on the determined target calibrating parameter and the target morphological value, and wherein the determining the target calibrating parameter comprises: when the target scan condition is corresponded to a first scan condition, the target calibrating parameter is determined to a first calibrating parameter for calibrating a first morphological value which is obtained under the first scan condition and which is related the target element; and when the target scan condition is corresponded to a second scan condition, the target calibrating parameter is determined to a second calibrating parameter for calibrating a second morphological value which is obtained under the second scan condition different to the first scan condition and which is related the target element.

According to a device for analyzing a medical image disclosed in the present application, wherein the controller is configured to: when the target scan condition is corresponded to the first scan condition, calculate a first calibrated morphological index based on the target morphological value and the first calibrating parameter, and when the target scan condition is corresponded to the second scan condition, calculate a second calibrated morphological index based on the target morphological value and the second calibrating parameter; and when the target scan condition is corresponded to the first scan condition, output the first calibrated morphological index, and when the target scan condition is corresponded to the second scan condition, output the second calibrated morphological index.

According to a device for analyzing a medical image disclosed in the present application, wherein the first calibrating parameter includes a parameter for calculating an estimated morphological value under a third scan condition from a morphological value obtained under the first scan condition, and wherein the second calibrating parameter includes a parameter for calculating an estimated morphological value under the third scan condition from a morphological value obtained under the second scan condition, and wherein the controller is configured to: calculate the first calibrated morphological index by obtaining the first calibrated morphological value which is an estimated morphological value of the target element under the second scan condition, based on the target morphological value and the first calibrating parameter; and calculate the second calibrated morphological index by obtaining the second calibrated morphological value which is an estimated morphological value of the target element under the third scan condition, based on the target morphological value and the second calibrating parameter.

According to a device for analyzing a medical image disclosed in the present application, wherein the first calibrating parameter includes a first parameter set related to a first linear function for calculating an estimated morphological value under a third scan condition from a morphological value obtained under the first scan condition, and wherein the second calibrating parameter includes a second parameter set related to a second linear function for calculating an estimated morphological value under the third scan condition from a morphological value obtained under the second scan condition, and wherein the controller is configured to: calculate the first calibrated morphological index by obtaining the first calibrated morphological value, based on the target morphological value and the first linear function including the first parameter set; and calculate the second calibrated morphological index by obtaining the second calibrated morphological value, based on the target morphological value and the second linear function including the second parameter set.

According to a device for analyzing a medical image disclosed in the present application, wherein each of the first scan condition and the second scan condition is related to at least one of a magnetic field strength related to a resolution of the medical image of a medical image device, a manufacturer of the medical image device, and a setting parameter related to a magnetic field generated by the medical image device.

According to a device for analyzing a medical image disclosed in the present application, wherein the target medical image is obtained from an object having a first feature, wherein the first calibrating parameter or the second calibrating parameter are obtained from the first medical image and the second medical image obtained from an object having the first feature, and wherein the first feature is related to an age or a sex of an object.

According to a device for analyzing a medical image disclosed in the present application, the controller is configured to: obtain a target area related to the target element from the target medical image by performing a segmentation of the target medical image into a plurality of areas corresponding a plurality of elements including the target element; and obtain the target morphological value related to the target element based on a voxel data corresponding to the target area; wherein the segmentation is performed using a neural network for obtaining the plurality of areas corresponding to the plurality of elements based on the target medical image.

According to a device for analyzing a medical image disclosed in the present application, wherein the controller is configured to: convert the target medical image acquired under the target scan condition to medical image corresponding to image acquired under a scan condition other than the target scan condition, and perform the segmentation based on the converted medical image.

According to a device for analyzing a medical image disclosed in the present application, wherein when the first scan condition, the second scan condition and the target scan condition are related to the magnetic field strength, the first calibrating parameter includes a first parameter set for calibrating the first morphological value related to the target element obtained under the first magnetic field strength, and the second calibrating parameter includes a second parameter set for calibrating the second morphological value related to the target element obtained under the second magnetic field strength, wherein the controller is configured to: when the target scan condition is corresponded to the first scan condition, determine the target calibrating parameter as the first parameter set; and when the target scan condition is corresponded to the second scan condition, determine the target calibrating parameter as the second parameter set.

According to a method for analyzing a brain image disclosed in the present application, the method comprises: obtaining a first calibrating parameter for calibrating a first morphological value related to a first brain element; obtaining a second calibrating parameter for calibrating a second morphological value related to a second brain element different from the first brain element; obtaining a target brain image; by performing a segmentation the target brain image into a plurality of brain regions including a first region corresponding to the first brain element, a second region corresponding to the second brain element, and a skull region, obtaining the first region, the second region, and a third region related to an inner region of the skull region; obtaining a first brain morphological index related to the first brain element based on a voxel data corresponding to the first region, a voxel data corresponding to the third region and the first calibrating parameter; and obtaining a second brain morphological index related to the second brain element based on a voxel data corresponding to the second region, a voxel data corresponding to the third region and the second calibrating parameter.

According to a method for analyzing a brain image disclosed in the present application, the method further comprises: obtaining a reference morphological value related to the inner region based on a voxel data corresponding to the third region, wherein the obtaining the first brain morphological index comprises: obtaining a first target morphological value related to the first brain element based on voxel data corresponding the first region; and calculating the first morphological index based on the first calibrated morphological value and the reference morphological value;

wherein the obtaining the second brain morphological index comprises: obtaining a second target morphological value related to the second brain element based on voxel data corresponding the second region; and calculating the second morphological index based on the second calibrated morphological value and the reference morphological value.

According to a method for analyzing a brain image disclosed in the present application, wherein the first morphological value and the second morphological value are obtained under a first scan condition, the target brain image is obtained under the first scan condition, the first calibrating parameter includes a first parameter for calculating a third morphological value related to the first brain element obtained under a second scan condition different from the first scan condition based on the first morphological value, and the second calibrating parameter includes a second parameter for calculating a fourth morphological value related to the second brain element obtained under the second scan condition based on the first morphological value, wherein the calculating the first calibrated morphological value comprises: obtaining the first calibrated morphological value which is an estimated morphological value of the first brain element under the second scan condition based on the first target morphological value and the first calibrating parameter, wherein the calculating the second calibrated morphological value comprises: obtaining the second calibrated morphological value which is an estimated morphological value of the second brain element under the second scan condition based on the second target morphological value and the second calibrating parameter.

According to a method for analyzing a brain image disclosed in the present application, wherein the first calibrating parameter includes a first parameter set related to a first linear function for calculating the third morphological value based on the first morphological value, and the second calibrating parameter includes a second parameter set related to a second linear function for calculating the fourth morphological value based on the second morphological value, wherein the calculating the first calibrated morphological value comprises: obtaining the first calibrated morphological value based on the first target morphological value and the first parameter set related to the first linear function, wherein the calculating the second calibrated morphological value comprises: obtaining the second calibrated morphological value based on the second target morphological value and the second parameter set related to the second linear function.

According to a method for analyzing a brain image disclosed in the present application, wherein the first region corresponding to the first brain element is positioned adjacent to the skull region compared to the second region corresponding to the second brain element.

According to a method for analyzing a brain image disclosed in the present application, wherein the first brain element is related to an element performing a first brain function, and the second brain element is related to an element performing a second brain function different from the first brain function.

According to a method for analyzing a brain image disclosed in the present application, wherein each of the first scan condition and the second scan condition is related to at least one of a magnetic field strength related to a resolution of the brain image of a brain image device, a manufacturer of the brain image device, and a setting parameter related to a magnetic field generated by the brain image device.

According to a method for analyzing a brain image disclosed in the present application, wherein the target brain image is obtained from a first object having a first feature, wherein the first calibrating parameter and the second calibrating parameter are obtained from the first brain image and the second brain image obtained from a second object having the first feature, and wherein the first feature is related to an age or a sex of an object.

According to a method for analyzing a brain image disclosed in the present application, wherein the segmentation is performed using a neural network for obtaining the plurality of the brain regions corresponding to the plurality of the brain elements including the first brain element, the second element and the skull, based on the target brain image.

According to a method for analyzing a brain image disclosed in the present application, the method further comprises: preprocessing the target brain image, wherein the preprocessing the target brain image comprises: performing the preprocessing in a first method for the first region, and performing the preprocessing in a second method different from the first method for the second region, and the segmentation is performed based on the preprocessed target brain image.

According to a method for analyzing a brain image disclosed in the present application, wherein the first calibrated morphological value is a volumetric value related to the first brain element obtained from the target brain image, wherein the second calibrated morphological value is a volumetric value related to the second brain element obtained from the target brain image, the first brain morphological index is calculated as the first calibrated morphological value to the reference morphological value, and the second brain morphological index is calculated as the second calibrated morphological value to the reference morphological value.

According to a device for analyzing a brain image disclosed in the present application, the device comprises: an image acquisition unit obtaining a target brain image; and a controller providing a brain image analysis information based on the target brain image, wherein the controller is configured to:

obtain a first calibrating parameter for calibrating a first morphological value related to a first brain element; obtain a second calibrating parameter for calibrating a second morphological value related to a second brain element different from the first brain element; obtain a target brain image; by performing a segmentation the target brain image into a plurality of brain regions including a first region corresponding to the first brain element, a second region corresponding to the second brain element, and a skull region, obtain the first region, the second region, and a third region related to an inner region of the skull region; obtain a first brain morphological index related to the first brain element based on a voxel data corresponding to the first region, a voxel data corresponding to the third region and the first calibrating parameter; and obtain a second brain morphological index related to the second brain element based on a voxel data corresponding to the second region, a voxel data corresponding to the third region and the second calibrating parameter.

According to a device for analyzing a brain image disclosed in the present application, wherein the controller is configured to obtain a reference morphological value related to the inner region based on a voxel data corresponding to the third region, obtain a first target morphological value related to the first brain element based on voxel data corresponding the first region, calculate the first calibrated morphological value related to the first brain element based on the first target morphological value and the first calibrating parameter, calculate the first morphological index based on the first calibrated morphological value and the reference morphological value, obtain a second target morphological value related to the second brain element based on voxel data corresponding the second region, calculate the second calibrated morphological value related to the second brain element based on the second target morphological value and the second calibrating parameter, and calculate the second morphological index based on the second calibrated morphological value and the reference morphological value.

According to a device for analyzing a brain image disclosed in the present application, wherein the first morphological value and the second morphological value are obtained under a first scan condition, the target brain image is obtained under the first scan condition, the first calibrating parameter includes a first parameter for calculating a third morphological value related to the first brain element obtained under a second scan condition different from the first scan condition based on the first morphological value, and the second calibrating parameter includes a second parameter for calculating a fourth morphological value related to the second brain element obtained under the second scan condition based on the first morphological value,
  wherein the controller is configured to: calculate the first calibrated morphological value which is an estimated morphological value of the first brain element under the second scan condition based on the first target morphological value and the first calibrating parameter, and calculate the second calibrated morphological value which is an estimated morphological value of the second brain element under the second scan condition based on the second target morphological value and the second calibrating parameter.

According to a device for analyzing a brain image disclosed in the present application, wherein the first calibrating parameter includes a first parameter set related to a first linear function for calculating the third morphological value based on the first morphological value, and the second calibrating parameter includes a second parameter set related to a second linear function for calculating the fourth morphological value based on the second morphological value, wherein the calculating the first calibrated morphological value comprises: obtaining the first calibrated morphological value based on the first target morphological value and the first parameter set related to the first linear function,
  wherein the controller is configured to: calculate the first calibrated morphological value based on the first target morphological value and the first parameter set related to the first linear function and calculate the second calibrated morphological value based on the second target morphological value and the second parameter set related to the second linear function.

According to a device for analyzing a brain image disclosed in the present application, wherein the first region corresponding to the first brain element is positioned adjacent to the skull region compared to the second region corresponding to the second brain element.

According to a device for analyzing a brain image disclosed in the present application, wherein the first brain element is related to an element performing a first brain function, and the second brain element is related to an element performing a second brain function different from the first brain function.

According to a device for analyzing a brain image disclosed in the present application, wherein each of the first scan condition and the second scan condition is related to at least one of a magnetic field strength related to a resolution of the brain image of a brain image device, a manufacturer of the brain image device, and a setting parameter related to a magnetic field generated by the brain image device.

According to a device for analyzing a brain image disclosed in the present application, wherein the target brain image is obtained from a first object having a first feature, wherein the first calibrating parameter and the second calibrating parameter are obtained from the first brain image and the second brain image obtained from a second object having the first feature, and wherein the first feature is related to an age or a sex of an object.

According to a device for analyzing a brain image disclosed in the present application, wherein the segmentation is performed using a neural network for obtaining the plurality of the brain regions corresponding to the plurality of the brain elements including the first brain element, the second element and the skull, based on the target brain image.

According to a device for analyzing a brain image disclosed in the present application, wherein the controller is configured to: preprocess the target brain image, perform the preprocessing in a first method for the first region, and perform the preprocessing in a second method different from the first method for the second region, wherein the segmentation is performed based on the preprocessed target brain image.

According to a device for analyzing a brain image disclosed in the present application, wherein the first calibrated morphological value is a volumetric value related to the first brain element obtained from the target brain image, wherein the second calibrated morphological value is a volumetric value related to the second brain element obtained from the target brain image, the first brain morphological index is calculated as the first calibrated morphological value to the reference morphological value, and the second brain morphological index is calculated as the second calibrated morphological value to the reference morphological value.

MODE(S) FOR CARRYING OUT THE INVENTION

The above objects, features, and advantages of the present application will become more apparent from the following detailed description taken in conjunction with the accompanying drawings. However, since the present application may be variously modified and have several exemplary embodiments, specific exemplary embodiments will be shown in the accompanying drawings and described in detail.

Like reference numerals refer to like elements throughout the specification. Further, like reference numerals will be used to designate like elements within the same scope shown in the drawings of the embodiments, and a relevant description thereof will be omitted.

Detailed descriptions about well-known functions or configurations associated with the present application will be omitted in order not to unnecessarily obscure the subject matter of the present application. Also, ordinal numbers (e.g., first, second, etc.) used in the following description are merely identification symbols for distinguishing one element from another element.

The suffixes "module" and "unit" for elements used in the following embodiments are given or used interchangeably only for facilitation of preparing this specification, and thus they are not assigned a specific meaning or function.

As used herein, the singular forms "a," "an," and "one" are intended to include the plural forms as well, unless the context clearly indicates otherwise.

It should be further understood that the terms "comprises" and/or "comprising" used herein specify the presence of stated features or components but do not preclude the presence or addition of one or more other features or components.

The sizes of components depicted in the drawings may be exaggerated or reduced for convenience of description. For example, since the sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

In the following embodiments, when elements are connected to each other, the elements are connected to each other not only directly but also indirectly with other elements interposed therebetween.

For example, in the following embodiments, when elements are electrically connected to each other, the elements are electrically connected to each other not only directly but also indirectly with other elements interposed therebetween.

A brain image analysis device, a brain image analysis system, and a brain image analysis method of the present application will be described below. Here, brain image analysis may be performed by performing segmentation on a brain image to acquire a plurality of brain regions, computing brain-related morphological indices, and outputting the indices to a user.

In order to improve the accuracy and reliability of such brain image analysis, the present application discloses various techniques such as a technique of checking the quality of a brain image to improve the reliability of a brain image analysis result, a technique of correcting a morphological value or morphological index of a specific acquired brain region, a technique of computing a morphological value or morphological index of a specific brain region from a brain image itself to be analyzed and then providing a customized analysis result for a person, or a technique of providing only chosen information to a user to provide a user-friendly report.

A medical image analysis method, a medical image analysis device, and a medical image analysis system of the present application will be described below.

FIG. 1 is a schematic diagram of a medical image analysis system according to an embodiment of the present application. Referring to FIG. 1, the medical image analysis system according to an embodiment of the present application may include an image acquisition device 1000 and an image analysis device 2000.

The image acquisition device 1000 may acquire an image and transmit the image to the image analysis device 2000 over a network.

As an example, the image acquisition device 1000 may be a device for acquiring a magnetic resonance imaging (MRI) image. In this case, the MRI image acquired by the image acquisition device 1000 may be delivered to the image analysis device 2000 over a network.

As another example, the image acquisition device 1000 may be a device for acquiring a computed tomography (CT) image. In this case, the CT image acquired by the image acquisition device 1000 may be delivered to the image analysis device 2000 over a network.

As another example, the image acquisition device 1000 may be a device for acquiring a radiography image. In this case, the radiography image acquired by the image acquisition device 1000 may be delivered to the image analysis device 2000 over the network.

As another example, the image acquisition device 1000 may be a device for acquiring positron emission tomography (PET) images.

However, the above-described image acquisition device 1000 is merely an example, and the present invention is not limited thereto. The image acquisition device 1000 should be interpreted as encompassing any suitable device or system used for medical imaging.

An image acquired by the image acquisition device 1000 may be a two-dimensional (2D) image. In this case, the image may include pixel information regarding the coordinate, color, strength, and the like of a pixel.

An image acquired by the image acquisition device 1000 may be a three-dimensional (3D) image. In this case, the image may include pixel information regarding the coordinate, color, and strength of a voxel.

An image acquired by the image acquisition device 1000 may include information regarding image alignment. For example, the image acquisition device 1000 may also acquire data ijk related to the orientation of a captured image in consideration of a right-anterior-superior (RAS) orientation of a target subject 100. Specifically, the image acquisition device may acquire data ijk related to the orientation of a captured image in consideration of RAS information of a target subject 100 and coordinate axis information xyz of the image acquisition device.

The image acquisition device 1000 may acquire data related to magnetic field strength for an image, data related to the manufacturer of an imaging device, data related to setting parameters of an imaging device, data related to a target subject of an image, etc.

Data related to magnetic field strength may include data related to the strength of a magnetic field applied to a target subject when a medical image is acquired using the magnetic field (e.g., MRI). For example, when a target image is acquired under the condition of a magnetic field strength of 1.5 T (Tesla), data corresponding to "1.5 T" may correspond to data related to the magnetic field strength. However, the present invention is not limited to 1.5 T, and data corresponding to magnetic field strength generally used to obtain a medical image, such as 3 T, 7 T, 8 T, etc., may correspond to the data related to the magnetic field strength.

The setting parameters of the imaging device may include parameters that may be adjusted or controlled by the imaging device to acquire a medical image. For example, the setting parameters of the imaging device may include a repetition time (TR), which means the time between consecutive pulse sequences applied to the same slice, a time-to-echo (TE), which is a time between RF pulse delivery and an echo signal reception, a time constant T1, which is related to the rate at which excited protons return to equilibrium, a time constant T2, which is related to the rate at which excited protons reach equilibrium or go out of phase with each other, a proton density (PD), or any combination thereof.

However, the present invention is not limited to the above-described examples, and the setting parameters of the imaging device should be interpreted as including any parameters related to magnetic field characteristics. Also, the present invention is not limited to acquiring a target image using a magnetic field, and the setting parameters of the imaging device should be interpreted as including any parameters related to an imaging device that uses a CT method or an irradiation (e.g., X-ray) method.

In this case, the above-described data may be processed as metadata in an acquired image and transmitted to the image analysis device 2000 or delivered to the image analysis device 2000 separately from the image.

The image acquisition device 1000 may be a device for acquiring medical images such as MRI, CT, and X-ray images.

The image acquisition device 1000 may acquire images under various scan conditions.

For example, when an imaging device is an MRI device, an image may be acquired under a scan condition with a magnetic field strength of 1.5 Tesla (hereinafter referred to as T). Also, an image may be acquired under a scan condition with a magnetic field strength of 3 T. Also, an image may be acquired under a scan condition with a magnetic field strength of 7 T or 8 T.

As another example, when the image acquisition device 1000 is an MRI device, as described above, an image may be acquired under scan conditions of setting parameters including TR(Repetition Time), TE (Time to Echo), PD, a time constant T1, which is related to the rate at which excited protons return to equilibrium, and a time constant T2, which is related to the rate at which excited protons reach equilibrium or go out of phase with each other, of the image acquisition device 1000 or any combination thereof.

As another example, the image acquisition device 1000 may be a CT-related device. In this case, an image may be acquired under scan conditions of setting parameters related to voltage, current, exposure time, scanning time, and projection, which may be set in the CT device, and any combinations thereof.

As another example, the image acquisition device 1000 may be an X-ray-related device. In this case, an image may be acquired under scan conditions of setting parameters related to tube voltage, tube current, imaging time, a distance (SID) between an X-ray tube device and a detector, and the angle of an X-ray tube support device, which may be set in the X-ray imaging device, and any combinations thereof.

In addition, different images may be acquired depending on the tendency of an applicator who carries out irradiation. In this case, information on the applicator's tendency may be parameterized. Also, the parameter for the applicator's tendency may be used as one consideration factor in relation to correcting a morphological value or a morphological index in consideration of scan conditions to be described below. In other words, the morphological value or morphological index may be corrected according to the applicator's tendency. More specifically, the image analysis device 2000 according to an embodiment may acquire an applicator's identification information in relation to a scan condition. Also, the image analysis device 2000 may be implemented to acquire correction parameters for correcting the morphological value or morphological index on the basis of the applicator's identification information. For example, based on a correlation between a first morphological value computed from a first image captured by a first applicator and a second morphological value computed from a second image captured by a second applicator, the image analysis device 2000 may acquire a correction parameter for estimating a morphological value computed from a target image acquired from the first applicator as a morphological value related to the second applicator (or a correction parameter for estimating a morphological value computed from a target image acquired from the second applicator as a morphological value related to the first applicator).

As another example, the image acquisition device 1000 may be an MRI device or a CT device that uses positron emission tomography (PET). When PET is used, drugs related to radiopharmaceuticals may be used. For example, a drug (or tracer) such as 18F-florbetapir, 18F-florbetaben, 18F-flutemetamol, 18F-florapronol, etc. may be used to measure amyloid beta. A drug (or tracer) such as 18F-flortaucipir may be used to measure tau protein. A drug to be used may be used differently depending on the manufacturer of the image acquisition device. In this case, information on the drug to be used may be parameterized. Also, the parameter for the drug to be used for the image acquisition device may be used as a scan condition and may be used as one consideration factor in relation to correcting a morphological value or a morphological index in consideration of scan conditions to be described below. In other words, the morphological value or morphological index may be corrected based on the drug to be used and the manufacturer of the image acquisition device. More specifically, the image analysis device 2000 may acquire information on the manufacturer of the image acquisition device and the drug to be used and may be implemented to acquire a correction parameter for correcting a morphological value or a morphological index based on the information on the manufacturer of the image acquisition device and the drug to be used. For example, based on a correlation between a first morphological value computed from a first image captured using a first drug (e.g., 18F-florbetapir) and a second morphological value computed from a second image captured using a second drug (e.g., 18F-florbetaben), the image analysis device 2000 may acquire a first correction parameter for estimating a morphological value computed from a target image acquired using the first drug as a morphological value acquired using a second drug (or a correction parameter for estimating a morphological value computed from a target image acquired using the second drug as a morphological value acquired using the first drug). Also, based on a correlation between the second morphological value computed from the second image captured using the second drug and a third morphological value computed from a third image captured by a third drug, the image analysis device 2000 may acquire a second correction parameter for estimating a morphological value computed from a target image acquired using the second drug as a morphological value acquired using the third drug (e.g., 18F-flutemetamol) (or a correction parameter for estimating a morphological value computed from a target image acquired using the third drug as a morphological value acquired using the second drug). In this case, the first correction parameter may be different from the second correction parameter.

Also, the image acquisition device 1000 may acquire an image under a scan condition including at least one setting parameter. In other words, an image may be acquired under a scan condition based on various combinations of the above-described setting parameters.

For example, an image may be acquired under a first scan condition in which setting parameters are in a first combination. Also, an image may be acquired under a second scan condition in which setting parameters are in a second combination and a magnetic field strength is a first strength. The present invention is not limited thereto, and images acquired by the image acquisition device 1000 may be images acquired under various scan conditions corresponding to various combinations of setting parameters.

Also, the image acquisition device 1000 may include a plurality of image acquisition devices 1000.

In this case, the plurality of image acquisition device 1000 may be devices that may be manufactured by different manufacturers. Images acquired by the devices manufactured by different manufacturers have different characteristics, such as brightness and intensity, even if the scan conditions and setting parameters are the same. Therefore, even if a medical image is acquired for the same target subject, a morphological index based on the medical image may vary depending on the manufacturer's device.

Accordingly, a correction parameter acquisition operation is required to control a scan condition, a setting parameter, or a variable corresponding to the manufacturer of an imaging device by a correction parameter acquisition device 2400, which will be described below, according to an embodiment of the present application.

An image acquired by the image acquisition device 1000 may include information regarding an anatomical structure of a specific part of a human body. Also, the specific body part may correspond to any part for which medical imaging can be utilized. For convenience of description, the following drawings and specifications will focus on brain-related images. However, this is merely an example, and various embodiments disclosed in the present application may be applied to any suitable body part other than the brain (e.g., lung, breast, heart, joint, blood vessel, etc.).

Meanwhile, the image acquisition device 1000 according to an embodiment of the present application may be implemented in the form of a server. In this case, the server may be configured to store medical images and information regarding medical images. Also, the server may be implemented to modify or process medical images and information regarding medical images.

Also, medical images may be stored in a server or memory of the image analysis device 2000 and may be utilized to compute a correction parameter, perform quality control, or output an analysis result. This will be described in detail below.

Figure 2:
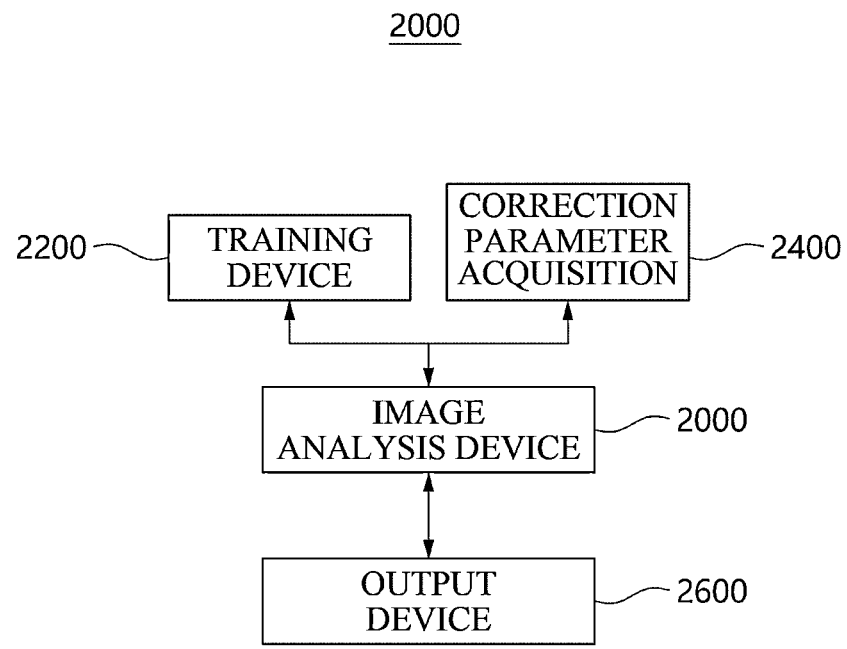
FIG. 2 is a schematic diagram of an image analysis device 2000, a training device 2200, a correction parameter acquisition device 2400, and an output device 2600 for image analysis according to an embodiment of the present application.

The image analysis device 2000, a training device 2200, a correction parameter acquisition device 2400, and an output device 2600 for image analysis according to an embodiment of the present application will be described below with reference to FIG. 2. FIG. 2 is a schematic diagram of the image analysis device 2000, the training device 2200, the correction parameter acquisition device 2400, and the output device 2600 for image analysis according to an embodiment of the present application.

The image analysis device 2000 performs an operation of segmenting an image acquired by the image acquisition device 1000 using an artificial neural network trained by the training device 2200 or an operation of computing a morphological index of a target element included in the image.

The training device 2200 may perform an operation of training a neural network model for image segmentation, a neural network model for image quality control, or the like using a plurality of image data sets.

The correction parameter acquisition device 2400 may perform an operation of computing a correction parameter for correcting a morphological value or morphological index related to a target element of a target image acquired by the image analysis device 2000 using data related to a scan condition and the plurality of image data sets.

The image analysis device 2000, the training device 2200, and the correction parameter acquisition device 2400 shown in FIG. 2 may be implemented to transmit and receive data to and from each other using any communication scheme.

For example, the image analysis device 2000, the training device 2200, and the correction parameter acquisition device 2400 may be implemented to share a server with each other.

As shown in FIG. 2, the image analysis device 2000, the training device 2200, and the correction parameter acquisition device 2400 are shown as being provided as separate devices. However, this is merely an example, and the image analysis device 2000, the training device 2200, and/or the correction parameter acquisition device 2400 may be implemented as a single device. Alternatively, one or some of the image analysis device 2000, the training device 2200, and the correction parameter acquisition device 2400 may be provided as a separate device(s), and the other device(s) may be implemented as a single device.

Figure 3:
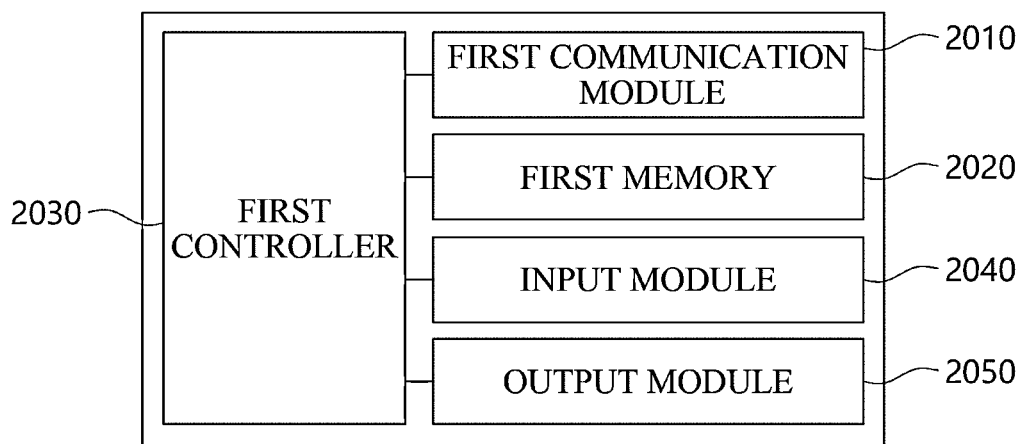
FIG. 3 is a block diagram of an image analysis device according to an embodiment of the present application.

The configuration of the image analysis device 2000 according to an embodiment of the present application will be described below with reference to FIG. 3. FIG. 3 is a block diagram of the image analysis device 2000 according to an embodiment of the present application.

The image analysis device 2000 according to an embodiment of the present application may include a first communication module 2010, a first memory 2020, and a first controller 2030.

The first communication module 2010 may perform communication with any external apparatus, including the image acquisition device 1000, the training device 2200, the correction parameter acquisition device 2400, and an output device 2600, which will be described below. In other words, through the first communication module 2010, the image analysis device 2000 may transmit and receive images to and from the image acquisition device 1000 or may transmit and receive data to and from the training device 2200, the parameter acquisition device 2400, the output device 2600, which will be described below, and external apparatuses including a router, a server, and the like.

For example, through the first communication module 2010, the image analysis device 2000 may receive an image acquired by the image acquisition device 1000, information on a neural network model trained by the training device 2200, and information regarding a correction parameter computed by the correction parameter acquisition device 2400. As another example, through the first communication module 2010, the image analysis device 2000 may transmit information regarding an image scan condition to the correction parameter acquisition device 2400 or may transmit information regarding an analysis result to the output device 2600. As another example, the image analysis device 2000 may access the Internet through the first communication module 2010 and upload various data related to images, information regarding scan conditions, and information regarding analysis results.

The first communication modules 2010 are largely divided into a wired-type module and a wireless-type module. Since the wired-type module and the wireless-type module each have advantages and disadvantages, in some cases, the image analysis device 2000 may be provided with both of the wired-type module and the wireless-type module.

Here, a representative example of the wired-type module may be local area network (LAN) or universal serial bus (USB) communication, but other communication schemes are possible.

Also, here, the wireless-type module may mainly use a wireless personal area network (WPAN)-based communication scheme, such as Bluetooth or Zigbee. However, since a wireless communication protocol is not limited thereto, the wireless communication module may use a wireless local area network (WLAN)-based communication scheme, such as Wi-Fi, or other known communication schemes.

The first memory 2020 may store various kinds of information. The first memory 2020 may temporarily or semi-permanently store various kinds of data. Examples of the first memory 2020 may include a hard disk drive (HDD), a solid-state drive (SSD), a flash memory, a read-only memory (ROM), a random access memory (RAM), etc.

The first memory 2020 may be built into or may be detachable from the image analysis device 2000. Various kinds of data necessary for the operation of the image analysis device 2000 may be stored in the first memory 2020 in addition to an operating system for driving the image analysis device 2000 or a program for operating each component of the image analysis device 2000. For example, various kinds of data related to images, information regarding scan conditions, and information regarding analysis results may be stored in the first memory 2020.

The first controller 2030 may control the overall operation of the image analysis device 2000. For example, the first controller 2030 may load a program for operating the image analysis device 2000 from the first memory 2020 and execute the program.

The first controller 2030 may be implemented as a central processing unit (CPU) or the like with hardware, software, or a combination thereof. The first controller 2030 may be provided in the form of an electronic circuit for processing an electrical signal to perform a control function when implemented with hardware and may be provided in the form of a program or code for driving a hardware circuit when implemented with software.

Meanwhile, referring to FIG. 3 again, the image analysis device 2000 according to an embodiment of the present application may include an input module 2040 and an output module 2050.

In this case, the image analysis device 2000 may acquire a user input and output information corresponding to the user input using the input module 2040 and the output module 2050. For example, the image analysis device 2000 may acquire a user input for requesting data acquisition, a user input for instructing preprocessing, a user input related to image segmentation, and a user input for a reference scan condition related to computation of a morphological index using the input module 2040 and may output corresponding information through the output module 2050.

As an example, a user may enter conditions or settings related to analysis of the image analysis device 2000 through the input module 2040.

For example, a user may set a reference scan condition related to a correction parameter for correcting a morphological value or a morphological index acquired from a target image through the input module 2040. In this case, the image analysis device 2000 may correct a morphological value or a morphological index on the basis of a reference scan condition received from the input module 2040.

The input module 2040 may be implemented in various forms, such as a mouse, a keyboard, and a touchpad.

The output module 2050 may be provided to output a notification or an image analysis result during an image analysis operation of the image analysis device 2000.

For example, when the image analysis device 2000 performs an operation of checking image quality, a notification window indicating that an artifact is present in a target image may be provided through the output module 2050.

As another example, when the image analysis device 2000 performs an operation of checking image quality, a notification window indicating that significant artifacts are present in the target image may be provided through the output module 2050 to select whether to perform image analysis.

As another example, when the image analysis device 2000 performs an operation of segmenting a target image, a segmentation result may be provided through the output module 2050.

As another example, when the image analysis device 2000 completes the analysis of the target image, a result of analyzing the target image may be provided through the output module 2050.

The output module 2050 may be implemented in various forms, such as a display.

Also, the image analysis device 2000 may further include a user interface for acquiring a user input through the input module 2040 and outputting information corresponding to the user input through the output module 2050.

In FIG. 3, the image analysis device 2000 according to an embodiment of the present application is shown as including the input module 2040 and the output module 2050, but this is merely an example. Alternatively, the image analysis device 2000 may be provided without the input module 2040 and the output module 2050.

Meanwhile, the image analysis device 2000 according to an embodiment of the present application may be implemented in the form of a server. In this case, the server may be configured to store medical images and information regarding medical images which are transmitted from the image acquisition device 1000. Also, the server may be configured to modify or process medical images and information regarding medical images which are transmitted from the image acquisition device 1000.

Also, the server of the image analysis device 2000 may be implemented separately from the server of the image acquisition device 1000, but the present invention is not limited thereto. The server of the image acquisition device 1000 and the server of the image analysis device 2000 may be implemented in a single form. In other words, the image acquisition device 1000 and the image analysis device 2000 may be implemented as having a common server.

Referring to FIG. 2 again, the image analysis device 2000 according to an embodiment of the present application may be implemented to perform communication with the output device 2600.

The output device 2600 according to an embodiment of the present application may be implemented to receive an analysis result of the image analysis device 2000 and visually output an image analysis result to a user.

In an embodiment, the output device 2600 according to an embodiment of the present application may be implemented to receive information regarding image quality from the image analysis device 2000 and output the information to a user. For example, the output device 2600 may be implemented to output a comment associated with the reliability of an index related to image quality or an image analysis result related to image quality.

In an embodiment, the output device 2600 according to an embodiment of the present application may be implemented to receive an analysis result related to a morphological index from the image analysis device 2000 and output the analysis result to a user.

For example, the output device 2600 may be implemented to output, to a user, a result of comparing and analyzing statistical data of a comparison group and an analysis result related to a morphological index of a target subject. In this case, the result of comparing and analyzing statistical data of a comparison group for target subjects may be processed and output as statistical information in the form of any suitable graph. Also, the output device 2600 may be implemented to provide analysis results related to morphological indices of a plurality of parts of a target subject together.

As another example, the output device 2600 may be provided to output an analysis result related to a morphological index of a target subject while visually outputting information regarding where a body part related to the morphological index corresponds.

In an embodiment, the output device 2600 according to an embodiment of the present application may be implemented to receive a segmentation result for an image from the image analysis device 2000 and output the segmentation result to a user. For example, the segmentation result of the image analysis device 2000 may be a result labeled in the image. In this case, the image analysis device 2000 or the output device 2600 may visually process an image according to a human body's anatomical structure on the basis of the labeled result, and the output device 2600 may be implemented to output an image obtained by visually distinguishing the anatomical structure of the human body to a user.

In an embodiment, the output device 2600 according to an embodiment of the present application may be implemented to receive a report from the image analysis device 2000 and output the report to a user.

Figure 4:
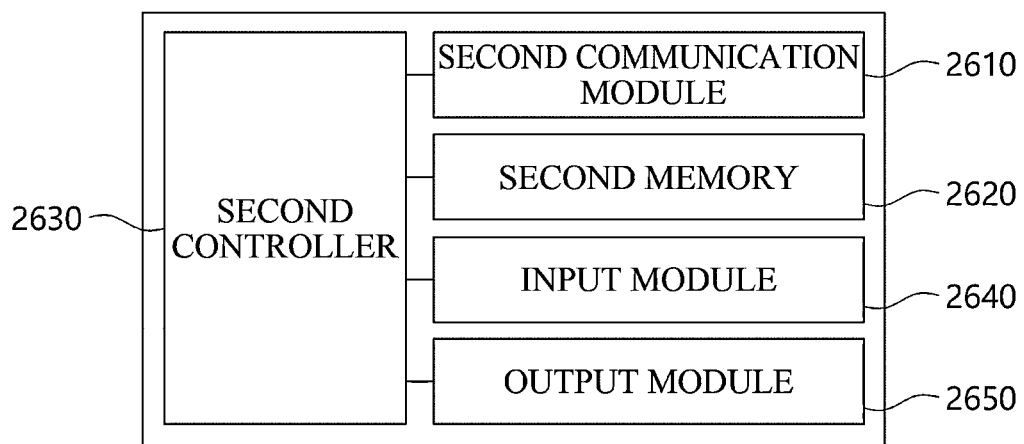
FIG. 4 is a block diagram of an output device according to an embodiment of the present application.

The configuration and operation of the output device 2600 according to an embodiment of the present application will be described below with reference to FIG. 4. FIG. 4 is a block diagram of an output device according to an embodiment of the present application.

The output device 2600 according to an embodiment of the present application may include a second communication module 2610, a second memory 2620, and a second controller 2630.

The second communication module 2610 may perform communication with any external apparatus including the image acquisition device 1000 and the image analysis device 2000. In other words, through the second communication module 2610, the output device 2600 may transmit and receive images to and from the image acquisition device 1000 and may transmit and receive an image analysis result to and from the image analysis device 2000. Also, the output device 2600 may transmit and receive data to and from any external apparatuses, including a router, through the second communication module 2610.

For example, through the second communication module 2610, the output device 2600 may receive images acquired from the image acquisition device 1000, data related to the reliability of an analysis result related to image quality acquired from the image analysis device 2000, data on a segmentation result for an image, data such as a morphological index, and the like. As another example, through the second communication module 2610, the output device 2600 may transmit data related to a user input received from an input module 2640, which will be described below, to the image analysis device 2000 or may transmit data processed by the output device 2600 to the image analysis device 2000. As another example, the output device 2600 may access the Internet through the second communication module 2610 and upload the data related to the user input and the data processed by the output device 2600.

The second communication modules 2610 are largely divided into a wired-type module and a wireless-type module. Since the wired-type module and the wireless-type module each have advantages and disadvantages, in some cases, the image analysis device 2000 may be provided with both of the wired-type module and the wireless-type module.

Here, a representative example of the wired-type module may be local area network (LAN) or universal serial bus (USB) communication, but other communication schemes are possible.

Also, here, the wireless-type module may mainly use a wireless personal area network (WPAN)-based communication scheme such as Bluetooth or Zigbee. However, since a wireless communication protocol is not limited thereto, the wireless communication module may use a wireless local area network (WLAN)-based communication scheme, such as Wi-Fi, or other known communication schemes.

The second memory 2620 may store various kinds of information. The second memory 2620 may temporarily or semi-permanently store various kinds of data. Examples of the second memory 2620 may include a hard disk drive (HDD), a solid-state drive (SSD), a flash memory, a read-only memory (ROM), a random access memory (RAM), etc.

The second memory 2620 may be built into or may be detachable from the output device 2600. Various kinds of data necessary for the operation of the output device 2600 may be stored in the second memory 2620 in addition to an operating system for driving the output device 2600 or a program for operating each component of the output device 2600. For example, various kinds of data related to images, information regarding an analysis result, and user input data may be stored in the second memory 2620.

The second controller 2630 may control the overall operation of the output device 2600. For example, the second controller 2630 may load a program for operating the output device 2600 from the second memory 2620 and execute the program.

The second controller 2630 may be implemented as a central processing unit (CPU) or the like with hardware, software, or a combination thereof. The second controller 2630 may be provided in the form of an electronic circuit for processing an electrical signal to perform a control function when implemented with hardware and may be provided in the form of a program or code for driving a hardware circuit when implemented with software.

Meanwhile, referring to FIG. 4 again, the output device 2600 according to an embodiment of the present application may include an input module 2640 and an output module 2650.

In this case, the output device 2600 may acquire a user input and output information corresponding to the user input using the input module 2640 and the output module 2650.

For example, the output device 2600 may acquire a user input for requesting data acquisition, a user input for instructing preprocessing, a user input related to image segmentation, and a user input for a reference scan condition related to computation of a morphological index using the input module 2640 and may output corresponding information through the output module 2650.

In this case, the output device 2600 may further include a user interface for acquiring a user input through the input module 2640 and outputting information corresponding to the user input through the output module 2650.

In an embodiment, a user may enter conditions or settings related to the output of the output device 2600 or select some of a plurality of pieces of output data through the input module 2640.

As an example, a user may set a reference scan condition related to a correction parameter for correcting a morphological value or a morphological index acquired from a target image through the input module 2640. In this case, the output device 2600 may be implemented to output an analysis result corresponding to the corrected morphological value or the corrected morphological index on the basis of the reference scan condition (e.g., the magnetic field strength, manufacturer, setting parameter of an imaging device, etc.) received from the input module 2640.

For example, when, by changing magnetic field strength, a user wants to receive an image analysis result according to the changed magnetic field strength, a scan condition for the magnetic field strength may be input through the input module 2640. In this case, the output device 2600 may be implemented to output a corrected image analysis result on the basis of the scan condition for the magnetic field strength input by the user. In this case, the output device 2600 may transmit input data related to the scan condition for the magnetic field strength input by the user to the image analysis device 2000, and the image analysis device 2000 may modify the image analysis result and deliver the modified image analysis result to the output device 2600 on the basis of a correction parameter acquired based on a received user input. It will be appreciated that the output device 2600 may be implemented to receive a correction parameter from the image analysis device 2000, modify an image analysis result, and output the modified image analysis result.

This will be described in more detail below with reference to FIGS. 66 and 67.

However, the above description is merely an example, and the present invention is not limited thereto. The output device 2600 may be implemented to receive a user input through the input module 2640 in order to output any type of information that the user wants to receive.

The input module 2640 may be implemented in various forms, such as a mouse, a keyboard, and a touchpad.

The output module 2650 may be provided to output an image analysis result or the like received from the image analysis device 2000.

For example, the output device 2600 transmits, through the output module 2650, information on whether an artifact is present in a target image received from the image analysis device 2000 and on the reliability of the analysis result thereof in text or any suitable visual form.

As another example, the output device 2600 may output, through the output module 2650, a result of segmenting a target image received from the image analysis device 2000. In this case, the output device 2600 may be implemented to divisionally output, as the segmentation result, a human body's anatomical structure in a visual graphic form.

As another example, the output device 2600 may output, through the output module 2650, a result of analyzing a target image received from the image analysis device 2000. In this case, the result of analyzing the target image may be output in the format of a report. Also, the output device 2600 may be implemented such that a morphological value or a morphological index of the anatomical structure included in the result of analyzing the target image is output using a statistical technique such as a graph. Also, the output device 2600 may be implemented such that the morphological value or morphological index of the anatomical structure included in the result of analyzing the target image is output using a statistical technique such as a graph in comparison to statistical data of a comparison group for target subjects.

The output module 2650 may be implemented in various forms, such as a display.

The image analysis device 2000 and the output device 2600 have been described as separate devices. However, this is merely an example, and the image analysis device 2000 and the output device 2600 may be implemented as a single device.

The image analysis device 2000 may receive a medical image delivered from the image acquisition device 1000 and perform preprocessing such as alignment of the medical image, normalization of brightness or intensity of the medical image, and noise removal.

Also, the image analysis device 2000 may receive a medical image delivered from the image acquisition device 1000 and perform segmentation on the medical image. In this case, the segmentation of the medical image according to an embodiment of the present application may be performed using a trained neural network model.

The image analysis device 2000 according to an embodiment of the present application may perform an operation of controlling the quality of a medical image. Therefore, with the image analysis device 2000 according to an embodiment of the present application, it is possible to increase the reliability of a medical image analysis result.

The image analysis device 2000 according to an embodiment of the present application may perform an operation of computing a morphological index on the basis of a medical image acquired from a target subject. Therefore, with the image analysis device 2000 according to an embodiment of the present application, it is possible to accurately compute a morphological index in relation to an anatomical structure of a target subject's body. Thus, there is an advantageous effect of being able to provide an accurate and objective index for a target subject's disease. In particular, since image segmentation is performed without matching a brain image related to a target subject to a standard brain model, it is possible to provide a personalized auxiliary diagnostic index related to a brain disease.

The image analysis device 2000 according to an embodiment of the present application may perform an operation of correcting a morphological value or a morphological index in consideration of a body part or a scan condition where a medical image is acquired. Therefore, with the image analysis device 2000 according to an embodiment of the present application, it is possible to accurately compute a morphological index in relation to an anatomical structure of a target subject's body. In other words, the computed morphological value may have a slight error depending on the scan condition or the body part. In this case, the image analysis device 2000 according to an embodiment of the present application may first correct the computed morphological value or morphological index in consideration of the scan condition or the body part. Thus, there is an advantageous effect of being able to provide an accurate and objective index for a target subject's disease.

The image analysis device 2000 according to an embodiment of the present application may perform an operation of giving priorities to various image analysis results according to the diagnostic field or the state of the target subject and outputting image analysis results chosen based on the priorities. Therefore, with the image analysis device 2000 according to an embodiment of the present application, it is possible to improve user convenience by selectively providing index information necessary for a user among various pieces of index information acquired through the analysis of a target medical image.

Some operations performed by an embodiment of the image analysis device 2000 will be described in more detail below.

For convenience of description, the following description will focus on an embodiment of analyzing an image related to a brain. However, the present invention is not limited to the brain, and the various embodiments disclosed in the present application may be applied to medical images of any suitable body part other than the brain.

Also, hereinafter, medical images, brain images, and target images are used interchangeably, but this is only for convenience of description. All of the medical images, brain images, and target images should be construed as referring to images to be analyzed by the image analysis devices 2000, 3000, and 4000.

Also, the following description may be performed by the image analysis devices 2000, 3000, and 4000 according to an embodiment of the present application. The reference numerals designating the image analysis devices are merely used to distinguish and describe operations of the image analysis devices for convenience of description, and the image analysis devices are not limited by the reference numerals.

The image analysis device 2000 according to an embodiment of the present application may acquire a brain image and information regarding the brain image.

Specifically, the image analysis device 2000 may acquire a brain image from the image acquisition device 1000. Also, the image analysis device 2000 may acquire information regarding the brain image from the image acquisition device 1000 or any external device (e.g., a server).

More specifically, the image analysis device 2000 may acquire a brain image and data related to the brain image from the image acquisition device 1000 through the first communication module 2010.

In this case, the format of the brain image may include various formats of medical images. For example, the brain image may be in the Digital Imaging and Communications in Medicine (DICOM), the Neuroimaging Informatics Technology Initiative (NIfTI), or any suitable format.

The data related to the brain image may encompass data included in the brain image, data related to a scan condition in which the brain image is acquired, and data on a target subject of the brain image.

In this case, the data included in the brain image may be data related to a pixel or voxel included in the brain image, data related to a direction of the brain image, and any metadata structured for the brain image.

In particular, the data related to the scan condition in which the brain is acquired or the data for the target subject of the brain image may be structured for the brain image as metadata.

Meanwhile, the data related to the scan condition in which the brain image is acquired may be data that is related to the magnetic field strength of the image acquisition device 1000 from which the brain image is acquired, a setting parameter of an imaging device of the image acquisition device 1000, or the manufacturer of the imaging device.

Since morphological figures acquired from the brain image may be affected according to the scan condition, the image analysis device 2000 according to an embodiment of the present application may obtain the scan condition-related data and perform correction on the morphological figures. This will be described in detail below with reference to FIGS. 58 to 67.

The data related to the target subject of the brain image may be personal information or medical information about the target subject of the target image to be analyzed by the image analysis device 2000. For example, the data related to the target subject of the brain image may include personal information regarding the target subject's gender, age, etc., and various kinds of medical information including questionnaire information regarding brain diseases (e.g., dementia, Alzheimer's disease, depression, stroke, etc.) or information regarding an underlying disease or the like.

In particular, since gender and age are important variables in brain diseases, data related to the target subject's gender and age may be a basis for the image analysis device 2000 to determine or acquire a correction parameter. For example, when a target image to be analyzed is acquired from a first target subject with a first characteristic related to gender and age, the image analysis device 2000 may determine a correction parameter for correcting a morphological value or a morphological index acquired from the target image as a correction parameter acquired from a first brain image and a second brain image acquired from a second target subject with the first characteristic. For example, the image analysis device 2000 may determine a correction parameter acquired from a second target subject having a similar age and the same gender as the first target subject of the target image as the correction parameter for correcting the morphological value or the morphological index acquired from the target image.

Alternatively, the data related to the target subject's gender and age may be considered in order to output the relative percentage of the morphological index of the target subject according to the gender and age using a statistical technique.

Also, the image analysis device 2000 according to an embodiment of the present application may acquire information regarding an operation related to brain image analysis.

Specifically, the image analysis device 2000 may acquire information regarding a template related to a brain from any external device so as to preprocess or align a brain image. This will be described in detail with reference to FIGS. 5, 6, and 48.

Also, the image analysis device 2000 may acquire information regarding a brain atlas serving as a reference for segmenting a brain image from any external device.

As an example, the information regarding the brain atlas may be information regarding an atlas related to a brain structure. For example, the atlas related to the brain structure may be Automated Anatomical Labeling (Tzourio-Mazoyer 2002), Desikan-Killiany Atlas (Desikan 2006), Destrieux Atlas (Destrieux 2010), Harvard-Oxford cortical/subcortical atlases (Makris 2006), MICCAI 2012 Multi-Atlas Labeling Workshop and Challenge (Neuromorphometrics), Hammersmith atlas (Hammers 2003, Gousias 2008, Faillenot 2017), HCP MMP 1.0 (Glasser 2016), JuBrain/Juelich histological atlas (Eickhoff 2005), or MarsAtlas (Auzias 2016).

As another example, the information regarding the brain atlas may be information regarding an atlas related to a brain function. For example, the atlas related to the brain function may be Mindboggle 101 (Klein 2012), Cortical Area Parcellation from Resting-State Correlations (Gordon 2016), Consensual Atlas of REsting-state Network (CAREN, Doucet 2019), Brainnetome Atlas parcellation (Fan 2016), Local-Global Parcellation of the Human Cerebral Cortex (Schaefer 2018), Human Motor Area Template (Mayka 2005), Sensorimotor Area Tract Template (Archer 2017), AICHA: An atlas of intrinsic connectivity of homotopic areas (Joliot 2015), Yeo 2011 functional parcellations (Yeo 2011), PrAGMATiC (Huth 2016), fMRI-based random parcellations (Craddock 2011), Voxelwise parcellations (Lead-DBS), SUIT Cerebellar parcellation (Diedrichsen 2006), or Buckner functional cerebellar parcellation (Buckner 2011).

The image analysis device 2000 may transmit information on the brain atlas related to the brain to the training device 2200, and the training device 2200 may be implemented to train a neural network model for segmenting the brain image on the basis of the information on the brain atlas.

However, the above-described information on the atlas related to the brain structure or the atlas related to the brain function is just an example, and the image analysis device 2000 may be implemented to acquire any suitable brain-related atlas information and train an artificial neural network model for image segmentation of the training device 2200 on the basis of the acquired atlas information.

The image analysis device 2000 may receive a user input from the input module 2040 of the image analysis device 2000 or the input module 2640 of the output device 2600.

The image analysis device 2000 may acquire a user input related to a disease to be diagnosed. For example, the image analysis device 2000 may acquire a user input related to a brain disease (e.g., dementia, depression, stroke, etc.) corresponding to the disease to be diagnosed, which is related to the target image.

The image analysis device 2000 may acquire a user input related to a patient. For example, the image analysis device 2000 may acquire a user input related to a patient's gender, age, name, etc., which is related to the target image.

The image analysis device 2000 may acquire a user input related to image analysis.

As an example, the image analysis device 2000 may acquire a user input related to image preprocessing. For example, the image analysis device 2000 may acquire a user input related to image processing including correcting the intensity of the target image or removing noise.

As an example, the image analysis device 2000 may acquire a user input related to segmentation. For example, the image analysis device 2000 may acquire a user input for modifying a brain atlas considered for segmentation and labeling data output from the neural network model.

As an example, through an input module, the image analysis device 2000 may receive a user input for a scan condition in which the target image is captured. Information on the scan condition in which the target image is captured may be acquired by being included as metadata of the target image or may be acquired from a user input.

As an example, the image analysis device 2000 may receive, through the input module, a user input for a reference scan condition related to a reference for a correction parameter for correcting a brain-related morphological value or morphological index computed based on the segmentation result. In this case, the image analysis device 2000 may acquire the correction parameter and correct the brain-related morphological value or morphological index on the basis of a user input for the reference scan condition or the like. This will be described in detail below with reference to FIGS. 66 and 67.

As another example, when image analysis results are output, the image analysis device 2000 may select some of the output results or receive a user input for assigning priorities through the input module. In this case, the image analysis device 2000 may be implemented to selectively output information on an analysis result to be output or implemented to output an analysis result reflecting a user's priority on the basis of the user input. This will be described in detail below with reference to FIGS. 68 to 81.

The data acquired by the image analysis device 2000 may be stored in the first memory 2020 of the image analysis device 2000 or any external device (e.g., a server) of the image analysis device 2000. Also, the data acquired by the image analysis device 2000 may be transmitted to the training device 2200 or the correction parameter acquisition device 2400. Alternatively, the data acquired by the image analysis device 2000 may be transmitted to the output device 2600 or transmitted to any external device (e.g., a server).

The image analysis device 2000 according to an embodiment of the present application may perform image preprocessing. The image analysis device 2000 may perform preprocessing for improving image analysis accuracy. The image analysis device 2000 may be provided to perform preprocessing on an image to derive a more accurate segmentation result before performing a segmentation operation on the image.

As an example, the image analysis device 2000 may be provided to perform transformation on the format of the image acquired by the image acquisition device 1000. Specifically, by standardizing the formats of images to be analyzed, it is possible to more stably and accurately train the neural network model. More specifically, it may be more stable and accurate to perform image analysis using an image having the same format as an image used to train the neural network model. Accordingly, the image analysis device 2000 according to an embodiment of the present application may be provided to perform transformation on the format of the image acquired by the image acquisition device 1000.

As an example, the image analysis device 2000 according to an embodiment of the present application may perform an operation of transforming an image of a first format acquired from the image acquisition device 1000 into an image of a second format. For example, the format of the image acquired by the image acquisition device 1000 may be a DICOM format that is generally used in a medical image. In this case, it is possible to perform image segmentation or compute a morphological index on the basis of images of the DICOM format.

However, in analyzing a brain image, it may be relatively easy for a brain image analysis system to analyze an image or train an artificial neural network using a brain image of the NIfTI format. Accordingly, the image analysis device 2000 according to an embodiment of the present application may be provided to transform the format of an image acquired by the image acquisition device 1000 into the NIfTI format.

However, the above-described format is merely an example, and the image analysis device 2000 may be provided to perform a transformation operation into any suitable format other than the NIfTI format, if necessary. Also, the format of the image acquired by the image acquisition device 1000 may be a medical image of any format other than the DICOM format, and even in this case, the image analysis device 2000 may be provided to perform a transformation operation into any suitable format.

As an example, the image analysis device 2000 may be provided to perform correction on an artifact or remove noise that may be present in the image acquired by the image acquisition device 1000. For example, in order to remove noise, a blurring technique and a technique of using a median filter may be utilized. By removing noise and performing correction on an artifact, the image analysis device 2000 may derive a segmentation result on a more accurate image and may compute a morphological index on the basis of a segmentation result with improved accuracy. Thus, it is possible to provide an objective auxiliary diagnostic index for a brain-related disease with high reliability.

As an example, the image analysis device 2000 may be provided to perform an operation of correcting the intensity of the image acquired by the image acquisition device 1000. By appropriately correcting the intensity, noise that may be present in the image may be removed, and an image specialized for allowing the anatomical structure of a brain to be analyzed may be acquired.

As an example, the image analysis device 2000 may be provided to perform an operation of smoothing the image acquired by the image acquisition device 1000. For example, as the image smoothing method, a technique of using a Gaussian filter or performing blurring may be used.

As an example, the image analysis device 2000 may be provided to perform an operation of proportioning or cutting the image acquired by the image acquisition device 1000. For example, the image analysis device 2000 may be implemented to utilize any suitable cropping technique to cut an image. Alternatively, the image analysis device 2000 may be implemented to utilize any suitable image resizing technique such as Ondemand image resizing, Lambda image resizing, a resizing method using CILanczosScaleTransform filter, and a resizing method using CIFilter in order to proportion an image.

As an example, the image analysis device 2000 may be provided to perform an operation of transforming the image acquired by the image acquisition device 1000 into an image captured under a scan condition different from a scan condition in which the image is acquired. For example, the image analysis device 2000 may be provided to perform an operation of transforming an image captured under a first scan condition of an MRI device into an estimated image such as an image captured under a second scan condition of the MRI device. Such an image transformation operation may be performed using a magnetic resonance (MR) transforming technique or an artificial intelligence model. However, the present invention is not limited thereto, and the image analysis device 2000 may be provided to perform image transformation in consideration of a scan condition using any suitable software or image processing technology.

As an example, the image analysis device 2000 may be implemented to perform a preprocessing operation corresponding to an image preprocessing operation in the training device 2200 to be described below. For example, when the training device 2200 trains the neural network model using a first preprocessing technique for an image, the image analysis device 2000 may be implemented to preprocess a target image in a preprocessing technique corresponding to the first preprocessing technique. Thus, it is possible to more stably and accurately implement image segmentation using the neural network model.

An image alignment-related operation of the image analysis device 2000 according to an embodiment of the present application will be described below with reference to FIGS. 5 and 6.

Figure 5:
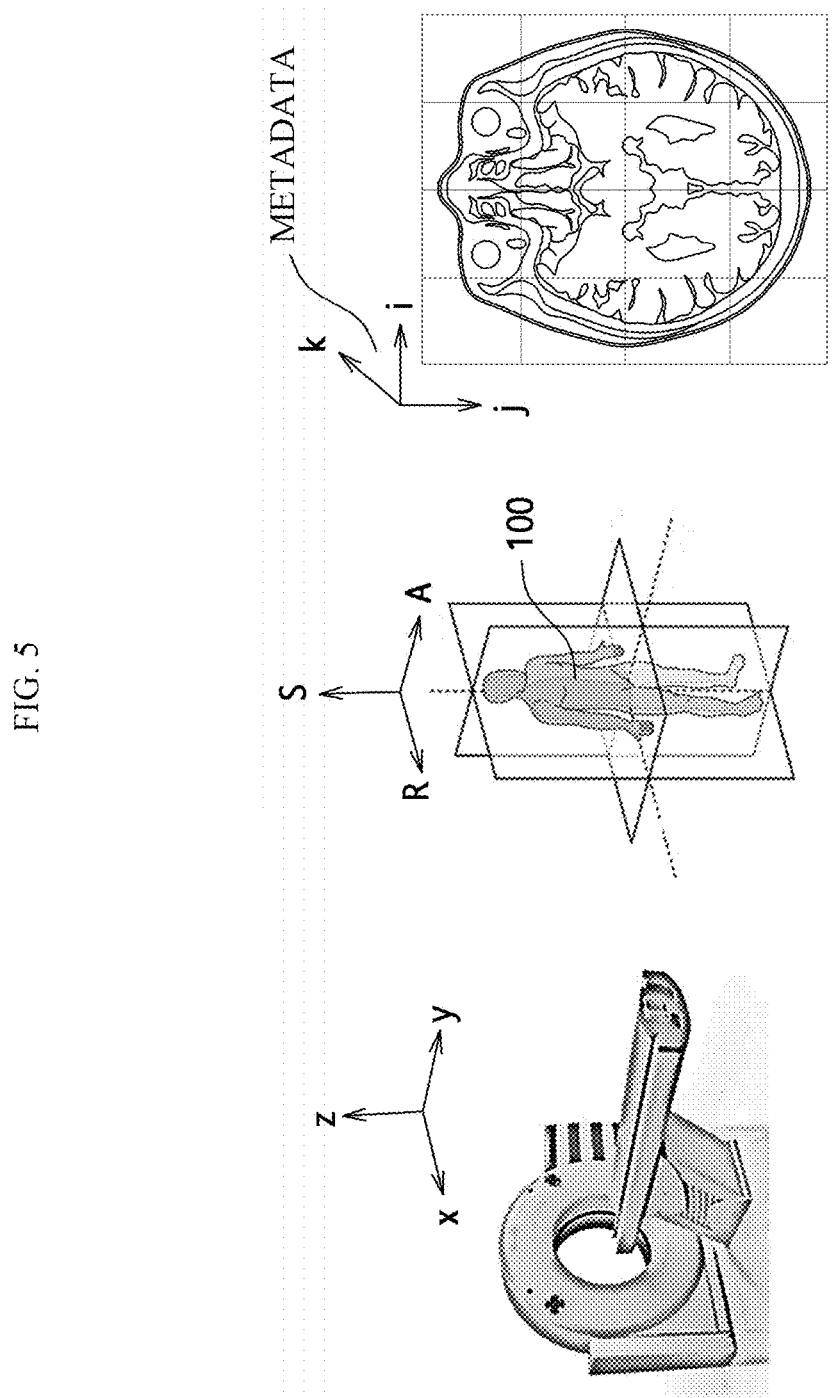
FIG. 5 shows an example of an image alignment operation of the image analysis device 2000.

FIG. 5 shows an example of an image alignment operation of the image analysis device 2000.

Figure 6:
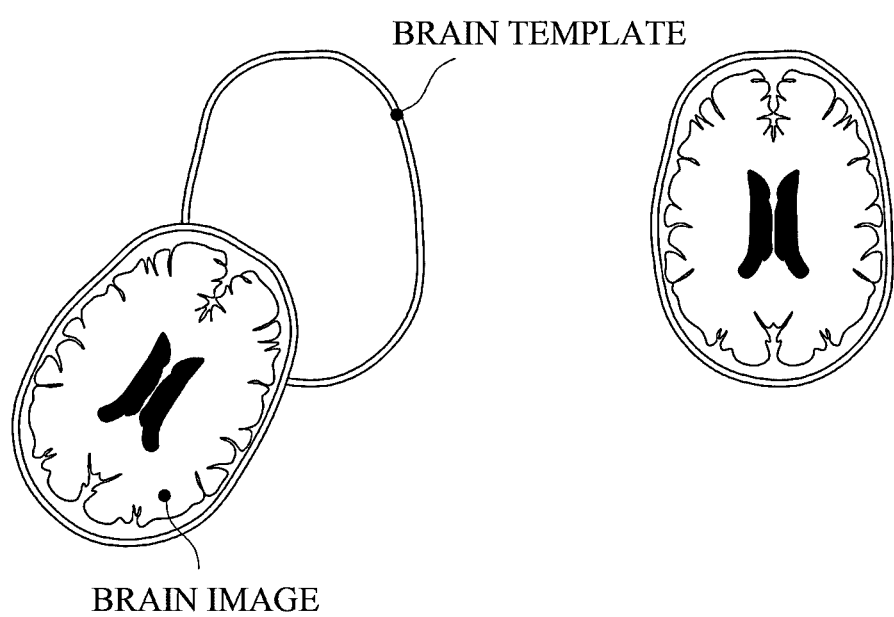
FIG. 6 shows an example of an image alignment operation of the image analysis device 2000.

FIG. 6 shows an example of an image alignment operation of the image analysis device 2000.

The image analysis device 2000 may be implemented to perform an operation of aligning a brain image on the basis of data related to a direction of the brain image included in the brain image.

As an example, the image analysis device 2000 may be implemented to perform an operation of aligning a brain image before performing an image segmentation operation.

For example, referring to FIG. 5, the image acquisition device 1000 may also acquire data i, j, k related to the direction of the captured image in consideration of the direction of the reference coordinate axis (R-A-S) of the target subject 100. Specifically, the image acquisition device 1000 may acquire data (i, j, k) related to the direction of the captured image in consideration of the information (R-A-S) on the reference coordinate axis of the target subject 100 and the information x, y, z on the coordinate axis of the image acquisition device 1000.

The data related to the direction of the image may be structured as metadata for the image. Alternatively, the data related to the direction of the image may be delivered to the image analysis device 2000 separately from the image.

The image analysis device 2000 may be implemented to align an image to correspond to the RAS direction of the target subject 100 on the basis of the data (i-j-k) related to the image direction.

With the above-described image alignment operation of the image analysis device 2000, brain images, which are the basis for segmentation, may be aligned in the common direction before performing the segmentation operation. Thus, it is possible to prevent an inaccurate segmentation result and secure the stability of the segmentation operation of the neural network.

The image analysis device 2000 may be implemented to perform spatial normalization of a brain image.

Specifically, an artificial neural network model for brain image segmentation may be stably driven with respect to a brain image corresponding to a spatial distribution of a training image used as "training data." In other words, when the brain image has a different spatial distribution from the training image, there is a possibility that the trained artificial neural network may not be driven stably.

Therefore, the image analysis device 2000 may be implemented to perform spatial normalization of a brain image in order to reduce spatial uncertainty in the brain image.

As an example, the image analysis device 2000 according to an embodiment of the present application may be implemented to perform spatial normalization of a brain image on the basis of a brain template. Specifically, by matching the brain image to the brain template, the image analysis device 2000 may transform the coordinates of the brain image such that the spatial distribution of the brain image is optimal for the artificial neural network model.

For example, the brain template for matching the brain image may be an MNI template, a Talairach template, or the like.

It has been described above that the image analysis device 2000 performs an operation of matching the brain image to the brain template. In this case, the term "matching" may simply refer to an operation of matching the positional space of the brain image, rather than an operation of mapping the internal elements of the brain in the brain image to the internal elements of the brain in the brain template.

By the above-described spatial normalization operation of the image analysis device 2000, the spatial uncertainty of an image can be removed. Thus, it is possible to secure the stability of a segmentation operation using a neural network and also possible to acquire a segmentation result with improved accuracy.

Also, by matching the brain image to the brain template, data related to the transformed coordinates may be generated. The data related to the transformed coordinates may be used to transform the coordinates of the brain image into original coordinates after segmentation, which will be described below, is completed. In other words, the image analysis device 2000 may be implemented to perform an operation of transforming a segmentation result acquired based on the spatial distribution of the brain template to correspond to the original brain image using the data related to the transformed coordinates.

Through such an operation of the image analysis device 2000, a user can receive an analysis result for a brain image with respect to original coordinates.

For example, when a morphological index related to a brain image is output through an output module, a morphological index corrected by using a correction parameter or the like may be output. Meanwhile, when visual information of a brain (e.g., Info.13 shown in FIG. 57 or a segmentation result) is output through an output module, visual information regarding the brain may be output on the basis of an image obtained through inverse transformation based on the above-described transformed coordinates, i.e., the original brain image.

An operation related to image segmentation of the image analysis device 2000 and the training device 2200 according to an embodiment of the present application will be described in detail below with reference to FIGS. 7 to 17.

According to an embodiment of the present application, the image segmentation operation may be performed using a trained neural network model. However, even when a neural network model is not used, the image segmentation operation according to an embodiment of the present application may be implemented using any suitable method.

The following description will focus on an operation of training a neural network model for image segmentation and an operation of performing image segmentation using the trained neural network model.

Figure 7:
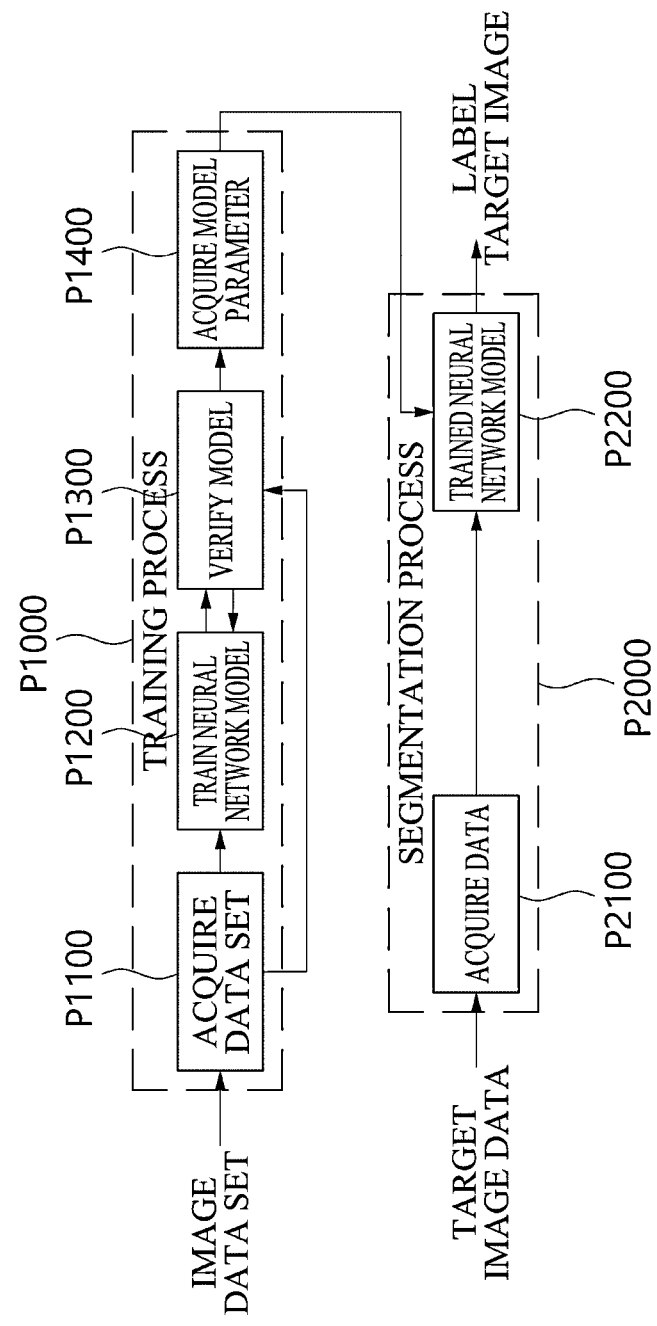
FIG. 7 is a diagram showing a flowchart of an image segmentation process according to an embodiment of the present application.

Reference will be made to FIG. 7. FIG. 7 is a diagram showing a flowchart of an image segmentation process according to an embodiment of the present application.

Referring to FIG. 7, the image segmentation process according to an embodiment of the present application may include a process of training an artificial neural network model for image segmentation (P1000) and a process of segmenting a target image using the trained artificial neural network (P2000).

In this case, the training process P1000 may be implemented by the training device 2200 according to an embodiment of the present application.

Also, the segmentation process P2000 may be implemented by the image analysis device 2000 according to an embodiment of the present application.

In this case, parameters of the neural network model acquired by the training process P1000 implemented by the training device 2200 may be transmitted to the image analysis device 2000 through any suitable communication module.

In this case, the image analysis device 2000 may be implemented to perform segmentation of a target image on the basis of the parameters of the neural network model acquired by the training process P1000.

The training process P1000 according to an embodiment of the present application may include a process of acquiring an image data set (P1100), a process of training a neural network model (P1200), a process of verifying the neural network model (P1300), and a process of acquiring parameters of the neural network model (P1400).

Figure 8:
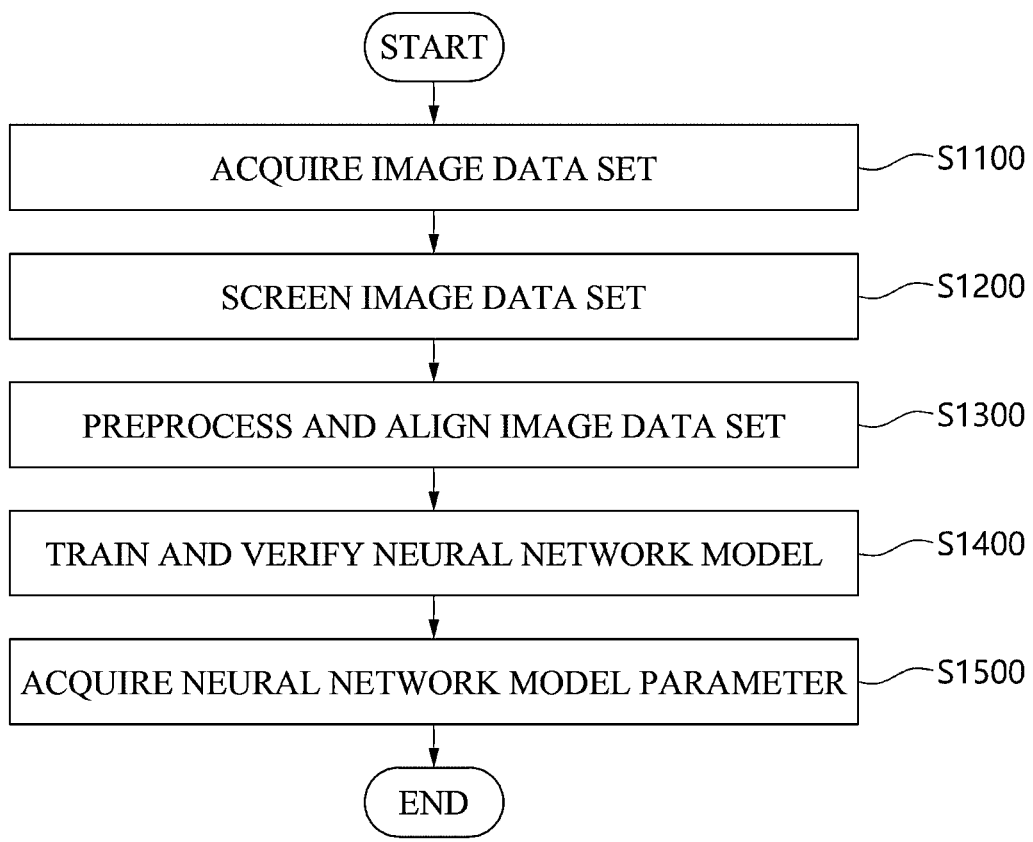
FIG. 8 is a sequence diagram illustrating a method of training a neural network model by the training device 2200 according to an embodiment of the present application.

The method of training the neural network model by the training device 2200 according to an embodiment of the present application will be described below with reference to FIG. 8. FIG. 8 is a sequence diagram illustrating a method of training a neural network model by the training device 2200 according to an embodiment of the present application.

Referring to FIG. 8, the method of training the neural network model by the training device 2200 according to an embodiment of the present application may include an operation of acquiring an image data set (S1100), an operation of screening the image data set (S1200), an operation of preprocessing and aligning the image data set (S1300), an operation of training and verifying a neural network model (S1400), and an operation of acquiring a neural network model parameter (S1500).

In the operation of acquiring the image data set (S1100), the training device 2200 according to an embodiment of the present application may acquire image data sets from the image acquisition device 1000 or any external devices.

Figure 9:
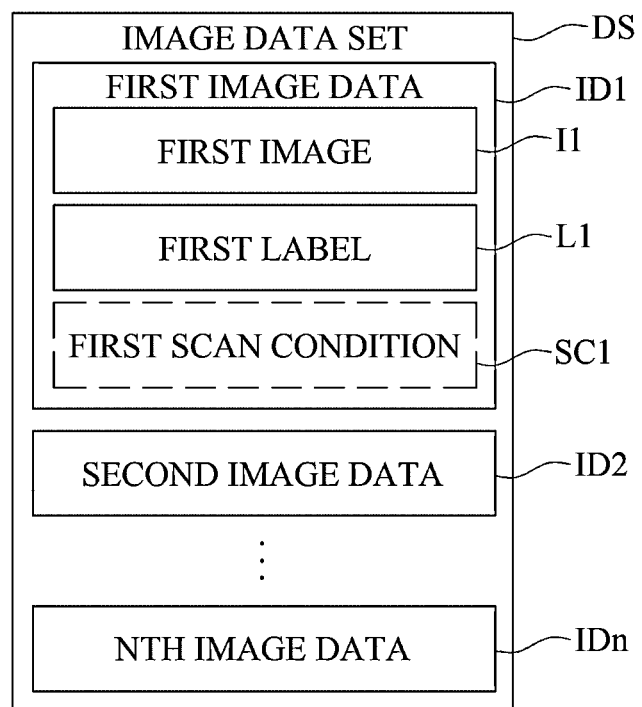
FIG. 9 is an exemplary structural diagram of an image data set according to an embodiment of the present application.

Reference will be made to FIG. 9. FIG. 9 is an exemplary structural diagram of an image data set according to an embodiment of the present application.

An image data set DS acquired by the training device 2200 may include at least one piece of image data. In other words, the image data set DS acquired by the training device 2200 may include at least one of first image data ID1, second image data ID2, and nth image data IDn.

In this case, image data included in the image data set DS acquired by the training device 2200 may include image-related data and label-related data.

For example, referring to FIG. 9, the first image data ID1 included in the image data set DS may include data related to a first image I1 and a first label L1.

Specifically, the first label L1 may be acquired by manually labeling the first image I1 by a clinician who can diagnose a brain disease. Alternatively, the first label L1 may be acquired through automatic labeling using any suitable image segmentation technique.

The image-related data and the label-related data included in the image data may be a basis for training and verifying an artificial neural network model in relation to a training method according to an embodiment of the present application.

Meanwhile, the image data included in the image data set DS may include data related to a scan condition. In this case, the scan condition-related data may be data related to magnetic field strength, a setting parameter of an imaging device, and/or data related to the manufacturer of the imaging device, as described above. Also, the scan condition-related data may be structured as metadata for the image data.

As an example, referring to FIG. 9, the first image data ID1 may include data related to a first scan condition SC1 related to a scan condition which was used for capturing the first image data ID1. For example, when the first image data ID1 is captured under a magnetic field strength of 3 T, information regarding the magnetic field strength corresponding to 3 T may be structured as metadata for the first image data ID1 and acquired by the training device 2200 through the data set acquisition operation (S1100).

The scan condition-related data included in the image data may be considered to acquire a correction parameter for correcting a morphological value or a morphological index corresponding to a target element acquired from a target image, which will be described below.

FIG. 9 shows only the data included in the first image data ID1, but this is merely an example Image data of the image data set including the second image data ID2 or the nth image data IDn may include data related to images, labels, and scan conditions.

Additionally, the training device 2200 may be implemented to acquire information regarding a brain atlas related to a brain structure or a brain function for segmentation related to a brain image.

Specifically, the training device 2200 may acquire the above-described information regarding the brain atlas related to the brain structure or brain function from the image analysis device 2000 or any external device.

In this case, the training device 2200 may be implemented to train or verify an artificial neural network model, which will be described below, in consideration of the information regarding the brain atlas.

In the operation of screening the image data set (S1200), the training device 2200 according to an embodiment of the present application may be implemented to perform an operation of screening the image data set acquired in the operation of acquiring the image data set (S1100) or choosing only some of the image data included in the image data set.

As an example, some image data in the acquired image data set may not be suitable for training an artificial neural network model for segmentation. For example, some image data may contain significant artifacts or significant noise. Such image data may not be suitable for training an artificial neural network model.

Therefore, the training device 2200 may be implemented to screen image data included in the acquired image data set or choose image data that is valid for training an artificial neural network model.

In the operation of preprocessing and aligning the image data set (S1300), the training device 2200 according to an embodiment of the present application may be implemented to perform a preprocessing operation for removing noise or artifacts of the image included in the image data set or correcting the intensity of the image.

Also, the training device 2200 according to an embodiment of the present application may be implemented to perform an operation of aligning an image on the basis of data related to a direction of the image or aligning an image through spatial normalization by matching the image to a brain template.

In this regard, the above-described preprocessing operation of the image analysis device 2000 and the image alignment operation described above with reference to FIGS. 5 and 6 may be provided and implemented in the training device in the same way. Alternatively, the image analysis device 2000 may be implemented to perform an operation of preprocessing and aligning an image through transmission or reception between the training device 2200 and the image analysis device 2000 and then deliver the image to the training device 2200.

In the operation of training and verifying a neural network model (S1400), the training device 2200 for image segmentation according to an embodiment of the present application may train an artificial neural network model for image segmentation.

Specifically, the artificial neural network module may include an input layer for receiving image data, an output layer for outputting a labeling result, which is a segmentation result, and a hidden layer including at least one node.

In this case, the training device 2200 may be implemented to receive the image data included in the acquired image data set through the input layer and acquire a labeling result for the image data acquired by the neural network model through the output layer.

For example, the training device 2200 may be implemented to train an artificial neural network configured to receive the first image data ID1 as an input and output a first-prime label L1' through the output layer. Also, the training device 2200 may input second image data ID2 to the input layer and acquire a second-prime label L2' output through the output layer.

Also, the training device 2200 according to an embodiment of the present application may train the artificial neural network in consideration of the above-described brain atlas related to a brain structure or related to a brain function.

The training device according to an embodiment may train the neural network model to divide a brain image on the basis of a predetermined brain atlas. The brain atlas may include a plurality of brain regions including a first brain region and a second brain region. The training device may use an image in which a first region corresponding to the first brain region and a second region corresponding to the second brain region are labeled and may train the neural network model to acquire the first region and the second region by using the image as an input.

For example, the training device 2200 according to an embodiment of the present application may be implemented to train an artificial neural network model for segmentation of image data included in image data sets on the basis of the Desikan-Killiany Atlas (Desikan 2006). The Desikan-Killiany Atlas (Desikan 2006) is an atlas in which a cerebral cortex including a plurality of brain regions, including a first brain region and a second brain region, is used to acquire regions corresponding to the plurality of brain regions.

In this case, the training device 2400 may train the neural network model for segmenting a brain's cerebral cortex using image data in which the first region corresponding to the first brain region and the second region corresponding to the second brain region are labeled in consideration of the Desikan-Killiany Atlas (Desikan 2006).

However, the above-described brain atlas is merely an example, and any suitable brain atlas may be considered according to a region of interest (ROI) or the purpose of segmentation of the image data.

Also, the training device 2200 according to an embodiment of the present application may be implemented to train the neural network model according to a scan condition in which the image data is captured.

For example, the training device 2200 may be implemented to use a first neural network model to segment a first image acquired in a first scan condition into a plurality of regions. On the other hand, the training device 2200 may be implemented to use a second neural network model to segment a second image acquired in a second scan condition into a plurality of regions. In other words, the training device 2200 may train the neural network model differently depending on the scan condition in which the image is captured.

Also, in the segmentation process P2000, the image analysis device 2000 according to an embodiment of the present application may be implemented to segment a target image acquired under the first scan condition using the trained first neural network model and segment a target image acquired under the second scan condition using the trained second neural network model.

Thus, since the image analysis device 2000 according to an embodiment of the present application can perform segmentation on a target image using an optimal neural network model for each scan condition, it is possible to more stably and accurately acquire a plurality of regions.

An example of an artificial neural network model that can be used by the training device 2200 according to an embodiment of the present application will be described below with reference to FIGS. 10 and 11.

Figure 10:
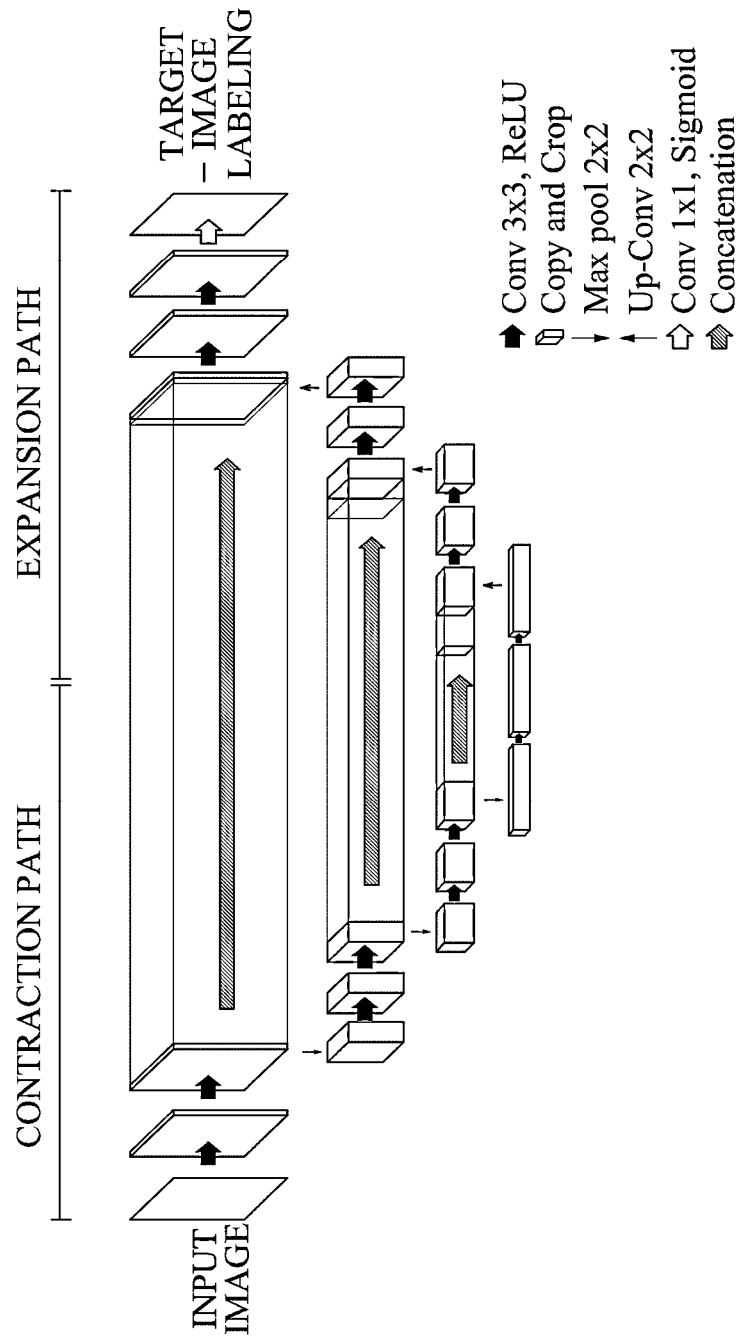
FIG. 10 is an example of an artificial neural network model that can be used by the training device 2200 according to an embodiment of the present application.

FIG. 10 is an example of an artificial neural network model that can be used by the training device 2200 according to an embodiment of the present application.

Figure 11:
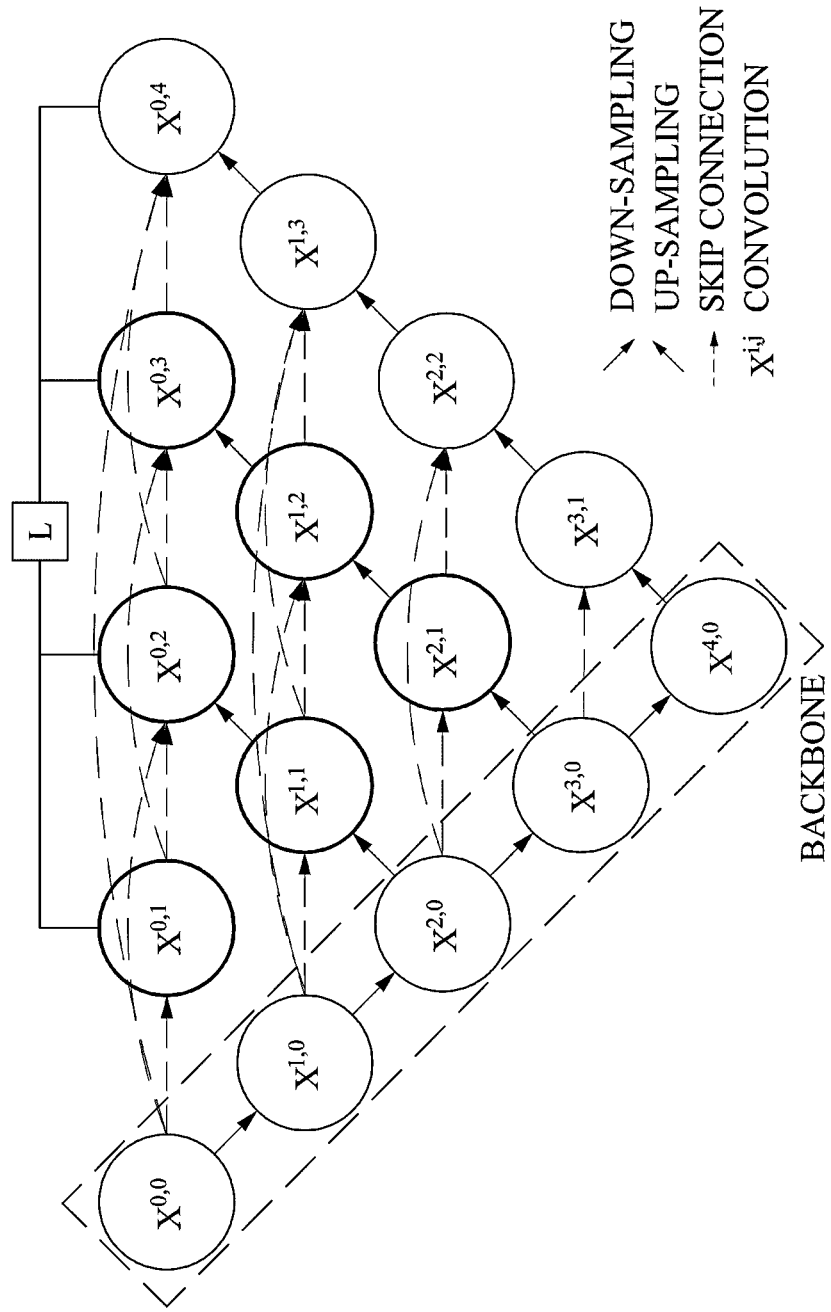
FIG. 11 is another example of an artificial neural network model that can be used by the training device 2200 according to an embodiment of the present application.

FIG. 11 is another example of an artificial neural network model that can be used by the training device 2200 according to an embodiment of the present application.

Referring to FIG. 10, the training device 2200 according to an embodiment of the present application may utilize the U-net as an artificial neural network for image segmentation.

The U-net utilized for image segmentation may have an architecture including a contraction path and an expansion path.

Specifically, the contraction path of the U-net may be configured such that two convolutions and max-pooling are successively performed. In this case, image-related characteristics may be extracted from the contraction path of the U-net.

However, since the size of a characteristic map is also reduced in the contraction path, the U-net may be configured to recover the size of the characteristic map by additionally including the expansion path.

The expansion path of the U-net may be configured such that up-convolution and two convolutions are successively performed. In this case, the size of the characteristic map and the image may be extracted from the expansion path of the U-net.

Additionally, the U-net has an architecture configured to concatenate the characteristic map of the same level and thus may provide characteristic-related location information from the contraction path to the expansion path.

At this time, based on the difference between the label of the input image and the label of the output segmentation map, a weight or a parameter of at least one node of a layer included in the U-net may be adjusted such that the difference between the label of the input image and the label of the output segmentation map is minimized.

Also, referring to FIG. 11, the training device 2200 according to an embodiment of the present application may utilize the U-net$^{++}$ as the artificial neural network for image segmentation. The U-net$^{++}$ is an artificial neural network model using a high-density block idea of DenseNet to improve the performance of the U-net and differs from the U-net in that a convolution layer is present in a skip path to connect a semantic gap between encoder and decoder feature maps and in that a dense skip connection is present in the skip path to improve gradient flow.

Specifically, the training device 2200 may be implemented to input an input image to an input layer of a U-net$^{++}$ neural network model and acquire label information output through an output layer. In this case, the training device 2200 may adjust a weight or a parameter of at least one node of a hidden layer included in U-net$^{++}$ on the basis of the difference between label information included in the input image and the label information output from the neural network model.

Specifically, the training device 2200 may be implemented to repeatedly perform the above-described operation of adjusting a weight or a parameter of at least one node and thus may acquire a weight or a parameter of a node in which the difference between label information included in the input image and the label information output from the neural network model is minimized.

As described above, the training device 2200 according to an embodiment of the present application may perform an operation of training the artificial neural network model on the basis of the output label result.

Specifically, in the operation of training the artificial neural network model (S1400), the label-related data included in the image data acquired in the operation of acquiring the image data set (S1100) may be acquired.

In this case, the training device 2200 may be implemented to train the artificial neural network model on the basis of labeling data output through the output layer of the neural network model and the image data.

More specifically, the training device 2200 may be implemented to train the neural network model by adjusting a weight or a parameter of at least one node included in the hidden layer of the neural network model on the basis of the difference between labeling data included in the input data and the labeling data output through the output layer of the neural network model.

As an example, the training device 2200 may input the first image data ID1 to the input layer of the artificial neural network and acquire labeling data corresponding to a first-A label (L1A). In this case, the training device may train the neural network model on the basis of labeling data corresponding to a first label L1 included in the first image data ID1 and labeling data related to the first-A label L1A. For example, the training device 2200 may be implemented to train the neural network model by adjusting a weight or a parameter of at least one node included in the hidden layer of the neural network model on the basis of the difference between the first label L1 and the first-A label L1A.

As another example, the training device 2200 may input an ith image data IDi to the input layer of the artificial neural network and acquire labeling data corresponding to an ith-A label LiA. In this case, the training device may train the neural network model on the basis of labeling data corresponding to an ith label Li included in the ith image data IDi and the labeling data related to the ith-A label LiA. For example, the training device 2200 may be implemented to train the neural network model by adjusting a weight or a parameter of at least one node included in the hidden layer of the neural network model on the basis of the difference between the ith label Li and the ith-A label LiA. Here, i may be any number.

In the operation of verifying the artificial neural network model (S1400), the training device 2200 according to an embodiment of the present application may verify the artificial neural network model.

As an example, the training device 2200 according to an embodiment of the present application may acquire labeling data output through the trained neural network model on the basis of at least one piece of image data included in the image data set DS. In this case, the training device 2200 may verify the trained neural network model on the basis of labeling data related to at least the piece of image data and the labeling data output through the trained neural network model.

For example, the training device 2200 may verify whether a weight or a parameter of a node of a hidden layer of the trained neural network model is appropriate by comparing how similar the labeling data related to at least the piece of image data and the labeling data output through the trained neural network model are.

In the operation of acquiring the artificial neural network model (S1500), the training device 2200 according to an embodiment of the present application may acquire a neural network model including at least one node having a weight or a parameter in which the difference between the label-related data included in the image data and the label-related data output from the artificial neural network is minimized, by repeatedly performing the operation of training the artificial neural network model with image data included in the image data set and verifying the artificial neural network model.

The acquired weight or parameter of the node may be used by the artificial neural network model for image segmentation in the segmentation process P2000.

The above description has focused on segmentation using the artificial neural network, but the image analysis device 2000 disclosed in the present application may use various image segmentation algorithms, including image segmentation using the artificial neural network.

As an example, the image segmentation algorithm may be provided as a machine learning model. A representative example of the machine learning model may be an artificial neural network. Specifically, a representative example of the artificial neural network is a deep-learning-based artificial neural network including an input layer that receives data, an output layer that outputs a result, and a hidden layer that is between the input layer and the output layer to process data. Detailed examples of the artificial neural network are a convolutional neural network, a recurrent neural network, a deep neural network, a generative adversarial network, and the like. Here, the artificial neural network should be interpreted in a comprehensive sense including the above-described artificial neural networks, various other types of artificial neural networks, and all combinations of the artificial neural networks, and does not necessarily have to be based on deep learning.

In addition, the machine learning model does not necessarily have to be in the form of an artificial neural network model. In addition, the machine learning model may include the k-nearest neighbors (KNN) algorithm, Random Forest, support vector machine (SVM), principal component analysis (PCA), and the like and may include ensembles of the aforementioned techniques or various other combinations thereof. Meanwhile, it should be noted that the artificial neural network can be replaced with another machine learning model unless otherwise stated in the embodiments mentioned focusing on the artificial neural network.

Furthermore, the image segmentation algorithm herein is not necessarily limited to the machine learning model. That is, the image segmentation algorithm may include various decision algorithms other than the machine learning model.

Therefore, the image segmentation algorithm herein should be understood in a comprehensive sense including all types of algorithms that perform segmentation using image data.

Referring to FIG. 7 again, the segmentation process P2000 according to an embodiment of the present application may include a data acquisition process P2100 and a segmentation process P2200 using the trained neural network model.

The segmentation process P2000 may be implemented by the image analysis device 2000 according to an embodiment of the present application.

Figure 12:
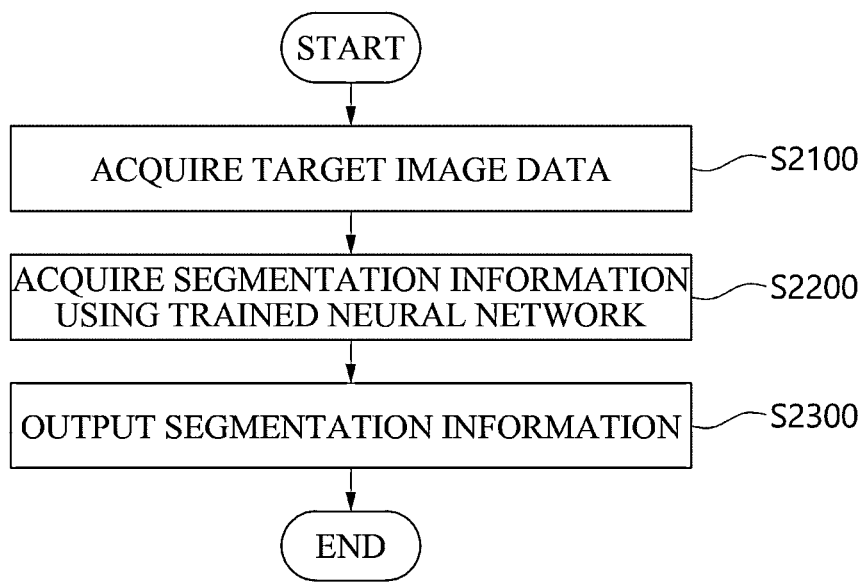
FIG. 12 is a flowchart of an image segmentation method using a neural network model of the image analysis device 2000 according to an embodiment of the present application.

The image segmentation method using the neural network model of the image analysis device 2000 according to an embodiment of the present application will be described below with reference to FIG. 12. FIG. 12 is a flowchart of an image segmentation method using a neural network model of the image analysis device 2000 according to an embodiment of the present application.

Referring to FIG. 12, the image segmentation method using the neural network model of the image analysis device 2000 according to an embodiment of the present application may include an operation of acquiring target image data (S2100), an operation of acquiring segmentation information using the trained neural network (S2200), and an operation of outputting the segmentation information (S2300).

Specifically, in the operation of acquiring the target image data (S2000), the image analysis device 2000 may acquire a target image from the image acquisition device 1000. Also, the image analysis device 2000 may acquire target subject information regarding the target image or information regarding a scan condition which was used for capturing the target image from the image acquisition device 1000 or any external device.

In this case, the target subject information regarding the target image or the information regarding the scan condition in which the target image is captured may be considered to acquire a correction parameter, which will be described below. This will be described in detail below with reference to FIGS. 58 to 67.

Figure 13:
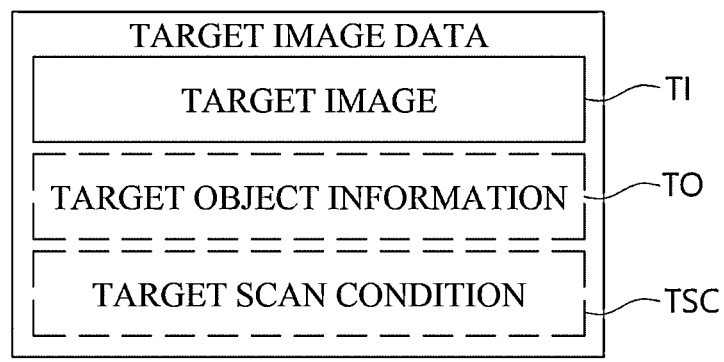
FIG. 13 is an exemplary structural diagram of a target image according to an embodiment of the present application.

Reference will be made to FIG. 13. FIG. 13 is an exemplary structural diagram of a target image according to an embodiment of the present application.

As an example, target image data acquired by the image analysis device 2000 according to an embodiment of the present application may include information on a target image TI. For example, the information on the target image TI may include information regarding pixel coordinates, intensity, color, etc.

As another example, the target image data may include target subject information TO. For example, information on the target subject information TO may be information on personal data of the subject target (e.g., a patient subjected to brain disease screening) related to the target image TI. For example, the information on the target subject information TO may be information regarding the name, age, gender, etc. of the target subject (e.g., a patient subjected to brain disease screening). In this case, the image analysis device 2000 may acquire the information on the target subject information TO from any external device. Alternatively, the image analysis device 2000 may acquire the information on the target subject information TO by recognizing metadata structured for the target image data.

As another example, the target image data may include information on a target scan condition TSC. For example, the information on the target scan condition TSC may be information regarding a scan condition in which the target image TI is captured. For example, the information on the target scan condition TSC may be information regarding magnetic field strength in which the target image TI is captured, a setting parameter of an imaging device that captures the target image TI, or the manufacturer of the imaging device that captures the target image TI. In this case, the image analysis device 2000 may acquire information on the target scan condition TSC from any external device. Alternatively, the image analysis device 2000 may acquire the information on the target scan condition TSC by acquiring metadata structured for the target image data.

Referring to FIG. 7 again, the image analysis device 2000 may be implemented to input target image data acquired in the data acquisition process P2100 to the input layer of the trained neural network model.

In this case, the image analysis device 2000 may be implemented to apply a parameter and/or a weight of a node of the artificial neural network model acquired according to the training process P1000 implemented in the above-described training device 2200 to the artificial neural network model for segmenting the target image data.

Referring to FIG. 12 again, in the operation of acquiring the segmentation information using the trained neural network model (S2200), the neural network model trained based on the parameter and/or weight of the node acquired from the training device 2200 may be provided to receive the target image data through the input layer and output a result of labeling the target image TI through the output layer as a result of segmenting the target image TI. In this case, the image analysis device 2000 may acquire segmentation information regarding the labeling of the target image through the output layer of the trained neural network model.

In this case, a result output through the output layer of the artificial neural network model may include a plurality of target regions acquired from the target image of the target image data.

A result output through the output layer of the neural network model may be in a labeling form corresponding to a plurality of target regions acquired from the target image. For example, the result output through the output layer of the neural network model may be in the form of labeling data including a first label defining a first region and a second label defining a second region, which are acquired from the target image.

In this case, the result output through the output layer of the neural network model may be in a form in which the first region of the target image is overlaid with a first color and the second region of the target image is overlaid with a second color on the basis of the first label. Thus, the first region and the second region may be more easily distinguished. However, the above description is merely an example, and the output result may be configured in any form for distinguishing the first region and the second region.

Also, the segmentation information output through the output layer of the neural network model may be in a form in which the target image is partitioned into a plurality of regions on the basis of a predetermined brain atlas. For example, as described above, the training device may train the neural network model to divide a training image into a first region corresponding to a first brain region and a second region corresponding to a second brain region on the basis of a predetermined brain atlas. In this case, since the neural network model trained based on the predetermined brain atlas is used, the segmentation information output through the output layer of the neural network model may be output in a form in which the target image is partitioned into a plurality of regions including the first region corresponding to the first brain region and the second region corresponding to the second brain region.

The image analysis device 2000 may perform an operation of computing a morphological figure corresponding to a specific region on the basis of the segmentation information output through the output layer.

As an example, the image analysis device 2000 may be implemented to compute a morphological figure indicating a morphological character related to the first brain region on the basis of first-region-related segmentation information output through the output layer. For example, the morphological character may be related to volume, thickness, length, shape, etc.

In the operation of outputting the segmentation information (S2300), the image analysis device 2000 may be implemented to overlay a plurality of brain regions with visual graphics and display the brain regions to a user through the output module 2650 of the output device 2600 or the output module 2050 of the image analysis device 2000 on the basis of the segmentation information output through the output layer.

Figure 14:
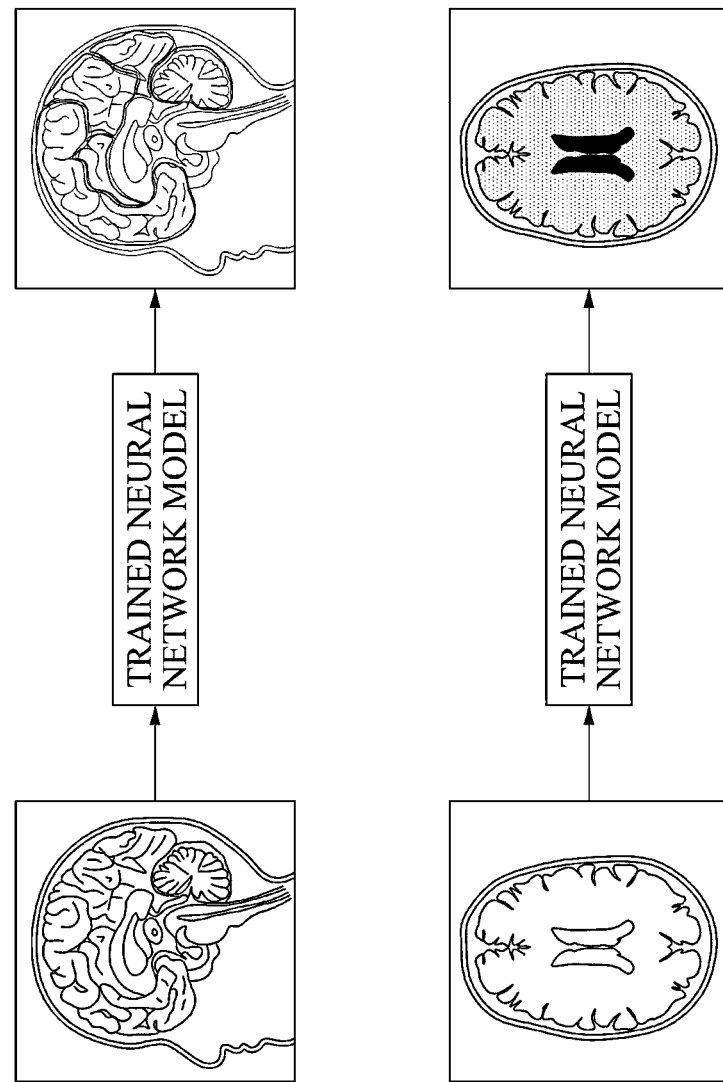
FIG. 14 shows examples of an image acquired based on a result value acquired by a segmentation process of the image analysis device 2000 according to an embodiment of the present application.

Reference will be made to FIG. 14. FIG. 14 shows examples of an image acquired based on segmentation information acquired by a segmentation process of the image analysis device 2000 according to an embodiment of the present application.

In particular, the drawing shown on the upper side of the FIG. 14 is an example of an image output based a segmentation result for an image acquired from the T1-MRI. The drawing shown on the lower side of FIG. 14 is an example of an image output based on a segmentation result for an image acquired from the T2-Flair MRI.

For example, the image analysis device 2000 according to an embodiment of the present application may acquire segmentation information corresponding to frontal lobe, temporal lobe, parietal lobe, occipital lobe, lateral ventricle, amygdala, and hippocampus regions by a segmentation process for the image obtained from the T1-MRI.

For example, the image analysis device 2000 according to an embodiment of the present application may acquire segmentation information corresponding to white matter, grey matter, ventricle, and white matter hyperintensity (WMH) regions by a segmentation process for the image obtained from the T2-Flair MRI.

According to the above-described image segmentation operation of the image analysis device 2000, a user can visually check the segmentation result and thus can easily confirm the segmentation result. Also, an advantageous effect of improving the user's understanding of an auxiliary index for diagnosing a brain disease may be provided.

Meanwhile, the artificial neural network model used in FIG. 7 may be implemented as at least one artificial neural network model.

A flowchart of an image segmentation process using at least one artificial neural network model according to an embodiment of the present application will be described below with reference to FIGS. 15 to 17. Specifically, the following description will focus on characteristics when using a plurality of artificial neural network models in relation to the process P1200 of training the artificial neural network model of FIG. 7. The description with reference to FIGS. 7 to 14 may be analogically applied to embodiments to be described below with reference to FIGS. 15 to 17.

Figure 15:
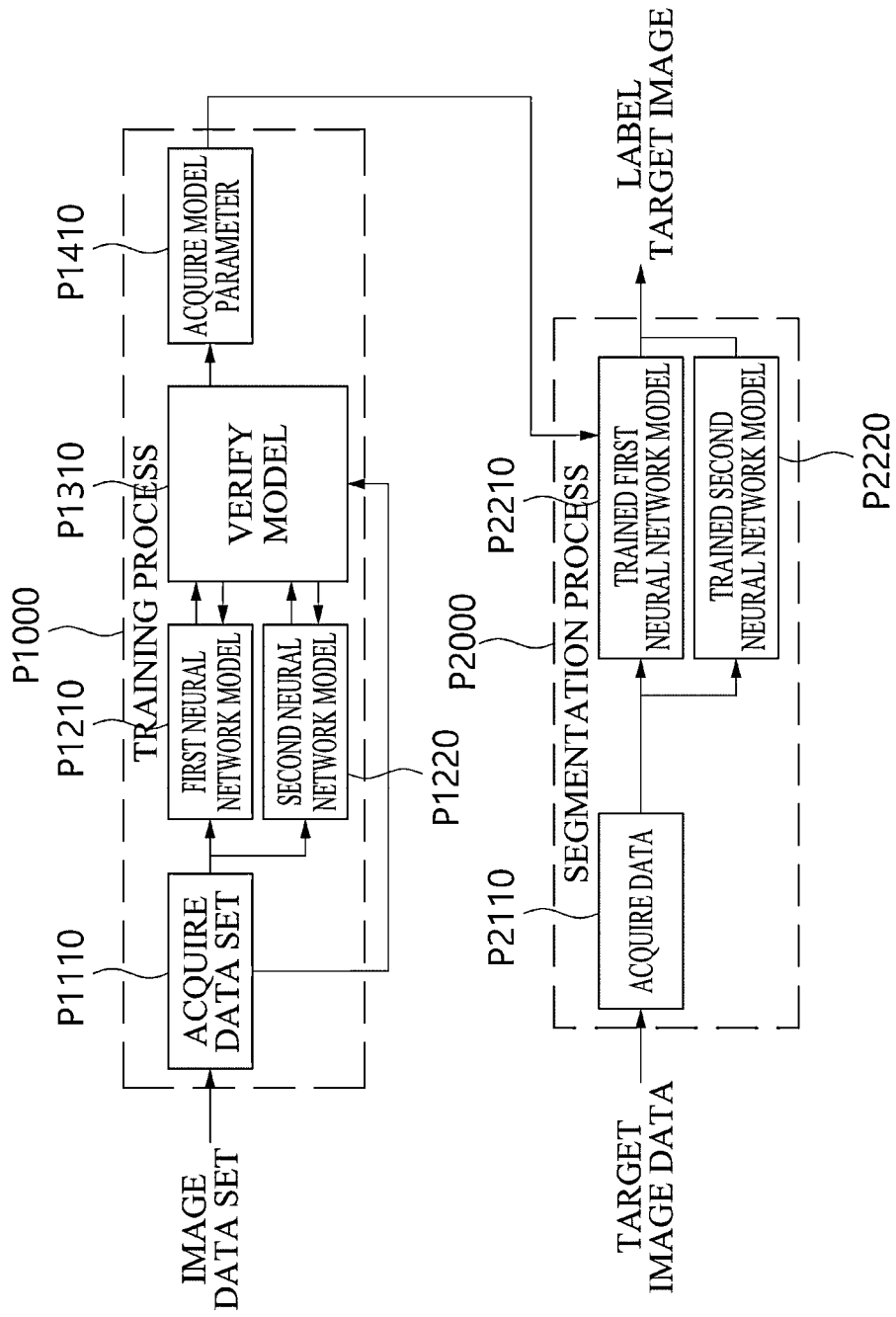
FIG. 15 is a diagram showing a flowchart of an image segmentation process according to an embodiment of the present application.

FIG. 15 is a diagram showing a flowchart of an image segmentation process according to an embodiment of the present application.

As an example, referring to FIG. 15, the neural network model training process P1200 of the training process P1000 of FIG. 7 may include a process of training a first neural network model (P1210) and a process of training a second neural network model (P1220).

As an example, the first neural network model may be trained to acquire a first region corresponding to a first brain region and a second region corresponding to a second brain region. In this case, the second neural network model may be trained to acquire a third region and a fourth region included in the first region, which may be acquired from the first neural network model. In other words, the first neural network model may be trained to acquire regions corresponding to a brain's macroscopic structure (e.g., a skull region, a cerebrospinal fluid (CSF) region, a cortical region, and a medullary region), and the second neural network model may be trained to acquire regions corresponding to a brain's detailed structure (e.g., a region corresponding to brain elements located within the cortex and a region corresponding to brain elements located in the medulla).

As another example, the first neural network model may be trained to acquire regions corresponding to brain regions corresponding to a first brain atlas. On the other hand, the second neural network model may be trained to acquire regions corresponding to brain regions corresponding to a second brain atlas.

As another example, the first neural network model may be trained to acquire regions corresponding to a brain's macroscopic structure (e.g., a skull region, a cerebrospinal fluid (CSF) region, a cortical region, and a medullary region). On the other hand, the second neural network model may be trained to acquire regions corresponding to brain regions corresponding to a brain atlas. For example, the second neural network model may be trained to acquire regions corresponding to a plurality of brain regions based on the Desikan-Killiany Atlas (Desikan 2006), and the second neural network model trained based on the Desikan-Killiany Atlas (Desikan 2006) may be trained to acquire regions including a frontal lobe, temporal lobe, parietal lobe, occipital lobe, lateral ventricle, amygdala, and hippocampus.

The process of training the first neural network model (P1210) and the process of training the second neural network model (P1220) may be performed independently.

Specifically, data set used for the process of training the first neural network model (P1210) and data set used for the process of training the second neural network model (P1220) may be independent from each other.

Figure 16:
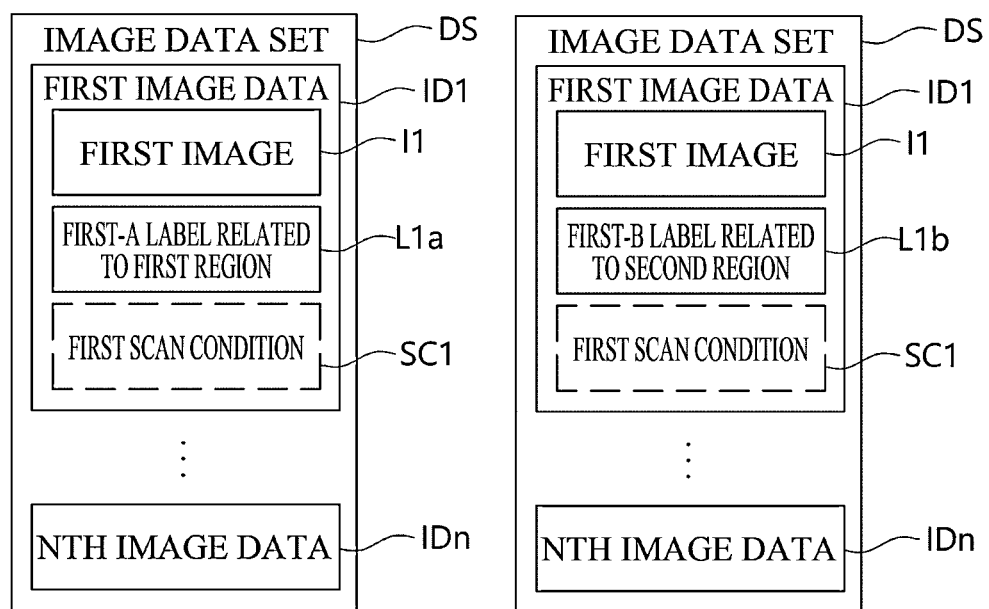
FIG. 16 is an exemplary structural diagram of image data sets according to an embodiment of the present application.

Reference will be made to FIG. 16. FIG. 16 is an exemplary structural diagram of image data sets according to an embodiment of the present application. Specifically, the image data set shown on the left side of FIG. 16 may be an image data set for training the first neural network model. On the other hand, the image data set shown on the right side of FIG. 16 may be an image data set for training the second neural network model.

For example, the image data set DS for training the first neural network model may include first image data including information regarding a first-a label L1a related to first regions and the first image I1. On the other hand, the image data set DS for training the second neural network model may include first image data including information regarding a first-b label L1b related to second regions and the first image I1.

In this case, by using the first neural network model, the training device may input the first image data ID1 to the input layer of the artificial neural network and acquire output labeling data corresponding to the first-a label L1a' related to the first regions. In this case, the training device may train the artificial neural network model on the basis of labeling data corresponding to the label L1a related to the first regions included in the first image data ID1 and output labeling data related to a first-a' label L1a' related to the first region. For example, the training device 2200 may be implemented to adjust a weight or a parameter of at least one node included in a hidden layer of the neural network model on the basis of the difference between the first-a label L1a and the first-a' label L1a'. Also, by repeatedly performing the above-described process of training the first neural network model, the training device 2200 may acquire a parameter related to the first neural network model related to the first region.

On the other hand, by using the second neural network model, the training device may input the first image data to the input layer of the artificial neural network and acquire output labeling data corresponding to the first-b' label L1b' related to the second regions. In this case, the training device may train the artificial neural network model on the basis of labeling data corresponding to the first-b label L1b related to the second regions included in the first image data ID1 and output labeling data related to a first-b label L1b' related to the second region. For example, the training device 2200 may be implemented to adjust a weight or a parameter of at least one node included in a hidden layer of the neural network model on the basis of the difference between the first-b label L1b and the first-b' label L1b'. Also, by repeatedly performing the above-described process of training the second neural network model, the training device 2200 may acquire a parameter related to the second neural network model related to the second region.

Also, a parameter related to the first neural network model acquired in the training process P1000 may be used in the first neural network model for image segmentation corresponding to the first region of the segmentation process P2000 (P2210), and a parameter related to the second neural network model acquired in the training process P1000 may be used in the second neural network model for image segmentation corresponding to the second region of the segmentation process P2000 (P2220).

However, according to FIG. 16, it is shown that the first-a label included in the image data related to the first neural network model is a label related to the first region and the first-b label included in the image data related to the second neural network model is a label related to the second region. However, this is merely an example, and the present invention is not limited thereto. For example, the image data of the first and second neural network models may include label information regarding the first region and label information regarding the second region. Only the label information regarding the first region may be used when the first neural network model is trained, and only the label information regarding the second region may be used when the second neural network model is trained.

Also, the first neural network model and the second neural network model have been described as being independent, but the present invention is not limited thereto. The first neural network model and the second neural network model may share at least some layers. In other words, the first neural network model and the second neural network model may include at least one common layer.

Meanwhile, the process of training the first neural network model and the process of training the second neural network model may be independent or related to each other. Here, the term "related training" may include using data output from one of the two neural network models as input data of the other neural network model and may mean encompassing any form in which any data generated in one of the two neural network models is used by the other neural network model.

Figure 17:
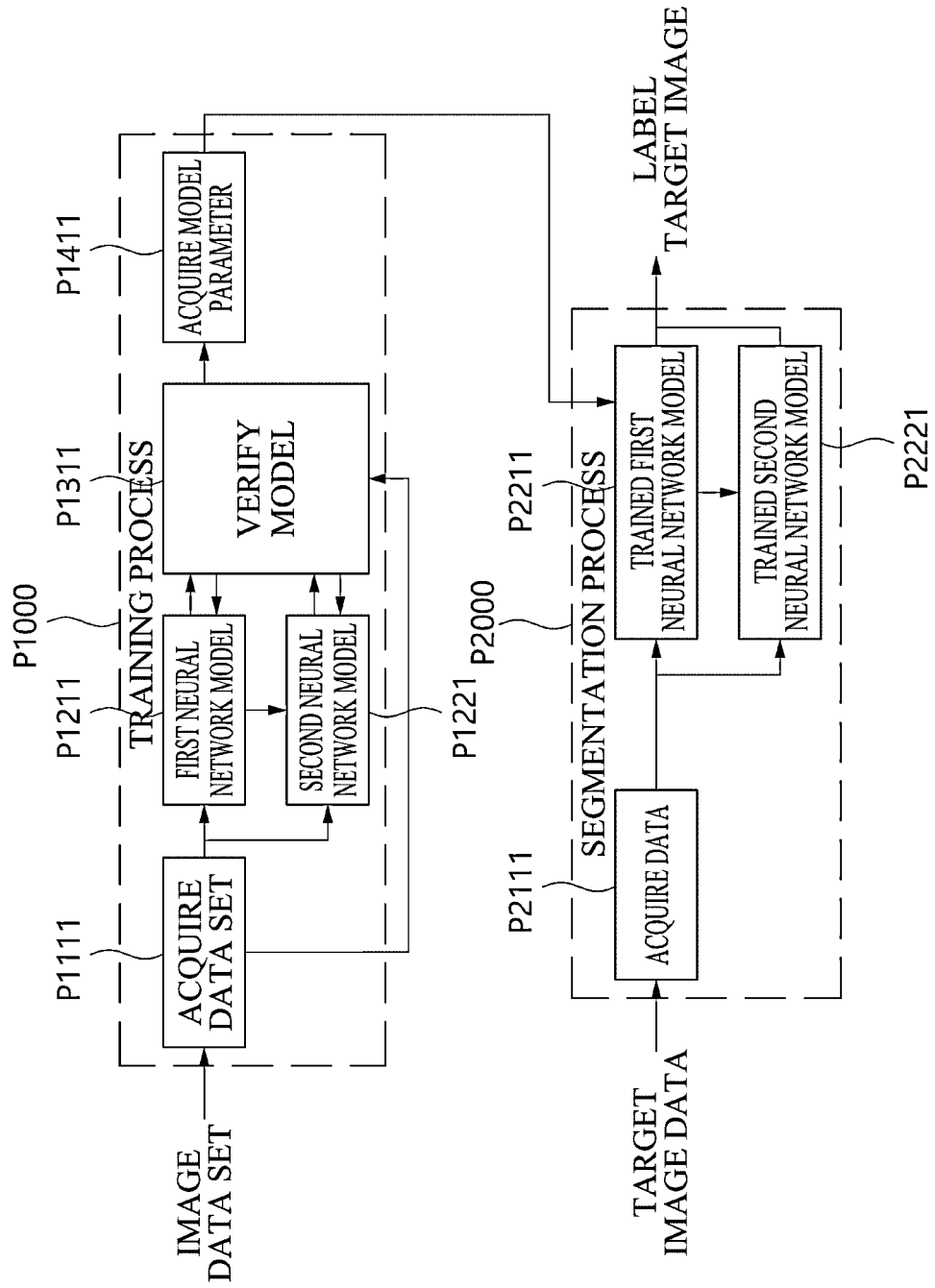
FIG. 17 is a diagram showing a flowchart of an image segmentation process according to an embodiment of the present application.

Reference will be made to FIG. 17. FIG. 17 is a diagram showing a flowchart of an image segmentation process according to an embodiment of the present application.

In an embodiment, the process of training the neural network model (P1200) in the training process P1000 according to an embodiment of the present application may include a process of training the first neural network model (P1211) and a process of training the second neural network model (P1221) and may be implemented such that data related to a result output from the first neural network model may be input to the second neural network mode as input data.

As an example, the training device 2200 may be configured such that the second neural network model receives labeling data related to a first region. In this case, the labeling data related to the first region may be acquired by manually labeling the first region corresponding to the first brain region in the image data or by using any automatic labeling software.

For example, the labeling data related to the first region may be data that is manually labeled by a clinician with respect to the image data input to the first neural network model.

As another example, the first neural network model may be trained to output the labeling data related to the first region. In this case, the labeling data related to the first region input to the second neural network model may be labeling data that is output from the first neural network model.

In this case, the second neural network model may be trained to output labeling data related to a second region on the basis of the image data and the labeling data related to the first region.

Accordingly, the training device 2200 according to an embodiment of the present application may be implemented to acquire the labeling data related to the first region through the first neural network model and acquire the labeling data related to the second region through the second neural network model. Therefore, the training device 2200 may train the first neural network model and the second neural network model to acquire the labeling data related to the first region and the labeling data related to the second region.

Also, the training device 2200 may be provided to adjust a weight or a parameter of at least one node of the first neural network model or adjust a weight or a parameter of at least one node of the second neural network on the basis of the difference between labeling data related to labels related to the first region and the second region and labeling data related to the first region and the second region of the image data set.

Also, the parameters related to the first neural network model and the second neural network model acquired in the training process P1000 may be used in the first neural network model and the second neural network model for image segmentation corresponding to the first region and the second region of the segmentation process P2000.

In this case, the first region or the second region may be a region related to a brain's anatomical structure and may be one of the regions obtained through partitioning based on the above-described brain atlas. Also, the first region or the second region may be a region indicating a significant association with a brain disease.

However, the above-described training process of the neural network model is merely an example, and a parameter of the neural network model may be acquired by training the neural network model with the image segmentation operation and verifying the neural network model using various combinations or connections of at least one neural network model having any suitable form, type, and parameter.

Meanwhile, in the segmentation process P2000, the image analysis device 2000 according to an embodiment of the present application may be implemented to update the trained artificial neural network model.

As an example, the image analysis device 2000 may be implemented such that segmentation information obtained by segmenting the target image by the segmentation process P2200 using the trained neural network model can be modified manually or using any software. In this case, the image analysis device 2000 may be implemented to update the artificial neural network model by modifying a weight or a parameter of at least one node of the trained neural network model on the basis of the modified segmentation information.

The image analysis device according to an embodiment may perform a function of determining image quality. The image analysis device may have a quality criterion for determining image quality and may determine whether an input image satisfies the quality criterion.

More specifically, the image quality determination may mean determining whether a medical image acquired by the image acquisition device has quality above a certain level. In other words, the image quality determination may mean determining whether it is possible to acquire medical information with a reliability above a certain level from a medical image acquired by the image acquisition device.

The image quality determination may be performed along with sub-operations constituting the image analysis operation. For example, the image quality determination operation may be performed together with an image acquisition operation, an image preprocessing operation, an image segmentation operation, and/or a medical information output operation, which are described herein.

The image quality determination operation may be performed before or after at least one sub-operation is performed. The image quality determination operation may be performed based on information obtained as a result of performing the sub-operations. The image quality determination operation may be performed to determine whether a criterion for performing the sub-operations is satisfied.

The image quality determination may be performed based on image data. The image quality determination may be performed based on image raw data. The image quality determination may be performed based on a preprocessed medical image. As another example, the image quality determination may be performed based on a result of segmenting a medical image. As another example, the image quality determination may be performed based on a result of analyzing a medical image.

The image quality determination may be performed based on non-image data related to image data. The image quality determination may be performed based on at least one of information on metadata for a medical image, information on artifacts included in a medical image, or information on a region of interest (ROI) obtained through the medical image segmentation.

According to an embodiment, the image quality determination may be performed differently for each sub-operation.

For example, first quality determination may be performed based on raw data before a preprocessing operation. In this case, the preprocessing operation may be performed on an image that satisfies a first quality criterion. For example, second quality determination may be performed based on a processed image or raw data before a segmentation operation. In this case, the segmentation operation may be performed on an image that satisfies a second quality criterion. For example, third quality determination may be performed based on raw data, a preprocessed image, or an image segmentation result before image analysis. The image analysis may be performed on an image that satisfies a third quality criterion. The first to third quality criteria may be different from each other.

Information acquired through the image quality determination may be output. The information acquired through the image quality determination may include information serving as a basis for the image quality determination. The information serving as a basis for the image quality determination may include whether a defect is present in the image, format information of the image, an acquisition condition for the image, etc. The information acquired through the image quality determination may be used to generate or provide information regarding whether to perform subsequent operations.

A specific embodiment of the image quality determination will be described below.

The image analysis device 2000 according to an embodiment of the present application may be provided to perform an operation of computing a morphological index of a target subject's brain on the basis of a result of segmenting a target image.

Specifically, the image analysis device 2000 may acquire an internal region of a skull and a region corresponding to a target element on the basis of the segmentation result. Also, the image analysis device 2000 may additionally perform an operation of modifying a boundary corresponding to the internal region of the skull in order to compute a morphological index of the target element.

Also, the image analysis device 2000 may additionally perform an operation of aligning a brain image in order to modify a boundary of the internal region of the skull.

An operation of computing a morphological index of a target subject's brain by the image analysis device 2000 according to an embodiment of the present application will be described in detail below with reference to FIGS. 48 to 57.

The image analysis device 2000 according to an embodiment of the present application may be provided to perform an operation of correcting the morphological value or morphological index of the brain computed based on the result of segmenting the target image.

Specifically, the image analysis device 2000 may acquire a region corresponding to the target element and pixel or voxel data corresponding to the target element on the basis of the segmentation result. In this case, the image analysis device 2000 may acquire the morphological value of the target element on the basis of the pixel or voxel data corresponding to the target element.

Also, the image analysis device 2000 may perform an operation of correcting the morphological value of the target element in consideration of a scan condition in which the target image is acquired or the location of the target element in the target image so as to more accurately output the morphological value.

In this case, the image analysis device 2000 may acquire a correction parameter from the correction parameter acquisition device 2400 in consideration of the scan condition or the location of the target element in order to correct the morphological value of the target element and may be provided to perform an operation of outputting a morphological index of the target element on the basis of the correction parameter and the morphological value of the target element.

An operation of correcting the morphological index or morphological value of the brain by the image analysis device 2000 according to an embodiment of the present application will be described in detail below with reference to FIGS. 58 to 67.

An image output device according to an embodiment may provide auxiliary diagnostic information to a user on the basis of various pieces of medical information acquired through image analysis. Here, the auxiliary diagnostic information may include information acquired by processing various pieces of medical information acquired from a medical image. For example, the auxiliary diagnostic information may include information acquired by processing medical information, for example, diagnostic information, analysis information, prescription information, and the like which are based on the medical information.

An operation of providing the auxiliary diagnostic information may be performed together with sub-operations constituting the image output operation. For example, the operation of providing auxiliary diagnostic information may be performed together with an operation of acquiring an image, an operation of acquiring medical information from the image, an operation of acquiring auxiliary diagnostic information among the acquired information, an operation of outputting the auxiliary diagnostic information, and/or an operation of providing a comment based on the auxiliary diagnostic information, which are described herein. The above operations will be described in detail below.

An image output device according to another embodiment may selectively provide index information necessary for a user among various pieces of medical information acquired through image analysis. Here, the selective information provision may include selectively providing only necessary medical information to the user among various pieces of medical information that may be acquired through the image analysis device.

An operation of selectively providing information may be performed together with the sub-operations constituting the image output operation. For example, the operation of selectively providing information may be performed together with an operation of acquiring an image, an operation of acquiring medical information from the image, an operation of acquiring selective information among the acquired information, an operation of outputting the selective information, and/or an operation of providing a comment based on the selective information, which are described herein. The above operations will be described in detail below.

The configuration and operation of the image analysis device 2000 according to an embodiment of the present application have been described above. An image analysis method according to this embodiment will be described in detail below.

The image analysis method according to an embodiment of the present application will be described below as being performed by the image analysis device 2000, the training device 2200, the correction parameter acquisition device 2400, or the output device 2600, which has been described above. However, since this is only for convenience of description, a device capable of performing the image analysis method according to an embodiment of the present application is not limited to the image analysis device 2000, the training device 2200, the correction parameter acquisition device 2400, or the output device 2600, which has been described above. That is, the image analysis method, which will be described below, does not necessarily have to be performed only by the image analysis device 2000, the training device 2200, the correction parameter acquisition device 2400, or the output device 2600. The image analysis method may be performed by another system or device having a function similar to that of the image analysis device 2000, the training device 2200, the correction parameter acquisition device 2400, or the output device 2600, which has been described above.

A variety of information is acquired from a medical image to determine a patient's health state. In order to acquire accurate information, analysis should be performed based on a medical image that has quality above a certain level and satisfy necessary conditions.

More specifically, a medical image acquired by the image acquisition device may have a quality (or characteristic) that is not suitable for image analysis. For example, an image may have a formal or substantial defect that is inappropriate for medical data acquisition. For example, a medical image may not have quality above a certain level because of various defects that may occur in the image due to the brightness of the image, the resolution of the image, a body part which is captured, a direction in which a body part is captured, an angle at which a body part is captured, or other problems that may occur during capture. Alternatively, the format of the image, such as the format and size of an image file, may not satisfy requirements.

When analysis is performed based on a medical image that does not have quality above a certain level, the analysis result may also not have a reliability above a certain level. Accordingly, in order to derive an analysis result having a higher level of reliability, image quality determination should be made as to whether an image acquired by the image acquisition device has quality above a certain level.

In the past, an inspector directly determined whether a medical image acquired through imaging equipment has a defect. However, the determination result might not be constant depending on the inspector's point of view, experience, and condition, and thus there was a limitation in that it was difficult to make a quality determination with a certain level of accuracy.

According to an embodiment, artificial intelligence may be utilized to overcome the above-described limitation and to determine improved quality for a captured medical image. That is, the image analysis device according to an embodiment may perform high-level quality determination on a medical image by utilizing artificial intelligence.

Figure 18:
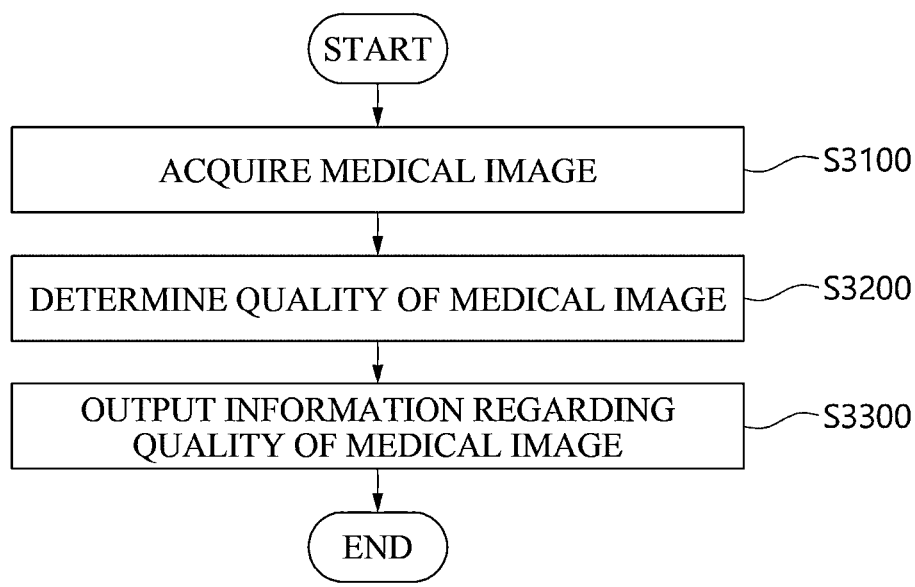
FIG. 18 is a diagram illustrating an image quality determination process according to an embodiment.

FIG. 18 is a diagram illustrating an image quality determination process according to an embodiment.

Referring to FIG. 18, the image quality determination process according to an embodiment may include an operation of acquiring a medical image (S3000), an operation of determining the quality of the medical image (S3300), and an operation of outputting information regarding the quality of the medical image (S3500). In this case, the operation of outputting information regarding the quality of the medical image (S3500) may be omitted. Meanwhile, the image quality determination process may further include an operation of preprocessing a medical image and/or an operation of segmenting a medical image.

Figure 19:
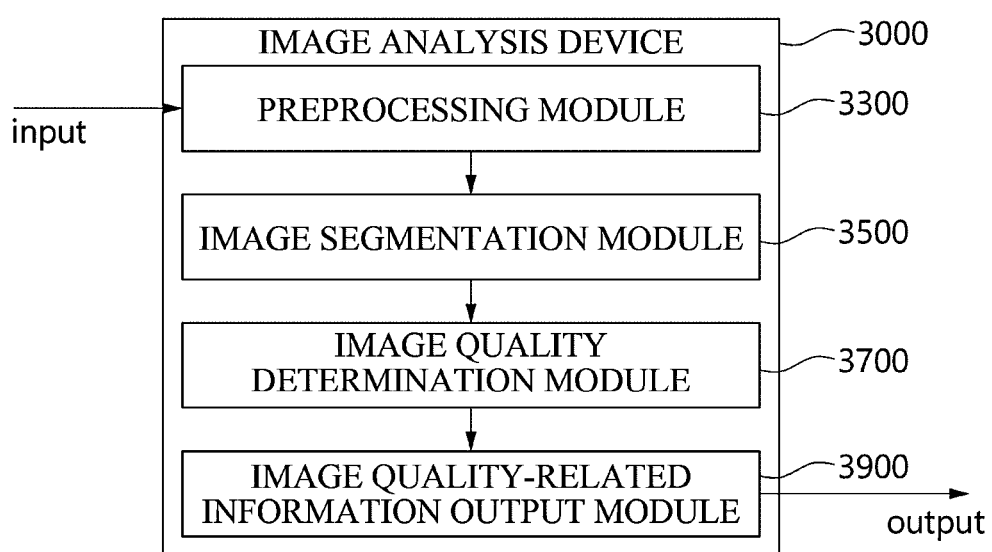
FIG. 19 is a diagram illustrating an image analysis device for performing an image quality determination process.

FIG. 19 is a diagram illustrating an image analysis device 3000 for performing an image quality determination process.

Referring to FIG. 19, the image analysis device 3000 may perform an image quality determination process. The image analysis device 3000 may include one or more modules for performing image quality determination. For example, the image analysis device 3000 may include at least one of a preprocessing module 3300, an image segmentation module 3500, an image quality determination module 3700, or an image quality-related information output module 3900.

Hereinafter, each operation of the image quality determination process will be described in detail below with more specific examples. The image quality determination process, which will be described below, may be performed by the above-described image analysis device 3000 or a device or system described throughout this specification.

An image acquisition device according to an embodiment may acquire a medical image. For example, a medical image may include, but is not limited to, CT images, MRI images, X-ray images, and the like. In this case, MRI images may include various types of images that can be captured by MRI imaging equipment, for example, a T1-weighted image, a T2-weighted image, or a FLAIR image. Also, MRI images may include images captured on various types of planes where imaging is captured by MRI imaging equipment, e.g., axial, coronal, and sagittal planes.

The image acquisition device may acquire a medical image having at least a portion not entirely captured. For example, the image acquisition device 3000 may acquire a medical image in which at least a portion of a target region is missing or improperly captured.

For example, the image acquisition device may acquire a medical image with quality below a certain level. The image acquisition device may acquire a medical image from which it is difficult to expect to extract medical information with a reliability above a certain level. As another example, the image acquisition device may acquire a medical image that has an abnormal file structure or that does not contain patient information. As another example, the image acquisition device may acquire a medical image that includes at least one type of noise. Here, the term "noise" may refer to various types of defects or states that affect image-based information acquisition.

The image quality determination process according to an embodiment may include an operation of preprocessing a medical image. For example, the image quality determination process according to an embodiment may include an operation of preprocessing a medical image acquired by the image acquisition device such that the medical image is suitable for the image quality determination to be performed.

For example, the image preprocessing operation may include performing various preprocessing processes, including correcting the brightness, size, ratio, direction, or resolution of the image, to facilitate the detection of artifacts included in the medical image. As another example, the image preprocessing operation may include performing various preprocessing processes, including correcting the brightness, size, ratio, direction, or resolution of the image, to facilitate the acquisition of information on an anatomical structure included in the medical image.

In addition, the image preprocessing operation may include performing various preprocessing processes for image quality determination. However, this has been described in detail above, and thus a redundant description thereof will be omitted.

The image quality determination process according to an embodiment may include an operation of segmenting a medical image. For example, the image quality determination process according to an embodiment may include an operation of segmenting a medical image acquired by the image acquisition device to determine image quality.

For example, the image segmentation operation may include performing image segmentation in order to acquire information regarding an artifact included in the medical image. As a more specific example, the image segmentation operation may include segmenting a region corresponding to an artifact included in the medical image.

The segmentation of the region corresponding to the artifact may be performed using a neural network model that is trained to acquire the region corresponding to the artifact included in the medical image. The segmentation of the artifact region may be performed using a neural network trained using training data including one or more medical images where an artifact region is labeled.

As another example, the image segmentation operation may include segmenting a medical image such that image quality determination may be made based on at least some regions of a human body included in the medical image. As a more specific example, the image segmentation operation may include segmenting a medical image in order to obtain information on a human body's anatomical or functional structure that may be the basis for image quality determination. The image segmentation operation may include segmenting a region corresponding to a human body's structure included in the medical image. The image segmentation operation may include acquiring a region corresponding to a structure used for image quality determination.

The segmentation of the region corresponding to the human body's structure may be performed using a neural network model. The segmentation of the region corresponding to the structure may be performed using a neural network model trained to segment a region included in the medical image. The image segmentation operation may include segmenting the medical image using a pre-trained neural network model to acquire at least one segmented region. In this case, at least the segmented region may correspond to a different anatomical or functional structure. Also, at least the segmentation region may include a region corresponding to a human body's structure used for quality determination. The contents related to the image segmentation that has been described through this specification may be similarly applied to the segmentation of the region corresponding to the anatomical or functional structure.

Figure 20:
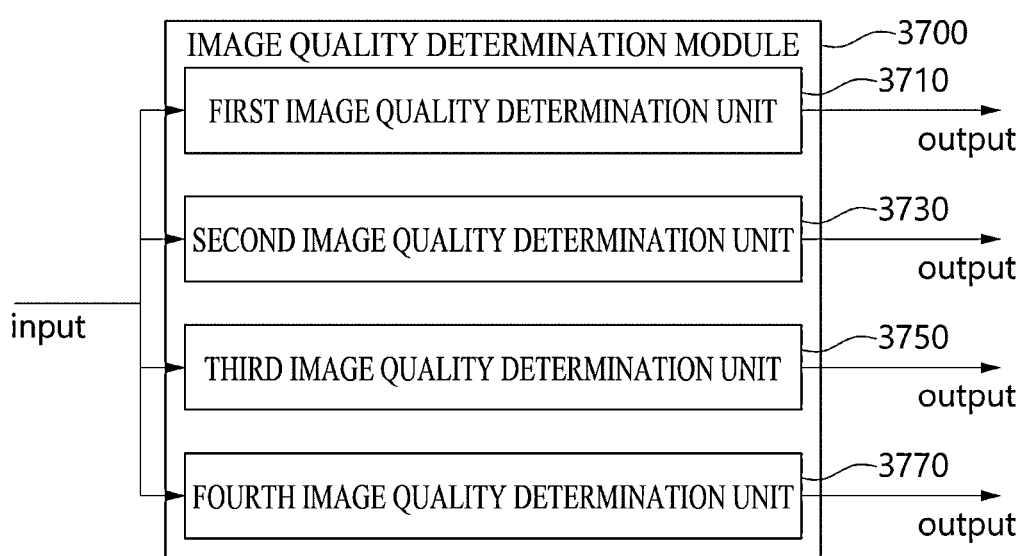
FIG. 20 is a diagram illustrating an image quality determination module.

FIG. 20 is a diagram illustrating an image quality determination module 3700.

Referring to FIG. 20, the image quality determination module 3700 may include at least one of a first image quality determination unit 3710, a second image quality determination unit 3730, a third image quality determination unit 3750, and a fourth image quality determination unit 3770.

For example, the first image quality determination unit 3710 may determine image quality on the basis of metadata information, the second image quality determination unit 3730 may determine image quality on the basis of noise information, the third image quality determination unit 3750 may determine image quality on the basis of segmentation information obtained through anatomical segmentation, and the fourth image quality determination unit 3770 may determine image quality on the basis of the relationship between segmentation information obtained through anatomical segmentation and complex information, e.g., noise information. The first to fourth image quality determination units 3710 to 3770 will be described in detail below.

A neural network model for performing image quality determination according to an embodiment may be trained and performed differently depending on the type of medical image acquired by the image acquisition device. For example, when the type of medical image acquired by the image acquisition device is a CT image, the image quality determination model of the image analysis device 3000 may be a model that is trained and performed based on the CT image. As another example, when the type of medical image acquired by the image acquisition device is MRI, the image quality determination model of the image analysis device 3000 may be a model that is trained and performed based on an MRI image.

The first image quality determination unit 3710 according to an embodiment may be performed based on metadata information in order to determine whether image analysis may be performed normally. In this case, the metadata information may include information on the medical image acquired by the image acquisition device. More specifically, the metadata information may include at least one of file structure information of the medical image or patient information input to the medical image.

Figure 21:
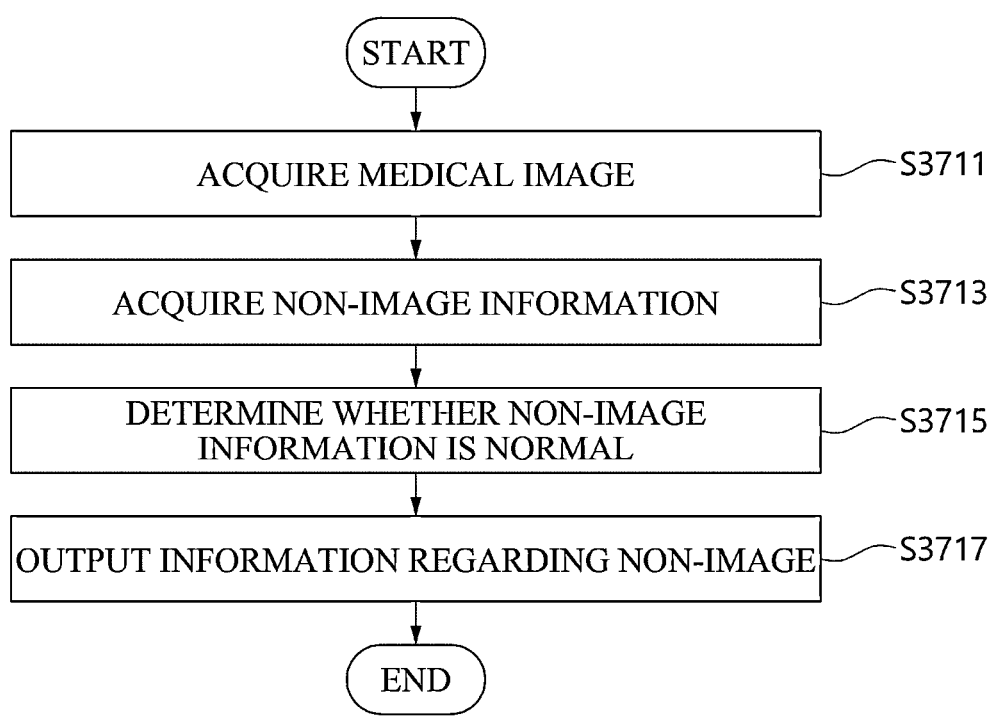
FIG. 21 is a diagram illustrating a first image quality determination process.

FIG. 21 is a diagram illustrating a first image quality determination process.

Referring to FIG. 21, the first image quality determination process may include an operation of acquiring a medical image (S3711), an operation of acquiring non-image information (S3713), an operation of determining whether the non-image information is normal (S3715), and an operation of outputting information regarding the non-image (S3717).

The operation of acquiring non-image information (S3713) may include acquiring medical image information from the medical image. The operation of acquiring non-image information (S3713) may include acquiring non-image information from the medical image. Here, the non-image information may include file structure information of the medical image or patient information input to the medical image.

In this case, the file structure information of the medical image may include, but is not limited to, information on the file format of the medical image, the format of the medical image, or the size of the file. Also, the patient information may include, but is not limited to, information regarding a patient's personal data such as name and age, information regarding when a medical image of the patient is captured, information on a patient's health state, etc.

The operation of determining whether the non-image information is normal (S3715) may include performing image quality determination based on the non-image information extracted from the medical image. The operation of determining whether the non-image information is normal (S3715) may include performing image quality determination based on at least one of the patient information or the file structure information of the medical image.

According to an embodiment, the operation of determining whether the non-image information is normal (S3715) may determine whether the file structure of the medical image is abnormal. Here, the file structure of the medical image may mean, but is not limited to, the file format of the medical image, the format of the medical image, or the size of the file.

For example, since the file format or format of the medical image has to be a file format or format suitable for image analysis performed by the image analysis device 3000, the operation of determining whether the non-image information is normal (S3715) may include determining whether the file format or format of the medical image is a file format or format suitable for image analysis to be performed by the image analysis device 3000. Accordingly, the operation of determining whether the non-image information is normal (S3715) may include acquiring information on whether image analysis can be performed normally on the basis of the file structure information of the medical image.

According to another embodiment, the operation of determining whether the non-image information is normal (S3715) may include determining whether the patient information is missing from the medical image acquired by the image acquisition device. Here, the patient information may include, but is not limited to, information on a patient's personal data such as name and age or a patient's health state.

For example, when the patient information is not included in the medical image, a patient related to the image analysis result by the image analysis device 3000 is unknown. Thus, the operation of determining whether the non-image information is normal (S3715) may include determining whether the patient information is included in the medical image. Accordingly, the operation of determining whether the non-image information is normal (S3715) may include acquiring information on whether the patient information is input to the medical image.

Figure 22:
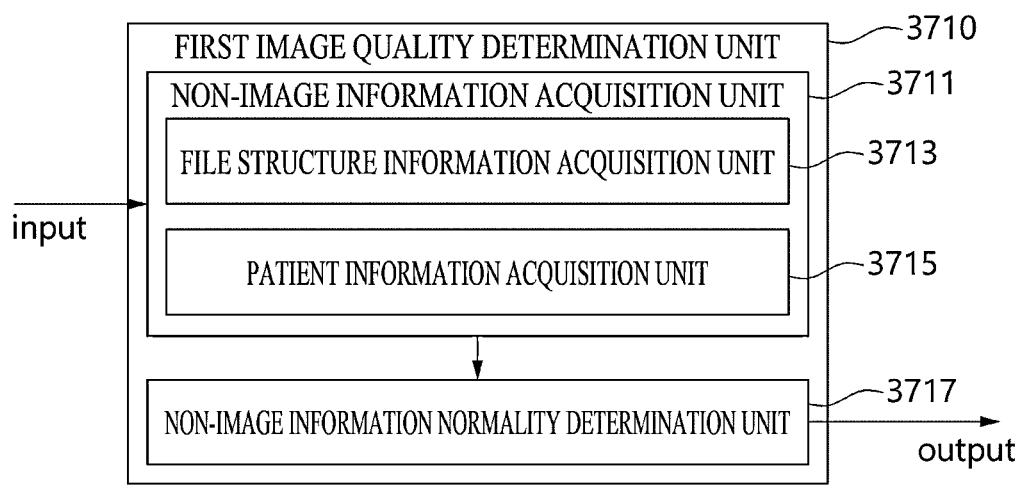
FIG. 22 is a diagram illustrating a first image quality determination unit.

FIG. 22 is a diagram illustrating the first image quality determination unit 3710.

Referring to FIG. 22, the first image quality determination unit 3710 may include at least one of a non-image information acquisition unit 3711 or a non-image information normality determination unit 3717.

The non-image information acquisition unit 3711 may include a file structure information acquisition unit 3713 or a patient information acquisition unit 3715. The non-image information acquisition unit 3711 may acquire non-image information on the basis of an acquired medical image. In this case, the acquired medical image may include raw data before a preprocessing operation or an image after a preprocessing operation.

The non-image information normality determination unit 3717 may determine whether the non-image information is normal on the basis of the non-image information acquired by the non-image information acquisition unit 3711. The non-image information normality determination unit 3717 may output information regarding a result of determining whether the non-image information is normal. For example, the non-image information normality determination unit 3717 may output information on whether image analysis can be performed normally or information on whether the patient information is input to the medical image on the basis of the file structure information of the medical image.

The second image quality determination unit 3730 according to an embodiment may perform a function of extracting noise information included in the image. Here, the term "noise information" may refer to various types of defects or states that affect image-based information acquisition. For example, the noise information may include information regarding the resolution of the image, information regarding the brightness of the image, or information on an artifact generated in the image. In addition, the noise information may mean various image defects generated as a result of improper image sampling.

Figure 23:
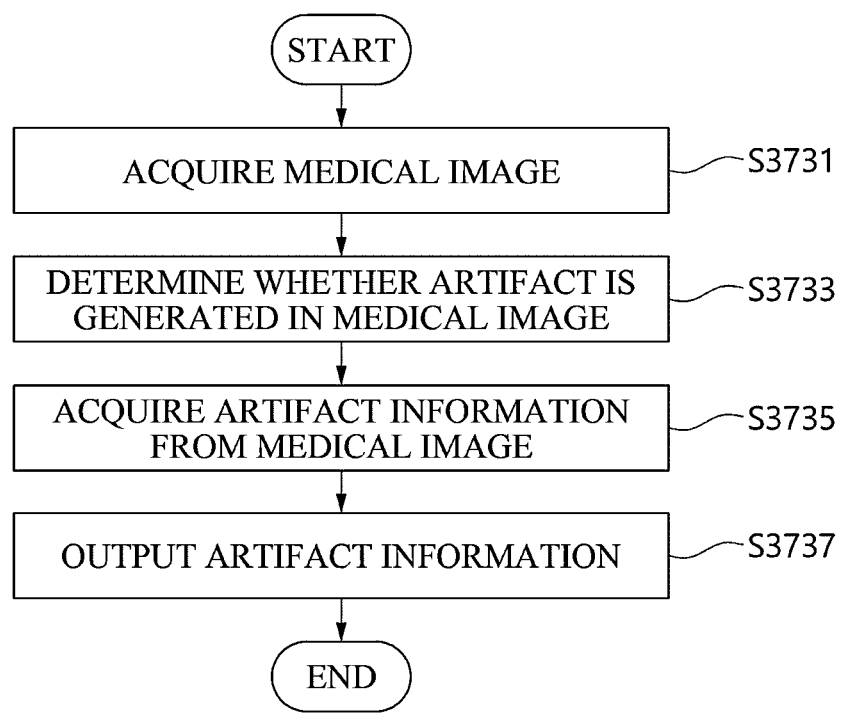
FIG. 23 is a diagram illustrating a second image quality determination process.

FIG. 23 is a diagram illustrating a second image quality determination process.

Referring to FIG. 23, the second image quality determination process may include an operation of acquiring a medical image (S3731), an operation of determining whether an artifact is generated in the medical image (S3733), an operation of acquiring artifact information from the medical image (S3735), and an operation of outputting the artifact information (S3737).

The operation of determining whether an artifact is generated in the medical image (S3733) may include determining whether an artifact is included in a medical image. Here, the artifact may include noise related to a pixel that does not faithfully show an anatomical structure in the medical image. For example, the artifact may include a motion artifact, a bias artifact, a zipper artifact, a ghost artifact, a spike artifact, and the like, but the present invention is not limited thereto. The artifact may include various types of known artifacts.

The operation of acquiring artifact information from the medical image (S3735) may include acquiring information on an artifact that is generated in the medical image. Here, the artifact information may include information regarding an artifact, e.g., information on whether an artifact is generated, information on where an artifact is generated, information on the type of generated artifact, information on the degree to which an artifact is generated, etc.

According to an embodiment, the operation of determining whether an artifact is generated in the medical image (S3733) or the operation of acquiring artifact information from the medical image (S3735) may include performing the operation using a trained neural network model. The operation of determining whether an artifact is generated in the medical image (S3733) may include determining whether an artifact is generated in the medical image using the trained neural network model. In the drawing, the operation of determining whether an artifact is generated in the medical image (S3733) and the operation of acquiring artifact information from the medical image (S3735) are expressed separately, but each operation may include acquiring information on whether an artifact is generated and information regarding an artifact using one neural network model.

The neural network model may acquire whether an artifact is generated based on the medical image. The neural network model may acquire whether an artifact is present in a specific region of the acquired medical image on the basis of the input medical image.

Also, the neural network model may acquire artifact information on the basis of the medical image. The neural network model may acquire information on whether an artifact is generated, information on where an artifact is generated, information on the type of generated artifact, and information on the degree to which an artifact is generated based on the input medical image.

The artifact information may be acquired based on the medical image acquired by the image acquisition device. For example, the artifact information may be acquired using a neural network model trained to acquire the artifact information on the basis of the medical image.

A classifier algorithm that classifies or predicts an input image with respect to one or more labels may be used to acquire the artifact information. For classification or prediction, various types of algorithms may be used. For example, a k-nearest neighbors (KNN) algorithm, a support-vector machine algorithm, an artificial neural network algorithm, a decision tree algorithm, a self-organizing map, a logistic regression algorithm, or the like may be used.

The artificial neural network may be a hybrid classifier, an ensemble classifier, a linear regression neural network, or the like. The artificial neural network may include a convolutional neural network (CNN). The artificial neural network may be a model subjected to supervised training, unsupervised training, or reinforcement training.

Figure 25:
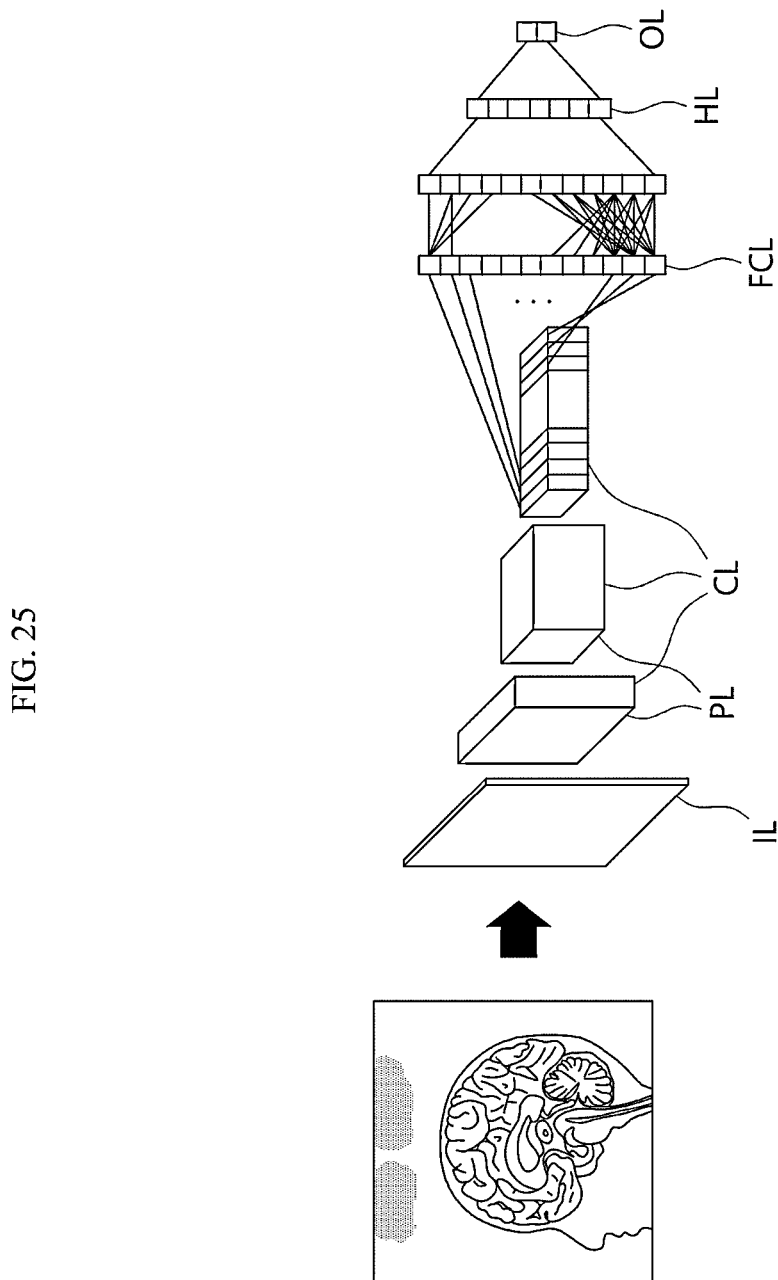
FIG. 25 is a diagram illustrating a neural network model for acquiring artifact information according to an embodiment.

FIG. 25 is a diagram illustrating a neural network model for acquiring artifact information according to an embodiment. Referring to FIG. 25, the neural network model according to an embodiment may be provided in the form of a classifier. According to an embodiment, the neural network model may include an input layer (IL), a pooling layer (PL), a convolutional neural network layer (CL), a fully connected layer (FCL), a hidden layer (HL), and an output layer (OL) and may acquire a feature vector on the basis of an input image. The neural network model may be provided in the form of a classifier that classifies an input image into one or more labels. Alternatively, the neural network model may be provided in the form of a regression model. The neural network model may be provided as a regression model that acquires a linear output value for specific artifact information on the basis of an input image.

The neural network model may acquire output information by using a medical image acquired by capturing a specific region of a human body as an input. The output information may indicate whether the input image includes a target object. For example, the output layer of the neural network model may include an output node to which a probability function is assigned. The output layer of the neural network model may include an output node to which a probability function indicating whether a target image includes a target object is assigned. The output layer may include an output node to which one or more probability functions indicating whether an input image includes one or more corresponding target objects is assigned.

The neural network model may be trained to acquire the artifact information. The neural network model may be trained to acquire the artifact information on the basis of training data including one or more medical images labeled with the artifact information. The neural network model may be trained to acquire an artifact region on the basis of training data including one or more medical images labeled with the artifact region.

Artifact training data may include a plurality of medical images. Artifact training data may include medical images captured in various ways, e.g., CT, MRI, or X-ray images. Artifact training data may include a plurality of medical images including artifacts of various kinds, ranges, sizes, shapes, or locations.

Artifact training data may include a medical image assigned an artifact label indicating whether an artifact is generated. Artifact training data may include medical images that are acquired by capturing various parts of a human body and that are assigned an artifact label indicating whether an artifact is generated. Here, the artifact label may be assigned differently depending on where the artifact is generated, the degree to which the artifact is generated, a shape in which the artifact is generated, or the type of artifact.

Artifact training data may include a medical image in which an artifact region is masked. Artifact training data may include a medical image in which one or more artifact regions are masked (or labeled). Artifact training data may include a medical image in which multiple types of artifact regions are differently masked (or labeled). For example, artifact training data may include a medical image in which a first type of artifact generation is shown in a first color and a second type of artifact generation is shown in a second color.

The neural network model may be trained using the artifact training data. The neural network model may be subject to supervised training, unsupervised training, or reinforcement training using the artifact training data to acquire the artifact information on the basis of the medical image. The neural network model may be trained using backpropagation.

The neural network model may be trained to classify the medical image according to whether an artifact is included by using artifact training data including a medical image labeled with whether the artifact is generated. The neural network model may be trained to classify the medical image according to the type of an artifact included in the medical image. The neural network model may be trained to acquire whether a target image includes each of a plurality of types of artifacts through artifact training data including a medical image labeled with whether a plurality of types of artifacts are present.

The neural network model may be trained to acquire artifact region information through the artifact training data. The neural network model may be trained to detect an artifact region from the target image using artifact training data including a medical image in which artifact regions of one or more types of artifacts are masked. The neural network model may be trained to acquire, through artifact training data including a medical image in which a plurality of types of artifact regions are labeled, artifact region information for the region and/or type of each of a plurality of artifacts included in the medical image.

The neural network model may be trained using a plurality of pieces of artifact training data. The neural network model may be trained using first artifact training data including a medical image with a first type of artifact and second artifact training data including a medical image with a second type of artifact.

Meanwhile, a plurality of neural network models may be trained and used. A first neural network model may be trained based on the first artifact training data, and a second neural network model may be trained based on the second artifact training data. The second artifact training data may be at least partially different from the first artifact training data.

Figure 24:
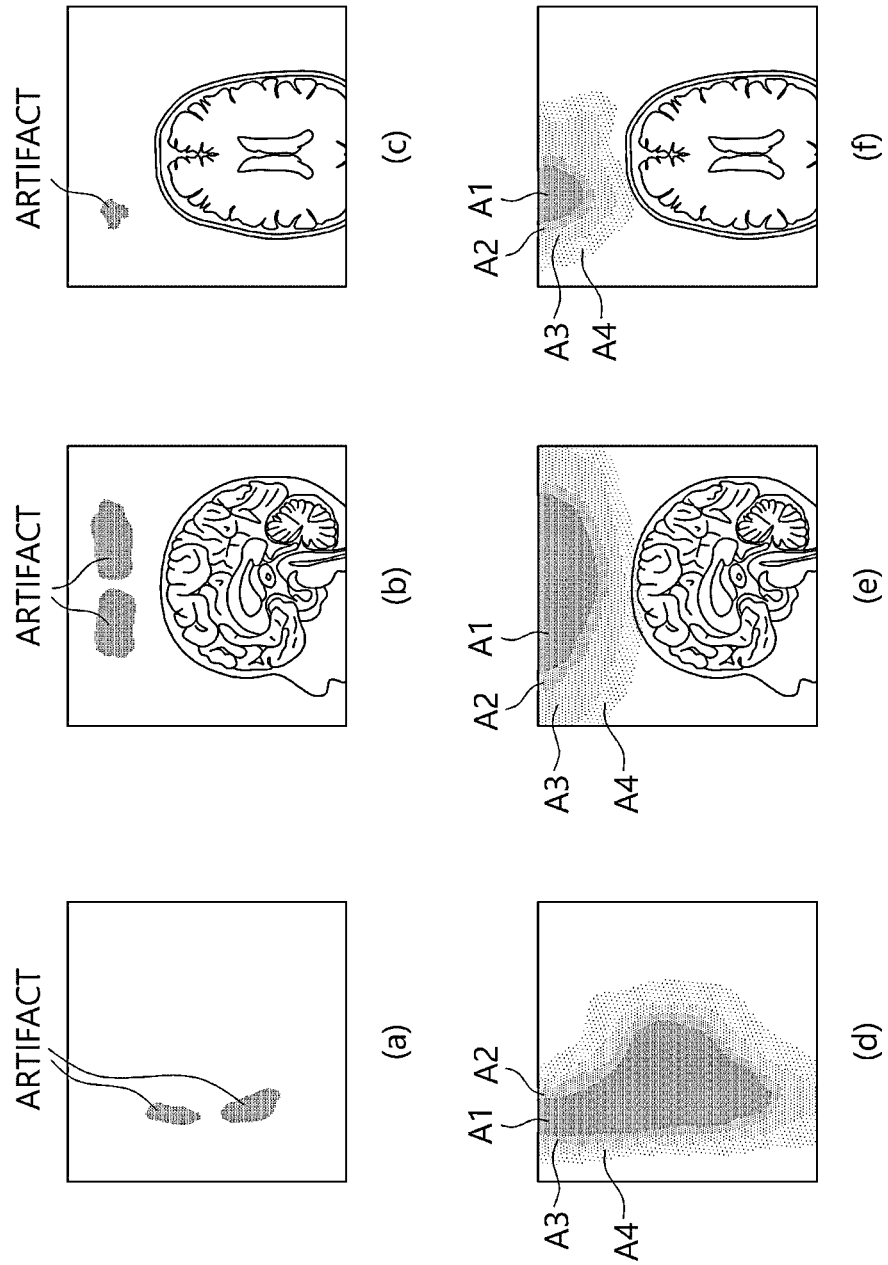
FIG. 24 is a diagram exemplarily illustrating that the second image quality determination process determines an artifact location in a medical image using an artificial neural network model.

FIG. 24 is a diagram exemplarily illustrating that the second image quality determination process determines an artifact location in a medical image using an artificial neural network model. Referring to FIG. 24, the neural network model may acquire artifact region information regarding where an artifact is generated by using a medical image acquired through the image acquisition device as an input.

Referring to FIG. 24, the operation of acquiring artifact information from the medical image (S3735) may include acquiring artifact region information in the medical image.

The artifact region information may be provided in the form of a mark for indicating a region where an artifact is likely to be located in a medical image, for example, a saliency map in the form of a heatmap. The artifact region information may be a feature map acquired from a neural network model for determining whether an artifact is present or a neural network model for acquiring artifact information.

The artifact region may be a region of a feature map, which is acquired from a trained neural network model and related to a target artifact present in a target medical image, where a relevance to a target artifact is greater than or equal to a reference value on the basis of the feature map. The artifact region may include a first region and a second region located within the first region. The first region may be a region of the feature map where the relevance to the target artifact is greater than or equal to a first reference value. The second region may be a region of the feature map where the relevance to the target artifact is greater than or equal to a second reference value, which is greater than the first reference value.

Referring to FIGS. 24A to 24C, the operation of acquiring artifact information from the medical image (S3735) may include acquiring a first original image (a), a second original image (b), and a third original image (c) including the artifact. In this case, the first original image (a), the second original image (b), and the third original image (c) may be images captured in different planes. The first original image (a), the second original image (b), and the third original image (c) may be images captured for the same subject at the same time.

Referring to FIGS. 24D to 24F, the operation of acquiring artifact information from the medical image (S3735) may include acquiring a first artifact image (d), a second artifact image (e), and a third artifact image (f) in which the locations of the artifacts are expressed. Here, the first artifact image (d) may be an image obtained by marking, on the first original image (a), artifact region information acquired based on the first original image (a). The second artifact image (e) may be an image obtained by marking, on the second original image (b), artifact region information acquired based on the second original image (b). The third artifact image (f) may be an image obtained by marking, on the third original image (c), artifact region information acquired based on the third original image (c).

Also, referring to FIGS. 24D to 24F, the first to third artifact images may be images obtained by marking the first to fourth regions A1 to A4 of the medical image in descending order of the probability that an artifact will be located in the medical image. Here, the first to fourth regions A1 to A4 may be regions corresponding to the region where an artifact is located in the image. The first to fourth regions A1 to A4 may be regions including at least a portion of the region where an artifact is located in the image. The first region A1 may be a region included in the second region A2. The second region A2 may be a region included in the third region A3. The third region A3 may be a region included in the fourth region A4.

Although not shown in the drawing, the artifact region information may include a bounding box for displaying a region where an artifact is located in a medical image. The artifact region information may include coordinate information, pixel information, etc., regarding where an artifact is located in a medical image. For example, the second image quality determination unit 3730 may use an artificial neural network model such as a backpropagation based method (BBMs), an activation based method (ABMs), or a perturbation based method (PBMs) to acquire artifact location information. BBMs may include layer-wise relevance propagation (LRP), DeepLIFT, SmoothGrad, VarGrad, etc. ABMs may include Class Activation Map (CAM), Gradient-weighted Class Activation Mapping (Grad-CAM), etc. PBMs may include Local Interpretable Model-agnostic Explanation (LIME), etc.

The third image quality determination unit 3750 according to an embodiment may perform quality determination in consideration of whether segmentation information satisfies a quantitative criterion on the basis of the segmentation information obtained by anatomically segmenting a medical image acquired by an image acquisition device. As a more specific example, the third image quality determination unit 3750 may determine whether at least a portion of the anatomical structure included in the medical image satisfies a predetermined quantitative criterion.

The third image quality determination unit 3750 may determine whether a value related to a predetermined region corresponding to a part of a human body included in an image satisfies a criterion. The third image quality determination unit 3750 may determine whether at least a portion of a human body's anatomical structure captured through the image capture device is entirely captured.

For example, when a specific part of a human body is captured through the image capture device and then analyzed, a disease may be determined through a morphological index of the captured part of the human body. In this case, when each region of the human body is not entirely captured, a disease determination result cannot have a reliability above a certain level. Accordingly, since each region of a human body should be entirely captured, the third image quality determination unit 3750 may perform a function of determining whether each region of the human body is entirely captured in consideration of whether a morphological index based on a human body's anatomical region included in a medical image satisfies a generally required reference value.

As a more specific example, when the image analysis device 3000 analyzes an MRI image of a brain, the image analysis device 3000 may determine a disease by computing the volume proportion of each anatomical region of the brain. In this case, when the volume of the captured specific region of the brain does not satisfy a generally required reference value, a disease determination result cannot have a reliability above a certain level. In this case, when the specific region of the brain is not entirely captured and disease determination is made based on the volume of the corresponding region, the result of the disease determination may be inaccurate. Accordingly, the third image quality determination unit 3750 may perform a function of determining whether each region of the brain is entirely captured in consideration of whether a morphological index of the corresponding region of the brain included in the MRI image satisfies a generally required reference value.

Figure 26:
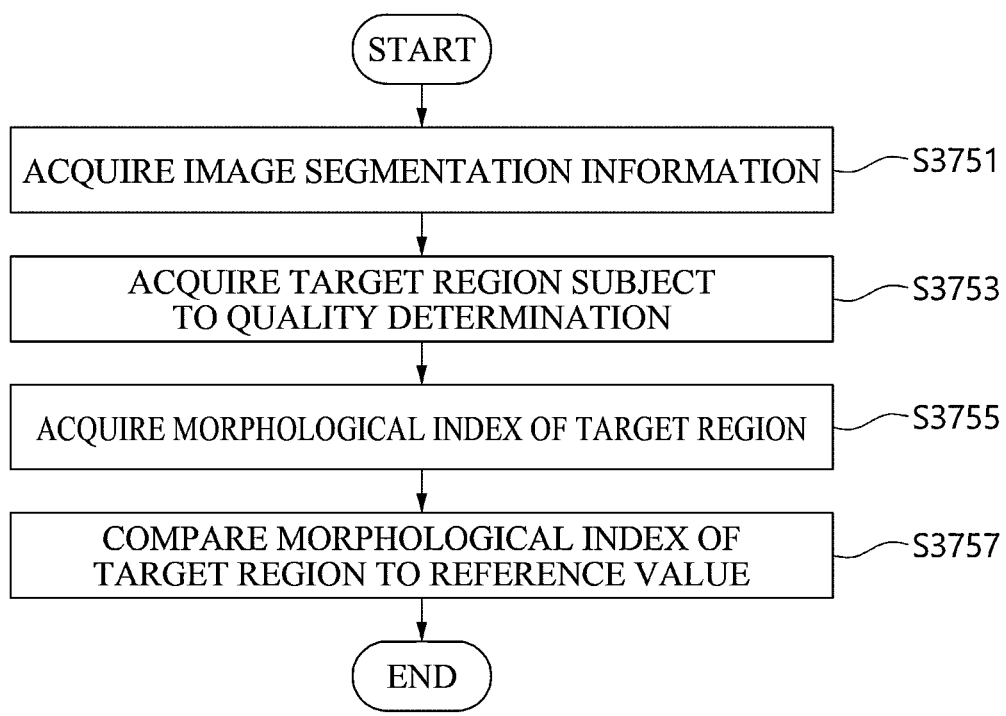
FIG. 26 is a diagram illustrating a third image quality determination process.

FIG. 26 is a diagram illustrating a third image quality determination process.

Referring to FIG. 26, the third image quality determination process may include an operation of acquiring image segmentation information (S3751), an operation of acquiring a target region subject to quality determination (S3753), an operation of acquiring a morphological index of the target region (S3755), and an operation of comparing the morphological index of the target region to a reference value (S3757).

The operation of acquiring image segmentation information (S3751) may include acquiring segmentation information on the basis of a medical image segmented by the image segmentation module 3500.

The segmentation information may include information on a human body's anatomical structure obtained by segmenting the medical image. The segmentation information may include a morphological index of at least a partial region of the human body's anatomical structure obtained by segmenting the medical image. Also, the segmentation information may include a morphological value of at least a partial region of the human body's anatomical structure obtained by segmenting the medical image.

The morphological index may be acquired based on the morphological value. The morphological index may be acquired based on a plurality of morphological values, for example, a first morphological value and a second morphological value. For example, the morphological index may be acquired based on a ratio of the first morphological value to the second morphological value. In this case, the first morphological value may indicate cerebellum, the second morphological value may indicate an anatomical region in a skull, and the morphological index acquired by the ratio of the first morphological value and the second morphological value may refer to an intracranial volume (ICV) value. The morphological value may be information on the area, volume, location, or shape of at least a partial region of the human body's anatomical structure.

The operation of acquiring a target region subject to quality determination (S3753) may include specifying a target region subject to third image quality determination on the basis of the segmentation information. Here, the target region may include at least a partial region of the human body's anatomical structure acquired through the medical image segmentation. Also, the target region may include at least a partial region that may affect the reliability of the disease determination result in the human body's anatomical structure.

For example, the target region may include an outermost region farthest from the center of the medical image in the human body's anatomical structure acquired through the medical image segmentation. The target region may include a region serving as a basis for disease diagnosis in the human body's anatomical structure acquired through the medical image segmentation. The target region may include any one of a leftmost, rightmost, uppermost, or lowermost region in the human body's anatomical structure acquired through the medical image segmentation. When image quality is determined based on a medical image of a brain, the target region may include at least a portion of the internal region of the skull of the brain acquired through the medical image segmentation.

The operation of acquiring a morphological index of the target region (S3755) may include the operation of acquiring a morphological index of a specified target region. For example, the operation of acquiring a morphological index of the target region (S3755) may include acquiring the morphological index of the target region on the basis of at least some of a plurality of medical images obtained by the image acquisition device. The operation of acquiring a morphological index of the target region (S3755) may include acquiring a morphological value of the target region on the basis of at least some of a plurality of medical images obtained by the image acquisition device.

The operation of comparing the morphological index of the target region to a reference value (S3757) may include comparing the morphological index or the morphological value of the target region to a predetermined reference value. Here, the predetermined reference value may mean the average of the morphological values of the target region for a large number of ordinary people. The predetermined reference value may mean an index or measurement value related to the target region when medical information with a reliability above a certain level can be obtained upon disease determination based on the morphological index of the target region.

Figure 27:
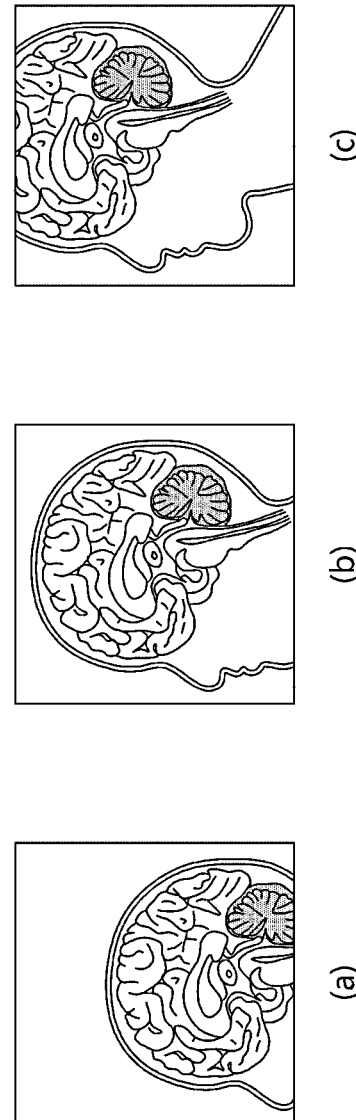
FIG. 27 is a diagram illustrating an embodiment of the third image quality determination process.

FIG. 27 is a diagram illustrating an embodiment of the third image quality determination process.

Referring to FIGS. 27A to 27C, the third image quality determination process according to an embodiment may include performing quality determination based on a medical image of a brain. According to an embodiment, the third image quality determination process may include performing quality determination on whether segmentation information obtained by anatomically segmenting the medical image of the brain satisfies a quantitative criterion on the basis of the segmentation information.

The operation of acquiring image segmentation information (S3751) may include receiving segmentation information obtained by anatomically segmenting an MRI image of a brain. The operation of acquiring a target region subject to quality determination (S3753) may include specifying a target region subject to quality determination, e.g., a predetermined region corresponding to a cerebellum, from among anatomically segmented regions of the brain.

For example, when the target region subject to quality determination is the predetermined region corresponding to the cerebellum, the segmentation information received in the operation of acquiring image segmentation information (S3751) may be information acquired based on an MRI image in which a predetermined region corresponding to a portion of the brain is not entirely captured. Here, a criterion applied with regard to whether the cerebellum has been entirely captured may be the same as a criterion for defining the internal region of the skull on the basis of the morphological value of the cerebellum in the section for describing ICV in this specification.

Referring to FIG. 27A, the operation of acquiring image segmentation information (S3751) may include receiving segmentation information acquired based on a first target region image in which at least a portion of a predetermined region corresponding to the cerebellum out of the regions of the brains is not captured.

Referring to FIG. 27B, the operation of acquiring image segmentation information (S3751) may include receiving segmentation information acquired based on a second target region image in which the entirety of the predetermined region corresponding to the cerebellum out of the regions of the brains is captured.

Referring to FIG. 27C, the operation of acquiring image segmentation information (S3751) may include receiving segmentation information acquired based on a third target region image in which the entirety of the predetermined region corresponding to the cerebellum out of the regions of the brains is captured but at least a portion of a region corresponding to an anatomical structure other than the cerebellum is not entirely captured.

The operation of acquiring a morphological index of the target region (S3755) may include acquiring a morphological index of a target region subject to quality determination, for example, the volume of the cerebellum specified as the target region subject to the quality determination. The operation of acquiring a morphological index of the target region (S3755) may include comparing the morphological index of the target region to a reference value. The operation of acquiring a morphological index of the target region (S3755) may include comparing the volume of the cerebellum specified as the target region to a predetermined reference value to determine whether a quantitative criterion is satisfied.

For example, the predetermined reference value may mean a morphological index of the cerebellum acquired based on the second target region image in which a predetermined region corresponding to the cerebellum is entirely captured. The predetermined reference value may be acquired based on a morphological index of the cerebellum acquired based on a plurality of images in which the predetermined region corresponding to the cerebellum is entirely captured. The predetermined reference value may be the average of the volumes of the cerebellum acquired based on a plurality of images.

In this case, the operation of comparing the morphological index of the target region to a reference value (S3757) may include comparing a morphological index of the cerebellum acquired based on the first target region image in which at least a portion of a predetermined region corresponding to the cerebellum is not captured, as shown in FIG. 27A, to a morphological index of the cerebellum acquired based on the second target region image of FIG. 27B, that is, a predetermined reference value, to determine whether a quantitative criterion is satisfied. The operation of comparing the morphological index of the target region to a reference value (S3757) may include performing image quality determination based on whether the difference between the volume of the cerebellum acquired based on the first target region image of FIG. 27A and the predetermined reference value is greater than or equal to a certain range.

Referring to FIG. 27C, in the case of a third target region image in which a region corresponding to the cerebellum specified as the target region is entirely captured but at least a portion of a region corresponding to an anatomical structure other than the cerebellum is not entirely captured, the third image quality determination process may include performing image quality determination after re-specifying a target region subject to quality determination.

Referring to FIG. 27C, when image quality determination is performed based on a region corresponding to the cerebellum, it is possible to determine the absence of an inferior image, but it may be difficult to determine the absence of a superior image. In order to prevent such a problem, an index other than the region corresponding to the cerebellum may be used as an index for image quality determination. For example, the volume (or ICV) of a region corresponding to the skull or cerebrum may be utilized as an index for quality determination.

Alternatively, when a morphological index acquired based on the region corresponding to the cerebellum (e.g., an ICV value of the cerebellum) is greater than or equal to a reference value, it may be determined that a region other than the cerebellum is incompletely captured.

The fourth image quality determination unit 3770 according to an embodiment may perform image quality determination on the basis of the relationship between segmentation information obtained by anatomically segmenting a medical image acquired by an image acquisition device and artifact information extracted from the medical image acquired by the image acquisition device. For example, the fourth image quality determination unit 3770 may determine whether an artifact generated in the medical image overlaps at least a portion of the anatomical structure included in the medical image.

For example, when a specific part of a human body through the image capture device is captured and then analyzed, the image analysis device 3000 may determine a disease on the basis of segmentation information obtained by anatomically segmenting each region of the human body. In this case, when an artifact is generated in the segmentation information, which may serve as a basis for disease determination, a result of the disease determination based on the corresponding medical image cannot have a reliability above a certain level. Conversely, when an artifact is generated in a medical image but the artifact does not affect segmentation information capable of serving as a basis for disease determination, for example, when an artifact is generated in a region that does not overlap with the segmentation information, a result of disease determination based on the corresponding medical image may have reliability that satisfies a certain level. Accordingly, even when an artifact is generated in a medical image, the fourth image quality determination unit 3770 may perform a function of determining whether the medical image may be normally analyzed in consideration of whether the artifact affects segmentation information capable of serving as a basis for disease determination.

As a more specific example, when analyzing an MRI image of a brain, the image analysis device 3000 may determine a disease on the basis of segmentation information obtained by anatomically segmenting each region of the brain. In this case, when an artifact is generated in at least a portion of the segmented anatomical regions of the brain, which may serve as a basis for disease determination, a result of the disease determination based on the corresponding medical image cannot have a reliability above a certain level. Accordingly, the fourth image quality determination unit 3770 may perform a function of determining whether the medical image may be normally analyzed in consideration of whether an artifact is generated in at least a portion of the anatomical structure of each region of the brain included in the MRI image.

Figure 28:
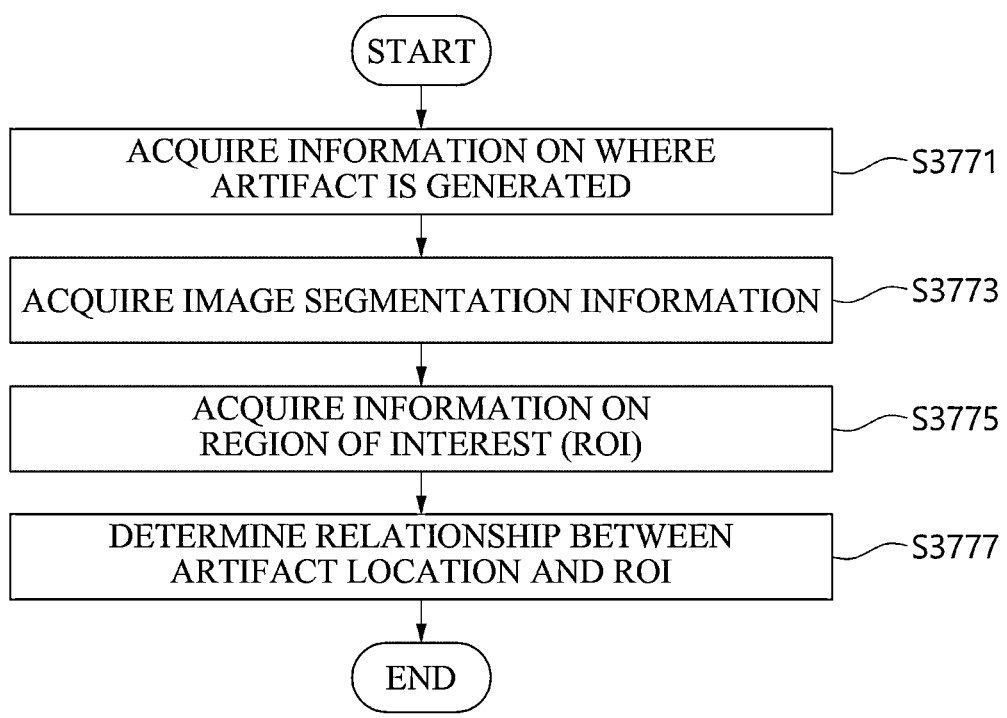
FIG. 28 is a diagram illustrating a fourth image quality determination process.

FIG. 28 is a diagram illustrating a fourth image quality determination process.

Referring to FIG. 28, the fourth image quality determination process may include an operation of acquiring information on an artifact location (S3771), an operation of acquiring image segmentation information (S3773), an operation of acquiring an ROI (S3775), and an operation of determining the relationship between the artifact location and the ROI (S3777).

The operation of acquiring information on an artifact location (S3771) may include acquiring information on where an artifact is generated. In this case, the artifact location information may be acquired from the image analysis device 3000. The artifact location information may include artifact region information regarding where an artifact is generated, for example, a saliency map in the form of a heatmap, indicating a region where an artifact is likely to be located in a medical image, a bounding box for displaying a region where an artifact is located in a medical image, and coordinate information or pixel information regarding where an artifact is located in a medical image. This has been described above in relation to the second image quality determination unit 3730, and thus a detailed description thereof will be omitted.

Here, the term "artifact" as used herein may include noise, for example, various types of defects or states that affect image-based information acquisition. Also, an artifact may include image resolution, image brightness, and various other image defects resulting from improper image sampling.

The operation of acquiring image segmentation information (S3773) may include acquiring segmentation information acquired on the basis of a medical image segmented by the image segmentation module 3500. Here, the image segmentation information may include information acquired by anatomically segmenting the medical image. The image segmentation information may include segmentation information acquired by anatomically segmenting an MRI image of a brain. This has been described above in relation to the third image quality determination unit 3750, and thus a detailed description thereof will be omitted.

The operation of acquiring an ROI (S3775) may include acquiring information regarding the ROI on the basis of the segmentation information obtained by anatomically segmenting a medical image. The operation of acquiring an ROI (S3775) may include acquiring information regarding the ROI from the segmentation information obtained by anatomically segmenting the medical image. The operation of acquiring an ROI (S3775) may include acquiring one or more regions by segmenting a medical image and acquiring a region corresponding to the ROI.

The ROI may include at least a partial region of a human body's anatomical structure acquired through the medical image segmentation. The ROI may be predefined as a region corresponding to a specific anatomical (or functional) element in the medical image. The ROI may include an outermost region farthest from the center of the medical image in the human body's anatomical structure acquired through the medical image segmentation. The ROI may include a region serving as a basis for disease diagnosis in the human body's anatomical structure acquired through the medical image segmentation. When image quality determination is performed based on an MRI image of a brain, the ROI may include at least a portion of the region of the skull and the internal region of the skull of the brain acquired through the medical image segmentation. The ROI may be a factor related to diagnosis of a target disease.

The operation of determining the relationship between the artifact location and the ROI (S3777) may include determining the relationship between the artifact location and the ROI. The operation of determining the relationship between the artifact location and the ROI (S3777) may include performing quality determination based on information on the ROI in the human body's anatomical structure obtained by segmenting the medical image and information on an artifact included in the medical image. The operation of determining the relationship between the artifact location and the ROI (S3777) may include performing quality determination based on whether the degree of overlap between the ROI and the artifact generated in the medical image affects the reliability of a disease determination result to a certain level or lower.

The operation of determining the relationship between the artifact location and the ROI (S3777) may include performing quality determination based on whether at least some artifacts generated in the medical image are located in the ROI or whether at least some artifacts generated in the medical image overlap the ROI.

The operation of determining the relationship between the artifact location and the ROI (S3777) may include determining the relationship between the artifact location and the ROI on the basis of the relationship between the ROI and a boundary related to the location of the artifact (an artifact boundary). Here, the artifact boundary may be an outer line of the artifact region. The artifact boundary may be acquired based on a saliency map (e.g., CAM) that is obtained from a neural network model for determining whether an artifact is present and related to the estimation of an artifact's location.

The operation of determining the relationship between the artifact location and the ROI (S3777) may include acquiring an outer line of the artifact region and an outer line of the ROI in the medical image and determining whether the artifact region overlaps the ROI on the basis of whether the outer line of the artifact region and the outer line of the ROI overlap in the medical image. In this case, when there are less than two intersections in which the outer line of the artifact region and the outer line of the ROI overlap in the medical image, the image analysis device 3000 may determine that the quality of the medical image is normal. Alternatively, when there are two or more intersections, the image analysis device 3000 may determine that the quality of the target medical image is abnormal.

The operation of determining the relationship between the artifact location and the ROI (S3777) may include acquiring the number of common pixels included in both the artifact region and the ROI of the medical image and determining the degree of overlap between the artifact and the ROI by using the number of common pixels. In this case, when the number of common pixels exceeds a predetermined reference value, the image analysis device 3000 may determine that the quality of the medical image is abnormal. Alternatively, when the number of common pixels is less than or equal to a predetermined reference value, the image analysis device 3000 may determine that the quality of the medical image is normal.

The operation of determining the relationship between the artifact location and the ROI (S3777) may include determining whether an artifact is generated in the ROI, e.g., at least a portion of the region of the skull or the internal region of the skull. The operation of determining the relationship between the artifact location and the ROI (S3777) may include determining whether an artifact overlaps the ROI, e.g., at least a portion of the region of the skull or the internal region of the skull.

FIG. 29 is a diagram illustrating an image in which an artifact is generated. An image quality determination process according to the range of the generated artifact will be described below with reference to FIGS. 28 and 29.

Referring to FIG. 29A, an image including an artifact overlapping the region of the skull and the internal region of the skull may be acquired. Referring to FIG. 29B, an image including an artifact overlapping a portion of the region of the skull may be acquired. Referring to FIGS. 29A and 29B, the ROI may be an internal region of the skull or a region corresponding to the skull.

Referring to FIG. 29A, when a target medical image includes an artifact overlapping the region of the skull and the internal region of the skull and the ROI is the region of the skull or the internal region of the skull, the operation of determining the relationship between the artifact location and the ROI (S3777) may include determining that the ROI and the artifact location overlap each other.

Referring to FIG. 29B, when a target medical image includes an artifact overlapping the region of the skull and the ROI is the internal region of the skull, the operation of determining the relationship between the artifact location and the ROI (S3777) may include determining that the ROI and the artifact location do not overlap each other.

Referring to FIG. 29B, when a target medical image includes an artifact overlapping the region of the skull and the ROI is the region of the skull, the operation of determining the relationship between the artifact location and the ROI (S3777) may include determining that the ROI and the artifact location overlap each other.

An artifact illustrated in FIG. 29 may mean a region determined as an artifact region. The region determined as an artifact region may be acquired through a segmentation neural network model for acquiring an artifact region or a classifier model for acquiring artifact information, and this will be described in detail below.

The fourth image quality determination may include acquiring a plurality of reference regions related to an artifact and determining the quality of the image on the basis of the overlap between each reference region and the ROI.

The operation of determining the relationship between the artifact location and the ROI (S3777) according to an embodiment may include performing the image quality determination on the basis of artifact information regarding the location of the artifact and a region including the ROI. The operation of determining the relationship between the artifact location and the ROI (S3777) according to an embodiment may include performing the image quality determination on the basis of information on the probability that an artifact will be located in a specific region of the medical image and information on the ROI. The operation of determining the relationship between the artifact location and the ROI (S3777) may include determining whether the degree of overlap between the artifact generated in the medical image and the ROI exceeds a predetermined reference value.

The information on the probability that an artifact will be located in a specific region of the medical image may include artifact region information. Here, the artifact region information may include first to nth artifact regions of the medical image in descending order of the probability that an artifact will be located. The artifact region may include a first region and a second region location within the first region as described above in the second image quality determination process. The first region may be a region in which a relevance to a target artifact in a feature map is greater than or equal to a first reference value, and the second region may be a region in which a relevance to a target artifact in a feature map is greater than or equal to a second reference value, which is greater than the first reference value.

Figure 30:
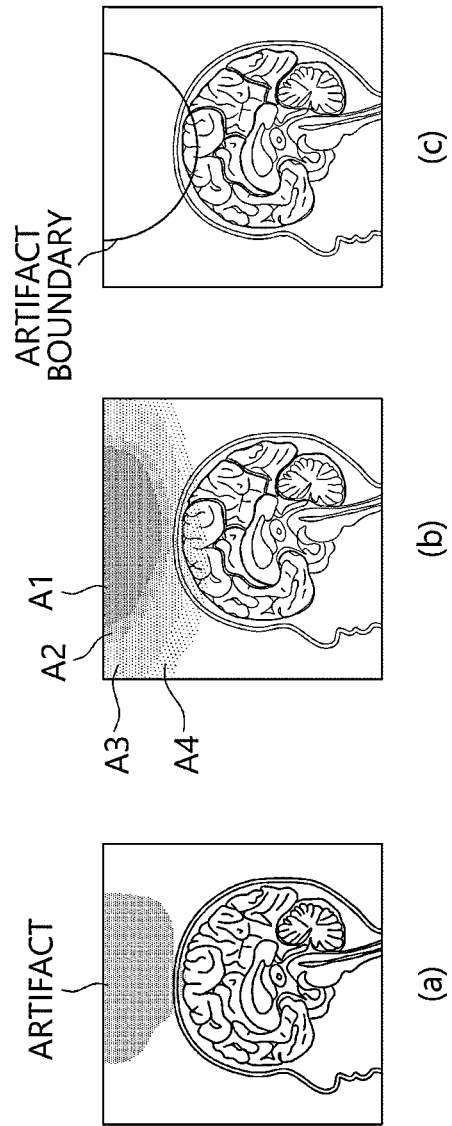
FIG. 30 is a diagram illustrating the determination of whether a generated artifact overlaps a region of interest (ROI) in the fourth image quality determination process according to another embodiment.

FIG. 30 is a diagram illustrating the determination of whether a generated artifact overlaps an ROI in the fourth image quality determination process according to another embodiment.

Referring to FIG. 30B, the artifact region may include a first artifact region AR1, a second artifact region AR2, a third artifact region AR3, or a fourth artifact region AR4 of the medical image in descending order of the probability that an artifact will be located. The first to fourth artifact regions AR1 to AR4 may include at least a portion of a region in which an artifact is located in the image. The artifact region may include a first artifact region AR1, a second artifact region AR2, a third artifact region AR3, and a fourth artifact region AR4 in descending order of the relevance to the artifact.

Alternatively, the artifact region may include a region in which a relevance to a target artifact in a feature map is greater than or equal to a first reference value (e.g., the third artifact region AR3 and the fourth artifact region AR4). The artifact region may include a region in which a relevance to a target artifact in a feature map is greater than or equal to a second reference value, which is greater than the first reference value (e.g., the first artifact region AR1 and the second artifact region AR2).

Referring to FIG. 30B, the degree of overlap between the artifact and the ROI may be determined using the number of common pixels included in both the artifact region and the ROI. For example, when the number of common pixels included in both the third artifact region A3 and the fourth artifact region A4 exceeds a predetermined reference value, the image analysis device 3000 may determine that the quality of the medical image is abnormal. As another example, when the number of common pixels included in all of the first artifact region A1, the second artifact region A2, and the ROI is less than or equal to a predetermined reference value, the image analysis device 3000 may determine that the quality of the medical image is normal.

Referring to FIG. 30C, an outer line of the artifact region may be used as an artifact boundary. The artifact boundary may be determined based on a feature map related to the artifact region as shown in FIG. 30A. The artifact boundary may be determined as a boundary of one of the first to fourth artifact regions AR1 to AR4 as shown in FIG. 30B. The artifact boundary may be determined as the average of the boundaries of the first to fourth artifact regions AR1 to AR4.

The artifact boundary may be an outer line of a first region (e.g., a region in which the relevance to the target artifact in the feature map is greater than or equal to the first reference value). The artifact boundary may be an outer line of a second region (e.g., a region in which the relevance to the target artifact in the feature map is greater than or equal to the second reference value, which is greater than the first reference value).

Determining the relationship between the location of the artifact and the ROI on the basis of the relationship between the artifact boundary and the ROI may include performing quality determination on the basis of whether the artifact boundary and the ROI overlap each other.

As shown in FIG. 30C, when there are more than two intersections at which the artifact boundary and the outer line of the ROI overlap in the medical image, the image analysis device 3000 may determine that the quality of the target medical image is abnormal.

When a plurality of artifacts are present in the target image, the operation of determining the relationship between the artifact location and the ROI (S3777) may include performing quality determination on the basis of whether the ROI overlaps one of the plurality of artifacts or the degree of overlap between the ROI and one of the plurality of artifacts.

The image output device may include an image quality-related information output module 3900. The image quality-related information output module 3900 may output a result of image quality determination performed by the image quality determination module 3700 of the image analysis device 3000. Also, the image quality-related information output module 3900 may output information generated based on a result of image quality determination performed by the image quality determination module 3700 of the image analysis device 3000.

The image output device or the image analysis device may acquire a user input indicating an additional operation in response to a selection window output.

Figure 31:
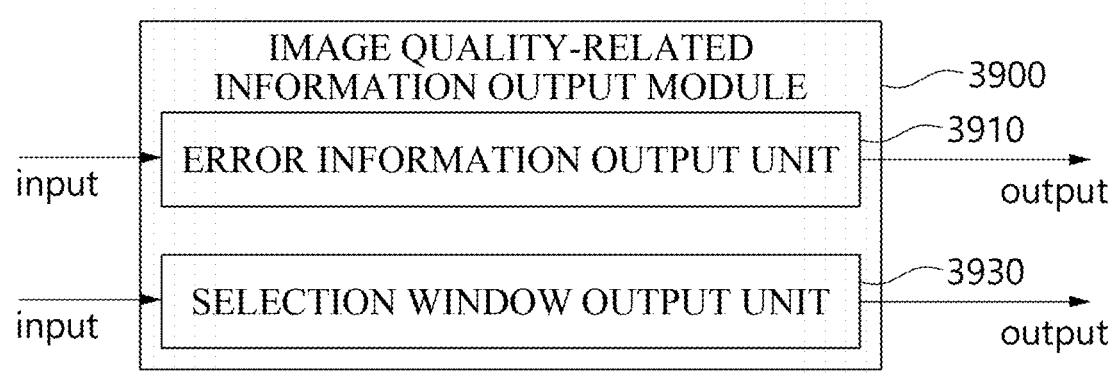
FIG. 31 is a diagram illustrating an image quality-related information output module according to an embodiment.

FIG. 31 is a diagram illustrating an image quality-related information output module according to an embodiment.

Referring to FIG. 31, the image quality-related information output module 3900 may include at least one of an error information output unit 3910 or a selection window output unit 3930. In this case, the error information output unit 3910 may output error information regarding information acquired based on the image quality determination result. The selection window output unit 3930 may output a selection window for the information acquired based on the image quality determination result.

The error information output unit 3910 and the selection window output unit 3930 may output information determined based on independent image quality determination results. For example, the error information output unit 3910 may output error information determined based on a first quality determination result, and the selection window output unit 3930 may output a selection window determined based on a second quality determination result.

Alternatively, the error information output unit 3910 and the selection window output unit 3930 may output information determined based on the same image quality determination result. The error information output unit 3910 may output error information determined based on the first quality determination result, and the selection window output unit 3930 may output a selection window determined based on the first quality determination result.

FIG. 31 exemplifies that the error information output unit 3910 and the selection window output unit 3930 are distinguished from each other, but this is merely an example. The error information output unit 3910 and the selection window output unit 3930 may be provided as one physical or logical component. For example, the image quality-related information output module 3900 may output error information generated based on a quality determination result and a selection window corresponding to the error information.

The selection window output unit 3930 may output a selection window for acquiring a user instruction related to an operation that may be additionally performed on the basis of a quality determination result.

The image quality-related information output module 3900 may output at least one of the error information or the selection window in the form of text or an image.

The image quality-related information output module 3900 may output the error information. In this case, the error information may include information acquired based on a result of image quality determination performed by the image quality determination module 3700. Also, the error information may include at least one of first error information regarding a first image quality determination result, second error information regarding a second image quality determination result, third error information regarding a third image quality determination result, and fourth error information regarding a fourth image quality determination result.

The image quality-related information output module 3900 may output a first error information screen. The first error information may include information acquired based on the first image quality determination result. The first error information may include information acquired based on metadata information of a medical image.

According to an embodiment, the image quality-related information output module 3900 may output a first error information screen when file structure information of a medical image acquired by an image acquisition device, e.g., a file type, a format, or file size of the medical image, is abnormal. In this case, the first error information screen may include a first notification window indicating that the file structure information of the medical image is abnormal or information regarding the file structure of the medical image.

According to another embodiment, when patient information, e.g., information regarding personal data such as a patient's name and age, information regarding when the medical image acquired by the image acquisition device is captured, information regarding a patient's health state, or the like is missing from the medical image, the image quality-related information output module 3900 may output the first error information screen. In this case, the first error information may include a first notification window indicating that patient information is missing from the medical image or the patient information that is missing from or included in the medical image.

Figure 32:
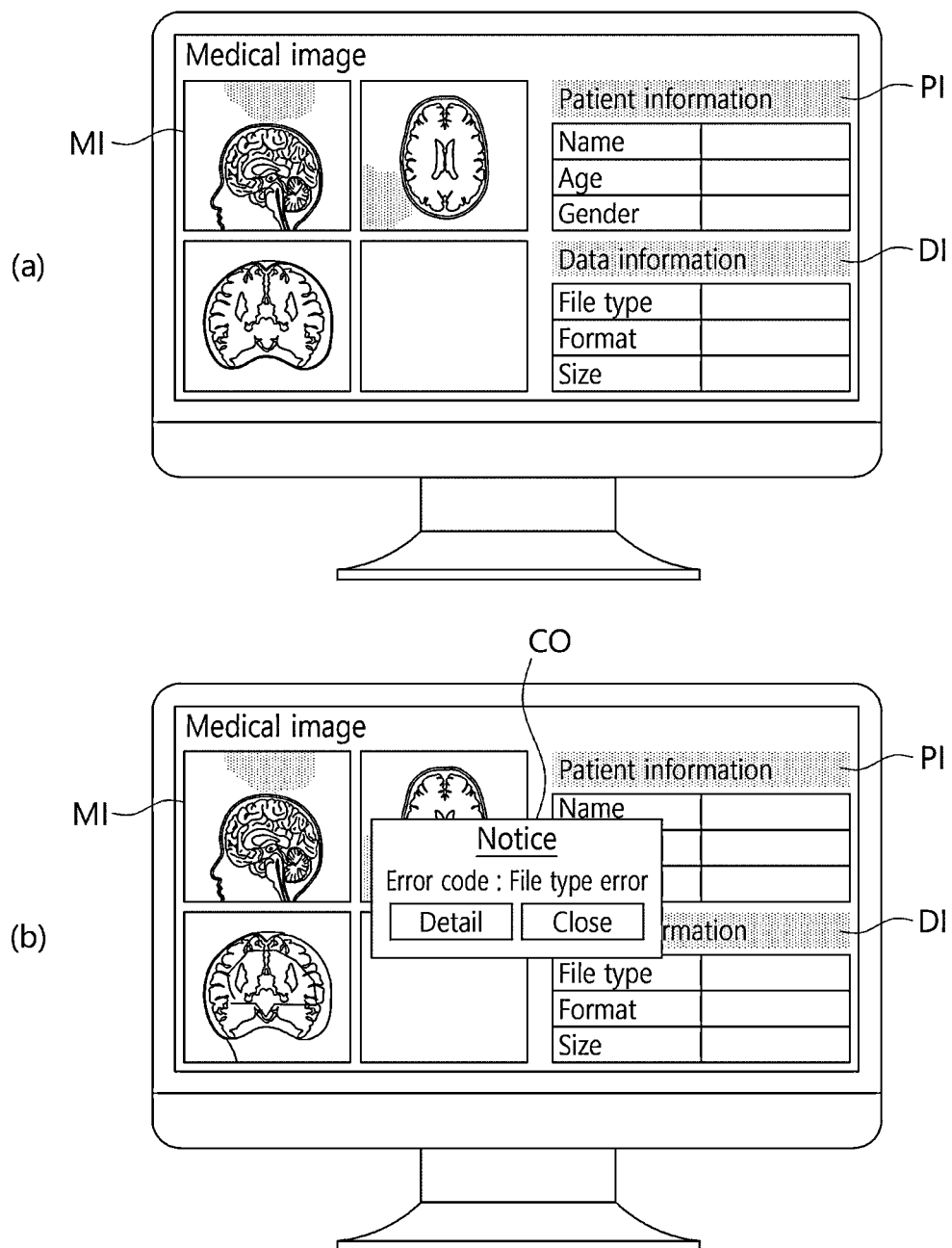
FIG. 32 is a diagram exemplarily illustrating a first error information screen.

FIG. 32 is a diagram exemplarily illustrating a first error information screen.

Referring to FIG. 32A, the first error information screen may include at least one of a medical image MI based on the first image quality determination, file structure information DI of the medical image, or patient input PI input to the medical image.

In this case, the medical image MI may be an image having a marked medical image used for the first image quality determination. The file structure information DI of the medical image may include first file structure information regarding the format of the medical image, second file structure information regarding the format of the medical image, or third file structure information regarding the size of the medical image. In this case, although not shown in the drawings, the first error information screen includes a detailed information object, and an output screen may additionally display more details (e.g., a patient's date of birth, a patient's address, a capture time, a capture place, a capture device, etc.) about the medical image MI or the file structure information DI according to a user's selection of the detailed information object.

Referring to FIG. 32B, the first error information screen may include a first notification window CO including first information indicating that a medical image is abnormal according to the first image quality determination result. For example, the first notification window CO may include an error code indicating that the file structure of the medical image is abnormal or that the patient information is missing from the medical image. In this case, the first error information screen includes a detailed information object, and an output screen may additionally display details (e.g., a description of the error code, a cause for an error message, a manual to respond to an error message, etc.) about the first information according to a user's selection of the detailed information object.

The image quality-related information output module 3900 may output a second error information screen. The second error information may include information acquired based on the second image quality determination result. The second error information may include information acquired based on noise information. The second error information may include information acquired based on various types of defects or states that affect image-based information acquisition.

According to an embodiment, the image quality-related information output module 3900 may output the second error information screen when a medical image acquired by an image acquisition device includes noise. The image quality-related information output module 3900 may output the second error information in the form of text or an image.

For example, the image quality-related information output module 3900 may output the second error information screen when an artifact is included in the medical image acquired by the image acquisition device. The second error information screen may include an error message stating that an artifact is included in the medical image. Also, the second error information may include one of information on the location of the artifact in the medical image, information on the degree to which the artifact is generated, information on the range in which the artifact is generated, or information on the type of artifact.

The second error information screen may include text or an image. For example, the second error information screen may include an indication for a region where an artifact is likely to be located in the medical image, for example, a heatmap-type image. As another example, the second error information screen may include an image showing a bounding box indicating the location of an artifact in the medical image. As another example, the second error information screen may include an image for indicating anatomical segmentation information of the medical image.

Figure 33:
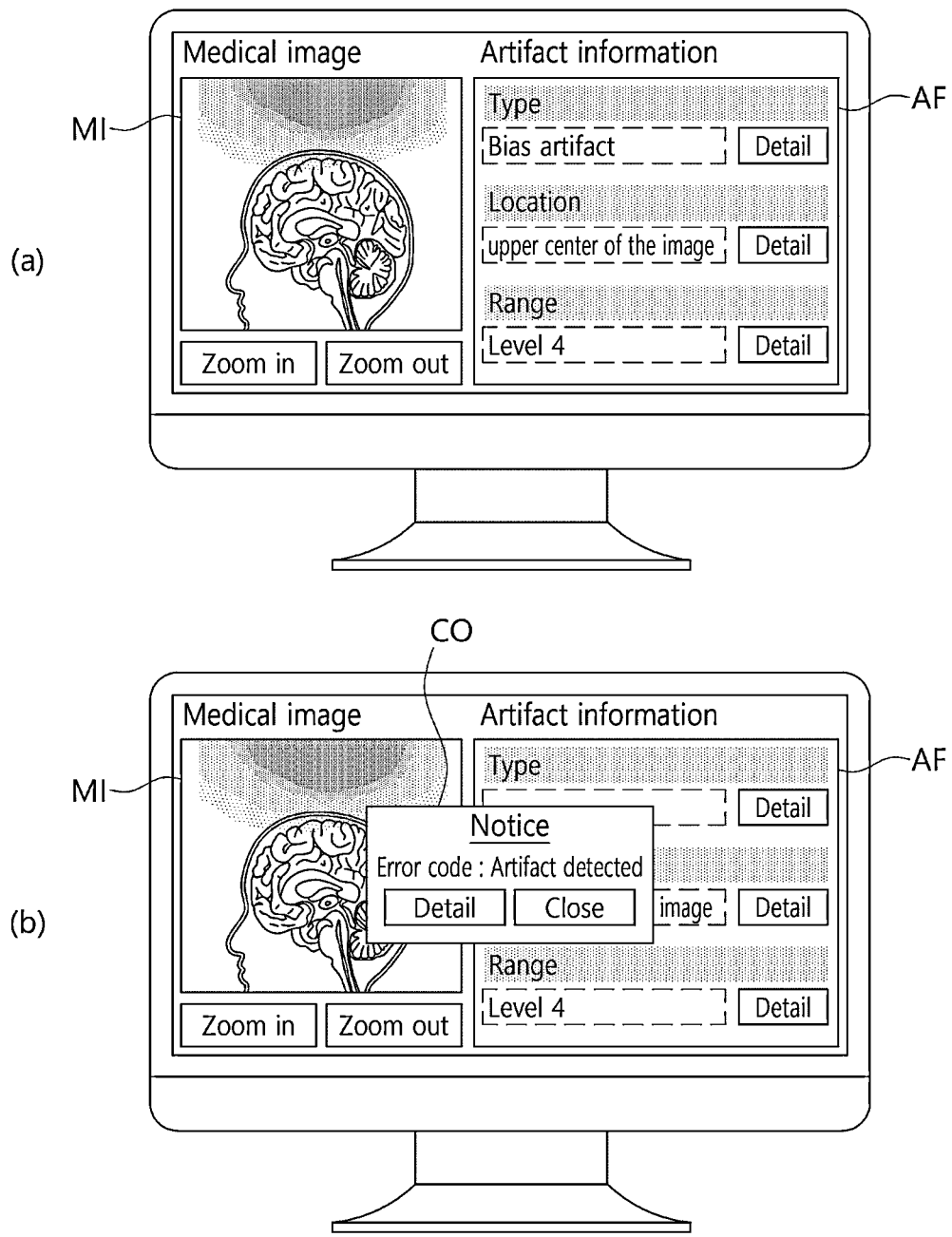
FIGS. 33 and 34 are diagrams exemplarily illustrating second error information screens.
Figure 34:
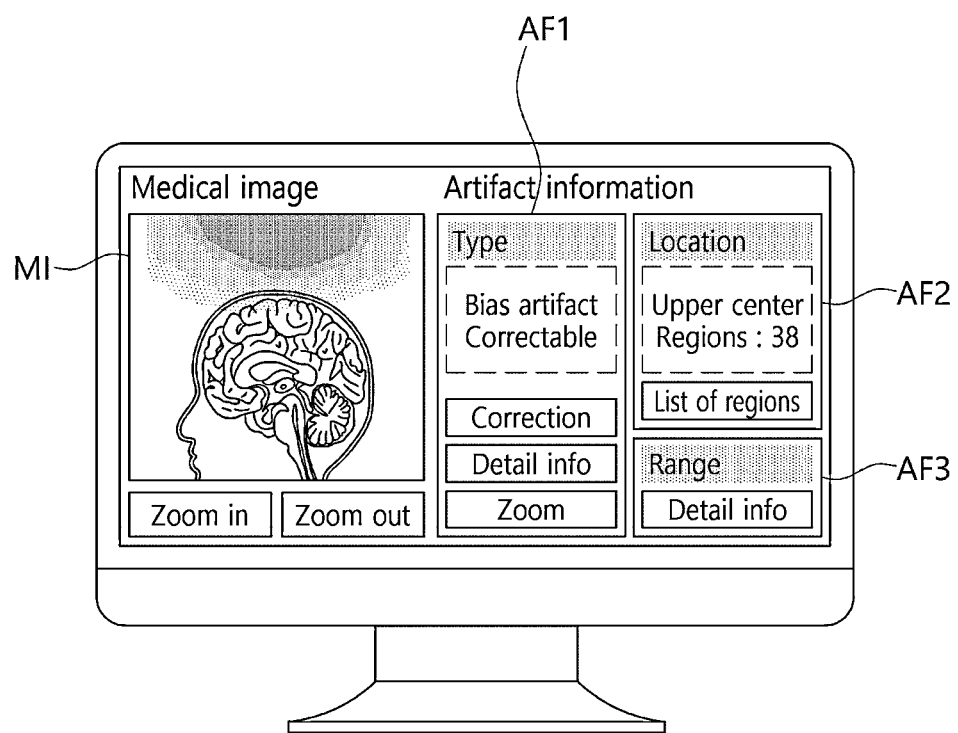

FIGS. 33 and 34 are diagrams exemplarily illustrating second error information screens.

Referring to FIG. 33A, the second error information screen may include a medical image (MI) display region related to the second image quality determination. The second error information screen may include an artifact information (AF) output region.

The medical image MI may be an image in which a region where an artifact is likely to be located in the medical image is emphasized based on the second image quality determination. The medical image MI may be an image in which a region determined as being highly related to an artifact is highlighted in the form of a heatmap. The medical image MI may be enlarged or reduced so that the type, generation range, shape, and the like of an artifact may be checked in more detail according to a user manipulation.

The artifact information AF may include at least one of information on the type of artifact, information on a region where an artifact is likely to be located, or information on the degree to which an artifact is generated. In this case, the second error information screen includes a detailed information object, and an output screen may additionally display more details (e.g., information on the probability that an artifact will be located in a specific region of the image, heatmap information or boundary information regarding the range in which an artifact is generated, etc.) about the medical image MI or the artifact information AF according to a user's selection of the detailed information object.

Referring to FIG. 33B, the second error information screen may include a second notification window CO including second information regarding an artifact included in the medical image. For example, the second notification window CO may include a message with a marked error code indicating that an artifact is generated in the medical image. In this case, the second error information screen includes a detailed information object, and an output screen may additionally display details (e.g., a description of the error code, a cause for an error message, a manual to respond to an error message, etc.) about the second information according to a user's selection of the detailed information object.

Referring to FIG. 34, the artifact information AF includes first artifact information AF1 including information on the type of artifact, and second artifact information AF2 including information on a region where an artifact is likely to be located, or third artifact information AF3 including information on the degree to which an artifact is generated.

The first artifact information AF1 may include information on the type of artifact, information on whether to correct an image in which an artifact is generated, and the like. In this case, the information on whether to correct an image in which an artifact is generated may include information acquired based on one of the type, location, range, or degree of the generated artifact.

The second artifact information AF2 may include information on a region where an artifact is likely to be located in the medical image and information on an analyzable region within a region corresponding to an anatomical structure in the medical image. In this case, the information on the analyzable region may be acquired based on anatomical segmentation information and artifact location information. For example, information on a diagnosis region may include information on a region that does not overlap an artifact within the region corresponding to the anatomical structure in the medical image or information on a region with a low degree of overlap with an artifact within the region corresponding to the anatomical structure in the medical image. In this case, diagnosable diseases may vary depending on the analyzable region.

The third artifact information AF3 may include information on the degree, level, range, and the like of the generated artifact. In this case, the image analysis device may determine whether to proceed with image analysis on the basis of the third artifact information AF3. For example, even when an artifact is generated in the medical image, the image analysis device may determine that the image analysis can be performed when it is determined that the degree of the generated artifact is lower than a predetermined reference value on the basis of the third artifact information AF3.

The image quality-related information output module 3900 may output a third error information screen. The third error information may include information acquired based on the third image quality determination result. Also, the third error information may include information acquired based on segmentation information obtained by anatomically segmenting a medical image acquired by the image acquisition device.

According to an embodiment, the image quality-related information output module 3900 may output the third error information screen when at least a portion of an anatomical structure included in a medical image acquired by an image acquisition device does not satisfy a predetermined quantity criterion. For example, the image quality-related information output module 3900 may output the third error information screen when a value related to a predetermined region, which is included in the medical image and corresponds to a part of a human body, does not satisfy a reference. As a more specific example, the image quality-related information output module 3900 may output the third error information screen when the volume of a predetermined region corresponding to a portion of a brain included in an MRI image of the brain does not satisfy a predetermined reference value. Also, the image quality-related information output module 3900 may output the third error information screen in the form of text or an image.

The third error information may include an error message stating that at least a portion of the anatomical structure in the medical image is abnormal or information on an abnormal anatomical structure. As a more specific example, the third error information may include information regarding a target region on which quality determination is to be performed based on the image segmentation result. The third error information may include information regarding at least a partial region that may affect the reliability of the disease determination result in the human body's anatomical structure.

The third error information may include information on a morphological index or morphological value, e.g., the area, volume, location, or shape, of at least a partial region of the human body's anatomical structure obtained by segmenting the medical image.

The third error information may include information on a result of comparing a morphological index or morphological value of a target region to a predetermined reference value. As a more specific example, the third error information may include information on whether at least a portion of the anatomical structure included in the medical image satisfies a predetermined quantitative criterion.

The third error information screen may include text or an image. The third error information screen may include text that numerically represents a morphological index or morphological value of at least a partial region of the human body's anatomical structure obtained by segmenting the medical image. The third error information screen may include an image obtained by marking, on the original medical image, a target region corresponding to an anatomical structure serving as a reference for quality determination.

Figure 35:
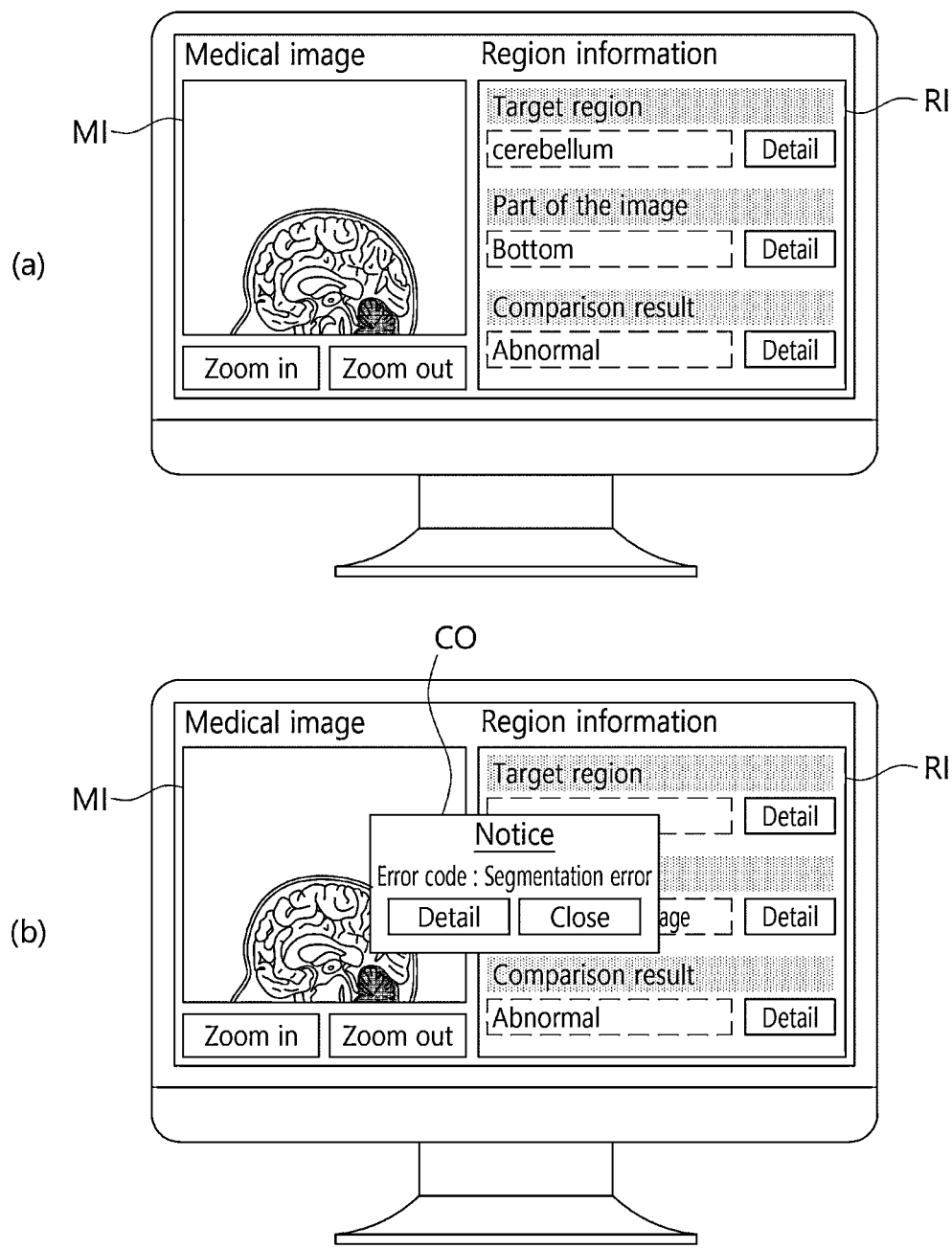
FIGS. 35 and 36 are diagrams exemplarily illustrating third error information screens.
Figure 36:
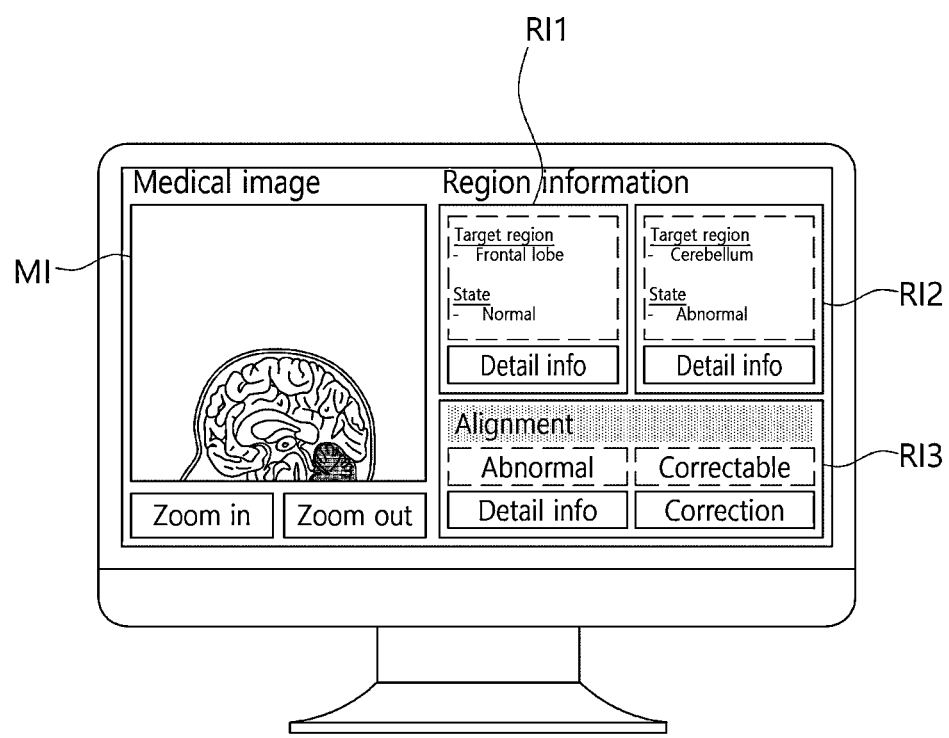

FIGS. 35 and 36 are diagrams exemplarily illustrating the third error information screen.

Referring to FIG. 35A, the third error information screen may include region information RI or a medical image MI related to third image quality determination.

In this case, the medical image MI may include information regarding a target region used for the third image quality determination on the basis of the image segmentation result. For example, when it is determined whether the lower side of the medical image is completely captured, the medical image may include an image obtained by representing information regarding a target region on which quality determination is to be performed, for example, a cerebellum. The third error information screen may include a button for enlarging or reducing the medical image MI in order to check information on a region corresponding to an anatomical structure in the medical image in more detail. Also, the region information RI may include one of information regarding the target region on which image quality determination is to be performed, information on a portion that is not completely captured in the medical image, or information on whether the target region satisfies a predetermined quantitative criterion. In this case, the third error information screen includes a detailed information object, and an output screen may additionally display more details (e.g., information on a region of a human body subject to quality determination, information on an image region subject to quality determination, etc.) about the medical image MI or the region information RI according to a user's selection of the detailed information object.

Referring to FIG. 35B, the third error information screen may include a third notification window CO including third information on a region corresponding to the anatomical structure in the medical image. For example, the third notification window CO may include a message that contains error information on the region corresponding to the anatomical structure in the medical image, e.g., an error code indicating that the segmentation information does not satisfy a predetermined quantitative criterion. In this case, the third error information screen includes a detailed information object, and an output screen may additionally display details (e.g., a description of the error code, a cause for an error message, a manual to respond to an error message, etc.) about the third information according to a user's selection of the detailed information object.

Referring to FIG. 36, the region information RI may include first region information RI1 including a first target region included in a first part of the medical image and information on whether the first target region satisfies a predetermined quantitative criterion, second region information RI2 including a second target region included in a second part of the medical image and information on whether the second target region satisfies a predetermined quantitative criterion, or third region information RI3 including information on the arrangement of the anatomical structure of the medical image and information on whether to correct the medical image.

For example, the first region information R1 may include information on whether a morphological index or morphological value of a target region located on an upper side of the medical image, for example, the frontal lobe, satisfies a predetermined quantitative criterion.

The second region information RI2 may include information on whether a morphological index or morphological value of a target region located on a lower side of the medical image, for example, a cerebellum, satisfies a predetermined quantitative criterion.

The third region information RI3 may include information on the arrangement of the anatomical structure in the medical image, for example, information on whether the captured anatomical structure in the medical image is inclined and information for determining whether to correct the medical image on the basis of the information on the inclination.

The image quality-related information output module 3900 may output a fourth error information screen. The fourth error information may include information acquired based on a fourth image quality determination result.

According to an embodiment, the image quality-related information output module 3900 may output the fourth error information screen when an artifact generated in the medical image overlaps at least a portion of the anatomical structure included in the medical image.

The fourth error information may include information acquired based on the relationship between segmentation information obtained by anatomically segmenting a medical image acquired by an image acquisition device and artifact information extracted from the medical image acquired by the image acquisition device. For example, the fourth error information may include information on whether an artifact is generated in at least a portion of an anatomical structure of each region of a brain included in an MRI image.

The fourth error information may include information on whether the artifact generated in the medical image overlaps at least a portion of the anatomical structure included in the medical image. Also, the fourth error information may include information on the degree of overlap between the artifact generated in the medical image and at least the portion of the anatomical structure included in the medical image. Also, the fourth error information may include information on the reliability of a result for disease determination performed through the analysis of the medical image on the basis of the degree of overlap between the artifact generated in the medical image and the anatomical structure included in the medical image.

The fourth error information may include information on the relationship between the probability that an artifact will be located in a specific region in the medical image and the ROI. Also, the fourth error information may include at least one of a first artifact region of the medical image where the probability that an artifact will be located is high, a second artifact region of the medical image where the probability that an artifact will be located is medium, and a third artifact region of the medical image where the probability that an artifact will be located is low. The first to third artifact regions may be visually highlighted on the original medical image. The first to third artifact regions may be displayed in the form of a heatmap to overlap the original medical image.

The fourth error information screen may include text or an image. For example, the fourth error information screen may include an image obtained by marking, on the human body's anatomical structure obtained by segmenting the medical image, artifact region information, e.g., a saliency map in the form of a heatmap that represents a region of the medical image where an artifact is likely to be located, a bounding box for indicating a region of the medical image where an artifact is located, and coordinate information or pixel information regarding where an artifact is located in the medical image.

Figure 37:
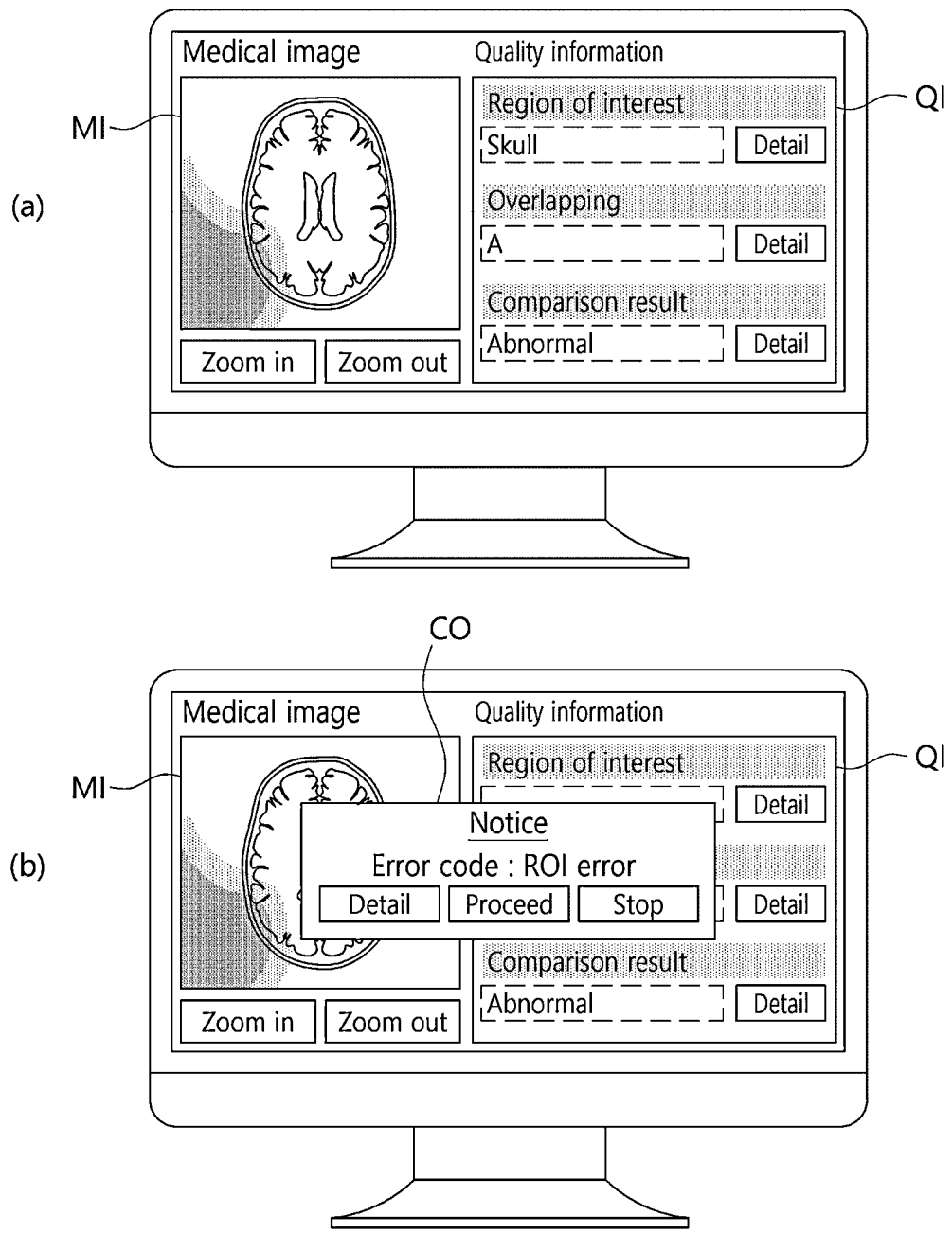
FIGS. 37 and 38 are diagrams exemplarily illustrating fourth error information screens.
Figure 38:
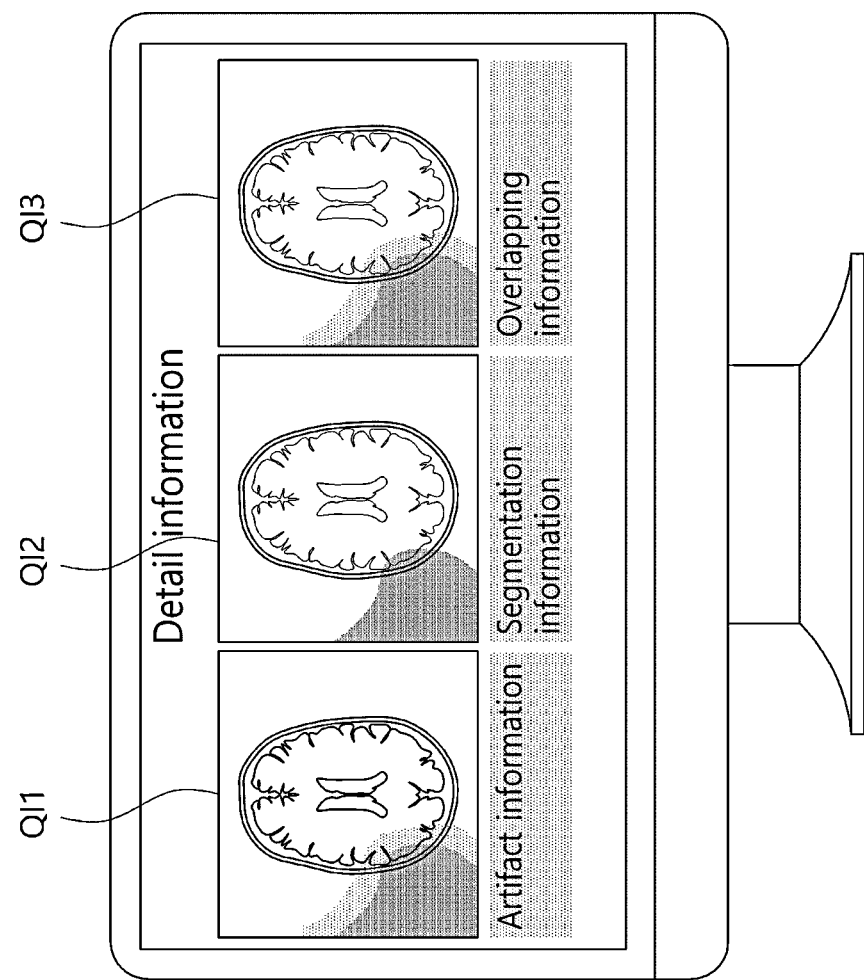

FIGS. 37 and 38 are diagrams exemplarily illustrating a fourth error information screen.

Referring to FIG. 37A, the fourth error information screen may include at least one of a medical image MI related to fourth image quality determination or information QI on the relationship between the artifact and the ROI.

The medical image MI may be an image with a marked ROI. The medical image MI may be an image with a marked specific region where an artifact is likely to be located The medical image MI may show the degree of overlap between an artifact and an ROI acquired based on the location information of the artifact. For example, the medical image MI may show information regarding the overlap region between the RIO and the artifact, e.g., the area, shape, and number of pixels of the overlap region. The medical image MI may show the ratio of the overlap region with the artifact to the ROI.

The medical image MI may be an image in which a relationship between the ROI and the probability that an artifact will be located in a specific region of the medical image is marked.

For example, the medical image MI may be an image in which a region corresponding to an artifact in a target medical image is visually highlighted. The medical image MI may be an image in which a region corresponding to an artifact is displayed in the target medical image in the form of a heatmap or in which a boundary of a region corresponding to an artifact, e.g., an outer line, is displayed.

Alternatively, the medical image MI may be an image in which a part where the artifact and the ROI overlap is visually highlighted. The medical image MI may be an image obtained by marking a region corresponding to an artifact on a target medical image. The medical image MI may be an image obtained by marking a boundary corresponding to an artifact, e.g., an outer line on a target medical image. The medical image MI may be an image obtained by marking a region corresponding to an artifact on a target medical image in the form of a heatmap.

The information QI on the relationship between the artifact and the ROI may include, but is not limited to, information on the type of ROI, information on the overlap between the ROI and the artifact, information on a quality determination result based on the overlap information, or the like.

In this case, the fourth error information screen includes a detailed information object, and an output screen may additionally display more details (e.g., information for expressing the degree of overlap between the ROI and the artifact using more sub-divisional operations, information for numerically representing the degree of overlap between the ROI and the artifact, detailed information regarding a part of the ROI overlapping the artifact, etc.) about the medical image MI or the information QI on the relationship between the artifact and the ROI according to a user's selection of the detailed information object.

Referring to FIG. 37B, the fourth error information screen may include a fourth notification window CO including fourth information on an ROI in the medical image.

The fourth notification window CO may include a message with a marked error code including information indicating that at least a portion of the ROI and the artifact overlap each other. In this case, the fourth error information screen includes a detailed information object, and an output screen may additionally display details (e.g., a description of the error code, a cause for an error message, a manual to respond to an error message, etc.) about the fourth information according to a user's selection of the detailed information object.

The fourth notification window CO includes an object for selecting whether to proceed with the image analysis when at least a portion of the ROI and the artifact overlap, and the image analysis device 3900 may proceed with the image analysis according to a user's selection of the image analysis process object.

When at least a portion of the ROI and the artifact overlap, the fourth notification window CO includes an object for stopping the image analysis, and the image analysis device 3900 may stop the image analysis according to a user's selection of the image analysis stop object.

Referring to FIG. 38, the information QI on the relationship between the artifact and the ROI may include at least one of artifact information QI1 on an artifact generated in the medical image, RIO information QI2 on a region corresponding to the anatomical structure in the medical image, or information QI3 on the degree of overlap between the artifact and the region corresponding to the anatomical structure. For example, when the ROI is specified as the skull, the fourth error information may include information on whether an artifact is generated in a predetermined region corresponding to the skull, information on the degree of overlap between the predetermined region corresponding to the skull and the artifact, etc.

Figure 39:
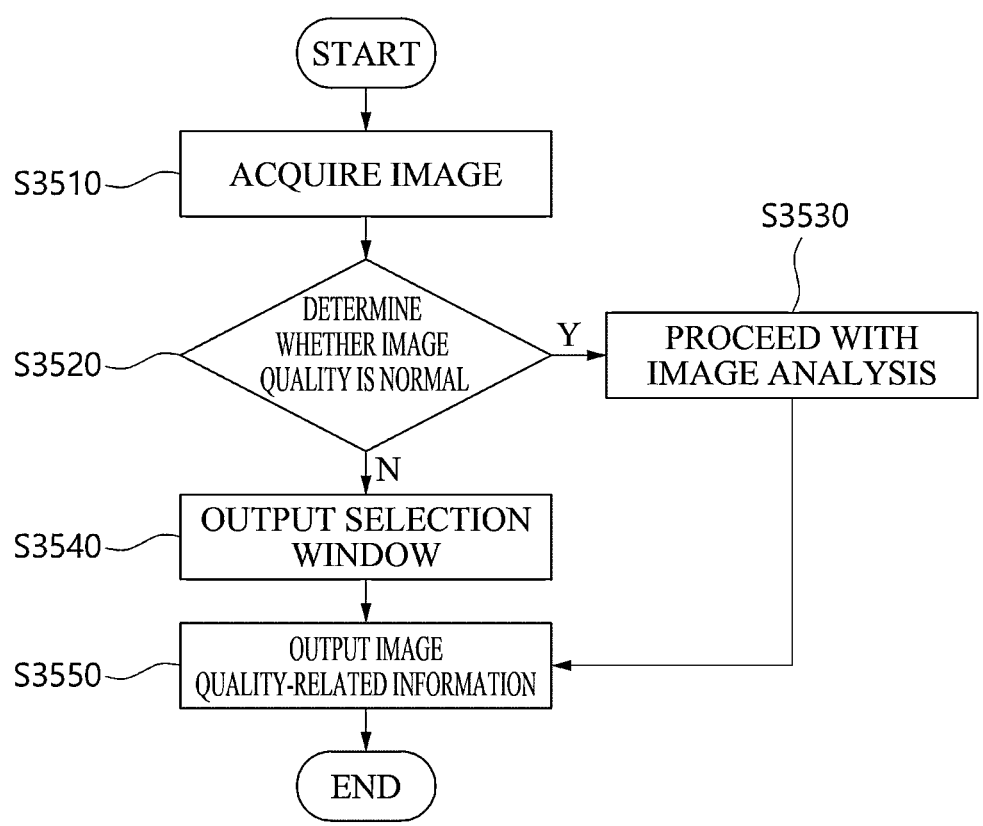
FIG. 39 is a diagram exemplarily illustrating a selection window that an image quality-related information output module 3900 outputs.
Figure 40:
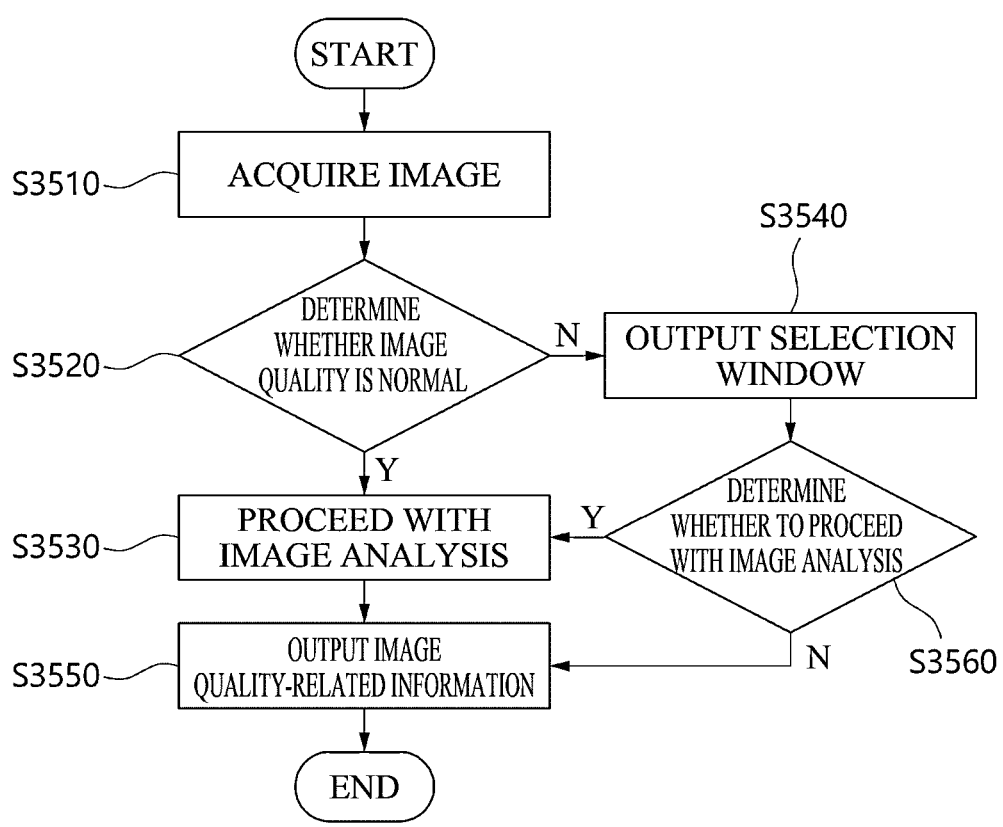
FIG. 40 is a diagram exemplarily illustrating a selection window that the image quality-related information output module 3900 outputs.

FIGS. 39 and 40 are diagrams exemplarily illustrating a selection window that the image quality-related information output module 3900 outputs.

As described above, when an inappropriate formal or substantial defect is present in acquired medical data, it may be difficult for a result of image analysis based on the medical data to have a reliability above a certain level.

However, even if a formal or substantial defect is present in the medical data, image analysis may be continuously performed when a predetermined criterion, for example, a criterion for the type or degree of defect present in the medical data, is satisfied. Thus, even if some defects are present in the medical data, the image analysis is not uniformly stopped. By determining whether to proceed with the image analysis according to a certain criterion or resuming the image analysis after the medical image is corrected or recaptured, it is possible to economically and efficiently perform the image analysis in terms of time and cost.

The image quality determination process of the present invention may include, when a certain defect is generated in the medical data, providing a criterion for determining whether the image analysis device can continue to perform the image analysis despite the defect. Also, the image quality determination process provides information regarding the quality of the medical data to the user and may provide a means for determining whether to proceed with image analysis according to a user's selection or for determining whether to re-proceed with the image analysis after correcting or recapturing the medical image.

Referring to FIG. 39, the image quality-related information output module 3900 may output a selection window on the basis of an image quality determination result. The image quality-related information output module 3900 may output a selection window when it is determined that the quality of the image is not normal through image quality determination. When it is determined that the quality of the image is normal through image quality determination, the image quality-related information output module 3900 may output information on the quality of the image after proceeding with the image analysis.

The selection window may include a message generated based on image quality determination. The selection window may include a message stating that the quality of the medical image is not suitable for an image analysis process to be performed on the basis of the image quality determination.

Referring to FIG. 40, the image quality-related information output module 3900 may output a selection window on the basis of an image quality determination result. When it is determined that the quality of the image is not normal through image quality determination, the image quality-related information output module 3900 may output a selection window for acquiring a user instruction related to the image analysis. Accordingly, even when a defect is generated in the medical data, the image analysis device may continue to perform image analysis according to a user's selection based on a certain criterion. Accordingly, even when a defect is generated in the medical data, the image analysis device may resume the image analysis after correcting or re-capturing the medical image according to a user's selection.

The selection window may include a message generated based on a result of image quality determination performed by the image quality determination module 3700. The selection window may include a message generated based on results performed by the first to fourth image quality determination units 3710 to 3770. The selection window may include a message generated based on image quality determination. The selection window may include a message stating that the quality of the medical image does not satisfy a certain level based on the image quality determination. The selection window may include a message stating that the quality of the medical image is not suitable for an image analysis process to be performed on the basis of the image quality determination.

The selection window may include a first button and a second button for acquiring whether the user agrees with the above-described message. The image analysis device may output an additional message for selecting whether to proceed with image analysis according to a user's selection of the first button. The image analysis device may output details about the message according to a user's selection of the second button.

The selection window may include a first selection window for acquiring a user instruction related to image analysis to be performed by the image analysis device. That is, the image quality-related information output module 3900 may output a first selection window for acquiring a user instruction for whether to proceed with image analysis performed by the image analysis device on the basis of a result obtained by the image quality determination module 3700.

The selection window may include a second selection window for acquiring a user instruction related to an operation of resuming the image quality determination process. That is, the image quality-related information output module 3900 may output a second selection window for acquiring a user instruction for whether to resume the image quality determination process on the basis of a result obtained by the image quality determination module 3700.

According to an embodiment, when it is determined, as a quality determination result of the second image quality determination unit 3730, that an artifact is included in the medical image, the image quality-related information output module 3900 may output the first selection window.

The first selection window may output a first message regarding information on an artifact included in the medical image, for example, whether an artifact is generated, the location of the generated artifact, the degree of the generated artifact, the range of the generated artifact, the type of artifact, etc.

When it is determined, as a quality determination result of the second image quality determination unit 3730, that an artifact is included in the medical image, the image quality-related information output module 3900 may output a second selection window for acquiring a user instruction related to the re-performance of the image quality determination process.

The second selection window may output a second message requesting a user instruction regarding whether to resume the image quality determination process after correcting an artifact included in the medical image. The second selection window may output a second message requesting a user instruction regarding whether to resume the image quality determination process after re-capturing the medical image.

According to another embodiment, when it is determined, as a quality determination result of the third image quality determination unit 3750, that segmentation information does not satisfy a quantitative criterion on the basis of segmentation information obtained by anatomically segmenting the medical image, the image quality-related information output module 3900 may output the first selection window.

The first selection window may include a first message on a morphological index or morphological value, e.g., the area, volume, location, or shape, of at least a portion of a region acquired through the medical image segmentation.

When it is determined, as a quality determination result of the third image quality determination unit 3750, that segmentation information does not satisfy a quantitative criterion on the basis of segmentation information obtained by anatomically segmenting the medical image, the image quality-related information output module 3900 may output the second selection window for acquiring a user instruction regarding an operation of re-performing the image quality determination process.

The second selection window may output a second message requesting a user instruction regarding whether to resume the image quality determination process after correcting anatomical segmentation information in the medical image. The second selection window may output a second message requesting a user instruction regarding whether to resume the image quality determination process after re-capturing the medical image.

According to an embodiment, when a quality determination result of the fourth image quality determination unit 3770 shows that an artifact generated in the medical image overlaps at least a portion of an anatomical structure included in the medical image, the image quality-related information output module 3900 may output the first selection window.

The first selection window may output a first message regarding information on the relationship between an ROI and an artifact included in the medical image, for example, the degree of overlap between the artifact and the ROI, information on the location of an artifact present in the ROI, etc.

When a quality determination result of the fourth image quality determination unit 3770 shows that an artifact generated in the medical image overlaps at least a portion of the anatomical structure included in the medical image, the image quality-related information output module 3900 may output a second selection window for acquiring a user instruction related to the re-performance of the image quality determination process.

The second selection window may output a second message requesting a user instruction regarding whether to resume the image quality determination process after correcting at least a portion of the anatomical structured included in the medical image. The second selection window may output a second message requesting a user instruction regarding whether to resume the image quality determination process after re-capturing the medical image.

A quality determination process according to various embodiments will be described below. Unless otherwise specified, the above description herein may be similarly applied to details about each operation.

Figure 41:
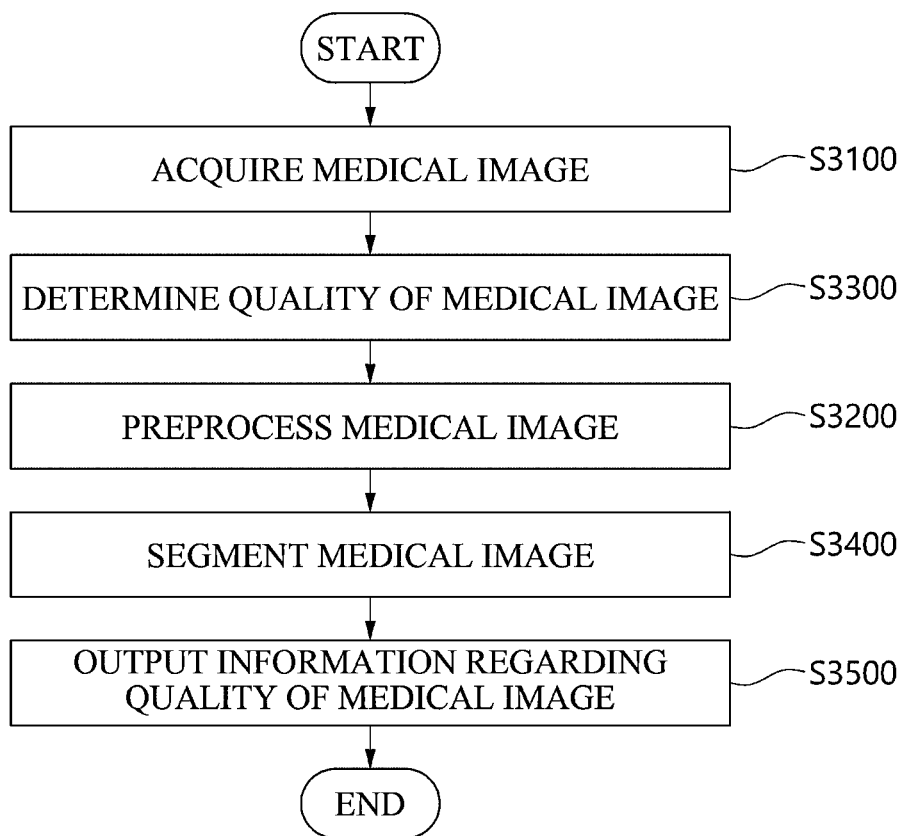
FIGS. 41 to 43 are diagrams illustrating first to third quality determination processes.
Figure 42:
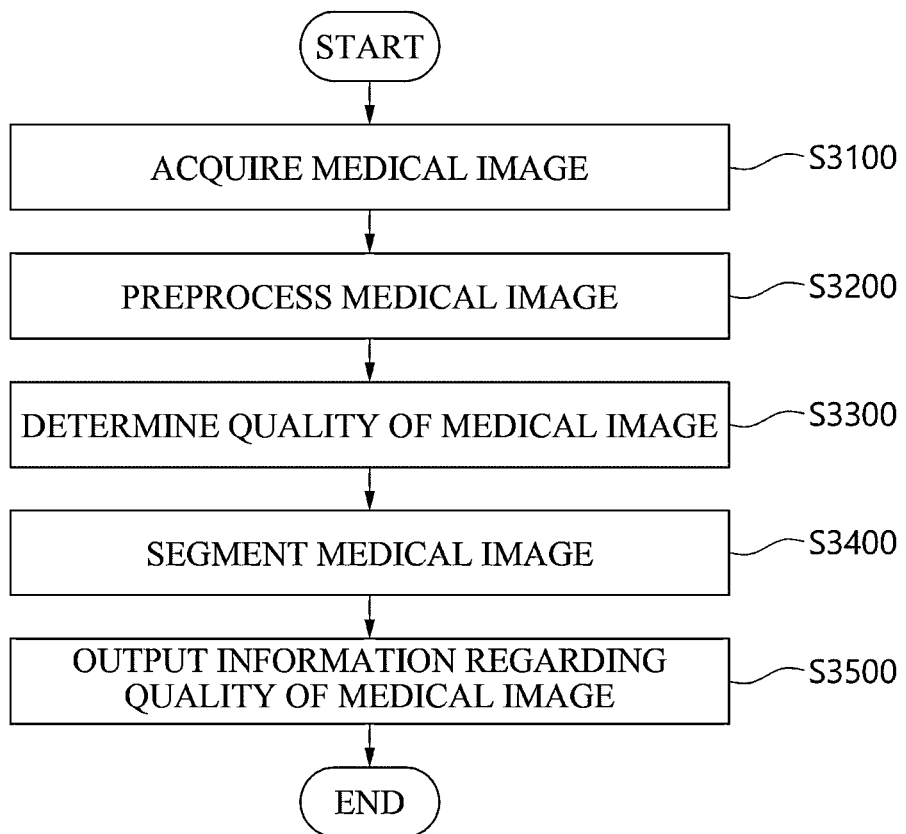
Figure 43:
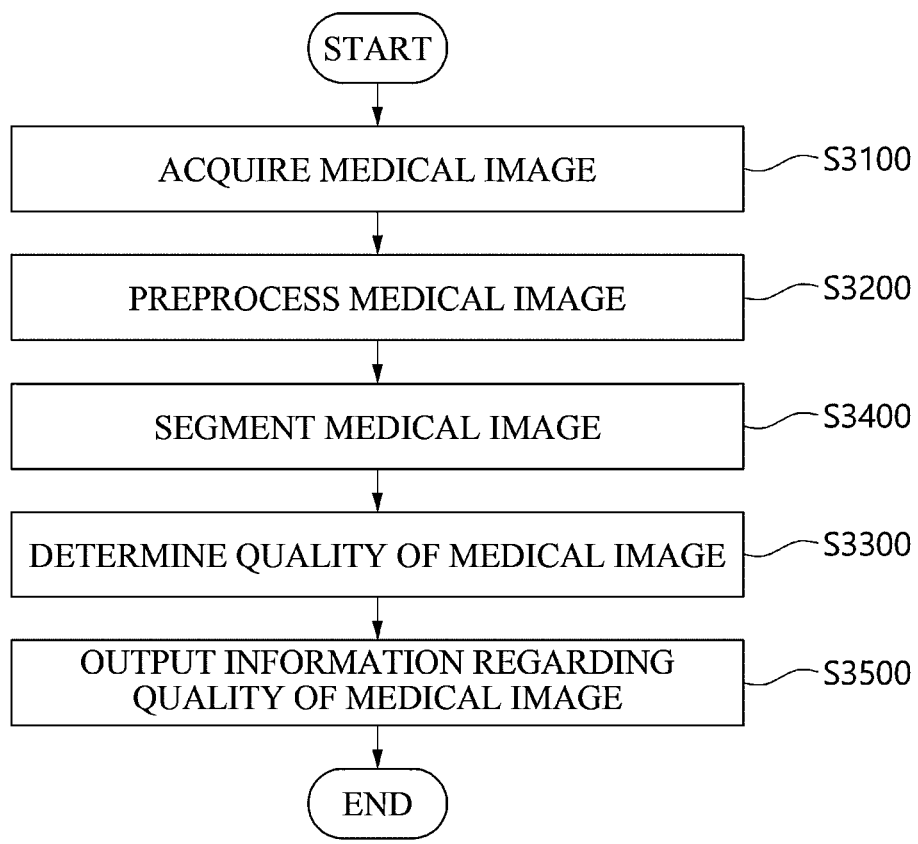

FIGS. 41 to 43 are diagrams illustrating first to third quality determination processes. The first to fourth quality determination processes may have different pieces of data, which are criteria for quality determination, different quality criteria, which are criteria for quality determination, different pieces of output quality information, etc.

Referring to FIGS. 41 to 43, the first to third quality determination processes may include an operation of acquiring a medical image (S3000), an operation of determining the quality of the medical image (S3300), an operation of preprocessing the medical image (S3200), an operation of segmenting the medical image (S3400), or an operation of outputting information regarding the quality of the medical image (S3500).

Referring to FIG. 41, the first quality determination process may include an operation of acquiring a medical image (S3000), an operation of determining the quality of the medical image (S3300), an operation of preprocessing the medical image (S3200), an operation of segmenting the medical image (S3400), and an operation of outputting information regarding the quality of the medical image (S3500) in sequence. In this case, the medical image quality determination operation S3300 may include performing the image quality determination on the basis of raw data before the preprocessing operation. The medical image preprocessing operation S3200 may include performing preprocessing on an image on which medical image quality determination has been performed.

Referring to FIG. 42, the second quality determination process may include an operation of acquiring a medical image (S3000), an operation of preprocessing the medical image (S3200), an operation of determining the quality of the medical image (S3300), an operation of segmenting the medical image (S3400), and an operation of outputting information regarding the quality of the medical image (S3500) in sequence. In this case, the medical image quality determination operation S3300 may include performing the image quality determination on the basis of a preprocessed image. The operation of segmenting the medical image (S3400) may include segmenting an image on which medical image quality determination is performed.

Referring to FIG. 43, the third quality determination process may include an operation of acquiring a medical image (S3000), an operation of preprocessing the medical image (S3200), an operation of segmenting the medical image (S3400), an operation of determining the quality of the medical image (S3300), and an operation of outputting information regarding the quality of the medical image (S3500) in sequence. In this case, the medical image quality determination operation S3300 may include performing the image quality determination on the basis of an image on which the preprocessing operation and the segmentation operation are performed.

Figure 44:
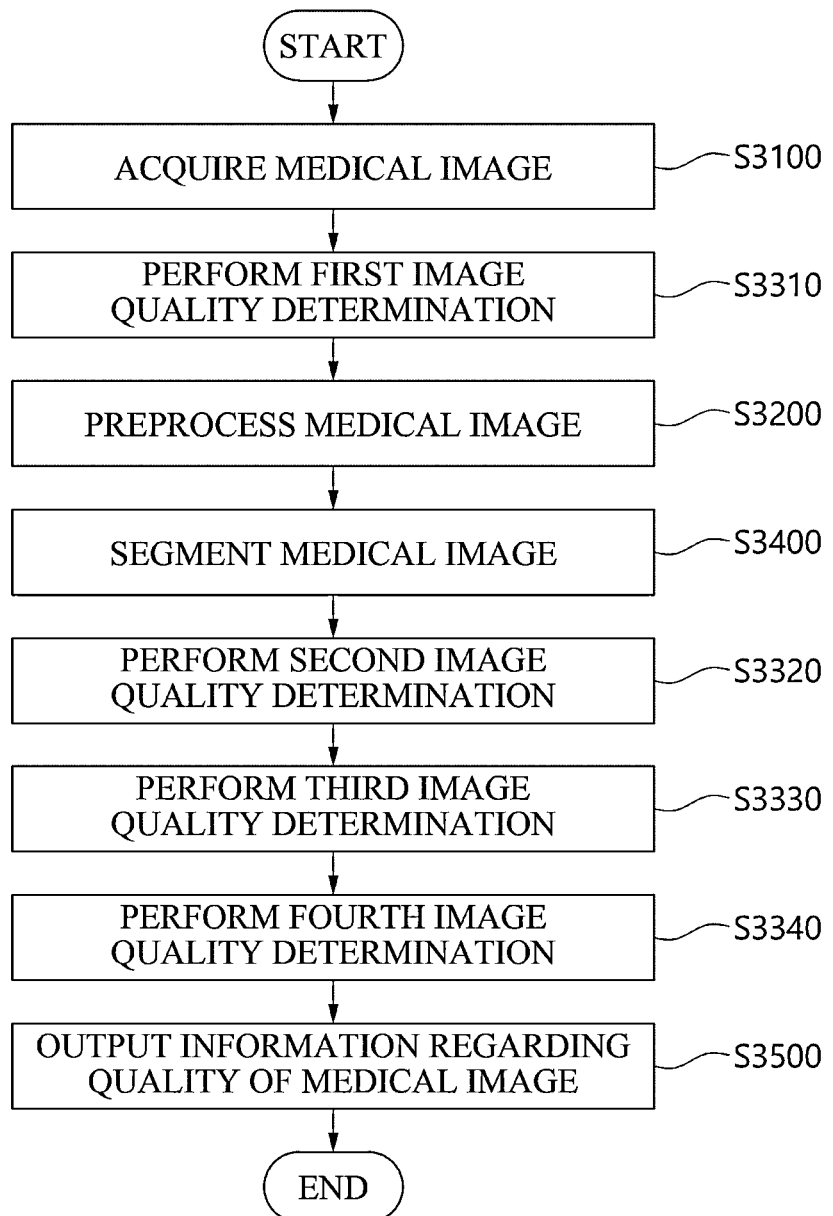
FIGS. 44 and 45 are diagrams illustrating a fourth quality determination process.
Figure 45:
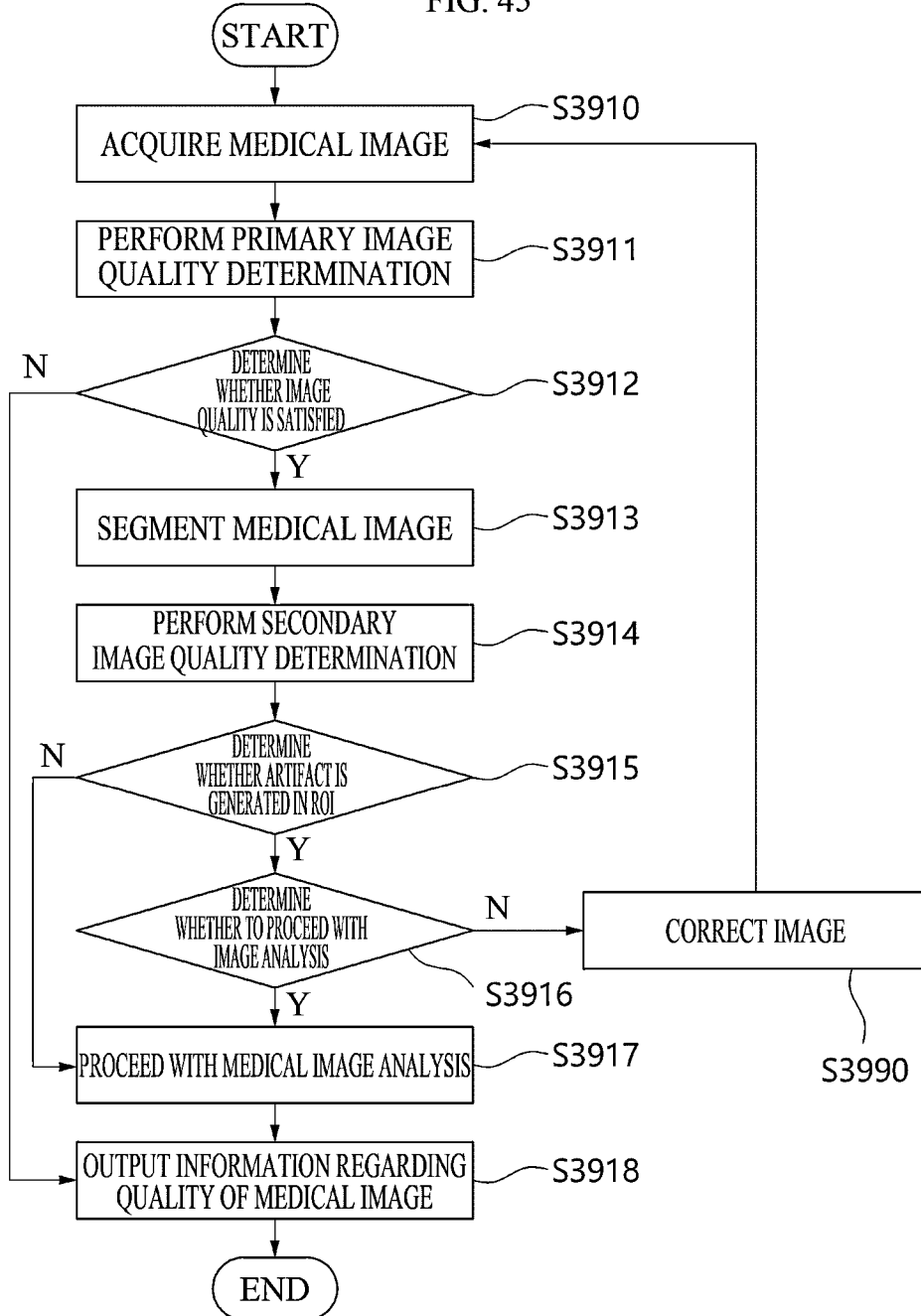

FIGS. 44 and 45 are diagrams illustrating a fourth quality determination process.

Referring to FIG. 44, the fourth quality determination process may include an operation of acquiring a medical image (S3000), an operation of first image quality determination (S3310), an operation of preprocessing the medical image (S3200), an operation of segmenting the medical image (S3400), an operation of second image quality determination (S3320), an operation of third image quality determination (S3330), an operation of fourth image quality determination (S3340), and an operation of outputting information regarding the quality of the medical image (S3500).

The operation of first image quality determination (S3310) may include performing the first image quality determination on the basis of raw data before the preprocessing operation. The operations of second to fourth image quality determination may include performing the second image quality determination on the basis of the image on which the preprocessing operation and the segmentation operation are performed. In this case, the order of the operations of second to fourth image quality determination does not limit the above description of the present invention and may be changed.

For example, the operation of second image quality determination (S3320) may be performed after the operation of third image quality determination (S3330) is performed on the basis of the image on which the preprocessing operation and the segmentation operation are performed. Alternatively, the operation of second image quality determination (S3320) and the operation of third image quality determination (S3330) may be performed in parallel on the basis of the image on which the preprocessing operation and the segmentation operation are performed.

Referring to FIG. 45, the image analysis device 3000 may acquire a medical image from an image acquisition device (S3910). The image analysis device 3000 may perform primary image quality determination on the basis of the acquired medical image (S3911). Here, the primary image quality determination may include a series of quality determination operations performed prior to the medical image segmentation operation. For example, the primary image quality determination may include quality determination performed based on metadata of the medical image.

In this case, when it is determined, as the primary image quality determination result, that the image quality does not satisfy a certain condition, the image analysis device 3000 may stop the image analysis and output information regarding the quality of the medical image (S3918).

When the primary image quality determination result shows that the image quality satisfies a certain condition, the image analysis device 3000 may perform medical image segmentation (S3913). Also, the image analysis device 3000 may perform secondary image quality determination (S3914) on the basis of the medical image on which the segmentation operation is performed.

When it is determined, as the secondary image quality determination result, that no artifact is generated in an ROI of the medical image, the image analysis device 3000 may proceed with medical image analysis (S3917) and then output information on the quality of the medical image (3918).

When it is determined, as the secondary image quality determination result, that an artifact is generated in an ROI of the medical image, the image analysis device 3000 may stop image analysis. In this case, the image analysis device 3000 may output the information on the quality of the medical image (S3918) after stopping image analysis. For example, when it is determined, as the secondary image quality determination result, that an artifact is generated in an ROI of the medical image, the image analysis device 3000 may stop image analysis, correct the medical image, and resume the image quality determination process. As another example, the image analysis device 3000 may stop the image analysis, re-capture a medical image, and then resume the image quality determination process.

When it is determined, as the secondary image quality determination result, that no artifact is generated in an ROI of the medical image, the image analysis device 3000 may proceed with the medical image analysis (S3917) and then output information regarding the quality of the medical image (S3918).

Figure 46:
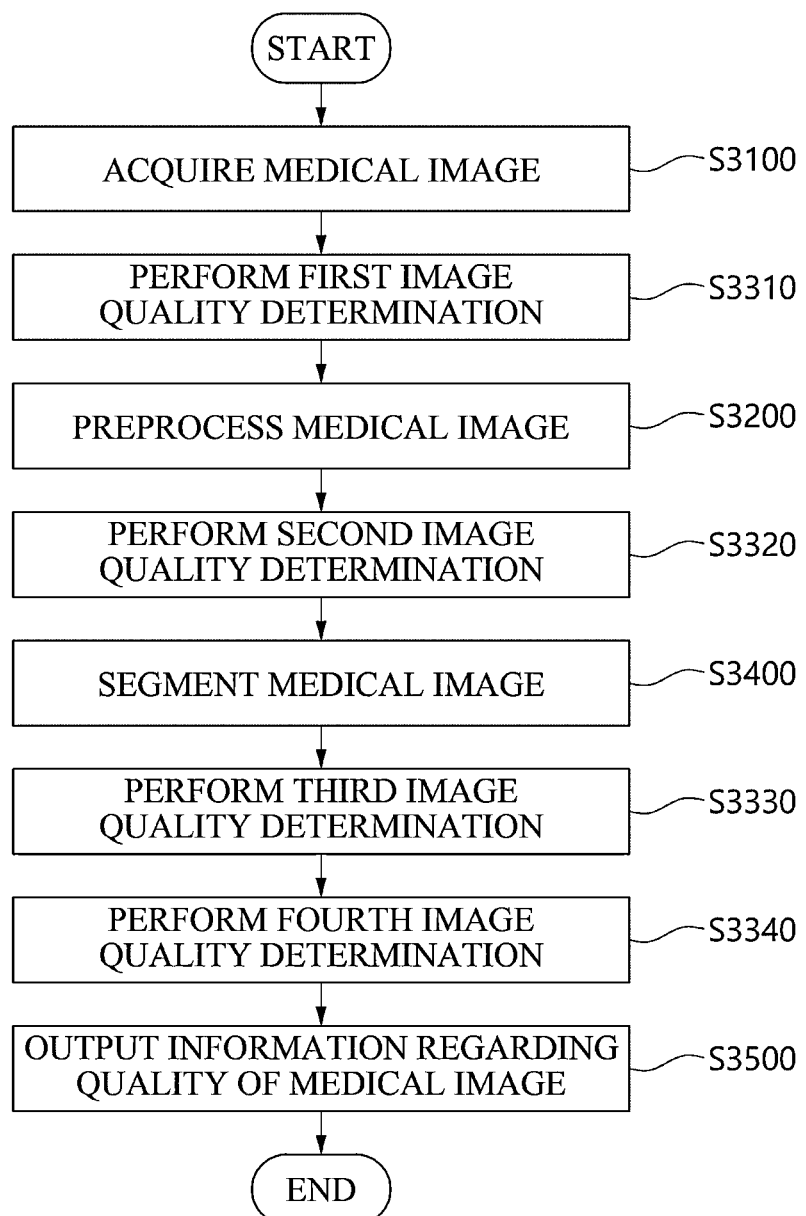
FIGS. 46 and 47 are diagrams illustrating a fifth quality determination process.
Figure 47:
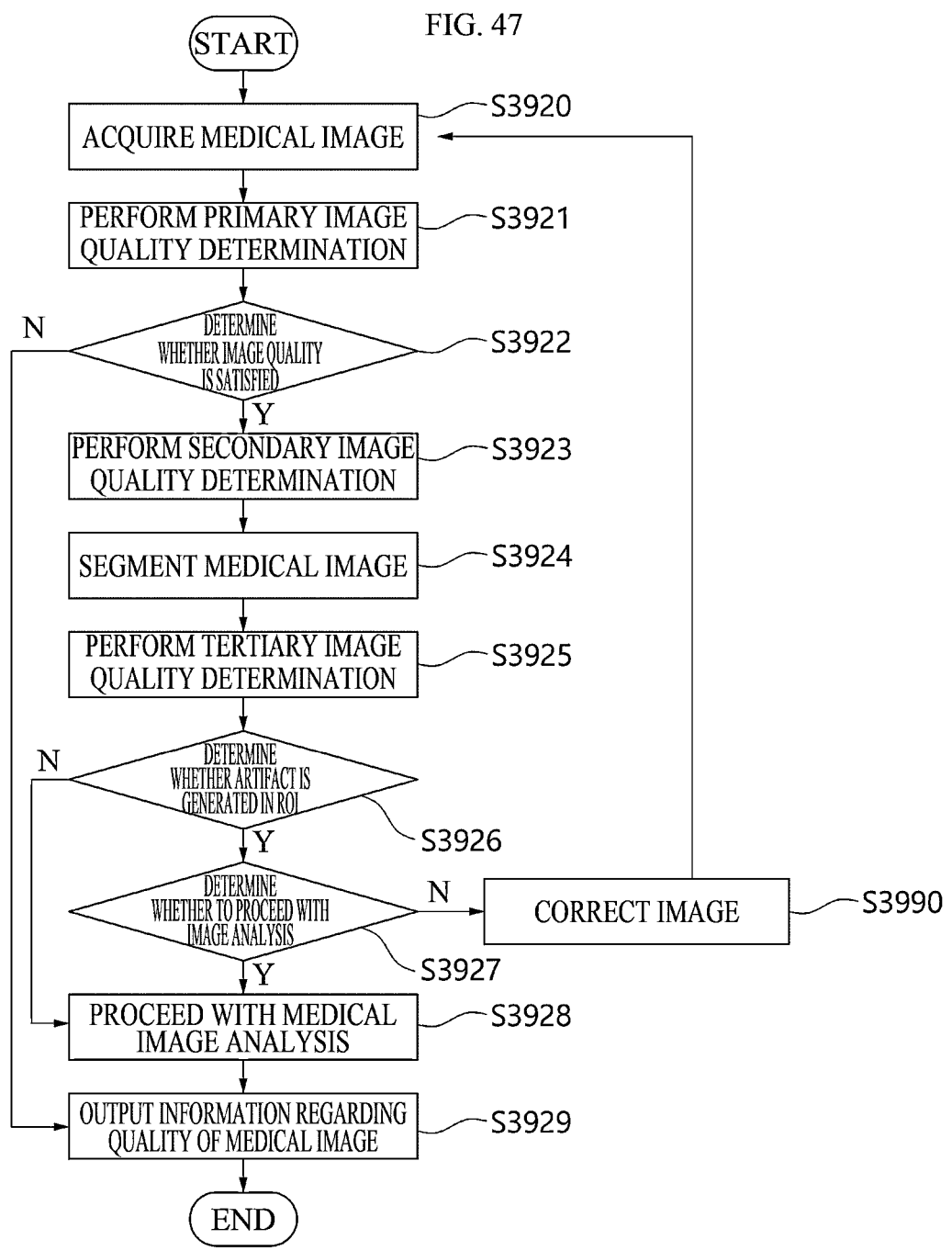

FIGS. 46 and 47 are diagrams illustrating a fifth quality determination process.

Referring to FIG. 46, the fifth quality determination process may include an operation of acquiring a medical image (S3000), an operation of first image quality determination (S3310), an operation of preprocessing the medical image (S3200), an operation of second image quality determination (S3320), an operation of segmenting the medical image (S3400), an operation of third image quality determination (S3330), an operation of fourth image quality determination (S3340), and an operation of outputting information on the quality of the medical image (S3500).

The operation of first image quality determination (S3310) may include performing the first image quality determination on the basis of raw data before the preprocessing operation. The operation of second image quality determination (S3320) may include performing the quality determination on the basis of the image on which the preprocessing operation is performed. The operation of third image quality determination (S3330) and the operation of fourth image quality determination (S3340) may include performing the quality determination on the basis of the image on which the segmentation operation is performed.

The order of the operation of third image quality determination (S3330) and the operation of fourth image quality determination (S3340) does not limit the above description of the present invention and may be changed. For example, the operation of third image quality determination (S3330) and the operation of fourth image quality determination (S3340) may be performed in parallel on the basis of the image on which the preprocessing operation and the segmentation operation are performed.

Referring to FIG. 47, the image analysis device 3000 may acquire a medical image from an image acquisition device (S3920). The image analysis device 3000 may perform primary image quality determination on the basis of the acquired medical image (S3921).

When it is determined, as the primary image quality determination result, that the image quality does not satisfy a certain condition, the image analysis device 3000 may stop the image analysis and output information on the quality of the medical image (S3929).

When it is determined, as the primary image quality determination result, that the image quality satisfies a certain condition, the image analysis device 3000 may perform secondary image quality determination (S3923). Here, the secondary image quality determination may include a series of quality determination operations performed prior to the image segmentation operation.

The image analysis device 3000 may perform medical image segmentation on the basis of a medical image on which the secondary image quality determination is performed (S3924). Also, the image analysis device 3000 may perform tertiary image quality determination (S3925) on the basis of segmentation information obtained by performing medical image segmentation. Here, the tertiary image quality determination may include a series of quality determination operations performed prior to the image segmentation operation.

When it is determined, as the tertiary image quality determination result, that no artifact is generated in an ROI of the medical image, the image analysis device 3000 may proceed with the medical image analysis and then output information regarding the quality of the medical image (S3929).

When it is determined, as the tertiary image quality determination result, that artifact is generated in an ROI of the medical image, the image analysis device 3000 may stop the medical image analysis and then output information regarding the quality of the medical image (S3929). Here, the information regarding the quality of the medical image may include information based on the primary, secondary, and tertiary image quality determination.

When it is determined, as the tertiary image quality determination result, that no artifact is generated in an ROI of the medical image, the image analysis device 3000 may proceed with the image analysis and then output information regarding the quality of the medical image (S3929). Here, the information regarding the quality of the medical image may include information based on the primary, secondary, and tertiary image quality determination.

The image quality determination process according to the present specification may be implemented in an order other than the order described in FIGS. 44 to 47.

In relation to brain-related diseases, particularly dementia, the degree of brain atrophy is indexed and used as an auxiliary index for dementia diagnosis. There are various indices related to the degree of brain atrophy, and as an example for acquiring the indices, intracranial volume (ICV) analysis is used to provide an auxiliary index related to dementia diagnosis. However, in the conventional analysis of the internal volume of the skull, a method of matching a target image of a target subject to a standard brain model was used. However, there was a problem in that the method of matching a target image of a target subject to a standard brain model could be inaccurate because volume analysis considering race was not properly reflected due to differences in the standard brain model between races. Also, since an individual brain structure was matched to a standard brain model, there was a problem in that volume analysis that reflects the characteristics of an individual's brain has limitations.

The image analysis device 2000 according to an embodiment of the present application may perform segmentation on a target image of a target subject, without matching the target image to a standard brain model, to acquire the region of the skull of the target subject and the internal region of the skull. Thus, advantageously, it is possible to improve the accuracy of the analysis of the internal volume of the skull based on the acquired regions.

A volume analysis method implemented by an image analysis device 2000 according to an embodiment of the present application will be described in detail below with reference to FIGS. 48 to 57.

Figure 48:
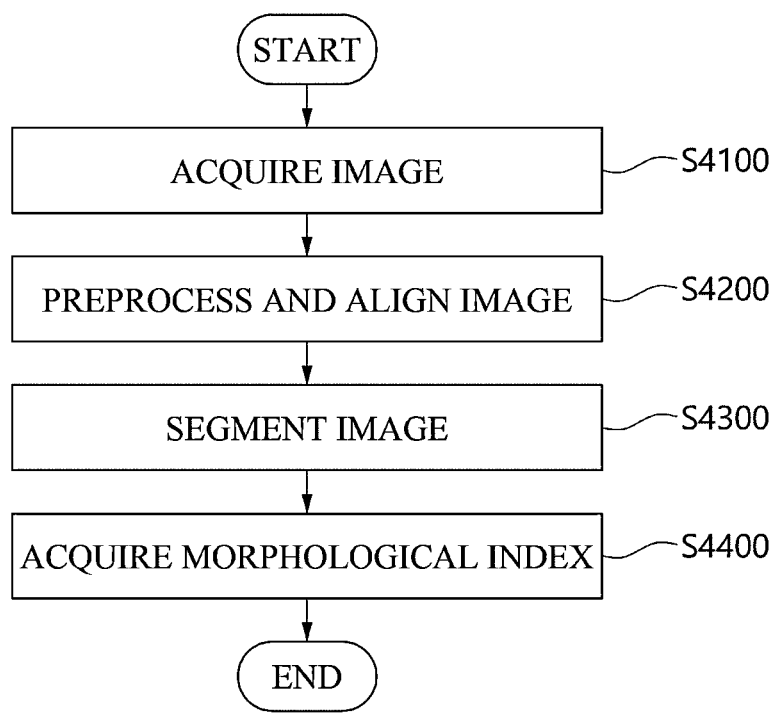
FIG. 48 is a flowchart showing one operation of an image analysis method implemented by an image analysis device 2000 according to an embodiment of the present application.

Reference will be made to FIG. 48. FIG. 48 is a flowchart showing one operation of an image analysis method implemented by an image analysis device 2000 according to an embodiment of the present application. Specifically, FIG. 48 is a flowchart showing an operation of acquiring a brain-related morphological index which is implemented by the image analysis device 2000 according to an embodiment of the present application.

The image analysis method according to an embodiment of the present application may include an operation of acquiring an image (S4100), an operation of preprocessing and aligning the image (S4200), an operation of segmenting the image (S4300), and an operation of acquiring a morphological index (S4400).

In the operation of acquiring an image (S4100), the image analysis device 2000 may acquire a target image from the image acquisition device 1000.

In the operation of preprocessing and aligning the image (S4200), the above-described preprocessing operations may be performed. For example, in the operation of preprocessing and aligning the image (S4200), the image analysis device 2000 may be implemented to perform a preprocessing operation, such as transformation of the format of the target image, removal of noise from the image, or correction of the intensity of the image, on a target image.

Also, in the operation of preprocessing and aligning the image (S4200), the image alignment operations described above with reference to FIGS. 5 and 6 may be performed. The image analysis device 2000 according to an embodiment of the present application may input a target image having a direction corresponding to the direction of an image of training data of a neural network model to the neural network model by aligning the target image and may derive an analysis result under a unified standard.

As an example, the image analysis device 2000 may be implemented to perform an operation of aligning the direction of the target image on the basis of data related to the direction of a brain image structured as metadata. For example, the image analysis device 2000 may perform an image alignment operation for matching the captured brain images with respect to the left and right, the anterior and posterior, and the superior and inferior using the metadata of the target image.

As another example, the image analysis device 2000 may be implemented to perform spatial normalization on the target image as one method of the image alignment operation. Specifically, the image analysis device 2000 may be implemented to perform spatial normalization on the target image on the basis of a brain template. More specifically, by matching the target image to the brain template, the image analysis device 2000 may convert the coordinates of the target image and align the target image so that the spatial distribution of the target image becomes optimal with respect to an artificial neural network model.

As an example, the image analysis device 2000 may be implemented to perform an operation of aligning the target image on the basis of a feature region of the target image.

Figure 49:
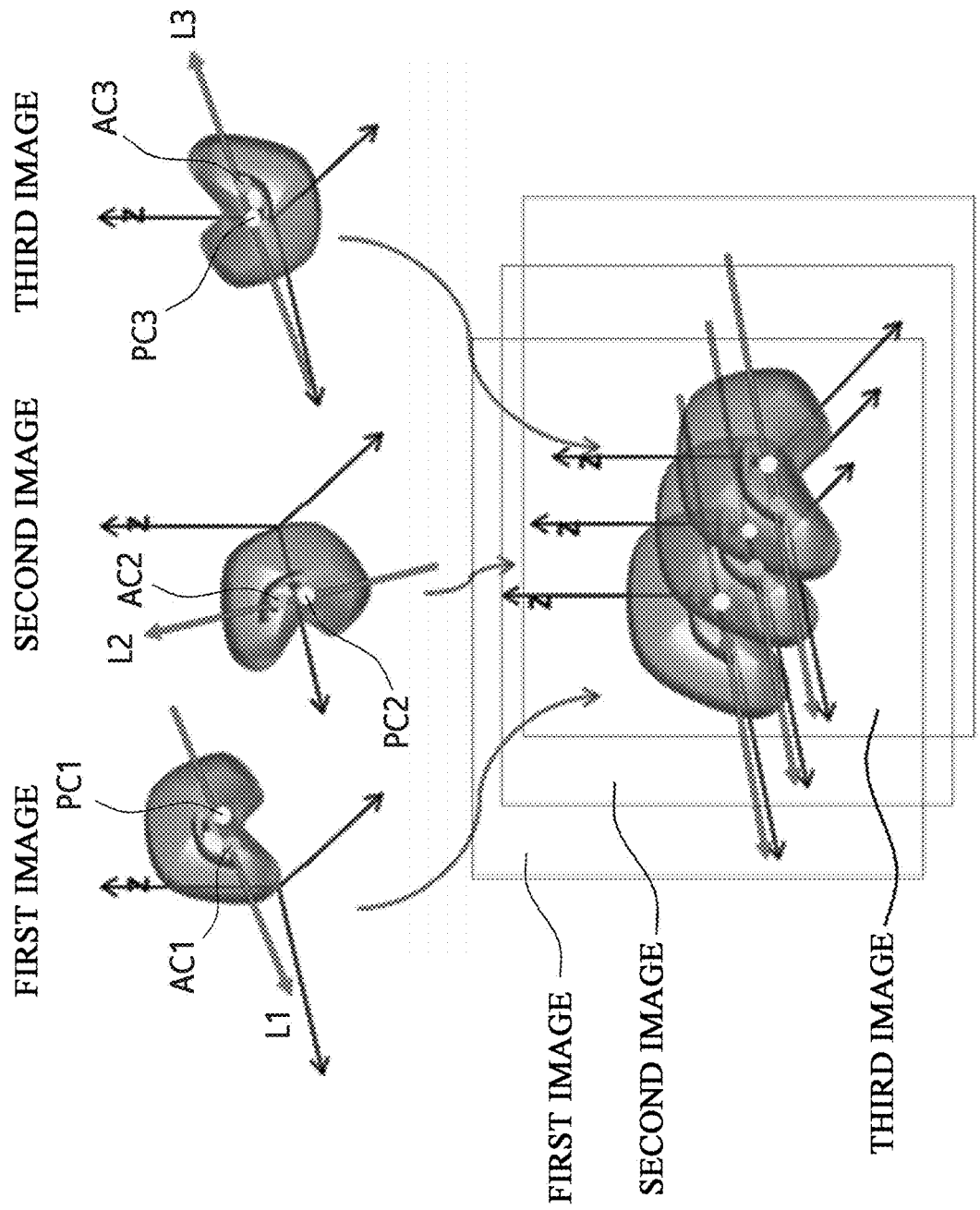
FIG. 49 is an exemplary diagram of an image alignment method implemented by the image analysis device 2000 according to an embodiment of the present application.

Reference will be made to FIG. 49. FIG. 49 is an exemplary diagram of an image alignment method implemented by the image analysis device 2000 according to an embodiment of the present application.

For example, referring to FIG. 49, feature regions corresponding to the anterior commissure AC and the posterior commissure PC may be present in a brain image. In this case, the image analysis device 2000 may be implemented to perform a spatial alignment operation of the target image on the basis of an AC-PC line that connects the anterior commissure AC and the posterior commissure PC.

For example, a first image may be captured in a first direction, a second image may be captured in a second direction, and a third image may be captured in a third direction. Since images were captured in random directions, the images acquired from the image acquisition device 1000 may not be spatially aligned. In this case, by spatially aligning each image, the image analysis device 2000 may unify the directions of the images.

For example, the first image may be acquired while an AC-PC line L1 connecting the anterior commissure AC1 and the posterior commissure PC1 is in the first direction, the second image may be acquired while an AC-PC line L2 connecting the anterior commissure AC2 and the posterior commissure PC2 is in the second direction, and the third image may be acquired while an AC-PC line L3 connecting the anterior commissure AC3 and the posterior commissure PC3 is in the third direction.

In this case, the image analysis device 2000 may be implemented to align the images such that the AC-PC lines L1, L2, and L3 of the images are spatially facing the same reference direction.

For example, the image analysis device 2000 may align the second image and the third image using, as the reference direction, the AC-PC line L1 from which the first image is acquired.

As another example, the image analysis device 2000 may acquire an input for the reference direction from a user and may align the first image, the second image, and the third image on the basis of the user's input.

However, the above description is merely an example, and a target image may be aligned with respect to any reference direction such that the directions of target images to be analyzed by the image analysis device 2000 are unified.

Also, as described above, although the anterior commissure and the posterior commissure have been described as feature regions in the image, this is merely an example, and any suitable feature region for performing spatial alignment on a target image may be utilized. For example, the image analysis device 2000 may be implemented to align an image such that the centers of two eyes and a line connecting the centers of two eyes are in the same direction.

Also, the image analysis device 2000 according to an embodiment of the present application may be implemented to align a target image by matching the target image to a template generated based on the above-described AC-PC line (or plane). In other words, a method of aligning a target image such that AC-PC lines of images included in the target image are in the same direction has been described with reference to FIG. 49, but the present invention is not limited thereto. A standard template including information on AC-PC lines may be generated, and a target image may be aligned by matching the target image to the standard template.

The image analysis device 2000 according to an embodiment of the present application may improve the accuracy of the segmentation of a target image using an artificial neural network by performing spatial alignment on the target image.

Also, in the case of volume analysis such as intracranial volume (ICV) analysis, it is necessary to define an internal region whose volume is to be computed. Since the image analysis device 2000 according to an embodiment can be implemented to define an internal region in a target image aligned according to the common criterion, it is possible to increase the accuracy or reproducibility of the volume analysis.

In the image segmentation operation (S4300), the image analysis device 2000 may perform segmentation on the target image according to the image segmentation operation that has been described with reference to FIGS. 7 to 17.

The image analysis device 2000 according to an embodiment of the present application may be implemented to acquire (a morphological volume value corresponding to a target element)/(a morphological volume value corresponding to a second internal region) as an example of a morphological index to be described. In this case, in order to compute the morphological index, the image analysis device 2000 should acquire at least a region corresponding to the target element of the target image and a region corresponding to the second internal region.

In this case, the second internal region may be a region included in the internal region of the skull. Accordingly, the image analysis device 2000 may be implemented to acquire at least a region corresponding to the skull and an internal region of the skull from the target image.

Also, the image analysis device 2000 may acquire the second internal region by modifying a boundary related to the internal region of the skull acquired from the target image. In this case, in order to modify the boundary related to the internal region of the skull, a reference region may be a basis. Accordingly, the image analysis device 2000 may be implemented to acquire a region corresponding to the reference region from the target image.

Accordingly, by the segmentation operation of the image analysis device 2000, the target image may be partitioned into a plurality of regions including at least the skull region and the region corresponding to the target element. Also, the reference region as a basis for modifying the boundary of the internal region of the skull, which will be described below, may be additionally acquired by the segmentation operation of the image analysis device 2000.

As an example, the reference region that is a basis for modifying the boundary of the internal region of the skull may be a region corresponding to a cerebellum or a region corresponding to cervical vertebrae. However, this is merely an example, and it is obvious that a region corresponding to any brain element may be acquired as a reference region if necessary in order to define the internal region of the skull.

The image analysis device 2000 according to an embodiment of the present application may acquire the internal region of the skull on the basis of the skull region acquired by the segmentation.

With the image analysis method according to an embodiment of the present application, the image analysis device 2000 may compute a morphological index (S4400). In this case, the morphological index may be interpreted as information including quantitative information or qualitative information that may be acquired from the image.

As an example, with the image analysis method according to an embodiment of the present application, a morphological index related to the brain's volume may be acquired as the morphological index.

The type of morphological index related to the brain's volume may vary.

For example, the morphological index may include the normalized brain parenchymal volume (NBN), the regional brain parenchymal volume (RBPV), etc.

As another example, the image analysis method according to an embodiment of the present application may be implemented to compute a morphological index related to the ICV. In this case, the morphological index related to the ICV may be defined as (a morphological volume value corresponding to the target element)/(a morphological volume value corresponding to the second internal region), and the morphological index related to the ICV may be used as an auxiliary index for diagnosis of a brain disease (e.g., depression, dementia, etc.).

The following description will focus on an image analysis method according to an embodiment of the present application to compute a morphological index related to ICV that is improved in accuracy and personalized.

In the operation of computing the morphological index (S4400), the image analysis device 2000 may be implemented to perform an operation of modifying the boundary of the internal region of the skull and computing the morphological index on the basis of the modified boundary.

Figure 50:
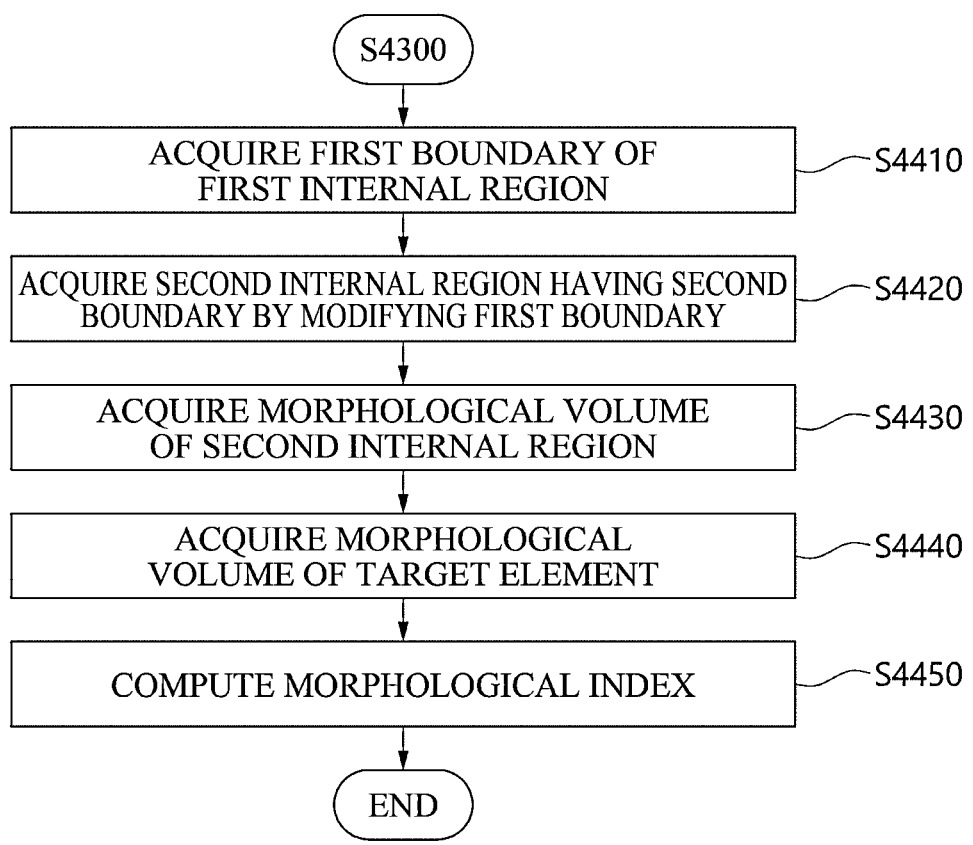
FIG. 50 is a flowchart of an image analysis method according to an embodiment of the present application.

The operation of computing the morphological index (S4400) will be described in more detail below with reference to FIG. 50. FIG. 50 is a diagram illustrating a flowchart of an image analysis method according to an embodiment of the present application and, specifically, is a diagram showing sub-operations of operation S4400 of FIG. 48.

Referring to FIG. 50, the operation of computing the morphological index (S4400) according to an embodiment of the present application may further include an operation of acquiring a first boundary of a first internal region of the skull (S4410), an operation of modifying the first boundary to acquire a second internal region having a second boundary (S4420), an operation of acquiring a morphological volume value of the second internal region (S4430), an operation of acquiring a morphological volume value of a region corresponding to a target element (S4440), and an operation of computing a morphological volume index (S4450).

Specifically, in the operation of computing the morphological index (S4400), the image analysis device 2000 may acquire a first internal region of the skull and a first boundary corresponding to the first internal region of the skull on the basis of the skull region acquired in the image segmentation operation (S4300).

Figure 51:
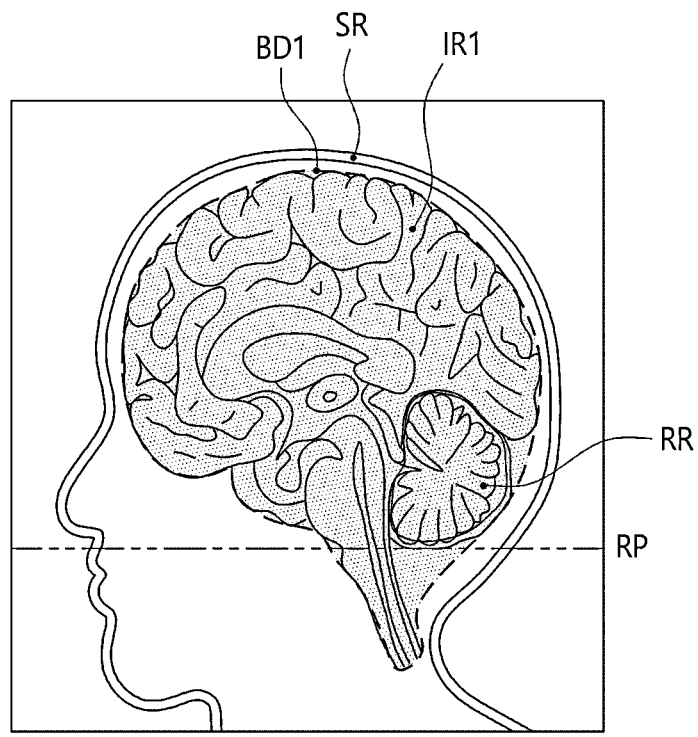
FIG. 51 is a diagram showing an example of a method of modifying a first boundary in a first internal region of a skull according to an embodiment of the present application.

Reference will be made to FIG. 51. FIG. 51 is a diagram showing an example of a method of modifying a first boundary in a first internal region of a skull according to an embodiment of the present application.

Referring to FIG. 51, the image analysis device 2000 may acquire a first internal region IR1 of the skull on the basis of a skull region SR acquired in the image segmentation operation (S4300). Also, the image analysis device 2000 may acquire a first boundary BD1 corresponding to the first internal region IR1 of the skull on the basis of the acquired first internal region IR1 of the skull.

As an example, the image analysis device 2000 may acquire a region corresponding to the cerebrospinal fluid (CSF) in the image segmentation operation (S4300) and may acquire a skull region on the basis of the region corresponding to the cerebrospinal fluid (CSF). For example, the image analysis device 2000 may acquire a skull region using an external boundary of the region corresponding to the cerebrospinal fluid (CSF) as an internal boundary of the skull region.

In this case, the image analysis device 2000 may acquire the external boundary of the region corresponding to the cerebrospinal fluid (CSF) as the first boundary BR1.

Alternatively, the image analysis device 2000 may acquire the internal boundary of the region corresponding to the cerebrospinal fluid (CSF) as the first boundary BR1.

However, the above-described first boundary is merely an example, and the image analysis device 2000 may acquire any regions between the external boundary and the internal boundary of the region corresponding to the cerebrospinal fluid (CSF) as the first boundary BD1.

The image analysis device 2000 according to an embodiment of the present application may smooth or correct a boundary corresponding to the acquired internal region of the skull (e.g., the first internal region or the second internal region which will be described below). Specifically, there may be a possibility that the boundaries corresponding to the acquired internal region of the skull are not clear or have errors. Accordingly, the image analysis device 2000 may smooth a boundary corresponding to the boundary corresponding to the acquired internal region of the skull or correct an error related to the boundary.

For example, when the boundary is not clear, the image analysis device 2000 may be implemented to use any suitable smoothing method and image intensity correction method, such as the above-described image preprocessing technique.

For example, when the acquired boundary has an error, the image analysis device 2000 may be implemented to acquire a user input for modifying the boundary through an input module and modify the boundary on the basis of the user input. Alternatively, the image analysis device 2000 may be implemented to use any suitable noise removal method such as the above-described image preprocessing technique.

The image analysis device 2000 according to an embodiment of the present application may perform an operation of modifying a portion of the first boundary BD1 related to the first internal region IR1 of the skull on the basis of the reference region RR acquired in the image segmentation operation S4300.

For each target image, the location or size of a region corresponding to a brain included in an acquired image may be different depending on the image capture method.

For example, a brain region included in the first internal region of the skull acquired by a first imaging scheme may be different from a brain region included in the first internal region of the skull acquired by a second imaging scheme.

Therefore, there is a need for a boundary definition scheme that includes a region necessary to provide information regarding auxiliary disease diagnosis and that is not affected by an image capture scheme.

Since the image analysis device 2000 according to an embodiment of the present application may perform an operation of modifying a portion of the first boundary corresponding to the first internal region of the skull and modifying a portion of the first boundary for the target image on the basis of a "common criterion," information meaningful to auxiliary disease diagnosis may be acquired, and an auxiliary disease diagnosis index may be acquired for each target image according to the common criterion.

Figure 52:
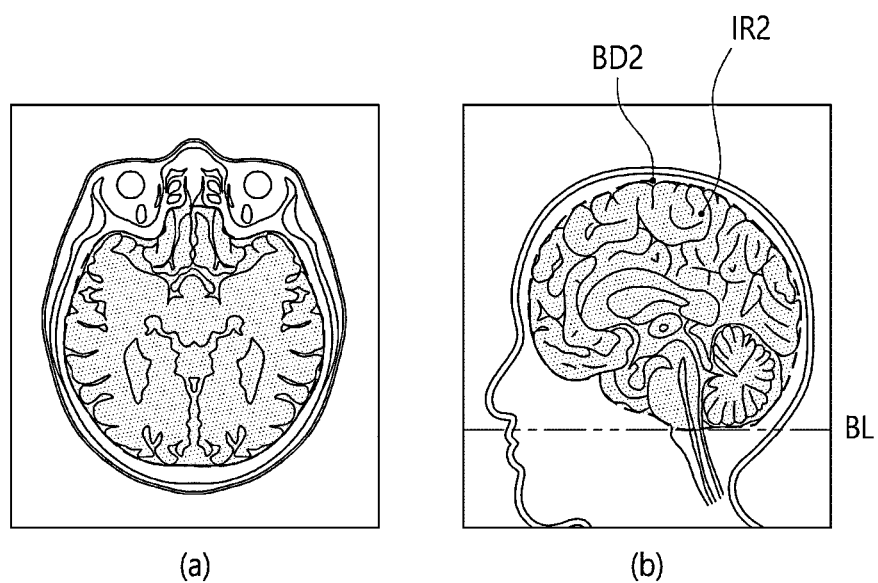
FIG. 52 is a diagram showing an example of a second internal region acquired according to the method of modifying a first boundary in a first internal region of a skull according to an embodiment of the present application.

An example of a method of modifying the first boundary of the first internal region of the skull according to an embodiment of the present application will be described below with reference to FIGS. 51 and 52. FIG. 52 is a diagram showing an example of a second internal region acquired according to the method of correcting a first boundary in a first internal region of a skull according to an embodiment of the present application.

The first boundary BD1 acquired in the above-described image segmentation operation (S4300) may be a 3D boundary.

In this case, the image analysis device 2000 may acquire a reference plane RP (or a 2D image slice), which is a modification basis, in order to modify the first boundary, which is 3D, to acquire a region necessary to provide the information meaningful to the auxiliary disease diagnosis. Also, in order to acquire the reference plane RP, the image analysis device 2000 may use a feature region included in a sagittal plane image, as shown in FIGS. 51 and 52.

For example, the image analysis device 2000 may acquire a reference plane RP related to a reference region RR. The image analysis device 2000 may acquire a reference plane RP adjacent to the reference region RR from a target image. For example, the image analysis device 2000 may acquire a plane adjacent to an inferior edge of a boundary defining the reference region RR as a reference plane RP. The reference plane RP may be a plane that is parallel to the transverse plane of the target image and vertical to the sagittal plane. In this case, the reference region RR may be a region corresponding to a cerebellum.

The image analysis device 2000 may acquire a second boundary BD2 by modifying a portion of the first boundary of the first internal region on the basis of the acquired reference plane RP. For example, the image analysis device 2000 may modify a portion of the first boundary BD1 located on the bottom side of the reference plane RP and acquire the second boundary BD2 on the basis of the first boundary BD1 located on the upper side of the reference plane RP.

More specifically, the image analysis device 2000 may be implemented to modify the first boundary by replacing the portion of the first boundary located on the bottom side of the reference plane RP with a reference line or a reference plane included in the reference plane RP.

The image analysis device 2000 may modify the first boundary to acquire the second boundary and may acquire a second internal region of the skull having the second boundary.

By modifying a portion of the first boundary BD1 on the basis of the reference plane RP, the image analysis device 2000 according to an embodiment of the present application may acquire a second internal region BD2, which is a region necessary to provide information meaningful to auxiliary disease diagnosis, and may compute a morphological index for the target image on the basis of the second internal region BD2 acquired according to the common criterion. Thus, information meaningful to auxiliary disease diagnosis may be acquired.

Referring to FIG. 52, the image analysis device 2000 may modify a portion of the first boundary BD1 on the basis of a reference plane RP adjacent to the reference region RR (e.g., a reference plane including an inferior edge of the reference plane RR) and acquire the second internal region IR2 of the skull having the second boundary BD2. At this time, as compared to FIG. 51, the portion of the first boundary BD1 located on the bottom side of the reference plane RP is replaced with a reference surface of the reference plane RP, and thus it can be confirmed that the first boundary BD1 is corrected. Also, by modifying the first boundary BD1, the second internal region IR2 having the second boundary BD may be acquired.

FIGS. 51 and 52 show an example of modifying a portion of the first boundary BD1 of the first internal region IR of the skull only for a brain image related to a sagittal plane among brain images, but the image analysis device 2000 may also perform a corresponding boundary modification operation on brain images related to a coronal plane and a transverse plane among the brain images.

Figure 53:
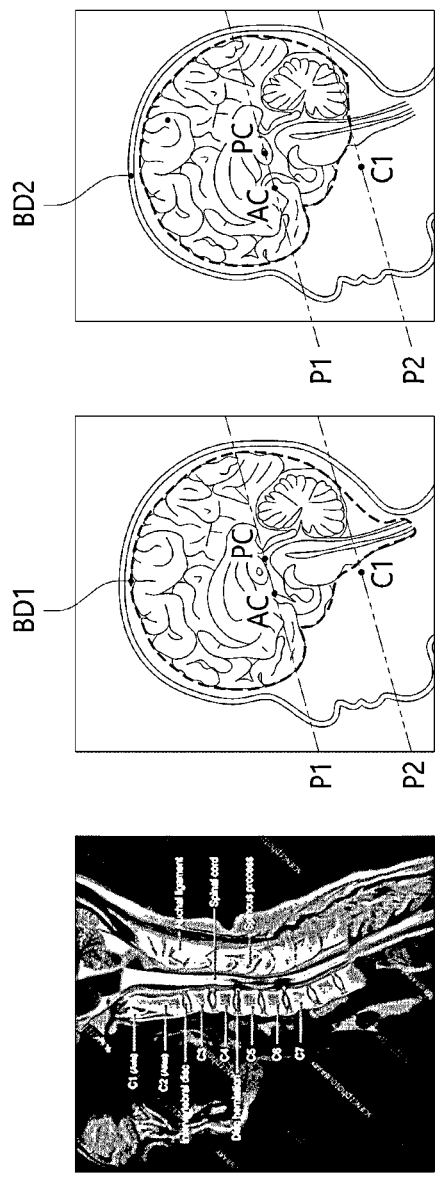
FIG. 53 is a diagram showing another example of the method of modifying a first boundary in a first internal region of a skull according to an embodiment of the present application.

Another example of a method of modifying the first boundary of the first internal region of the skull according to an embodiment of the present application will be described below with reference to FIG. 53. FIG. 53 is a diagram showing another example of the method of modifying the first boundary in the first internal region of the skull according to an embodiment of the present application.

Referring to FIG. 53, the image analysis device 2000 according to an embodiment of the present application may be implemented to modify a portion of the first boundary BD1 of the first internal region IR1 of the skull using a region corresponding to cervical vertebrae as the reference region RR.

As an example, the image analysis device 2000 may acquire region C1 related to cervical vertebrae. In this case, the image analysis device 2000 may modify a portion of the first boundary BD1 of the first internal region IR1 of the skull on the basis of region C1 related to cervical vertebrae.

The image analysis device 2000 may acquire a first feature region and a second feature region from a target image. For example, the first feature region may be a region corresponding to the anterior commissure AC, and the second feature region may be a region corresponding to the posterior commissure PC.

The image analysis device 2000 may be implemented to calculate a first feature point from the first feature region and calculate a second feature point from the second feature region.

For example, the image analysis device 2000 may calculate the first feature point on the basis of a region corresponding to the superior edge, the interior edge, or the like included in a boundary defining a region corresponding to the anterior commissure AC or the center of a region corresponding to the anterior commissure AC, which may be the first feature region. Also, the image analysis device 2000 may calculate the second feature point on the basis of a region corresponding to the superior edge, the interior edge, or the like included in a boundary defining a region corresponding to the posterior commissure PC or the center of a region corresponding to the posterior commissure PC, which may be a second feature region.

Also, the image analysis device 2000 may acquire a reference plane on the basis of the calculated first feature point and second feature point.

For example, the image analysis device 2000 may acquire a reference direction on the basis of the center of the anterior commissure AC and the center of the posterior commissure PC in a sagittal plane. For example, the image analysis device 2000 may acquire a reference direction in which the center of the anterior commissure AC and the center of the posterior commissure PC are connected. In this case, the image analysis device 2000 may acquire a reference plane P2 that is adjacent to the reference region RR and parallel to the reference direction.

As another example, the image analysis device 2000 may acquire a first plane P1 that includes the center of the anterior commissure AC and the center of the posterior commissure PC and that is vertical to a sagittal plane. In this case, the image analysis device 2000 may acquire a reference plane P2 that is adjacent to the reference region RR and parallel to the first plane P1.

The image analysis device 2000 may acquire a second boundary BD2 by modifying a portion of the first boundary B1 of the first internal region on the basis of the reference plane P2. For example, the image analysis device 2000 may modify a portion of the first boundary BD1 located on the bottom side of the reference plane P2 and acquire the second boundary BD2 on the basis of the first boundary BD1 located on the upper side of the reference plane P2.

More specifically, the image analysis device 2000 may be implemented to modify the first boundary BD1 by replacing the portion of the first boundary BD1 located on the bottom side of the reference plane P2 with a reference line or a reference plane included in the reference plane P2.

The image analysis device 2000 may acquire the second boundary BD2 on the basis of the modified first boundary and may acquire the second internal region IR2 of the skull having the second boundary BD2.

FIG. 53 shows an example of modifying a portion of the first boundary BD1 of the first internal region IR of the skull only for a brain image related to a sagittal plane among brain images, but the image analysis device 2000 may also perform a corresponding boundary modification operation on brain images related to a coronal plane and a transverse plane among the brain images.

Also, although a portion of the first boundary BD1 of the first internal region IR1 of the skull has been described as being modified based on region C1 of cervical vertebrae as illustrated in FIG. 53, the present invention is not necessarily limited to the modification of the first boundary BD1 based on region C1 of cervical vertebrae. For example, the image analysis device 2000 may be implemented to modify the first boundary BD1 on the basis of other regions of cervical vertebrae and modify the first boundary BD1 on the basis of a region with prominent features within a brain image.

Also, FIG. 53 illustrates the reference plane P2 as a plane parallel to the first plane P1 acquired based on the anterior commissure AC and the posterior commissure PC, but this is merely an example. The image analysis device 2000 may be implemented to acquire a plane that is parallel to the transverse plane of the target image and that includes region C1 as the reference plane P2 and may correct the first boundary BD1 based on the reference plane P2.

Also, FIGS. 51 to 53 show that a boundary is modified for a 2D image, but this is only for convenience of description. The present invention should be interpreted as acquiring the internal region by modifying the boundary for a 3D image.

Referring to FIG. 50, the image analysis method according to an embodiment of the present application may include an operation of acquiring a morphological volume value of the second internal region (S4430).

Specifically, in the operation of acquiring a morphological volume value of the second internal region (S4430), the image analysis device 2000 may compute a morphological volume value on the basis of the acquired second internal region. Specifically, the image analysis device 2000 may acquire a morphological volume value corresponding to the second internal region on the basis of voxel data corresponding to the second internal region.

Also, the image analysis method according to an embodiment of the present application may include an operation of acquiring a morphological volume value of a target element (S4440).

Specifically, in the operation of acquiring a morphological volume value of a target element (S4440), the image analysis device 2000 may compute the morphological volume value related to the target element on the basis of a region corresponding to the acquired target element in the image segmentation operation S4300. Specifically, the image analysis device 2000 may be provided to acquire a morphological volume value corresponding to the target element on the basis of voxel data corresponding to the target element.

Also, the image analysis method according to an embodiment of the present application may include an operation of computing a morphological index (S4450). Specifically, in the operation of computing a morphological index (S4450), the image analysis device 2000 may compute the morphological index on the basis of the morphological volume value corresponding to the second internal region acquired in operation S4430 and the morphological volume value corresponding to the target element acquired in operation S4450.

As an example, the morphological index may be an index defined as a ratio of the morphological volume value corresponding to the target element to the morphological volume value corresponding to the second internal region.

For example, the morphological index may be equal to (a morphological volume value corresponding to the target element)/(a morphological volume value corresponding to the second internal region).

Also, the computed morphological index may provide meaningful information as an auxiliary diagnosis index related to a brain disease such as dementia, depression, stroke, etc.

Although not shown in FIGS. 48 and 50, each of the morphological volume value corresponding to the second internal region acquired in operation S4430 and the morphological volume value corresponding to the target element acquired in operation S4440 may be corrected based on a correction parameter related to a scan condition or a correction parameter related to the location of the target element. In this case, the image analysis device 2000 may be implemented to finally compute a morphological index based on a morphologically corrected volume value corresponding to the second internal region and a morphologically corrected volume value corresponding to the target element. This will be described in detail below with reference to FIGS. 58 to 67.

An example of output morphological index-related information and an operation of the image analysis device 2000 outputting the information according to an embodiment of the present application will be described below with reference to FIGS. 54 to 57. FIGS. 54 to 57 are exemplary diagrams showing output morphological index-related information according to an embodiment of the present application.

The output morphological index-related information, which will be described below, may be output through the output device 2600 or the output module 2050 of the image analysis device 2000 according to an embodiment of the present application.

Figure 54:
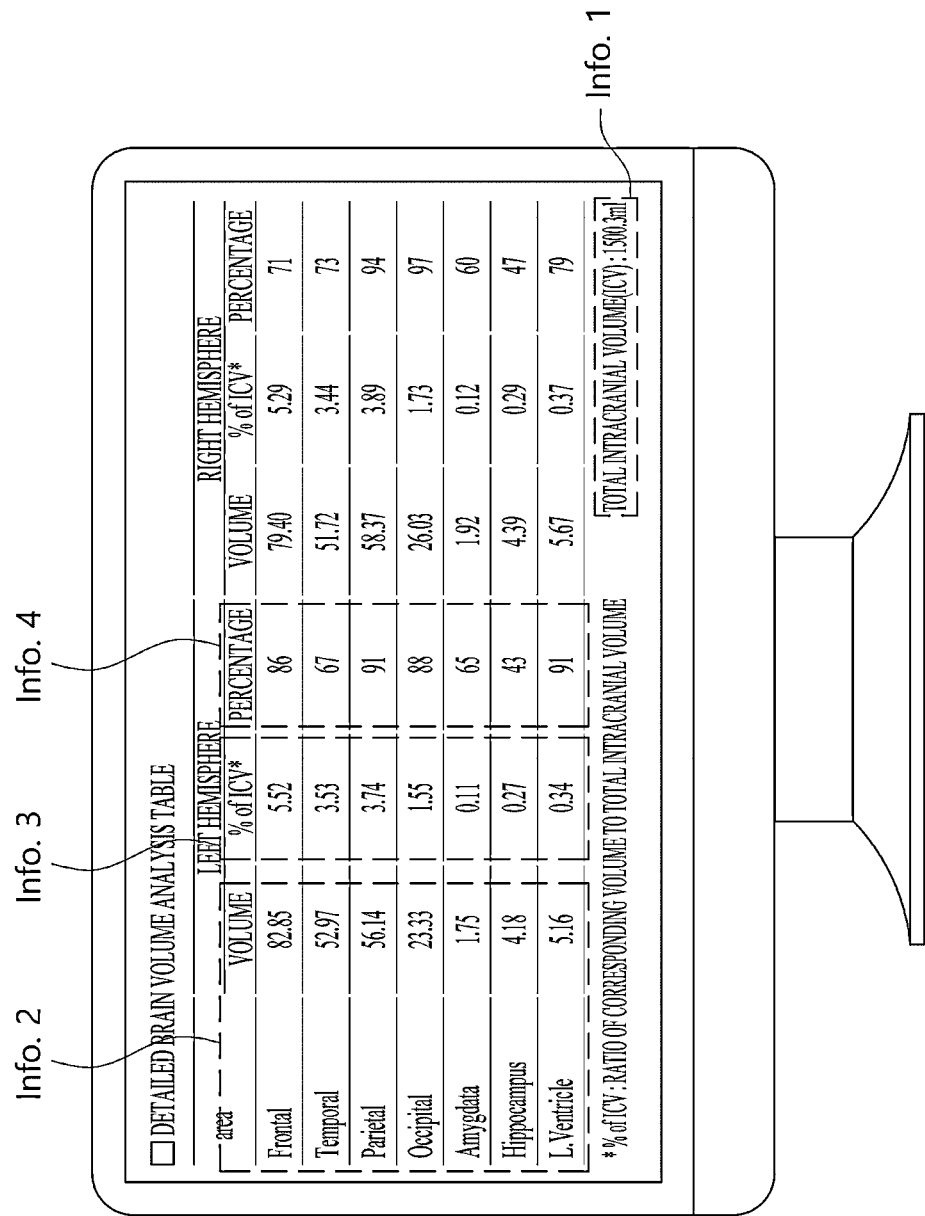
FIGS. 54 to 57 are exemplary diagrams showing output morphological index-related information according to an embodiment of the present application.

Referring to FIG. 54, morphological index-related information output from the image analysis device 2000 according to an embodiment of the present application may include the total intracranial volume ICV (Info.1).

For example, the total intracranial volume ICV (Info.1) may be a volume value acquired by the image analysis device 2000 according to an embodiment of the present application on the basis of voxel data corresponding to the internal region of the skull of the target image.

In this case, as described above, the image analysis device 2000 may modify a portion of the first boundary of the first internal region of the skull acquired based on the segmentation result for the target image and acquire the second internal region having the second boundary in order to define the internal region of the skull. In this case, according to a preferred embodiment, the total intracranial volume ICV (Info.1) may be a value acquired based on the voxel data of the target image corresponding to the second internal region.

Referring to FIG. 54 again, morphological index-related information output from the image analysis device 2000 according to an embodiment of the present application may include the volumes (Info.2) of target elements, morphological indices (Info.3), and percentage information (Info.4) of morphological indices. In other words, the image analysis device 2000 according to an embodiment of the present application may output morphological index-related information including the volumes (Info.2) of target elements, morphological indices (Info.3), and percentages (Info.4) of morphological indices.

The information output from the image analysis device 2000 according to an embodiment of the present application may be information regarding various regions located in a brain. In this case, the target element may be a region significantly associated with a brain disease. For example, the target element may be a region associated with a hippocampus, lateral ventricle, frontal lobe, temporal lobe, parietal lobe, occipital lobe, and amygdala related to a brain disease such as dementia.

The image analysis device 2000 according to an embodiment of the present application may be provided to segment the target image into a plurality of brain regions including the above-described regions and then acquire and output a volume value of each target element on the basis of voxel data corresponding to the regions.

Also, the image analysis device 2000 according to an embodiment of the present application may acquire the volume values of the target elements and may correct the volume value of the target elements in consideration of the locations of the target elements or a scan condition in which the target is captured.

In this case, the volumes (Info.2) of the target elements of FIG. 54 may be corrected volume values.

The morphological indices (Info.3) output from the image analysis device 2000 according to an embodiment of the present application may be a ratio of the volume of the region corresponding to the target element to the volume corresponding to the internal region of the skull. For example, referring to FIG. 54, the morphological indices (Info.3) output from the image analysis device 2000 may be a ratio of the volume values (Info.2) of the target elements to the total intracranial volume ICV (Info.1).

However, this is merely an example, and the present invention is not limited to the volume. The image analysis device 2000 may be provided to acquire and output morphological indices related to a shape, length, thickness, etc., which are associated with any suitable brain disease.

The image analysis device 2000 according to an embodiment of the present application may acquire a morphological index database and acquire percentages (Info.4) of morphological indices of a target subject on the basis of the morphological index database. The percentages (Info.4) of the morphological indices output from the image analysis device 2000 may be information regarding the percentages of the morphological indices (Info.3) of the target subject located in the morphological indices of a comparison group. In this case, the comparison group may be a target group acquired in consideration of the gender or age of the target subject of the target image.

Specifically, the image analysis device 2000 may acquire percentage information of the morphological index of the target subject using a morphological index database including one or more morphological indices acquired based on a brain image to be compared.

For example, the image analysis device 2000 may acquire ICV data including one or more morphological values or morphological indices related to ICV acquired from the morphological index database and may acquire percentages in the ICV data of the morphological value or the morphological index related to ICV acquired based on the target image of the target subject.

As an example, the image analysis device 2000 may acquire information of a target subject related to the gender or age of the target subject of the target image and may acquire a morphological index database on the basis of the information of the target subject. The morphological index database may include one or more morphological indices acquired based on a brain image of a comparison group having similar characteristics (gender, age, etc.) to those of the information of the target subject.

The image analysis device 2000 may acquire percentage information of the morphological index of the target subject using the acquired morphological index database.

For example, the image analysis device 2000 may acquire ICV data including one or more morphological values or morphological indices related to ICV acquired based on a brain image of a man in his 60s and may acquire percentages in the ICY data of the morphological values or morphological indices related to an ICV value acquired based on the brain image of the man in his 60s.

As another example, the image analysis device 2000 according to an embodiment of the present application may acquire information (e.g., age or gender) of the target subject related to the target image and may select brain images of a comparison group from among a plurality of brain images stored in the database or the memory 2020 in consideration of information on a target subject.

The image analysis device 2000 may acquire ICV data, which includes one or more morphological values or morphological indices related to the ICV corresponding to the target element from the selected brain images of the comparison group, through an operation similar to the operation of acquiring the morphological index from the target image The image analysis device 2000 may compare a morphological value or a morphological index related to an ICV value acquired from the target image to ICV data acquired from the brain images of the comparison group and may compute percentages in the ICV data of the morphological value or the morphological index related to the ICV value acquired from the target image.

Information regarding the volumes (Info.2) of target elements, morphological indices (Info.3), and percentages (Info.4) of morphological indices, which is output from the image analysis device 2000 according to an embodiment of the present application, may be individually acquired and output for the left and right hemispheres.

However, it will be appreciated that the morphological index-related information shown in FIG. 54 is merely an example and any suitable information may be additionally acquired and output from the image analysis device 2000.

Information regarding the volumes (Info.2) of target elements, morphological indices (Info.3), or percentages (Info.4) of morphological indices, which is output from the image analysis device 2000 according to an embodiment of the present application, may be output by processing the morphological index-related information in a statistical technique using any suitable graph.

An example of processing and outputting morphological index-related information by the image analysis device 2000 according to an embodiment of the present application will be described below with reference to FIGS. 55 to 57.

Figure 55:
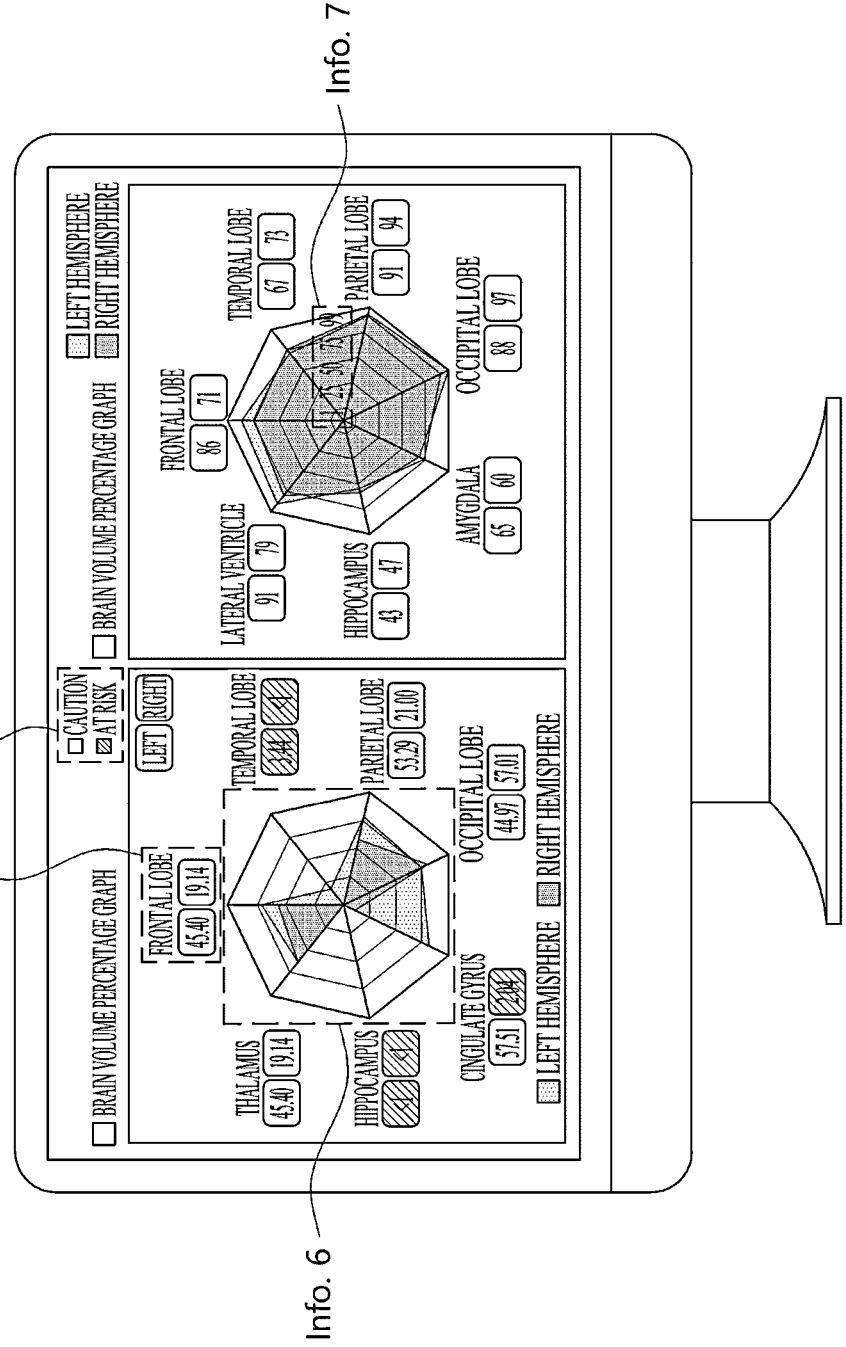

Referring to FIG. 55, morphological index-related information output from the image analysis device 2000 according to an embodiment of the present application may include information regarding the percentages (Info.5) of morphological indices, graphs (Info.6, 7) of percentages of morphological indices, and risk levels (Info.8) associated with brain diseases.

The percentages (Info.5) of the morphological indices output from the image analysis device 2000 according to an embodiment of the present application may be values acquired with respect to a target element located in the left hemisphere and a target element located in the right hemisphere.

For example, referring to FIG. 55, percentage values of morphological indices acquired for frontal lobe, temporal lobe, parietal lobe, occipital lobe, cingulate gyrus, hippocampus, and thalamus may be visually output. In this case, the percentages of the morphological indices for frontal lobe and the like located in the left hemisphere and the percentages of the morphological indices for frontal lobe and the like located in the right hemisphere may be visually output together.

Graphs (Info.6, 7) for the percentages of morphological indices output from the image analysis device 2000 according to an embodiment of the present application may be generated based on the percentage of the morphological index of the target subject computed by comparing the morphological index (Info.3) of the target subject and morphological indices acquired from brain images of a comparison group, which has been described with reference to FIG. 54.

In this case, the graph may be provided to visually display the percentage of the morphological index and may include a ruler (Info.7) related to the percentage indicating where the percentage of the morphological index of the target subject is distributed.

Also, the graph may be provided by distinguishing the percentages of the morphological indices for the left hemisphere and the percentages of the morphological indices for the right hemisphere.

Information regarding the risk levels (Info.8) related to brain diseases output from the image analysis device 2000 according to an embodiment of the present application may be provided such that the risk levels can be computed based on the percentages of the morphological indices of the target subject and such that the information is output visually differently according to the risk levels.

Specifically, the image analysis device 2000 may be provided such that a predetermined threshold is set for the percentage of the morphological index in relation to the risk level (Info.8) associated with brain diseases. In this case, the predetermined threshold may be preset differently depending on the degree of risk (e.g., cautious, at risk, normal).

In this case, the image analysis device 2000 may be implemented to visually output information indicating that the target subject may be at risk of a brain disease when the percentage of the morphological index of the target subject is less than a predetermined first threshold. For example, referring to FIG. 55, when the percentages of the morphological indices of the hippocampus located in the left and right hemispheres of the target subject are smaller than the predetermined first threshold, the image analysis device 2000 may be implemented to determine that the target subject is at risk and implemented to output the percentages of the morphological indices related to the hippocampus in a first color (e.g., red) on the basis of a result of determining that the target subject is at risk.

Also, when the percentage of the morphological index of the target subject is greater than a predetermined first threshold and is smaller than a predetermined second threshold, the image analysis device 2000 may be implemented to visually output information indicating that a target subject is likely to have a brain disease and thus needs to be cautious. For example, when the percentage of the morphological index of a specific target element located in the left and right hemispheres of the target subject is greater than a predetermined first threshold and smaller than a predetermined second threshold, the image analysis device 2000 may be implemented to determine that the target subject needs to be cautious and may be implemented to output the percentage of the morphological index of the specific target element in a second color (e.g., orange) on the basis of the determination that the target subject needs to be cautious.

However, outputting the percentage in different colors depending on the above-described risk level is merely an example, and the present invention is not limited thereto. It will be appreciated that the image analysis device 2000 may be implemented to provide information regarding a risk level associated with brain diseases utilizing any suitable method.

The image analysis device 2000 according to an embodiment of the present application may be implemented to provide information regarding the morphological index of the target subject acquired from the target image and morphological indices acquired from brain images of a comparison group.

Specifically, as described above with reference to FIG. 55, the image analysis device 2000 may acquire the morphological indices of the comparison group from the morphological index database on the basis of the information of the target subject including the age or gender of the target subject of the target image.

In this case, the image analysis device 2000 according to an embodiment of the present application may be implemented to output the morphological index of the target subject and the morphological indices of the comparison group according to the information of the target subject in the form of a visual graph. In this case, the morphological indices of the comparison group according to the information of the target subject may be implemented to be output reflecting the morphological indices of the comparison group corresponding to thresholds predetermined in relation to the risk levels for brain diseases and the average of the morphological indices of the comparison group.

Figure 56:
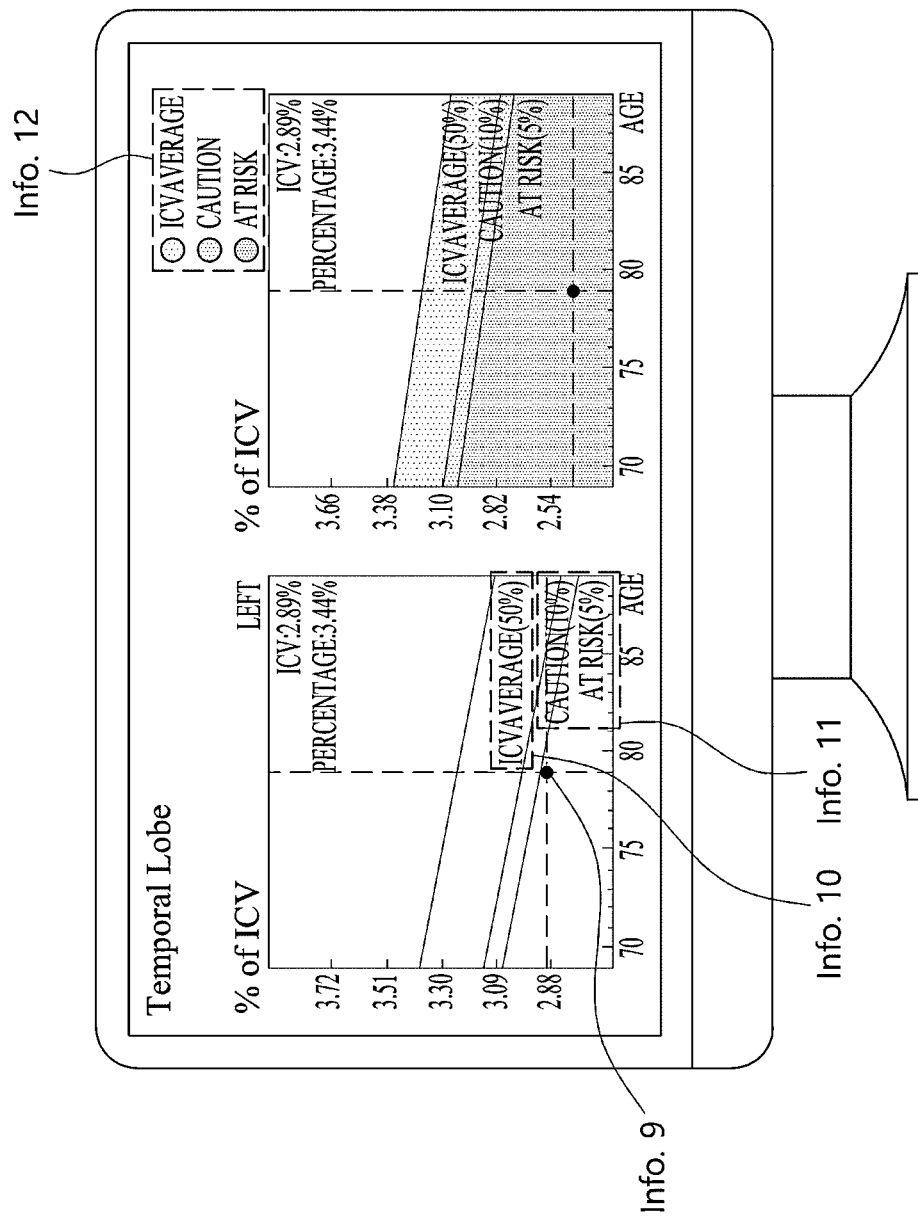

Reference will be made to FIG. 56. FIG. 56 is a graph showing an example of morphological index-related information output by the image analysis device 2000 according to an embodiment of the present application.

As an example, the morphological index output by the image analysis device 2000 according to an embodiment of the present application may be output as the morphological index (Info.9) of the target subject according to information (e.g., age or gender) of the target subject related to the target image.

In this case, the image analysis device 2000 according to an embodiment of the present application may be implemented to additionally output the morphological indices (Info.10, Info.11) of the comparison group together with the morphological index (Info.9) of the target subject in order to provide information regarding a brain disease of the target subject.

For example, the image analysis device 2000 may acquire morphological index information of comparison groups of 70- and 80-year-olds from the morphological index database in consideration of the age of the target subject (e.g., 79 years of age in FIG. 56), as described above. In this case, the image analysis device 2000 may be implemented to acquire and output the average (Info.10) of the morphological index information of the comparison group acquired in consideration of age.

As another example, the image analysis device 2000 may have thresholds related to the morphological indices of the comparison group that are set to provide information regarding a risk level associated with brain diseases. For example, the image analysis device 2000 may be implemented such that a threshold is preset to determine that the target subject is at risk when the percentage of the morphological index of the target subject is less than 5%. Alternatively, the image analysis device 2000 may be implemented such that a threshold is preset to determine that the target subject needs to be cautious when the percentage of the morphological index of the target subject is greater than 5% or less than 10%.

In this case, the image analysis device 2000 according to an embodiment of the present application may be implemented to output the morphological indices (Info.11) of the comparison group corresponding to a present threshold in relation to the risk level for brain diseases. In this case, the morphological indices (Info.11) of the comparison group may be output according to the information of the target subject such as the age of the target subject.

The image analysis device 2000 according to an embodiment of the present application may be provided to output information (Info.12) related to the risk level for brain diseases on the basis of a threshold preset in relation to the risk level for brain diseases and the percentage of the morphological index of the target subject.

For example, the image analysis device 2000 may be implemented such that a threshold is preset to determine that the target subject is at risk when the percentage of the morphological index of the target subject is less than 5%. In this case, the image analysis device 2000 may be implemented to visually output information indicating that the target subject may be at risk of a specific brain disease when the percentage of the morphological index of the target subject is less than 5%. For example, referring to FIG. 56, the image analysis device 2000 may be implemented such that the morphological index (Info.9) of the target subject is displayed and output in a first color (e.g., red).

Alternatively, the image analysis device 2000 may be implemented such that a threshold is preset to determine that the target subject needs to be cautious when the percentage of the morphological index of the target subject is greater than 5% or less than 10%. In this case, the image analysis device 2000 may be implemented to visually output information indicating that the target subject may need to be cautious about a specific brain disease when the percentage of the morphological index of the target subject is greater than 5% or less than 10%. For example, the image analysis device 2000 may be implemented such that the morphological index (Info.9) of the target subject is displayed and output in a second color (e.g., orange).

However, the above description is merely an example, and the present invention is not limited thereto. That is, the image analysis device 2000 may be implemented to output information regarding risk levels of brain diseases of the target subject using any suitable scheme.

The image analysis device 2000 according to an embodiment of the present application may be provided to visually output information regarding 3D brain information in order to provide information on where a target element or a 3D structure of a target element is located inside a brain. An example of morphological index-related information and an operation of the image acquisition device 2000 outputting the information according to an embodiment of the present application will be described below with reference to FIG. 57.

For example, the image analysis device 2000 may additionally acquire data related to a 3D brain template. Based on the data related to the 3D brain template and the region corresponding to the target element acquired by segmenting the target image, the image analysis device 2000 may output information on where the target element or the 3D structure of the target element is located in the brain in a visual graphic form (Info.13).

Also, based on the data related to the 3D brain template and the above computed percentage of the morphological index related to the target element, the image analysis device 2000 according to an embodiment of the present application may be implemented to overlay and output the 3D brain template with information on the percentage of the morphological index related to the target element. For example, the image analysis device 2000 according to an embodiment of the present application may be implemented to overlay the 3D brain template with different colors depending on the percentage of the morphological index related to the target element to provide information regarding volume shrinkage of the target element.

Also, the image analysis device 2000 according to an embodiment of the present application may be implemented to receive an input for outputting detailed morphological index-related information from a user through an input module and output an output corresponding to the user's input to the user through an output module. For example, when the user's input for a specific brain region of the 3D brain template shown in FIG. 57 is acquired, the image analysis device 2000 may be provided to output morphological index-related information (e.g., information shown in FIGS. 54 to 56) regarding the specific brain region corresponding to the acquired input.

Figure 57:
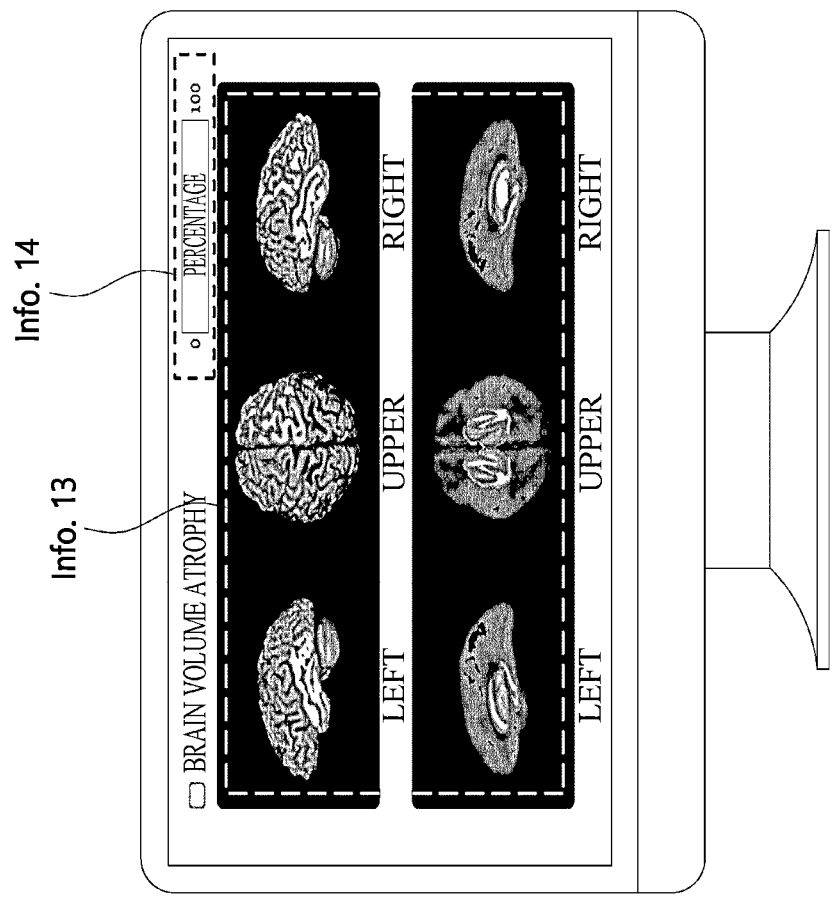

However, the morphological index-related information shown in FIG. 57 is merely an example, and the image analysis device 2000 according to an embodiment of the present application may be implemented to provide the information on the percentage of the morphological indices related to the target element in any suitable method in three dimensions.

Also, the image analysis device 2000 according to an embodiment of the present application may be implemented to output the morphological index-related information associated with the target subject according to temporal variables. For example, the image analysis device 2000 may be implemented to output morphological index-related information (e.g., information shown in FIGS. 54 to 57) acquired from the target subject at the first timing and morphological index-related information (e.g., information shown in FIGS. 54 to 57) acquired from the target subject at the second timing. In particular, although it is important to perform comparison to the morphological indices of the comparison group in relation to brain diseases, it may be important to analyze the morphological index of the target subject according to temporal variables.

The image analysis device 2000 according to an embodiment of the present application may acquire morphological index-related information at the first timing from a brain image acquired from the target subject at the first timing through the above-described image analysis operations and may acquire morphological index-related information at the second timing different from the first timing from a brain image acquired from the target subject at the second timing through the above-described image analysis operations. In this case, the image analysis device 2000 may be implemented to output the morphological index-related information at the first timing and the morphological index-related information at the second timing to the user through various statistical techniques.

However, the morphological index-related information described above with reference to FIGS. 54 to 58 is merely an example, and any suitable type of information regarding brain diseases may be output to the user in any suitable method.

An index that quantifies the degree of brain atrophy in relation to brain-related diseases, in particular, dementia, is being used as an auxiliary index for dementia diagnosis. In this case, a value related to the degree of brain atrophy may be measured differently depending on a scan condition in which the brain image is captured or the location of the target element. Here, the location of the target element may mean where the target element is distributed within the skull.

For example, a morphological index acquired for the same target subject, that is, a value related to the degree of brain atrophy, may depend on scan conditions including the strength of the magnetic field of the image acquisition device through which the brain image is captured, the manufacturer of the image acquisition device, and the setting parameters for the image acquisition device. As a specific example, the morphological index acquired for the same target subject may be measured differently depending on a variable called the strength of the magnetic field.

As another example, the morphological index acquired for the same target subject, i.e., the numerical number related to the degree of atrophy of the target element, may be measured differently depending on the location of the target element within the skull.

Accordingly, it is required to correct the morphological index according to the location of the target element or the scan condition in which the brain image is captured.

The image analysis device 2000 according to an embodiment of the present application may be implemented to perform an operation of correcting a morphological value or a morphological index of the target element in consideration of the scan condition in which the brain image is captured or the location of the target element.

Therefore, advantageously, the image analysis device 2000 according to an embodiment of the present application may more accurately acquire the morphological index related to the degree of brain atrophy associated with brain diseases and may provide a user with a more objective morphological index as auxiliary diagnostic information associated with brain diseases.

A method of correcting a morphological figure implemented by the image analysis device 2000 according to an embodiment of the present application will be described in detail below with reference to FIGS. 58 to 67. The following description will focus on a volume-related morphological figure, but the present invention is not limited thereto. The same correction method can be applied to any suitable morphological characters such as the shape, thickness, and length, other than volume, of a target part which will be an index for a brain disease.

Figure 58:
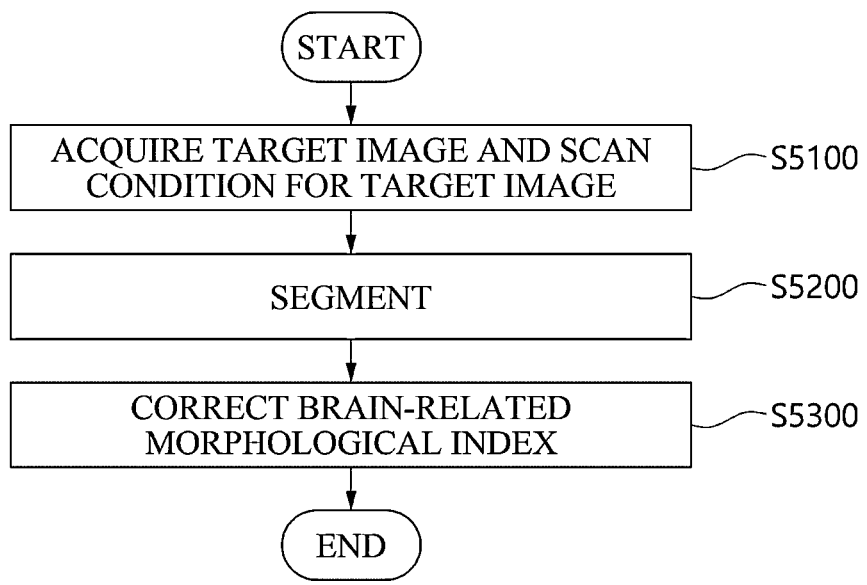
FIG. 58 is a flowchart showing one operation of a morphological figure correction method implemented by the image analysis device 2000 according to an embodiment of the present application.

Reference will be made to FIG. 58. FIG. 58 is a flowchart showing one operation of a morphological figure correction method implemented by the image analysis device 2000 according to an embodiment of the present application. Specifically, FIG. 58 is a flowchart showing an operation of correcting a brain-related morphological value or a brain-related morphological index, which is implemented by the image analysis device 2000 according to an embodiment of the present application.

The morphological figure correction method according to an embodiment of the present application may include an operation of acquiring a target image and a scan condition of the target image (S5100), an operation of segmenting the target image (S5200), and an operation of correcting a brain-related morphological index (S5300).

In the operation of acquiring a target image and a scan condition of the target image (S5100), an image analysis device 2000 may acquire a target image from an image acquisition device 1000. The term "target image" may encompass a brain image to be analyzed by the image analysis device 2000. In other words, the term "target image" may encompass a target brain image from which a morphological value or a morphological index of a target element is to be computed by the image analysis device 2000.

Also, in the operation of acquiring a target image and a scan condition of the target image (S5100), the image analysis device 2000 may acquire information regarding a scan condition in which the target image is captured from the image acquisition device 1000. As described above, information regarding the scan condition in which the target image is captured may be structured as metadata for the target image and may be acquired by acquiring the target image from the image acquisition device 1000. Alternatively, the information regarding the scan condition in which the target image is captured may be acquired from any external device separately from the target image.

In the operation of segmenting the target image (S5200), the image analysis device 2000 may segment the target image according to the image segmentation operation described above with reference to FIGS. 7 to 17.

According to an example, through the segmentation operation of the image analysis device 2000, at least one target element included in the target image may be acquired.

Also, the image analysis device 2000 may acquire the internal region of the skull, which will be described below, through the segmentation operation of the image analysis device 2000. In order to acquire the internal region of the skull, the image analysis device 2000 may be implemented to perform the operation of modifying a portion of the first boundary of the first internal region of the skull to obtain the second internal region of the skull having the second boundary, as described above with reference to FIGS. 48 and 57.

Also, a neural network model of the image analysis device 2000 that is provided may be trained to segment a brain image according to a scan condition. For example, a first neural network model trained from training data including a brain image acquired under a first scan condition may be provided to segment a target image acquired under the first scan condition. As another example, a second neural network model trained from training data including a brain image acquired under a second condition may be provided to segment a target image acquired under the second scan condition.

Referring to FIG. 58, although the preprocessing of the target image and the alignment of the target image are not shown, the operations of the image analysis device 2000 in the preprocessing of the image and the alignment of the image (S4200) described above with reference to FIG. 48 are applicable in the same way.

Figure 59:
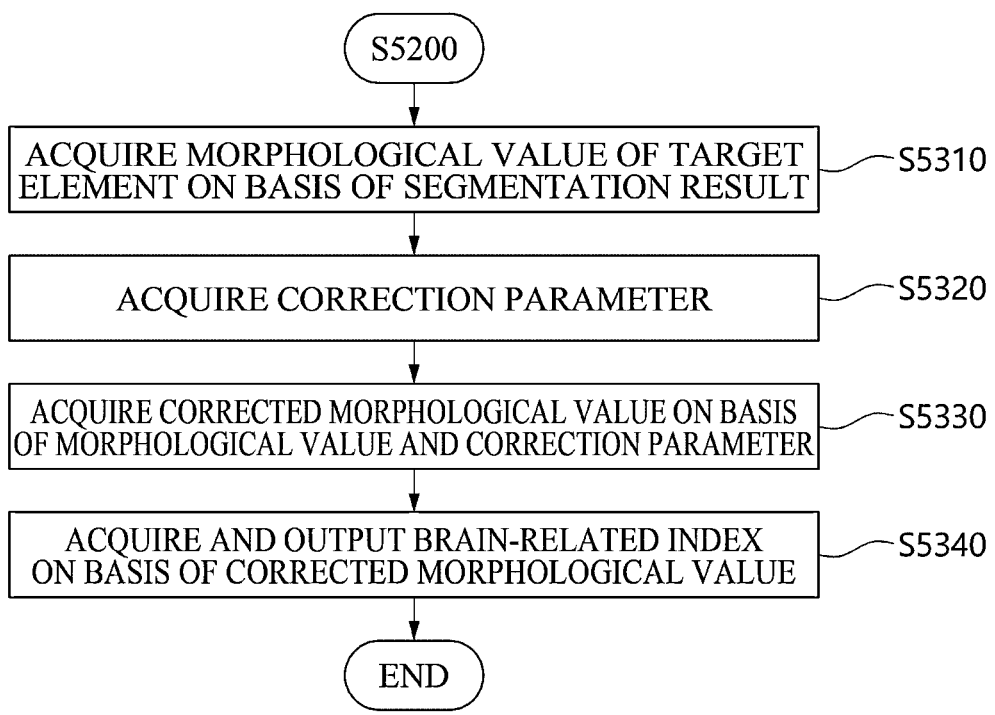
FIG. 59 is a flowchart of an image analysis method according to an embodiment of the present application.

An embodiment of the operation of correcting a brain-related morphological index (S5300) will be described in detail below with reference to FIG. 59. FIG. 59 is a diagram illustrating a flowchart of an image analysis method according to an embodiment of the present application and, specifically, is a diagram showing sub-operations of operation S5300 of FIG. 58.

Referring to FIG. 59, the operation of correcting a brain-related morphological index (S5300) according to an embodiment of the present application may further include an operation of acquiring a morphological value of a target element on the basis of a segmentation result (S5310), an operation of acquiring a correction parameter (S5320), an operation of acquiring a corrected morphological value on the basis of the morphological value and the correction parameter (S5330), and an operation of acquiring and outputting a brain-related morphological index on the basis of the corrected morphological value (S5340).

In the operation of acquiring a morphological value of a target element on the basis of a segmentation result (S5310), the image analysis device 2000 may acquire a morphological value related to a target element on the basis of voxel data of a target image related to a region corresponding to the target element acquired through the segmentation operation. Alternatively, the image analysis device 2000 may acquire a morphological value related to the internal region of the skull on the basis of voxel data of the target image related to the internal region of the skull acquired by the segmentation operation.

Also, in the operation of acquiring a morphological value of a target element on the basis of a segmentation result (S5310), the image analysis device 2000 may acquire a morphological index related to a target element on the basis of a morphological value related to the target element and a morphological value related to the internal region of the skull.

In this case, the morphological value of the target element or the brain-related morphological index may be a value related to morphological characters such as the volume, thickness, length, or shape of the target element.

In the operation of acquiring a correction parameter (S5320), the image analysis device 2000 may be implemented to perform an operation of acquiring a correction parameter from a parameter acquisition device 2400 and correcting a morphological value related to the target element or a morphological value related to the internal region of the skull.

Alternatively, in the operation of acquiring a correction parameter (S5320), the image analysis device 2000 may be implemented to perform an operation of acquiring a correction parameter from a parameter acquisition device 2400 and correcting a morphological index related to the target element. That is, referring to FIG. 59, it is illustrated that a correction is made by applying the correction parameter to the morphological value of the target element, but this is merely an example and the present invention is not limited thereto. The image analysis device 2000 may be implemented to apply the correction parameter to a brain-related morphological index computed based on the morphological value of the target element and the morphological value related to the internal region of the skull.

In this case, the parameter acquisition device 2400 may acquire correction parameters through a correlation analysis related to a morphological value corresponding to a scan condition or a location of the target element. An operation of the correction parameter acquisition device 2400 in relation to the operation of acquiring a correction parameter (5320) will be described in detail with reference to FIGS. 60 to 65.

In the operation of acquiring a corrected morphological value on the basis of the morphological value and the correction parameter (S5330), the image analysis device 2000 may be implemented to perform an operation of acquiring a corrected morphological value related to the target element on the basis of the correction parameter acquired from the correction parameter acquisition device 2400 and the morphological value corresponding to the target element.

The correction parameter may be a parameter for approximating or estimating a morphological value related to a target element acquired under a first scan condition to or as a morphological value acquired under a second scan condition.

For example, the image analysis device 2000 may acquire the corrected morphological value related to the target element on the basis of the morphological value corresponding to the target element and the correction parameter included in a transform function acquired from the correction parameter acquisition device 2400.

In this case, the transform function may be any nth-order function, and the correction parameter may mean a coefficient included in the transform function.

For example, the correction parameter may be acquired from a transform function acquired through a correlation analysis between a first morphological value related to the target element acquired under the first scan condition and a second morphological value related to the target element acquired under the second scan condition. For example, when a linear function acquired through the correlation analysis between the first morphological value and the second morphological value is y=a*x+b, a and b may represent correction parameters for approximating or estimating the morphological value of the target element acquired under the first scan condition to or as the morphological value acquired under the second scan condition. The image analysis device 2000 may approximate or estimate the morphological value acquired under the first scan condition to or as the morphological value acquired under the second scan condition by multiplying the morphological value related to the target element acquired from the target image acquired under the first scan condition by a correction parameter (a) and adding a correlation parameter (b) to the product.

Meanwhile, a difference between an actual morphological value (or a morphological reference value) and a measured morphological value of the target element may vary depending on the location of the target element acquired from the target image. The image analysis device 2000 according to an embodiment of the present application may correct the measured morphological value of the target element in consideration of the location of the target element.

For example, the image analysis device 2000 may acquire a first correction parameter from the correction parameter acquisition device 2400 in order to approximate a measured morphological value of a first brain element to an actual morphological value (or a morphological reference value) of the first brain element.

On the other hand, the image analysis device 2000 may acquire a second correction parameter from the correction parameter acquisition device 2400 in order to approximate a measured morphological value of a second brain element to an actual morphological value (or a morphological reference value) of the second brain element.

Also, the image analysis device 2000 according to an embodiment of the present application may acquire a correction parameter in consideration of all variables related to a scan condition and the location of the target element.

For example, the image analysis device 2000 may approximate a morphological value related to a first brain element of the target image acquired under a first scan condition to a morphological value acquired under a second scan condition using a first correction parameter. On the other hand, the image analysis device 2000 may approximate a morphological value related to a second brain element of the target image acquired under a first scan condition to a morphological value acquired under a second scan condition using a second correction parameter.

For example, when a linear function acquired through a correlation analysis between a first morphological value and a second morphological value of the first brain element is y=a1*x+b1, a1 and b1 may represent correction parameters for approximating the morphological value of the first brain element acquired under the first scan condition to the morphological value acquired under the second scan condition. On the other hand, when a linear function acquired through a correlation analysis between a first morphological value and a second morphological value of a second brain element is y=a2*x+b2, a2 and b2 may represent correction parameters for approximating the morphological value of the second brain element acquired under the first scan condition to the morphological value acquired under the second scan condition.

The image analysis device 2000 may approximate the morphological value acquired under the first scan condition to the morphological value acquired under the second scan condition by multiplying the morphological value related to the first brain element acquired from the target image acquired under the first scan condition by a correction parameter (a1) and adding a correlation parameter (b) to the product. On the other hand, the image analysis device 2000 may approximate the morphological value acquired under the first scan condition to the morphological value acquired under the second scan condition by multiplying the morphological value related to the second brain element related to the target image acquired under the first scan condition by a correction parameter (a2) and adding a correlation parameter (b2) to the product.

However, the above-described transform function is merely an example, and by acquiring any suitable function, it is possible to correct a morphological value in consideration of a scan condition.

The image analysis device 2000 according to an embodiment of the present application may approximate a morphological value to a value acquired under a uniform scan condition on the basis of values acquired under various scan conditions and thus may provide a uniform auxiliary diagnostic index related to brain diseases.

Also, the image analysis device 2000 according to an embodiment of the present application may acquire a correction parameter differently in consideration of the location of the target element to perform correction and thus it is possible to provide a more accurate auxiliary diagnostic index related to brain diseases.

Also, in the operation of acquiring and outputting a brain-related morphological index on the basis of the corrected morphological value (S5340), the image analysis device 2000 may be implemented to compute and output a brain-related morphological index on the basis of a first corrected morphological value related to the target element and a second corrected morphological value related to the internal region of the skull.

As an example, the brain-related morphological index may be defined as the first corrected morphological value with respect to the second corrected morphological value. However, this is merely an example, and the brain-related morphological index may be defined as any suitable auxiliary diagnostic index related to brain diseases.

Meanwhile, there may be a plurality of target elements. In other words, the target element may include a first brain element and a second brain element.

In this case, the image analysis device 2000 may segment the target image to acquire a first region corresponding to the first brain element, a second region corresponding to the second brain element, and a skull region. Also, the image analysis device 2000 may acquire the internal region of the skull on the basis of the skull region.

In this case, as described above, the image analysis device 2000 may compute the first brain element and a first corrected morphological value on the basis of a correction parameter and voxel data of the first region and may compute the second brain element and a second corrected morphological value on the basis of a correction parameter and voxel data of the second region. Also, the image analysis device 1000 may acquire a morphological reference value related to the internal region of the skull on the basis of voxel data corresponding to the internal region of the skull, and this value may be a basis for computing the brain-related morphological index. In this case, the correction parameter related to the first brain element may be different from the correction parameter related to the second brain element. This will be described in detail with reference to FIG. 64.

The image analysis device 2000 may compute a first brain-related morphological index related to the first brain element on the basis of the first corrected morphological value and the morphological reference value. Also, the image analysis device 2000 may compute a second brain-related morphological index related to the second brain element on the basis of the second corrected morphological value and the morphological reference value.

The image analysis device 2000 according to an embodiment of the present application may determine a correction parameter for correcting a morphological value acquired from a target image in consideration of characteristics, such as age and gender, of a target subject of the target image.

For example, when a target image is acquired from a first target subject having a first characteristic related to gender and age, the image analysis device 2000 may determine a correction parameter for correcting a morphological value acquired from the target image as a correction parameter acquired from a first brain image and a second brain image acquired from a second target subject having the first characteristic. For example, the image analysis device 2000 may determine a correction parameter acquired from a second target subject having a similar age and the same gender as the first target subject of the target image as the correction parameter for correcting the morphological value or the morphological index acquired from the target image.

In the operation of acquiring and outputting a brain-related morphological index on the basis of the corrected morphological value (S5340), the image analysis device 2000 may output information related to the acquired brain-related morphological index through the output module 2050 or the output module 2650 included in the output device 2600. Specifically, the image analysis device 2000 may be implemented to similarly visually output information related to FIGS. 54 to 57.

Meanwhile, FIG. 59 shows that the brain-related morphological index related to the target element is output after the morphological value related to the target element is corrected. However, the image analysis device 2000 and the parameter acquisition device 2400 may be implemented to compute the brain-related morphological index on the basis of the morphological value related to the target element, correct the brain-related morphological index in consideration of the correction parameter, and output the corrected brain-related morphological index.

According to this embodiment, the image analysis device 2000 may compute a target morphological value corresponding to a region related to a target element of a target image captured under a first scan condition as a morphological estimate value of the target element under a second scan condition or a third scan condition rather than the first scan condition.

Accordingly, the image analysis device 2000 according to this embodiment may freely correct a target morphological value to a morphological estimate value corresponding to a more accurate scan condition, and thus it is possible to output morphological index information with improved accuracy.

An operation in which the correction parameter acquisition device 2400 according to an embodiment of the present application acquires a correction parameter will be described in detail below with reference to FIGS. 60 to 65.

Figure 60:
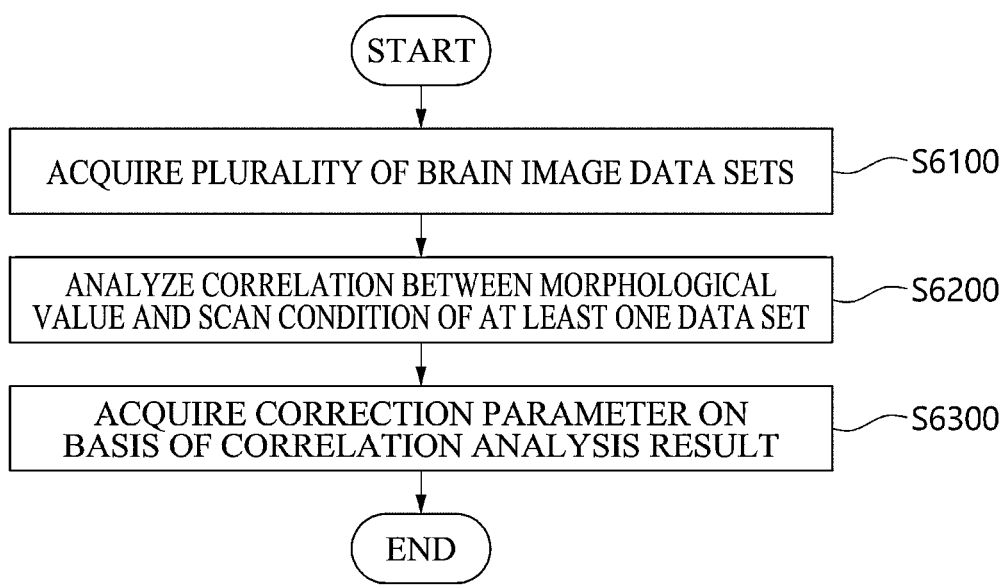
FIG. 60 is a flowchart showing one operation of a method of acquiring a correction parameter implemented by a correction parameter acquisition device 2400 according to an embodiment of the present application.

FIG. 60 is a flowchart showing one operation of a correction parameter acquisition method implemented by a correction parameter acquisition device 2400 according to an embodiment of the present application. The correction parameter, which will be described below, may be acquired by the correction parameter acquisition device 2400 according to an embodiment of the present application. In other words, the correction parameter acquisition operation disclosed in FIG. 60 may be implemented by the correction parameter acquisition device 2400.

Referring to FIG. 60, the correction parameter acquisition method according to an embodiment of the present application may include an operation of acquiring a plurality of brain image data sets (S6100), an operation of analyzing a correlation between morphological values corresponding to scan conditions of at least one of the data sets (S6200), and an operation of acquiring a correction parameter on the basis of a result of analyzing the correlation (S6300).

In the operation of acquiring a plurality of brain image data sets (S6100), the correction parameter acquisition device 2400 according to an embodiment of the present application may acquire a plurality of brain image data sets. In this case, the correction parameter acquisition device 2400 may acquire a plurality of brain image data sets from the image acquisition device 1000 or any external device.

Figure 61:
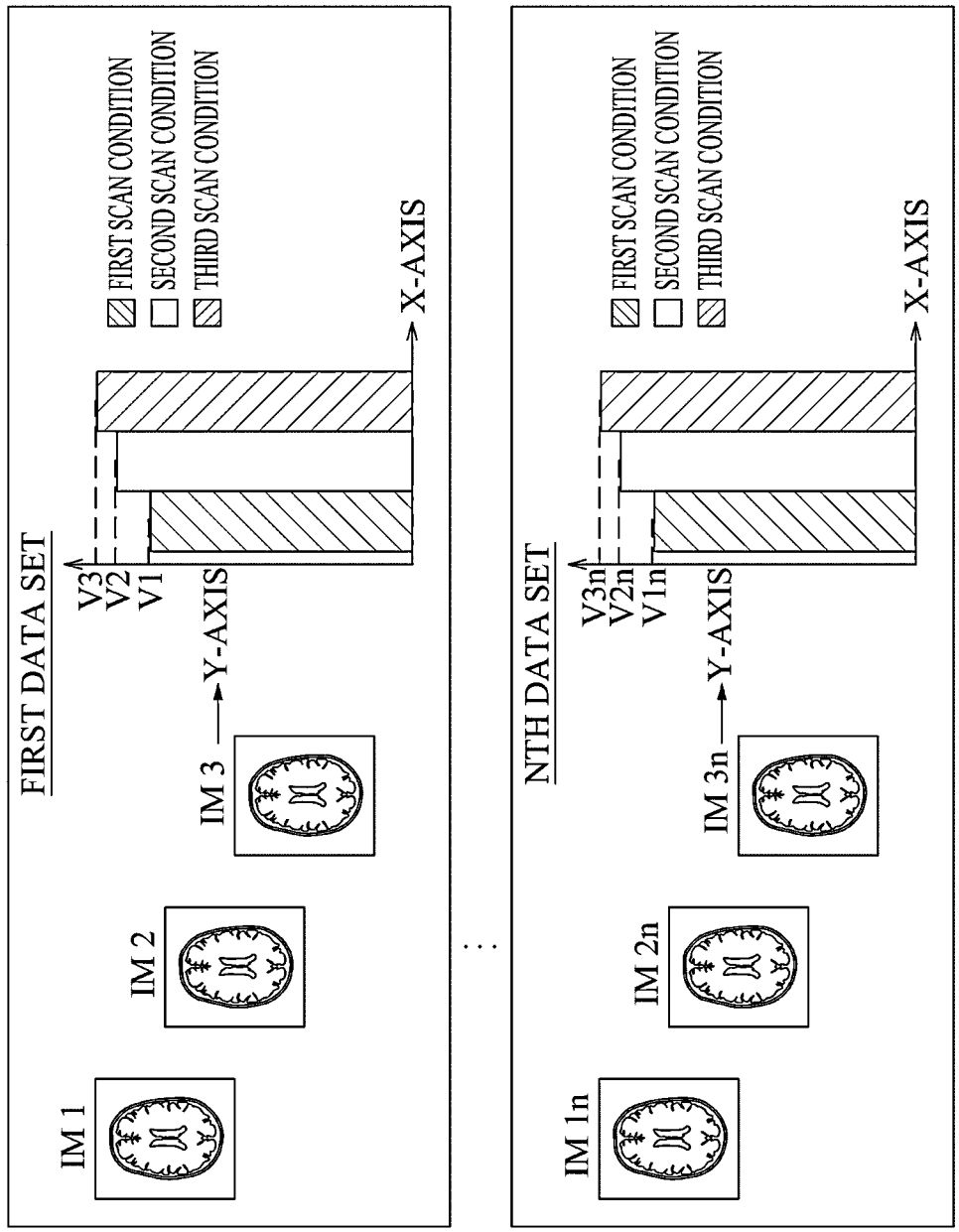
FIG. 61 is an exemplary diagram illustrating information included in a plurality of image data sets according to an embodiment of the present application.

Reference will be made to FIG. 61. FIG. 61 is an exemplary diagram illustrating information included in a plurality of brain image data sets according to an embodiment of the present application.

The plurality of brain image data sets may include information on a morphological figure or a morphological index of a region corresponding to the target element related to the brain image.

Also, the plurality of brain image data sets may include information on a scan condition in which the brain image is acquired or the location of the target element and information on a morphological figure or a morphological index acquired in relation to the scan condition or the location of the target element.

As an example, a first data set may include information regarding a first morphological figure (or a first morphological index V1) computed from a first brain image IM1 acquired under a first scan condition and information regarding a second morphological figure (or a second morphological index V2) computed from a second brain image IM2 acquired under a second scan condition. Also, the first data set may further include information regarding a third morphological figure (or a third morphological index V3) computed from a third brain image IM3 acquired under a third scan condition.

Also, the plurality of brain image data sets may further include a variety of brain data similar in form to the first data set. For example, an nth data set may include information regarding a first morphological figure (or a first morphological index V1$n$) computed from a first brain image IM1$n$ acquired under the first scan condition and information regarding a second morphological figure (or a second morphological index V2$n$) computed from a second brain image IM2$n$ acquired under the second scan condition. Also, the nth data set may further include information regarding a third morphological figure (or a third morphological index V3$n$) computed from a third brain image IM3$n$ acquired under the third scan condition.

Preferably, the plurality of brain image data sets may include a morphological figure (or a morphological index) corresponding to a scan condition of brain images acquired for the same target subject. For example, referring to FIG.

61, a first brain image IM1, a second brain image IM2, and a third brain image IM3 included in the first data set may be brain images acquired from a first target subject. Also, a first brain image IM1n, a second brain image IM2n, and a third brain image IM3n included in the nth data set may be brain images acquired from an nth target subject.

In this case, the first to third scan conditions include conditions related to the strength of a magnetic field (or the intensity of a magnetic field) related to image resolution of an image acquisition device, setting parameters related to the form of a generated magnetic field, which may be set in an image acquisition device, the type of manufacturer of an image acquisition device, or a combination thereof.

Meanwhile, the correction parameter acquisition device 2400 according to an embodiment of the present application may acquire a correction parameter using a data set that considers the characteristics of a target subject. The correction parameter acquisition device 2400 may acquire a correction parameter using a data set acquired from target subjects having one or more identical characteristics (e.g., age or gender). The correction parameter acquisition device 2400 may deliver one or more correction parameters to the image analysis device 2000 so that a correction parameter acquired based on a data set having a characteristic corresponding to the characteristic of a target subject corresponding to a target image can be used to analyze the target image.

Referring to FIG. 60 again, the correction parameter acquisition method according to an embodiment of the present application may include an operation of analyzing a correlation of a morphological value to a scan condition of at least one data set (S6200).

In the operation of analyzing a correlation between a morphological value to a scan condition of at least one data set (S6200), the correction parameter acquisition device 2400 according to an embodiment of the present application may be implemented to analyze a correlation between morphological figures (or morphological indices) corresponding to scan conditions included in at least one of a plurality of brain image data sets. In this case, a correlation analysis implemented by the correction parameter acquisition device 2400 according to an embodiment of the present application may be implemented using various statistical techniques such as linear analysis, nonlinear analysis, and regression analysis.

Also, the correction parameter acquisition method according to an embodiment of the present application may include an operation of acquiring a correction parameter on the basis of a result of the correlation analysis (S6300).

Specifically, the correction parameter acquisition device 2400 may acquire a first morphological figure V1$i$ acquired under a first scan condition, a second morphological figure V2$i$ acquired under a second scan condition, and a third morphological figure V3$i$ acquired under a third scan condition from an ith data set included in at least one of the plurality of brain image data sets.

Also, the correction parameter acquisition device 2400 may acquire a first morphological figure V1$j$ acquired under the first scan condition, a second morphological figure V2$j$ acquired under the second scan condition, and a third morphological figure V3$j$ acquired under the third scan condition from a jth data set as well as the ith data set.

In this case, the correction parameter acquisition device 2400 according to an embodiment of the present application may analyze a correlation between the first morphological figure and the second morphological figure acquired from the ith and jth data sets and may acquire a correction parameter between a morphological figure acquired under the first scan condition and a morphological figure acquired under the second scan condition on the basis of a result of the correlation analysis.

Also, the correction parameter acquisition device 2400 may analyze a correlation between the second morphological figure and the third morphological figure acquired from the ith and jth data sets and may acquire a correction parameter between a morphological figure acquired under the second scan condition and a morphological figure acquired under the third scan condition on the basis of a result of the correlation analysis.

Also, the correction parameter acquisition device 2400 may analyze a correlation between the first morphological figure and the third morphological figure acquired from the ith and jth data sets and may acquire a correction parameter between a morphological figure acquired under the first scan condition and a morphological figure acquired under the third scan condition on the basis of a result of the correlation analysis.

For example, the correction parameter acquisition device 2400 may acquire a correction parameter for transforming a morphological figure acquired under the first scan condition into a morphological figure measured under the second scan condition through the correlation analysis based on the first morphological figure acquired under the first scan condition and the second morphological figure acquired under the second scan condition. Alternatively, the correction parameter acquisition device 2400 may acquire a correction parameter for transforming a morphological figure acquired under the second scan condition into a morphological figure measured under the first scan condition.

For example, the correction parameter may be acquired from a transform function acquired through a correlation analysis between a first morphological value related to the target element acquired under the first scan condition and a second morphological value related to the target element acquired under the second scan condition. For example, when a linear function acquired through the correlation analysis between the first morphological value and the second morphological value is $y=a*x+b$, a and b may represent correction parameters for approximating the morphological value of the target element acquired under the first scan condition to the morphological value acquired under the second scan condition.

Also, through a correlation analysis in a manner similar to that described above, the correction parameter acquisition device 2400 may acquire a correction parameter for approximating a morphological value of the target element acquired under the second scan condition to a morphological value of the target element acquired under the third scan condition, a correction parameter for approximating a morphological value of the target element acquired under the first scan condition to a morphological value of the target element acquired under the third scan condition, a correction parameter for approximating a morphological value of the target element acquired under the second scan condition to a morphological value of the target element acquired under the first scan condition, or a correction parameter for approximating a morphological value of the target element acquired under the third scan condition to a morphological value of the target element acquired under the first scan condition.

Figure 62:
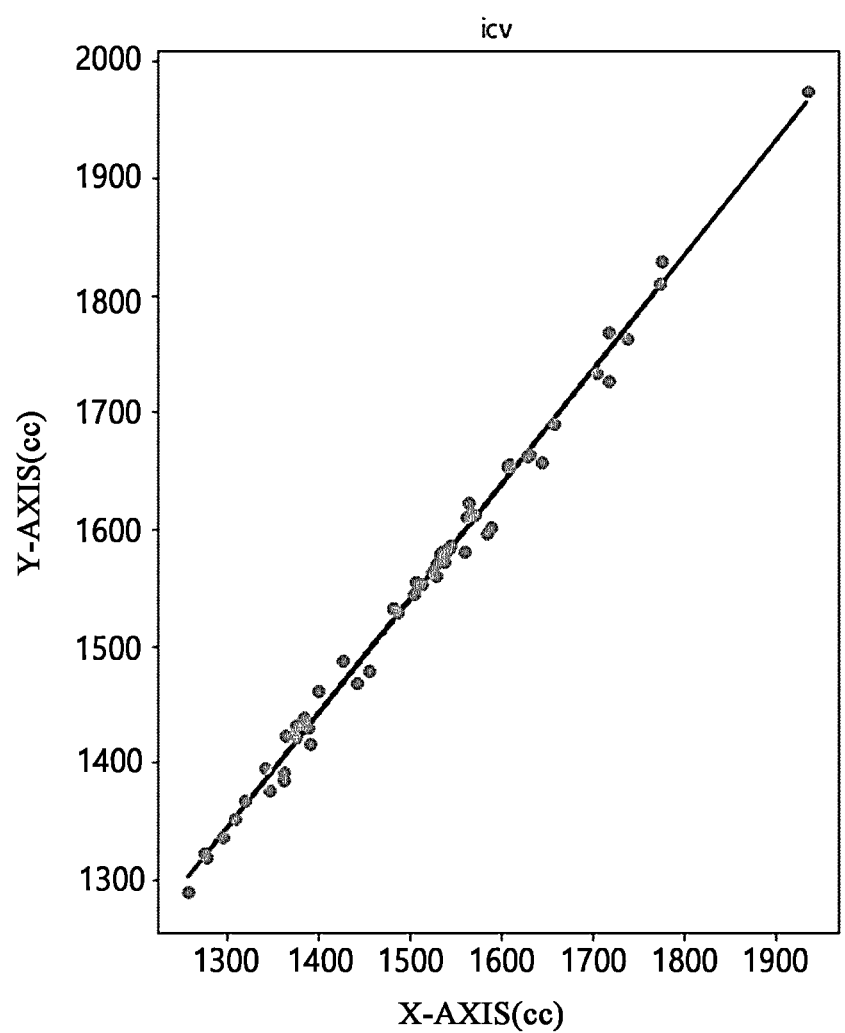
FIG. 62 is a graph showing an example of a correlation analysis for acquiring a correction parameter of the correction parameter acquisition device 2400 according to an embodiment of the present application.
Figure 63:
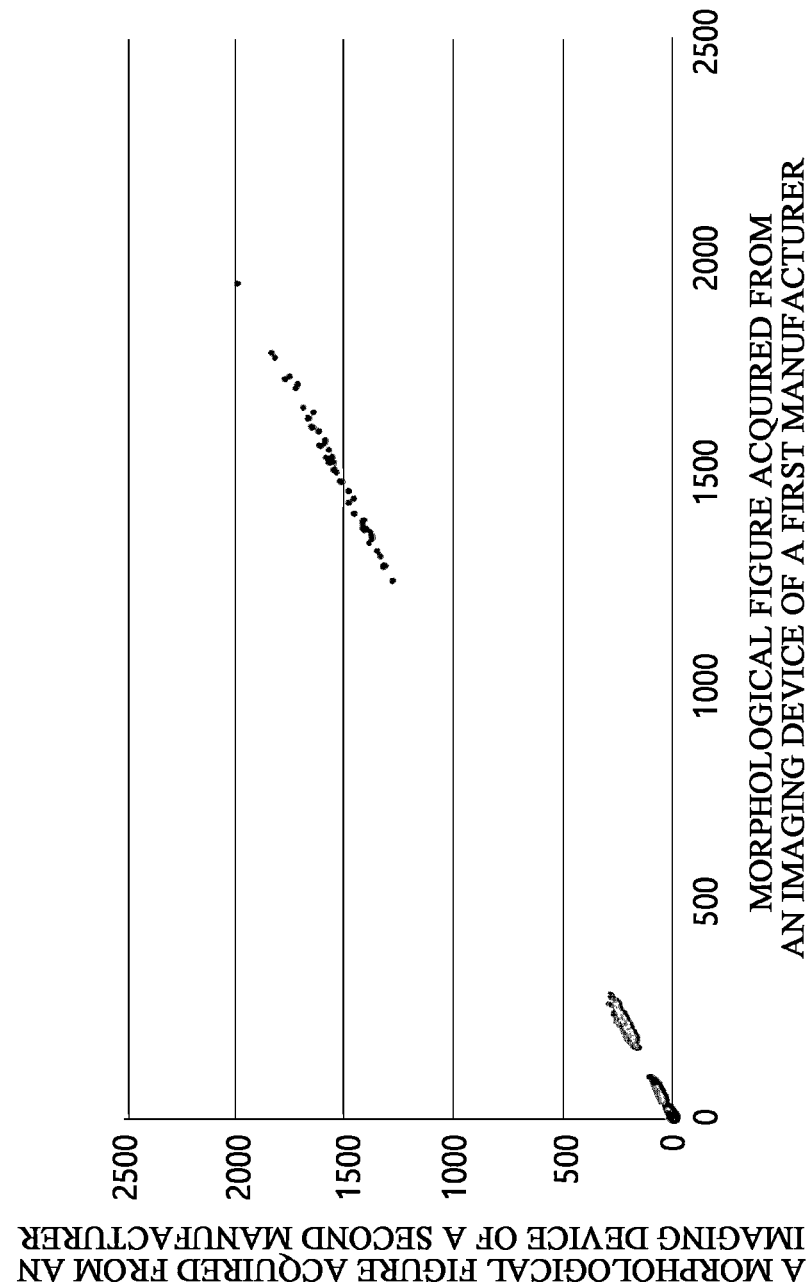
FIG. 63 is a graph showing another example of a correlation analysis for acquiring a correction parameter of the correction parameter acquisition device 2400 according to an embodiment of the present application.

Reference will be made to FIGS. 62 and 63.

FIG. 62 is a graph showing an example of a correlation analysis for acquiring a correction parameter of the correction parameter acquisition device 2400 according to an embodiment of the present application.

FIG. 63 is a graph showing another example of a correlation analysis for acquiring a correction parameter of the correction parameter acquisition device 2400 according to an embodiment of the present application.

Referring to FIG. 62, the correction parameter acquisition device 2400 may acquire, from an ith data set, a morphological figure (e.g., the volume of a target element) acquired under a first magnetic field strength (e.g., 1.5 T) and a morphological figure (e.g., the volume of a target element) acquired under a second magnetic field strength (e.g., 3 T or 8 T). In this case, the correction parameter acquisition device 2400 may acquire a correction parameter between a morphological figure acquired under the first magnetic field strength (e.g., 1.5 T) and a morphological figure acquired under the second magnetic field strength (e.g., 3 T or 8 T) by a correlation analysis method using any suitable statistical technique, such as linear analysis shown in FIG. 62. The correction parameter acquisition device 2400 may acquire a correction parameter for correcting a morphological figure acquired under the first magnetic field strength to a morphological figure acquired under the second magnetic field strength.

Referring to FIG. 63, the correction parameter acquisition device 2400 may acquire, from a jth data set, a morphological figure (e.g., the volume of a target element) acquired from an imaging device of a first manufacturer and a morphological figure (e.g., the volume of a target element) acquired from an imaging device of a second manufacturer. In this case, the correction parameter acquisition device 2400 may acquire a correction parameter between a morphological figure acquired from the imaging device of the first manufacturer and a morphological figure acquired from the imaging device of the second manufacturer by a correlation analysis method using any suitable statistical technique, such as linear analysis shown in FIG. 63. The correction parameter acquisition device 2400 may acquire a correction parameter for correcting a morphological figure acquired from a brain image acquired by the imaging device of the first manufacturer to a morphological figure acquired from a brain image acquired by the imaging device of the second manufacturer.

Figure 64:
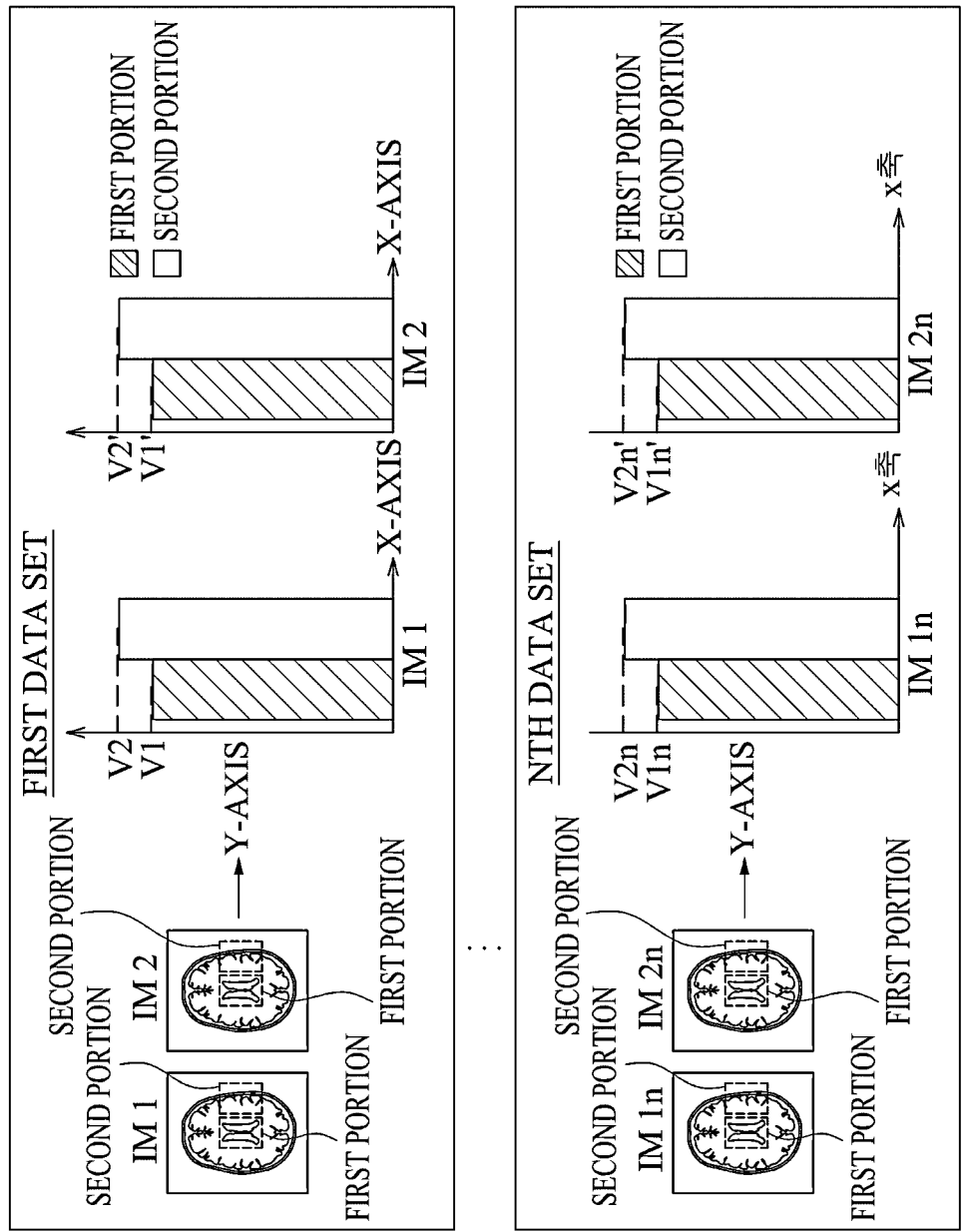
FIG. 64 is an exemplary diagram illustrating information included in a plurality of image data sets according to an embodiment of the present application.

However, the correlation analysis described in FIGS. 63 and 64 is merely an example, and it is possible to acquire a correction parameter between morphological figures corresponding to scan conditions by using any suitable statistical technique such as nonlinear analysis or regression analysis.

Also, FIGS. 63 and 64 illustrate a method of acquiring a correction parameter between morphological figures in consideration of variables such as a magnetic field strength and a manufacturer as scan conditions. However, it is obvious that a correction parameter can be acquired in consideration of a scan condition related to a setting parameter of an imaging device in such a similar way.

Also, it will be appreciated that a correction parameter between morphological figures corresponding to scan conditions can be acquired in consideration of at least two of a scan condition related to magnetic field strength, a scan condition related to a manufacturer, and a scan condition related to a setting parameter of an imaging device.

The following description refers to FIG. 60 again. A correction parameter acquisition method according to an embodiment of the present application may include an operation of analyzing a correlation between morphological values corresponding to scan conditions of at least one data set (S6200). In this case, the correction parameter acquisition device 2400 may be implemented to acquire a correction parameter by performing a correlation analysis in consideration of information regarding the location of the target element rather than the scan condition.

In other words, even under the same scan condition, parameters for correcting a morphological index may be different depending on the location of the target element. The correction parameter acquisition device 2400 according to an embodiment of the present application may be implemented to acquire a correction parameter for correcting a morphological index in consideration of the location of the target element.

Specifically, a difference between an actual morphological value (or a morphological reference value) and a measured morphological value of the target element may vary depending on the location of the target element acquired from the target image. The image analysis device 2000 according to an embodiment of the present application may correct the measured morphological value of the target element in consideration of the location of the target element.

For example, the image analysis device 2000 may acquire a first correction parameter from the correction parameter acquisition device 2400 in order to approximate a measured morphological value of a first brain element to an actual morphological value (or a morphological reference value) of the first brain element. On the other hand, the image analysis device 2000 may acquire a second correction parameter from the correction parameter acquisition device 2400 in order to approximate a measured morphological value of a second brain element to an actual morphological value (or a morphological reference value) of the second brain element.

As another example, the image analysis device 2000 may acquire a first correction parameter from the correction parameter acquisition device 2400 in order to approximate a measured morphological value of a first brain element to an actual morphological value (or a morphological reference value) of the first brain element. On the other hand, the image analysis device 2000 may determine that the measured morphological value of the second brain element is substantially the same as the actual morphological value (or the morphological reference value) of the second brain element. In this case, the image analysis device 2000 may be implemented not to acquire the second correction parameter of the correction parameter acquisition device 2400.

In other words, the image analysis device 2000 may be implemented to differently perform whether to correct the measured morphological value according to the location of the target element.

In this case, any type of threshold may be set for determining whether a measured morphological value of a brain element is substantially the same as an actual morphological value of the brain element.

The following description will focus on content that is changed from or added to the correction parameter acquisition method according to an embodiment of the present application in consideration of information regarding the location of the target element in addition to the scan condition.

In the operation of acquiring a plurality of brain image data sets (S6100), the correction parameter acquisition device 2400 according to an embodiment of the present application may acquire a plurality of brain image data sets from the image acquisition device 1000 or any external device. In this case, the correction parameter acquisition device 2400 may acquire a plurality of brain image data sets from a database or any external device.

Reference will be made to FIG. 64. FIG. 64 is an exemplary diagram illustrating information included in a plurality of image data sets according to an embodiment of the present application.

The plurality of brain image data sets may include information on a morphological figure or a morphological index of the location of a target element and a scan condition in which a brain image is acquired.

As an example, a first data set may include information regarding a morphological figure (or a morphological index V1) computed from a region corresponding to a first portion of a first brain image IM1 acquired under a first scan condition and information regarding a morphological figure (or a morphological index V2) computed from a region corresponding to a second portion of the first brain image IM1 acquired under the first scan condition. Also, a first data set may include information regarding a morphological figure (or a morphological index V1') computed from a region corresponding to a first portion of a second brain image IM2 acquired under a second scan condition and information regarding a morphological figure (or a morphological index V2') computed from a region corresponding to a second portion of the second brain image IM2 acquired under the second scan condition.

Also, the plurality of brain image data sets may further include a variety of brain data similar to the first data set. For example, an nth data set may include information regarding a morphological figure (or a morphological index V1n) computed from a region corresponding to a first portion of an nth brain image IMn acquired under a first scan condition and information regarding a morphological figure (or a morphological index V2n) computed from a region corresponding to a second portion of the first brain image IM1n acquired under the first scan condition. Also, an nth data set may include information regarding a morphological figure (or a morphological index V1n') computed from a region corresponding to a first portion of a second brain image IM2n acquired under a second scan condition and information regarding a morphological figure (or a morphological index V2n') computed from a region corresponding to a second portion of the second brain image IM2n acquired under the second scan condition.

In this case, the second portion may be located closer to the skull than the first portion. That is, the first portion and the second portion may be brain elements present in different locations in the skull.

Also, the first portion and the second portion may be anatomically distinguished.

Alternatively, the first portion and the second portion may perform different functions. In other words, the first portion may be a brain element that performs a first brain function while the second portion may be a brain element that performs a second brain function.

Referring to FIG. 60 again, the correction parameter acquisition method according to an embodiment of the present application may include an operation of analyzing a correlation between morphological values corresponding to a scan condition of at least one data set (S6200) and an operation of acquiring a correction parameter based on a result of the correlation analysis (S6300).

In this case, the correction parameter acquisition method according to an embodiment of the present application may include performing the correlation analysis based on morphological values corresponding to the scan conditions of at least one data set and "the locations of target elements."

Figure 65:
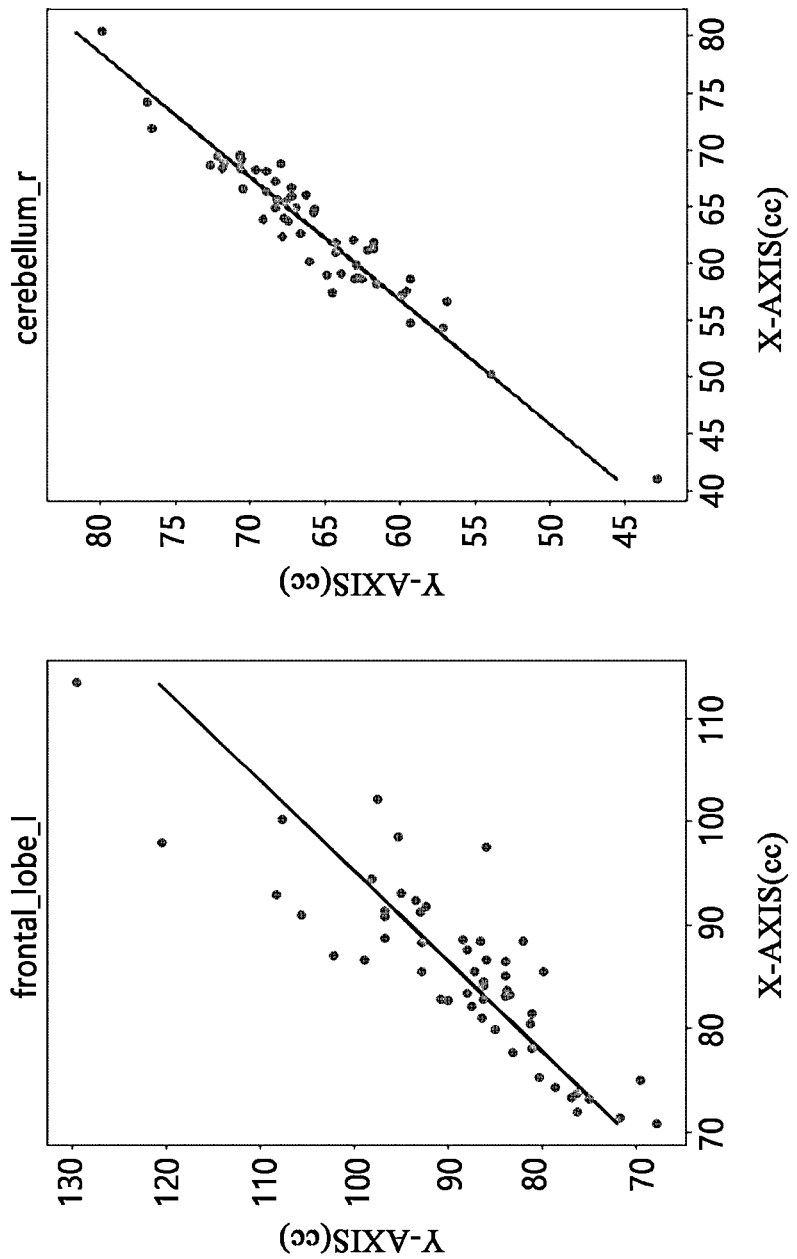
FIG. 65 is an exemplary diagram of a correlation analysis between morphological values corresponding to locations where a target element is distributed in a skull according to an embodiment of the present application.

Reference will be made to FIG. 65. FIG. 65 is an exemplary diagram of a correlation analysis between morphological values corresponding to locations of target elements according to an embodiment of the present application. In this case, the x-axis may be a morphological figure acquired under a first scan condition, and the y-axis may be a morphological figure acquired under a second scan condition.

As an example, referring to FIG. 65, the correction parameter acquisition device 2400 may acquire a first correction parameter for a first portion (e.g., a frontal lobe region) included in an ith data set on the basis of a morphological figure V1i acquired from an ith brain image IM1i captured under a first scan condition (e.g., 1.5 T) and a morphological figure V1i' acquired from an ith brain image IM2i captured under a second scan condition (e.g., 3 T or 8 T).

As another example, referring to FIG. 65, the correction parameter acquisition device 2400 may acquire a second correction parameter for a second portion (e.g., a cerebellum region) included in a jth data set on the basis of a morphological figure V2j acquired from a jth brain image IM1j captured under the first scan condition (e.g., 1.5 T) and a morphological figure V2j' acquired from a jth brain image IM2j captured under the second scan condition (e.g., 3 T or 8 T).

In this case, the first correction parameter for the first portion may be different from the second correction parameter for the second portion.

For example, the first correction parameter may include a parameter for approximating a morphological figure related to the first portion acquired under the first scan condition to a morphological figure related to the first portion acquired under the second scan condition. Alternatively, the first correction parameter may include a parameter for approximating a morphological figure related to the first portion acquired under the second scan condition to a morphological figure related to the first portion measured under the first scan condition.

For example, the first correction parameter may be acquired from a transform function acquired through a correlation analysis between the morphological value related to the first portion acquired under the first scan condition and the morphological value related to the first potion acquired under the second scan condition. For example, when a linear function acquired through the correlation analysis between the first morphological value and the second morphological value is $y=a1*x+b1$, a1 and b1 may represent parameters for approximating a morphological value of the first portion acquired under the first scan condition to a morphological value of the first portion acquired under the second scan condition.

On the other hand, the second correction parameter may include a parameter for approximating a morphological figure related to the second portion acquired under the first scan condition to a morphological figure related to the second portion measured under the second scan condition through the correlation analysis based on the morphological figure related to the "second portion" acquired under the first scan condition and the morphological figure related to the "second portion" acquired under the second scan condition. Alternatively, the second correction parameter may include a parameter for approximating a morphological figure related to the second portion acquired under the second scan condition to a morphological figure related to the second portion measured under the second scan condition.

For example, the second correction parameter may be acquired from a transform function acquired through a correlation analysis between the morphological value related to the second portion acquired under the first scan condition and the morphological value related to the second potion acquired under the second scan condition. For example, when a linear function acquired through the correlation analysis between the first morphological value and the second morphological value is y=a2*x+b2, a2 and b2 may represent correction parameters for approximating a morphological value of the second portion acquired under the first scan condition to a morphological value of the second portion acquired under the second scan condition.

Also, through a correlation analysis in a manner similar to that described above, the correction parameter acquisition device 2400 may acquire a correction parameter for approximating a morphological value of the first portion acquired under the second scan condition to a morphological value of the first portion under a third scan condition and a correction parameter for approximating a morphological value of the second portion acquired under the second scan condition to a morphological value of the second portion acquired under the third scan condition.

Also, through a correlation analysis in a manner similar to that described above, the correction parameter acquisition device 2400 may acquire a correction parameter for approximating a morphological value of the first portion acquired under the first scan condition to a morphological value of the first portion under the third scan condition and a correction parameter for approximating a morphological value of the second portion acquired under the first scan condition to a morphological value of the second portion acquired under the third scan condition.

Advantageously, the correction parameter acquisition device 2400 according to an embodiment of the present application may more accurately acquire a correction parameter for each portion in consideration of a variable for the location of a target element and may compensate for a morphological figure or index that is affected according to a scan condition for each portion.

Therefore, the image analysis device 2000 according to an embodiment of the present application can provide a user with a more accurate and objective morphological index and auxiliary diagnostic index related to brain diseases.

Additionally, the correction parameter acquisition device 2400 according to an embodiment of the present application may be implemented to perform the above-described correction parameter acquisition operation on target elements present in both the left and right hemispheres of a brain (e.g., a first brain element and a second brain element).

For example, in an example related to FIG. 65, the correction parameter acquisition device 2400 may acquire a correction parameter by performing a correlation analysis on a first portion (e.g., a frontal lobe) located in the left hemisphere.

Also, the correction parameter acquisition device 2400 may be implemented to acquire a correction parameter by performing a correlation analysis on a first portion (e.g., a frontal lobe) located in the right hemisphere. The correction parameters acquired for the first portion in the left and right hemispheres may be different from each other.

Meanwhile, there may be a need to modify a morphological value or a morphological index related to a target element output from the image analysis device 2000 into a morphological value or a morphological index corresponding to a scan condition targeted by a user of the image analysis device 2000. For example, when an output morphological value related to a target element or the like is a value acquired based on a morphological value acquired under a first scan condition, a user may want to receive morphological information regarding the target element as results corresponding to a morphological value acquired under the second scan condition rather than the first scan condition.

The image analysis device 2000 according to an embodiment of the present application may be implemented to acquire an input related to a reference scan condition from a user through an input module and output morphological information related to a target element corresponding to a user input.

Another embodiment for correcting a brain-related morphological index on the basis of a user input related to the reference scan condition will be described in detail below with reference to FIG. 66. FIG. 66 is a diagram illustrating a flowchart of an image analysis method according to an embodiment of the present application and, specifically, is a diagram showing sub-operations of operation S5300 of FIG. 58.

Figure 66:
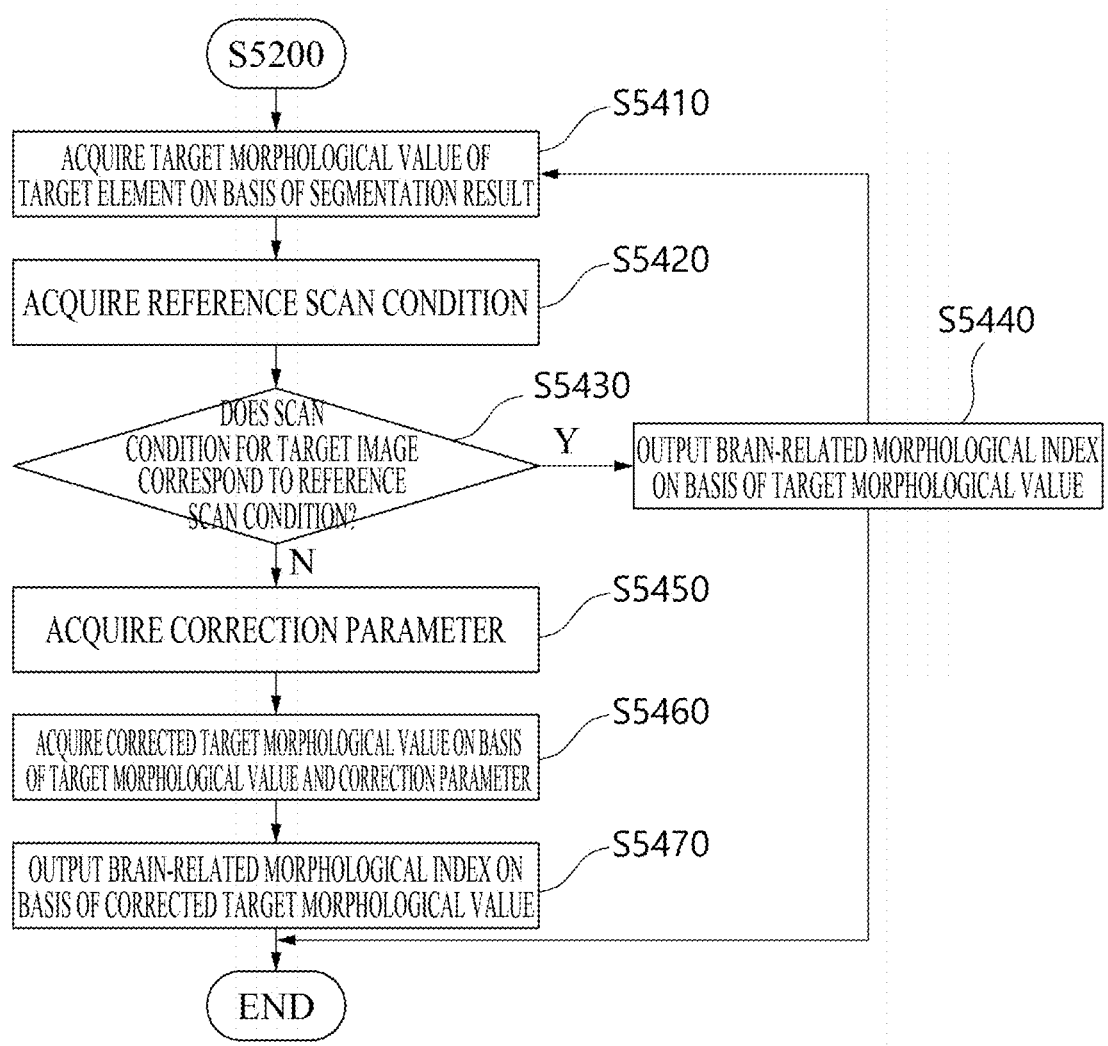
FIG. 66 is a flowchart of an image analysis method according to an embodiment of the present application.

Referring to FIG. 66, the operation of correcting a brain-related morphological index (S5300) according to an embodiment of the present application may include an operation of acquiring a target morphological value of a target element on the basis of a segmentation result (S5410), an operation of acquiring a reference scan condition (S5420), and an operation of determining whether the scan condition of the target image corresponds to the reference scan condition (S5430).

When the scan condition of the target image corresponds to the reference scan condition, the operation of correcting a brain-related morphological index (S5300) according to an embodiment of the present application may include an operation of outputting the brain-related morphological index on the basis of a target morphological value (S5440).

Meanwhile, when the scan condition of the target image does not correspond to the reference scan condition, the operation of correcting a brain-related morphological index (S5300) according to an embodiment of the present application may include an operation of acquiring a correction parameter (S5450), an operation of acquiring a corrected target morphological value on the basis of the target morphological value and the correction parameter (S5460), and an operation of outputting a brain-related morphological index on the basis of the corrected target morphological value (S5470).

In the operation of acquiring a target morphological value of a target element on the basis of a segmentation result (S5410), the image analysis device 2000 may acquire a target morphological value related to a target element on the basis of voxel data of a target image related to a region corresponding to the target element acquired through the segmentation operation.

Alternatively, the image analysis device 2000 may acquire a morphological value related to the internal region of the skull on the basis of voxel data of the target image related to the internal region of the skull acquired by the segmentation operation.

Also, in the operation of acquiring a target morphological value of a target element on the basis of a segmentation result (S5410), the image analysis device 2000 may acquire a brain-related morphological value related to a target element on the basis of a morphological value related to the target element and a morphological value related to the internal region of the skull.

In this case, the target morphological value or the brain-related morphological index may be a value related to a morphological character including volume, thickness, length, and shape.

In the operation of acquiring a reference scan condition (S5420), the image analysis device 2000 may acquire a user's input related to the reference scan condition through the input module 2040 included in the image analysis device 2000. Alternatively, the image analysis device 2000 may acquire a user's input related to the reference scan condition through the input module 2640 of the output device 2600.

Alternatively, the reference scan condition may be preset. The image analysis device 2000 may acquire information regarding the preset reference scan condition.

In this case, the reference scan condition may be a scan condition related to magnetic field strength, a setting parameter of an imaging device, or the manufacturer of an imaging device. Alternatively, the reference scan condition may be a scan condition that additionally considers the location of a target element for which a morphological index is to be acquired.

By acquiring the reference scan condition, the image analysis device 2000 may output or correct a brain-related morphological index or a morphological value of a target element corresponding to the reference scan condition. For example, by inputting the reference scan condition, the user may receive a brain-related morphological index or a morphological value related to a target element which is estimated as a value measured under the reference scan condition.

In the operation of determining whether the scan condition of the target image corresponds to the reference scan condition (S5430), the image analysis device 2000 may determine whether the acquired reference scan condition corresponds to the scan condition in which the target image is captured.

Specifically, the image analysis device 2000 may acquire information regarding the scan condition in which the target image is captured from the image acquisition device 1000 or any external device (e.g., a server).

For example, as described above, a scan condition in which a target image is captured may be structured as metadata with respect to the target image, and the image analysis device 2000 may acquire information regarding the scan condition in which the target image is captured by recognizing the metadata regarding the scan condition in which the target image is captured.

As another example, the image analysis device 2000 may acquire the scan condition in which the target image is captured by receiving the scan condition in which the target image is captured from a user through an input module.

As another example, as described above, information regarding the scan condition in which the target image is captured may be acquired from any external device.

In this case, the image analysis device 2000 may determine whether the acquired scan condition in which the target image is captured corresponds to the reference scan condition.

For example, when a target image is captured in a magnetic field with a strength of 1.5 T and information regarding a reference scan condition related to the magnetic field with the strength of 3 T is acquired from a user, the image analysis device 2000 may determine that the scan condition of the target image does not correspond to the reference scan condition.

n the other hand, when a target image is captured in a magnetic field with a strength of 3 T and a reference scan condition related to the magnetic field with the strength of 3 T is acquired from a user, the image analysis device 2000 may determine that the scan condition of the target image corresponds to the reference scan condition.

As another example, when a target image is captured by an imaging device manufactured by a first manufacturer and a reference scan condition related to a second manufacturer is acquired, the image analysis device 2000 may determine that the scan condition of the target image does not correspond to the reference scan condition.

In the other hand, when a target image is captured by an imaging device manufactured by a first manufacturer and a reference scan condition related to the first manufacturer is acquired, the image analysis device 2000 may determine that the scan condition of the target image corresponds to the reference scan condition.

In the operation of determining whether the scan condition of the target image corresponds to the reference scan condition (S5430), when determining that the scan condition of the target image corresponds to the reference scan condition, the image analysis device 2000 may be implemented to output a brain-related index on the basis of the target morphological value of the target element acquired based on the segmentation result.

In other words, when the scan condition of the target image corresponds to the reference scan condition, there is no need to perform correction to the scan condition that a user wants to be provided. Thus, the image analysis device 2000 may be implemented to output a brain-related morphological index on the basis of the target morphological value of the target element acquired based on the segmentation result.

On the other hand, in the operation of determining whether the scan condition of the target image corresponds to the reference scan condition (S5430), when determining that the scan condition of the target image does not correspond to the reference scan condition, the image analysis device 2000 may be implemented to acquire a correction parameter acquired based on a correlation analysis corresponding to the scan condition of the target image and the reference scan condition from the correction parameter acquisition device 2400.

For example, when a target image is captured in a magnetic field with a strength of 1.5 T and a reference scan condition related to a magnetic field with a strength of 3 T is acquired, the image analysis device 2000 may be implemented to acquire, from the correction parameter acquisition device 2400, a correction parameter for transforming or approximating a first morphological value acquired from a first image captured in a magnetic field with a strength of 1.5 T into a second morphological value acquired from a second image captured in a magnetic field with a strength of 3 T. Alternatively, the image analysis device 2000 may determine, as the correction parameter, a parameter for transforming or approximating a first morphological value acquired from a first image captured in a magnetic field with a strength of 1.5 T into a second morphological value acquired from a second image captured in a magnetic field with a strength of 3 T from a correction parameter database acquired from the correction parameter acquisition device 2400.

As another example, when a target image is captured by an imaging device manufactured by a first manufacturer and a reference scan condition related to a second manufacturer is acquired, the image analysis device 2000 may be implemented to acquire, from the correction parameter acquisition device 2400, a correction parameter for transforming or approximating a first morphological value acquired from a first image captured by the imaging device of the first manufacturer into a second morphological value acquired from a second image captured by the imaging device of the second manufacturer. Alternatively, the image analysis device 2000 may determine, as the correction parameter, a parameter for transforming or approximating a first morphological value acquired from a first image captured by the imaging device of the first manufacturer into a second morphological value acquired from a second image captured by the imaging device of the second manufacturer from a correction parameter database acquired from the correction parameter acquisition device 2400.

In the operation of acquiring a corrected target morphological value on the basis of the target morphological value and the correction parameter (S5460), the image analysis device 2000 may acquire a corrected target morphological value (or a corrected target morphological value) on the basis of the target morphological value of the target element acquired based on the segmentation result and the acquired correction parameter.

For example, when a target image is captured in a magnetic field with a strength of 1.5 T and a reference scan condition related to a magnetic field with a strength of 3 T is acquired, the image analysis device 2000 may acquire a first correction parameter for correcting a morphological value (or a morphological index) related to a target element acquired from a brain image captured in a magnetic field of 1.5 T to a morphological value (or a morphological index) corresponding to what is acquired in a magnetic field of 3 T. In this case, the image analysis device 2000 may acquire a corrected target morphological value by applying the first correction parameter to a target morphological value (or a target morphological index) related to the target element acquired based on the segmentation result of the target image.

As another example, when a target image is captured by an imaging device manufactured by a first manufacturer and a reference scan condition related to a second manufacturer is acquired, the image analysis device 2000 may acquire a second correction parameter for correcting a morphological value (or a morphological index) related to a target element acquired from a brain image captured by the imaging device of the first manufacturer to a morphological value (or a morphological index) corresponding to what is acquired by an imaging device of the second manufacturer. In this case, the image analysis device 2000 may acquire a corrected target morphological value by applying the second correction parameter to a target morphological value (or a target morphological index) related to the target element acquired based on the segmentation result of the target image.

In the operation of outputting a brain-related morphological index on the basis of the corrected target morphological value (S5470), the image analysis device 2000 may output a brain-related index associated with the target element on the basis of the corrected target morphological value.

For example, the image analysis device 2000 may be implemented to compute and output a brain-related morphological index associated with the target element on the basis of the corrected target morphological value and the morphological value corresponding to the internal region of the skull acquired according to the segmentation result of the target image. More specifically, the image analysis device 2000 may be implemented to compute and output a ratio of the corrected target morphological value to the morphological value corresponding to the internal region of the skull as the brain-related morphological index associated with the target element.

In this case, as described above, the morphological value corresponding to the internal region of the skull may be a value that is corrected by acquiring a correction parameter according to a user's input of a reference scan condition.

Although the above description has focused on magnetic field strength and the manufacturer of an imaging device as a scan condition, the present invention is not limited thereto. The above description may be similarly applicable to a scan condition for a setting parameter regarding an imaging device.

Also, referring to FIG. 66, it has been described that the image analysis device 2000 determines whether the scan condition of the target image corresponds to the reference scan condition, and a correction parameter is acquired or determined according to a result of the determination, but the present invention is not limited thereto. A process in which the image analysis device 2000 determines whether the scan condition of the target image corresponds to the reference scan condition will be omitted. For example, the image analysis device 2000 may be implemented to acquire a reference scan condition and a scan condition of a target image and acquire a corrected target morphological value or a brain-related morphological index on the basis of a correction parameter determined based on the scan condition of the target image and the reference scan condition.

A user interface for receiving an input related to a user's reference scan condition and an example of morphological index-related information output according to an embodiment of the present application will be described below with reference to FIG. 67. FIG. 67 is a diagram schematically showing a user interface according to an embodiment of the present application.

Figure 67:
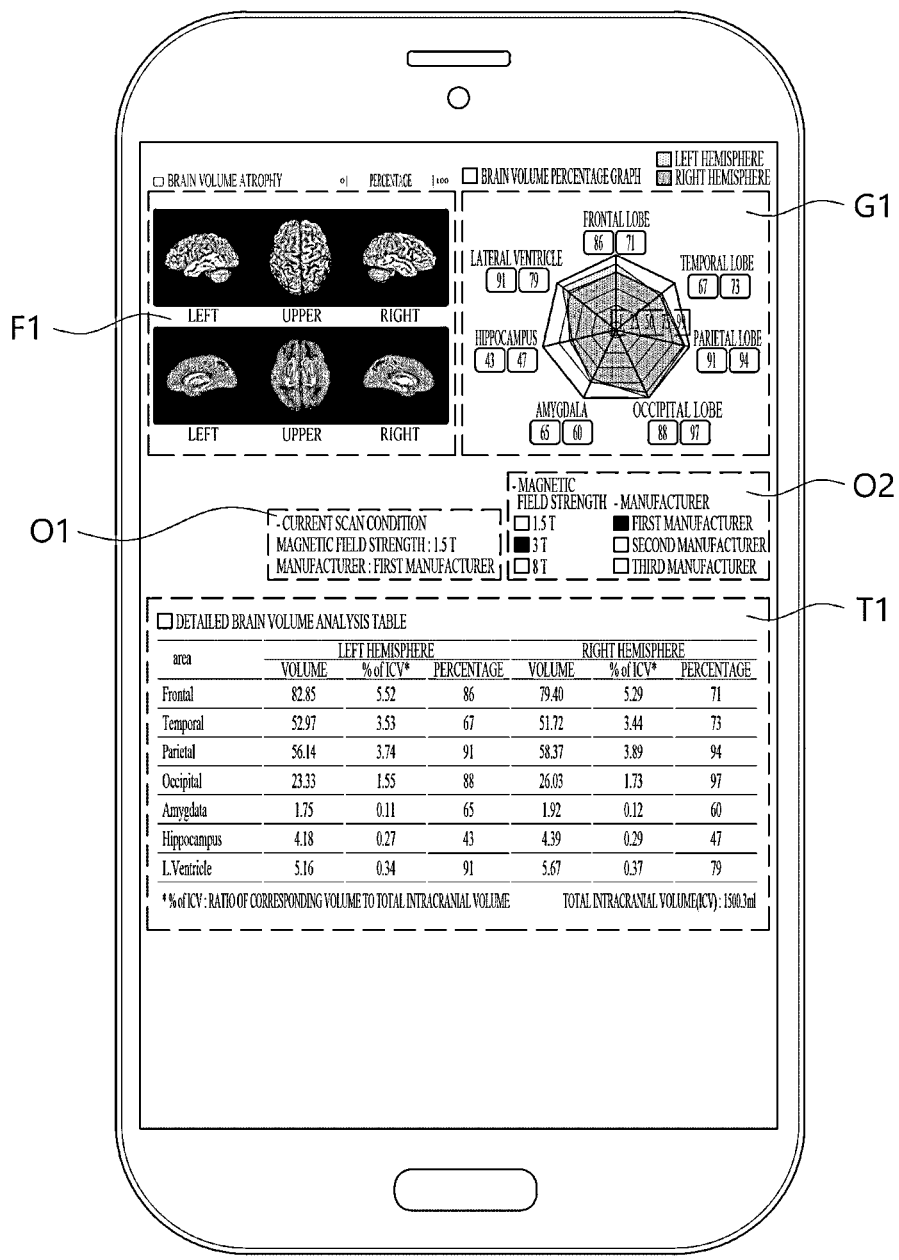
FIG. 67 is a diagram schematically showing a user interface according to an embodiment of the present application.

Referring to FIG. 67, the user interface according to an embodiment of the present application may be provided to acquire a user's input related to a reference scan condition through an input module 2040 or 2640 and output information corresponding to a user's input related to a reference scan condition through an output module 2050 or 2650. In this case, the output module 2050 or 2650 may be implemented in any suitable form such as a smartphone display and a monitor display.

As an example, the image analysis device 2000 may output morphological index-related information through the output module 2050 of the image analysis device 2000 or the output module 2650 of the output device 2600.

In this case, the image analysis device 2000 may be implemented to output information O1 on the current scan condition. Specifically, the image analysis device 2000 may be implemented to output information O1 on a scan condition to which the output morphological index-related information corresponds. For example, referring to FIG. 67 again, the morphological index-related information being currently output may include information indicating that a target image is acquired by an imaging device manufactured by a first manufacturer under a scan condition corresponding to a magnetic field of a strength of 1.5 T.

The user interface according to an embodiment of the present application may be implemented to output information O2 on reference scan conditions including checkboxes for acquiring a user's input to a reference scan condition.

In detail, the user interface may be implemented for a user to select a checkbox corresponding to a reference scan condition related to magnetic field strength through an input module, and the image analysis device 2000 may acquire the reference scan condition related to magnetic field strength through the user interface.

Also, the user interface may be implemented for a user to select a checkbox corresponding to the reference scan condition related to manufacturers through an input module, and the image analysis device 2000 may acquire the reference scan condition related to manufacturers through the user interface. The information O2 on reference scan conditions may be input through another type of input interface other than the checkbox.

For example, referring to FIG. 67, a user may enter, through an input module, input data for transforming morphological index-related information being currently output (information F1, G1, and T1 computed under scan conditions corresponding to an imaging device manufactured by a first manufacturer and a magnetic field with a strength of 1.5 T) into morphological index-related information such as what is acquired under scan conditions corresponding to an imaging device manufactured by a first manufacturer and a magnetic field with a strength of 3 T.

In this case, the image analysis device 2000 may be implemented to perform an operation of acquiring a corresponding correction parameter based on the acquired reference scan condition and correcting and outputting a morphological value (or a morphological index) as described with reference to FIG. 67.

In this case, the image analysis device 2000 may be implemented to change and output previously output morphological index-based information on the basis of the corrected morphological value or the corrected morphological index.

For example, a morphological value or a morphological index computed according to a reference scan condition acquired from a user may be changed. Based on this change, the image analysis device 2000 may be implemented to modify and output a brain volume percentage graph G1 based on the changed morphological value or morphological index through the output module 2050.

As another example, a morphological value or a morphological index computed according to a reference scan condition acquired from a user may be changed. Based on this change, the image analysis device 2000 may be implemented to modify and output values such as percentages related to the morphological value or the morphological index included in a detailed brain volume analysis table T1 through the output module 2050.

As another example, a morphological value or a morphological index computed according to a reference scan condition acquired from a user may be changed. Based on this change, the image analysis device 2000 may be implemented to modify and output a color corresponding to a percentage related to a morphological index included in a brain volume atrophy F1 through the output module 2050.

However, the user interface shown in FIG. 67 is merely an example, and the user interface may be implemented to acquire any suitable user input through any suitable method and output an analysis result of an image analysis device changed based on the user input through any suitable method.

According to this embodiment, the image analysis device 2000 may compute a target morphological value corresponding to a region related to a target element of a target image captured under a first scan condition as a morphological estimate value of the target element under a second scan condition or a third scan condition rather than the first scan condition.

Accordingly, the image analysis device 2000 according to this embodiment may freely correct a target morphological value to a morphological estimate value corresponding to a scan condition desired by a user, and thus it is possible to provide the user with morphological index information corresponding to the scan condition desired by the user.

Meanwhile, an example for correcting a morphological figure according to an embodiment of the present application may be performed even before the segmentation operation S5200 of FIG. 58. In other words, in order to more accurately acquire a morphological figure, the image analysis device 2000 may be implemented to perform a correction operation before the segmentation operation S5200.

In this case, according to an embodiment of the present application, correction related to a target image may be implemented differently for each scan condition in which the target image is obtained.

As an example, the image analysis device 2000 may be provided to perform an operation such as normalization of the intensity of a target image. In this case, a correction method for intensity regularization may be implemented differently for each scan condition in which the target image is acquired.

As another example, the image analysis device 2000 may be implemented to perform an operation of transforming the target image into a brain image corresponding to a scan condition related to target magnetic field strength or setting parameters. For example, the image analysis device 2000 may transform the target image into a brain image corresponding to the target scan condition using any suitable software such as an MR simulator, an image transform technique, or a trained artificial neural network. In this case, the correction of the target image may be performed by providing different image transformation parameters, such as the MR simulator, for each scan condition in which the target image is acquired, in particular, in consideration of setting parameters (e.g., TR, TE, etc.) in which the target image is acquired. In this case, considering a scan condition, the image analysis device 2000 may be implemented to acquire or compute a transformation parameter for transforming a target image into a brain image corresponding to a target scan condition.

Alternatively, correction related to a target image may be provided differently for each location of the target image.

As an example, the image analysis device 2000 may be implemented to perform preprocessing on a first region corresponding to a first brain element through a first method and perform preprocessing on a second region corresponding to a second brain element through a second method different from the first method.

For example, the first region corresponding to the first brain element may be located closer to the skull region than the second region corresponding to the second brain element. In this case, in relation to the resolution or sharpness of the target image, the first region may not be clearer than the second region. In this case, the image analysis device 2000 may be implemented to perform preprocessing on the first region to improve the sharpness of the first region using the first method and perform preprocessing on the second region to improve the accuracy of image analysis using any suitable second method.

As described above, the image analysis device 2000 according to an embodiment of the present application may correct a morphological figure (e.g., a morphological value or a morphological index) acquired based on the segmentation result and also perform additional correction in consideration of a scan condition or the like before the segmentation. Thus, it is possible to acquire more accurate morphological features.

Therefore, the image analysis device 2000 according to an embodiment of the present application can provide a user with an objective auxiliary diagnostic index related to brain diseases.

Various pieces of index information may be acquired by analyzing a medical image, and medical information that may be derived from the index information may also vary. For example, the medical information that may be derived from the index information may relate to diagnostic information, analysis information, or prescription information acquired by analyzing the index information.

In this case, information required for users among the acquired variety of index information may be different for each user. Accordingly, there is a need to selectively provide index information necessary for a user among a variety of index information included in a medical image. Alternatively, there is also a need to selectively provide index information selected according to a user's concern from among a variety of index information included in a medical image. That is, by providing necessary information to users differently depending on patient information or user information, it is possible for the users to easily acquire information compared to uniformly providing index information derived from a medical image.

According to an embodiment, an image output device may selectively provide a user with necessary index information among a variety of index information acquired by analyzing a captured medical image.

Figure 68:
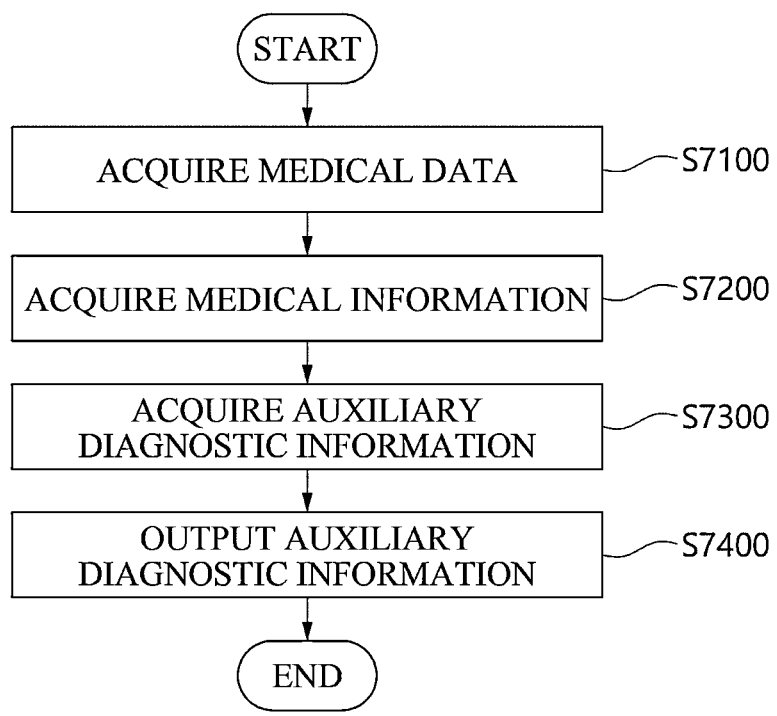
FIG. 68 is a diagram illustrating a medical information output process according to an embodiment.

FIG. 68 is a diagram illustrating a medical information output process according to an embodiment.

Referring to FIG. 68, the medical information output process according to an embodiment may include an operation of acquiring a medical image (S4100), an operation of acquiring medical information (S4200), an operation of acquiring auxiliary diagnostic information (S4300), and an operation of outputting the auxiliary diagnostic information (S4400).

Figure 69:
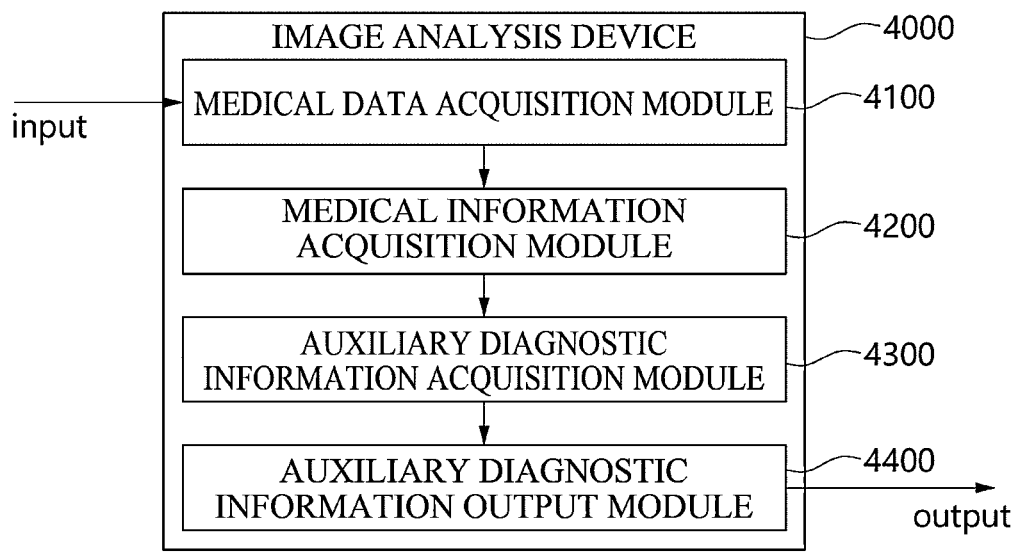
FIG. 69 is a diagram illustrating an image analysis device according to an embodiment.

FIG. 69 is a diagram illustrating an image analysis device according to an embodiment.

Referring to FIG. 69, an image analysis device 4000 according to an embodiment may output medical information. The image analysis device 4000 may include a medical data acquisition module 4100, a medical information acquisition module 4200, an auxiliary diagnostic information acquisition module 4300, and an auxiliary diagnostic information output module 4400.

Although medical data is shown as being acquired through the image analysis device in this drawing, medical data may be acquired by an image acquisition device.

Figure 70:
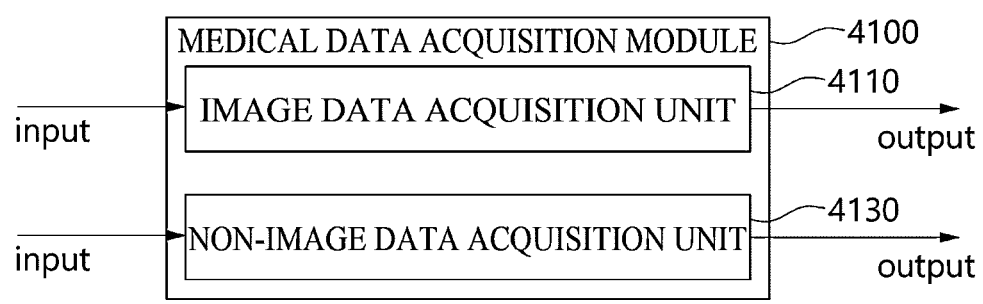
FIG. 70 is a diagram illustrating a medical data acquisition module.

FIG. 70 is a diagram illustrating a medical data acquisition module.

Referring to FIG. 70, a medical data acquisition module 4100 may include one of an image data acquisition unit 4110 or a non-image data acquisition unit 4130. The medical image may include one of image data or non-image data.

The image data acquisition unit 4110 may acquire image data. Here, the image data may include various kinds of medical images or medical videos. The image data may include a plurality of medical images or medical videos.

The non-image data acquisition unit 4130 may acquire non-image data. Here, the non-image data may include health-related questionnaire data. The non-image data may include non-image data acquired based on the image data.

Figure 71:
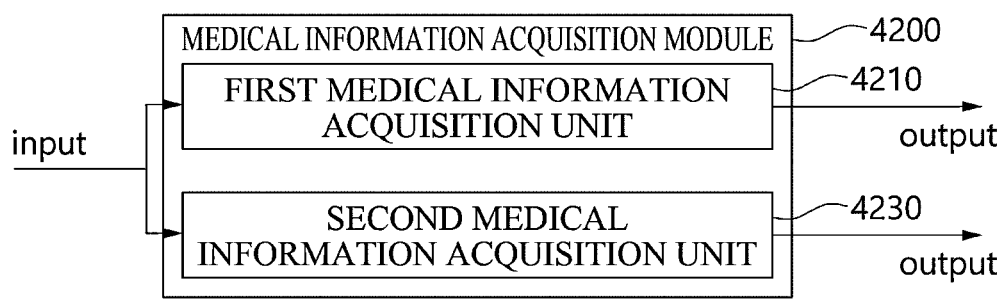
FIG. 71 is a diagram illustrating a medical information acquisition module.

FIG. 71 is a diagram illustrating the medical information acquisition module 4200.

The medical information acquisition module 4200 may acquire medical information on the basis of medical data. The medical information may include a variety of information related to a target subject's health state. The medical information may include a variety of index information related to a target subject, for example, the area, volume, location, or shape of a region of a human body.

Referring to FIG. 71, the medical information acquisition module 4200 may include one of a first medical information acquisition unit 4210 or a second medical information acquisition unit 4230.

The first medical information acquisition unit 4210 may acquire first medical information. The second medical information acquisition unit 4230 may acquire second medical information. In this case, the first medical information or the second medical information may include information that is acquired using a trained neural network on the basis of medical data. The first medical information or the second medical information may include medical data and raw data. The first medical information or the second medical information may include a morphological index or a morphological value acquired based on the medical data.

The first medical information acquisition unit 4210 and the second medical information acquisition unit 4230 may acquire medical information on the basis of respective independent pieces of medical data. The first medical information acquisition unit 4210 may acquire medical information on the basis of first medical data, and the second medical information acquisition unit 4230 may acquire medical information on the basis of second medical data. For example, the first medical information acquisition unit 4210 may acquire medical information on the basis of image data, and the second medical information acquisition unit 4230 may acquire medical information on the basis of non-image data.

Alternatively, the first medical information acquisition unit 4210 and the second medical information acquisition unit 4230 may acquire medical information on the basis of common medical data. The first medical information acquisition unit 4210 and the second medical information acquisition unit 4230 may acquire medical information on the basis of the first medical data. For example, the first medical information acquisition unit 4210 and the second medical information acquisition unit 4230 may acquire medical information on the basis of image data or non-image data.

FIG. 71 exemplifies that the first medical information acquisition unit 4210 and the second medical information acquisition unit 4230 are distinguished from each other, but this is merely an example. The first medical information acquisition unit 4210 and the second medical information acquisition unit 4230 may be provided as one physical or logical component.

Figure 72:
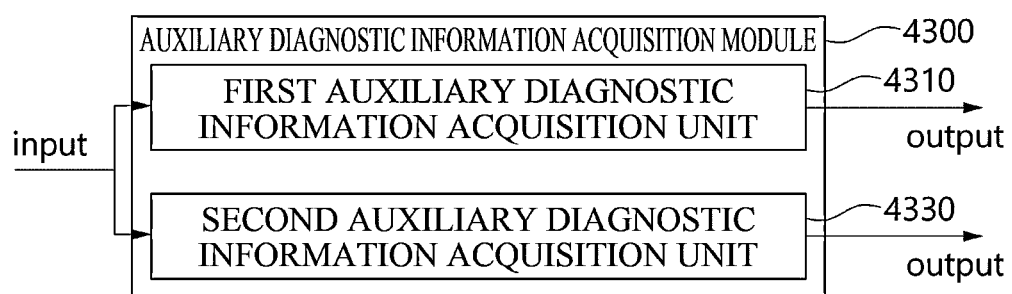
FIG. 72 is a diagram illustrating an auxiliary diagnostic information acquisition module.

FIG. 72 is a diagram illustrating the auxiliary diagnostic information acquisition module 4300.

The auxiliary diagnostic information acquisition module 4300 may acquire auxiliary diagnostic information. The auxiliary diagnostic information may be information that is acquired based on medical information using a trained neural network. The auxiliary diagnostic information may be information that is acquired by processing medical information. For example, the auxiliary diagnostic information may include disease diagnosis information, medical information analysis information, prescription information, and the like which are based on the medical information. The auxiliary diagnostic information may be in an image form or text form.

Also, the auxiliary diagnostic information may include image analysis-related information exemplified herein, for example, image quality-related information, ICV-related information, calibration-related information, or segmentation-related information.

Referring to FIG. 72, the auxiliary diagnostic information acquisition module 4300 may include one of a first auxiliary diagnostic information acquisition unit 4310 or a second auxiliary diagnostic information acquisition unit 4330.

The first auxiliary diagnostic information acquisition unit 4310 may acquire first auxiliary diagnostic information. The second auxiliary diagnostic information acquisition unit 4330 may acquire second auxiliary diagnostic information.

The first auxiliary diagnostic information acquisition unit 4310 and the second auxiliary diagnostic information acquisition unit 4330 may acquire auxiliary diagnostic information on the basis of respective independent pieces of medical data. The first auxiliary diagnostic information acquisition unit 4310 may acquire auxiliary diagnostic information on the basis of first medical information, and the second auxiliary diagnostic information acquisition unit 4330 may acquire auxiliary diagnostic information on the basis of second medical information. For example, the first auxiliary diagnostic information acquisition unit 4310 may acquire auxiliary diagnostic information on the basis of image data, and the second auxiliary diagnostic information acquisition unit 7313 may acquire auxiliary diagnostic information on the basis of non-image data.

Alternatively, the first auxiliary diagnostic information acquisition unit 4310 and the second auxiliary diagnostic information acquisition unit 4330 may acquire auxiliary diagnostic information on the basis of common medical information. The first auxiliary diagnostic information acquisition unit 4310 and the second auxiliary diagnostic information acquisition unit 4330 may acquire auxiliary diagnostic information on the basis of first medical information. For example, the first medical information may be image data or non-image data.

FIG. 72 exemplifies that the first auxiliary diagnostic information acquisition unit 4310 and the second auxiliary diagnostic information acquisition unit 4330 are distinguished from each other, but this is merely an example. The first auxiliary diagnostic information acquisition unit 4310 and the second auxiliary diagnostic information acquisition unit 4330 may be provided as one physical or logical component.

Figure 73:
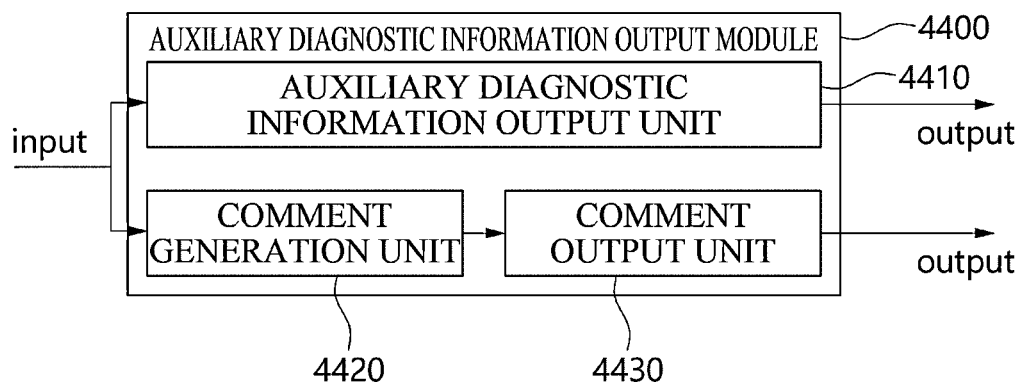
FIG. 73 is a diagram illustrating an auxiliary diagnostic information output module.

FIG. 73 is a diagram illustrating the auxiliary diagnostic information output module 4400.

Referring to FIG. 73, the auxiliary diagnostic information output module 4400 may include an auxiliary diagnostic information output unit 4410, a comment generation unit 4420, or a comment output unit 4430.

The auxiliary diagnostic information output unit 4410 may output auxiliary diagnostic information. The auxiliary diagnostic information output unit 4410 may output a plurality of pieces of auxiliary diagnostic information (e.g., prescription information and target disease-related index information). For example, the auxiliary diagnostic information output unit 4410 may output information based on first auxiliary diagnostic information and second auxiliary diagnostic information. The auxiliary diagnostic information output unit 4410 may output information obtained by processing auxiliary diagnostic information in an image form or a non-image form.

The comment generation unit 4420 may generate a comment determined based on the auxiliary diagnostic information. The comment generation unit 4420 may generate a comment determined based on a plurality of pieces of auxiliary diagnostic information. For example, the comment generation unit 4420 may generate a first comment on the basis of first auxiliary diagnostic information related to a first disease and second auxiliary diagnostic information related to a second disease. In this case, the first comment may include information regarding the first disease and/or information regarding prescription or medical treatment for the first disease.

The first comment may be generated based on first auxiliary information related to dementia, e.g., information on the degree of hippocampal atrophy, and second auxiliary information related to dementia, e.g., information on hippocampal shape.

The first comment may indicate a message stating that a target subject may correspond to an early stage of dementia with a dementia risk of 00%. Also, the first comment may indicate a message stating that a target subject may have reduced cognitive ability because the target subject corresponds to an early stage of dementia.

Meanwhile, the auxiliary diagnostic information output module may output auxiliary diagnostic information or comments differently according to a condition satisfied by acquired medical information on the basis of a plurality of predetermined conditions.

For example, the plurality of predetermined conditions may include a first condition that includes a reference value for one or more pieces of medical information and a second condition that includes a reference value for one or more pieces of medical information and that is at least partially different from the first condition. The auxiliary diagnostic information output module may output first auxiliary diagnostic information (or a first comment) when the plurality of pieces of acquired medical information satisfy the first condition and may output second auxiliary diagnostic information (or a second comment) when the plurality of pieces of acquired medical information satisfy the second condition.

The first condition may be related to the first disease and may include a first condition on first medical information and a second condition on second medical information. The first condition for the first medical information may include that the first medical information exceeds a first reference value, and the second condition for the second medical information may include that the second medical information exceeds a second reference value. The second condition may be related to the second disease and may be implemented similarly to the first condition.

Predetermined conditions that are based on the generation of auxiliary diagnostic information and/or comments will be described with reference to some embodiments.

FIG. 74 is a diagram illustrating indices related to some target diseases.

Referring to FIG. 74, Alzheimer's dementia may be associated with a temporal lobe atrophy index, a parietal lobe atrophy index, and a hippocampal atrophy index. Vascular dementia may be associated with a temporal lobe atrophy index, a parietal lobe atrophy index, a hippocampal atrophy index, a white matter lesions atrophy index, and a cingulate gyms atrophy index. Frontal-temporal lobe dementia (FTLD) may be associated with a frontal lobe atrophy index, a temporal lobe atrophy index, and a hippocampal atrophy index.

A correlation between each disease and a corresponding index may vary. For example, the hippocampal atrophy index may have a higher association with Alzheimer's dementia than the temporal lobe atrophy index and the parietal lobe atrophy index. The white matter lesions atrophy index may have a higher association with vascular dementia than the hippocampal atrophy index, and the hippocampal atrophy index may have a higher association with vascular dementia than the frontal lobe atrophy index, the temporal lobe atrophy index, and the parietal lobe atrophy index. The frontal lobe atrophy index and the temporal lobe atrophy index may have a higher correlation with frontal-temporal lobe dementia than the hippocampal atrophy index.

The auxiliary diagnostic information output module 4400 may output auxiliary diagnostic information generated based on a correlation between a disease and an index (medical information) illustrated in FIG. 74.

For example, referring to FIG. 74, according to the medical information, when the frontal lobe atrophy index, the temporal lobe atrophy index, and the hippocampal atrophy index are greater than respective thresholds, the auxiliary diagnostic information output module 4400 may output auxiliary diagnostic information indicating that a target subject is at risk for FTLD. Alternatively, when the hippocampal atrophy index, the temporal lobe atrophy index, and the parietal lobe atrophy index are greater than or equal to respective thresholds, the auxiliary diagnostic information output module 4400 may output auxiliary diagnostic information indicating that a target subject is at risk for Alzheimer's disease (AD).

Figure 75:
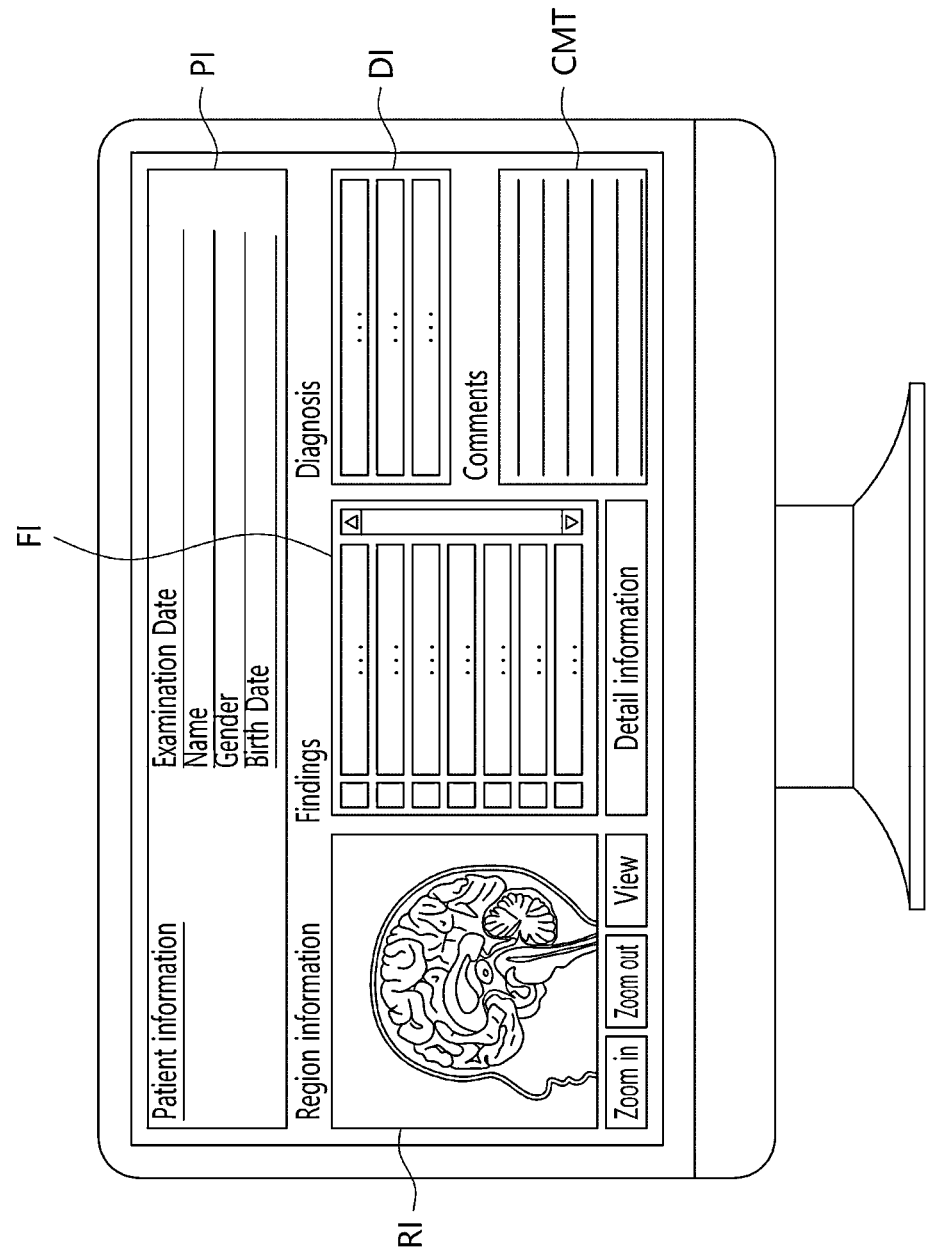
FIG. 75 is a diagram illustrating a medical information output screen according to an embodiment.

FIG. 75 is a diagram illustrating a medical information output screen according to an embodiment.

Referring to FIG. 75, the medical information output screen may include patient information PI, image information RI, index information FI, diagnostic information DI, or comment CMT.

Image information RI may include an image including a medical image related to auxiliary diagnostic information. Index information FI may include information related to medical information acquired from medical data. Diagnostic information DI may include auxiliary diagnostic information acquired from medical information, e.g., disease diagnosis information, medical information analysis information, prescription information, and the like.

Comment CMT may include a comment generated based on auxiliary diagnostic information. Referring to FIG. 74 together, when the frontal lobe atrophy index, the temporal lobe atrophy index, and the hippocampal atrophy index exceed respective thresholds, a comment may be provided which states that since the degrees of atrophy of the frontal and temporal lobes are higher than those of normal people and the degree of hippocampal atrophy is at a dangerous level, the occurrence of front-temporal lobe dementia (FTLD) is suspected.

Alternatively, when the hippocampal atrophy index, the temporal lobe atrophy index, and the parietal lobe atrophy index are greater than or equal to respective thresholds, a comment may be provided which states that since the degree of hippocampal atrophy is higher than that of normal people and the degree of atrophy of the temporal and parietal lobes are at dangerous levels, Alzheimer's disease (AD) is suspected.

Comment CMT may include prescription information generated based on auxiliary diagnostic information. Referring to FIG. 74 together, when the temporal lobe atrophy index, the parietal lobe atrophy index, and the hippocampal atrophy index are greater than or equal to respective thresholds, a comment may be provided which states that since Alzheimer's dementia is suspected, first prescription information, e.g., the prescription of platelet aggregation inhibitors such as aspirin, anticoagulants such as warfarin, blood circulation improving agents, and acetylcholinesterase inhibitors is required.

Alternatively, when the frontal lobe atrophy index, the temporal lobe atrophy index, and the hippocampal atrophy index are greater than or equal to respective thresholds, a comment may be provided which states that since frontal-temporal lobe dementia is suspected, a second prescription, e.g., the prescription of psychiatric drugs such as antipsychotic drugs, antidepressants, anti-anxiety drugs, and hypnotic drugs is required.

A variety of index information may be acquired through analysis of medical images. When the variety of index information are uniformly displayed or provided to users, inconveniently, a user (e.g., a clinician) has to selectively acquire information as needed. Accordingly, in order to improve user convenience, there is a need to provide medical information differently depending on user information or patient information.

An imaging device according to an embodiment may acquire medical data, acquire a plurality of pieces of medical information (e.g., ICV or other morphological indices) on the basis of the medical data, reconfigure the medical information, and provide the reconfigured information.

The reconfigured information may be information reconfigured based on user information or patient information. Here, the user information includes a user's selections of a medical subject, a category, preferred indices, etc., and the patient information includes patient personal information, information on a patient's health state, information obtained by analyzing a patient's medical data, a patient's medical history, etc.

Also, the reconfigured information may include information in which a priority order or an arrangement order of a plurality of pieces of medical information acquired based on the above-described user information or patient information is determined.

Alternatively, the reconfigured information may include some medical information preferentially selected from among a plurality of pieces of acquired medical information on the basis of the above-described user information or patient information.

The provision of the reconfigured information by the auxiliary diagnostic information output module 4400 may include displaying medical information with high priority on an upper portion on the user information or patient information. Alternatively, the provision of the reconfigured information by the auxiliary diagnostic information output module 4400 may include providing medical information selected based on the above-described user information or patient information.

A device and method for selectively providing medical information will be described in detail below.

Figure 76:
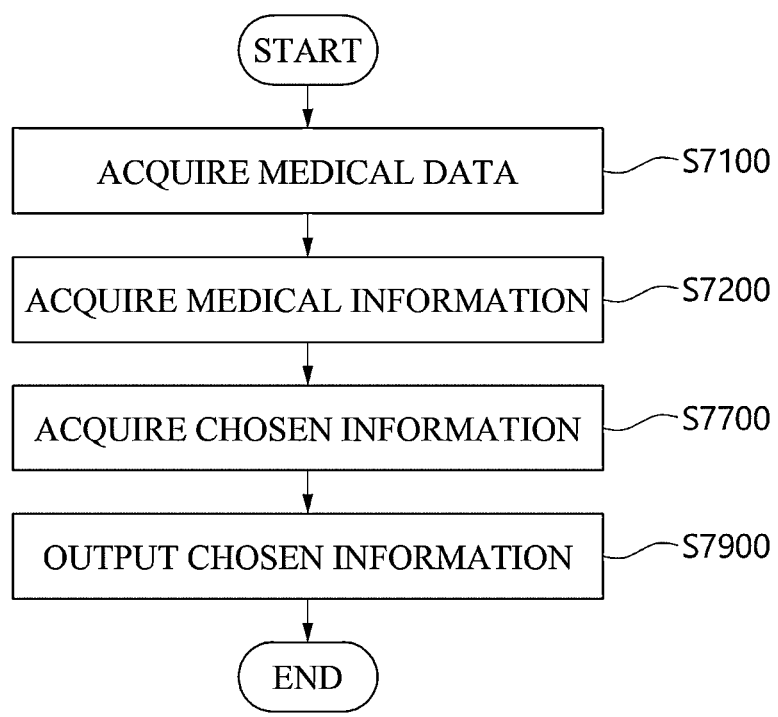
FIG. 76 is a diagram illustrating a medical information output process according to another embodiment.

FIG. 76 is a diagram illustrating a medical information output process according to another embodiment.

Referring to FIG. 76, the medical information output process according to another embodiment may include an operation of acquiring medical data (S4100), an operation of acquiring medical information (S4200), an operation of acquiring chosen information (S4700), and an operation of outputting the chosen information (S4900).

Figure 77:
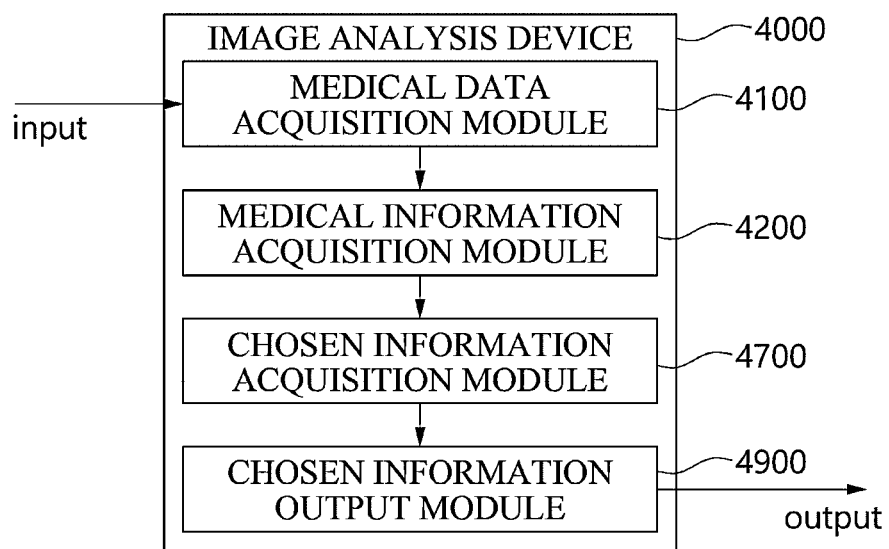
FIG. 77 is a diagram illustrating an image analysis device according to another embodiment.

FIG. 77 is a diagram illustrating an image analysis device according to another embodiment.

Referring to FIG. 77, an image analysis device 4000 according to another embodiment may output medical information. The image analysis device 4000 may include a medical data acquisition module 4100, a medical information acquisition module 4200, a chosen information acquisition module 4700, and a chosen information output module 4900. Although medical data is shown as being acquired through the image analysis device in this drawing, medical data may be acquired by an image acquisition device.

The chosen information acquisition module 4700 may acquire chosen information.

The chosen information may be information acquired based on the medical information. The chosen information may be information that is acquired based on medical information using a trained neural network model. The chosen information may be information that is a basis for determining a disease among the medical information. The chosen information may refer to information that is selected from the medical information using a trained neural network model.

The chosen information may refer to information that is selected from the medical information using a predetermined choice reference.

According to an embodiment, the choice criterion may be determined based on patient information. The choice criterion may be determined to select, from medical information acquired based on image data or non-image data, information related to a patient's state among medical information acquired based on image data.

The choice criterion may be determined such that information related to a patient's state is chosen among the medical information acquired based on the image data.

The choice criterion may be determined such that a predetermined set of medical information is chosen according to reference medical information. As a specific example, it is assumed that the reference medical information is the degree of hippocampal atrophy. When the degree of hippocampal atrophy is greater than or equal to a reference value, the choice criterion may be determined such that one or more predetermined pieces of medical information are output. In this case, one or more chosen pieces of medical information may be medical information related to hippocampal atrophy. For example, hippocampal atrophy has a high relevance to vascular dementia, and one or more chosen pieces of medical information may include temporal lobe atrophy information and parietal lobe atrophy information which are used to diagnose vascular dementia.

The choice criterion may be determined such that a predetermined set of medical information is chosen according to a user's selection. As a specific example, it is assumed that a user belongs to a first medical department (e.g., a radiology department). When the user is in the first medical department (e.g., a radiology department), the choice criterion may be determined such that one or more predetermined pieces of medical information are output. Based on a user input for selecting one of a plurality of medical departments (or items), the chosen information output module 4900 may selectively provide medical information corresponding to the selected medical department. In this case, one or more chosen pieces of medical information may be medical information handled by the first medical department (e.g., a radiology department). For example, when the user belongs to the first medical department, the chosen information output module 4900 may output medical information including a first index in response to a user input of selecting the first medical department. The first index may be predetermined to correspond to the first medical department. The first medical department (e.g., a radiology department) may have a high relevance to the first index (e.g., white matter lesions, etc.).

The choice criterion may be determined such that a predetermined set of medical information is chosen depending on the disease of interest to a doctor. As a specific example, it is assumed that a doctor is interested in the first disease (e.g., dementia). When the doctor is interested in the first disease (e.g., dementia), the choice criterion may be determined such that one or more predetermined pieces of medical information is output. Based on a user input of selecting one of a plurality of diseases of interest, the chosen information output module 4900 may selectively provide medical information corresponding to the selected disease. In this case, one or more chosen pieces of medical information may be medical information having a high relevance to the first disease (e.g., dementia).

Figure 78:
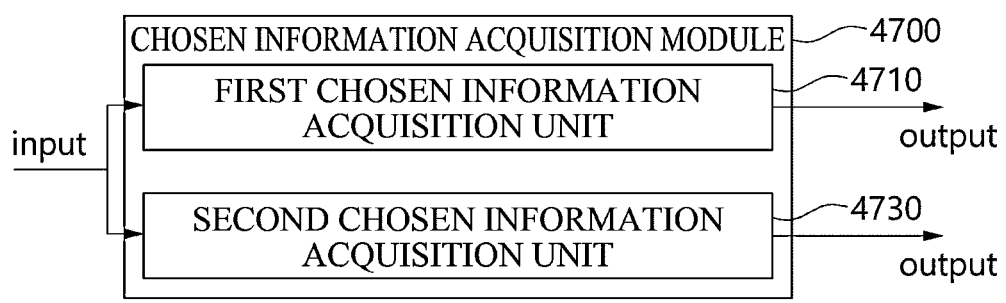
FIG. 78 is a diagram illustrating a chosen information acquisition module.

FIG. 78 is a diagram illustrating a chosen information acquisition module.

Referring to FIG. 78, the chosen information acquisition module 4700 may include a first chosen information acquisition unit 4710 or a second chosen information acquisition unit 4730.

The first chosen information acquisition unit 4710 may acquire first chosen information selected from the medical information according to a first choice criterion.

The second chosen information acquisition unit 4730 may acquire second chosen information selected from the medical information according to a second choice criterion.

The first choice criterion may be one of a criterion related to user information or a criterion related to patient information. The second choice criterion may be the other one of the criterion related to user information or the criterion related to patient information, which is different from the first choice criterion. As an example, the first choice criterion may be the criterion based on the user information (e.g., the type of a doctor's medical department, a doctor's interest) and the second choice criterion may be the criterion based on the patient information (e.g., a patient's personal information, information obtained by analyzing a patient's medical data, a patient's medical history).

Figure 79:
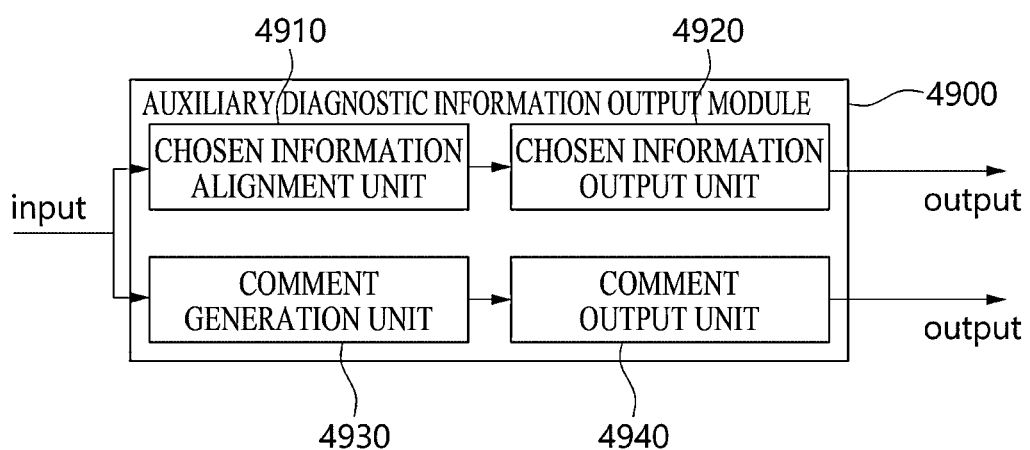
FIG. 79 is a diagram illustrating a chosen information output module.

FIG. 79 is a diagram illustrating the chosen information output module 4900.

Referring to FIG. 79, the chosen information output module 4900 may include a chosen information alignment unit 4910, a chosen information output unit 4920, a comment generation unit 4930, and a comment output unit 4940.

The chosen information alignment unit 4910 may align chosen information acquired through the chosen information acquisition module 4700 according to a predetermined alignment criterion. The alignment criterion may include a criterion in which the chosen information is aligned in descending order of satisfaction with the above choice criterion.

The chosen information alignment unit 4910 may align the chosen information according to a criterion determined such that the chosen information is aligned by type. For example, the chosen information alignment unit 4910 may include a criterion determined to classify and align chosen information related to a first disease and chosen information relate to a second disease. The chosen information alignment unit 4910 may be omitted.

The chosen information output unit 4920 may output chosen information. The chosen information output unit 4920 may output some of a plurality of pieces of medical information included in the chosen information. The chosen information output unit 4920 may output some information that highly satisfies the choice criterion among the plurality of pieces of medical information included in the chosen information.

The comment generation unit 4930 may generate a comment on the basis of the chosen information. The comment generation unit 4930 may generate a comment on the basis of a plurality of pieces of chosen information. For example, the comment generation unit 4930 may generate a first comment on the basis of first chosen information related to the first disease and second chosen information related to the first disease. In this case, the first comment may include information regarding the first disease and/or information regarding prescription or medical treatment for the first disease.

For example, the first comment may be generated based on first chosen information related to dementia, for example, information on the degree of hippocampal atrophy, and second chosen information related to dementia, e.g., information on a hippocampal shape. In this case, the first comment may indicate a message stating that a target subject may correspond to an early stage of dementia with a dementia risk of 00%. Also, the first comment may indicate a message stating that a target subject may have reduced cognitive ability because the target subject corresponds to an early stage of dementia. Also, the first comment may indicate prescription information based on the progression of dementia of the target subject.

Figure 80:
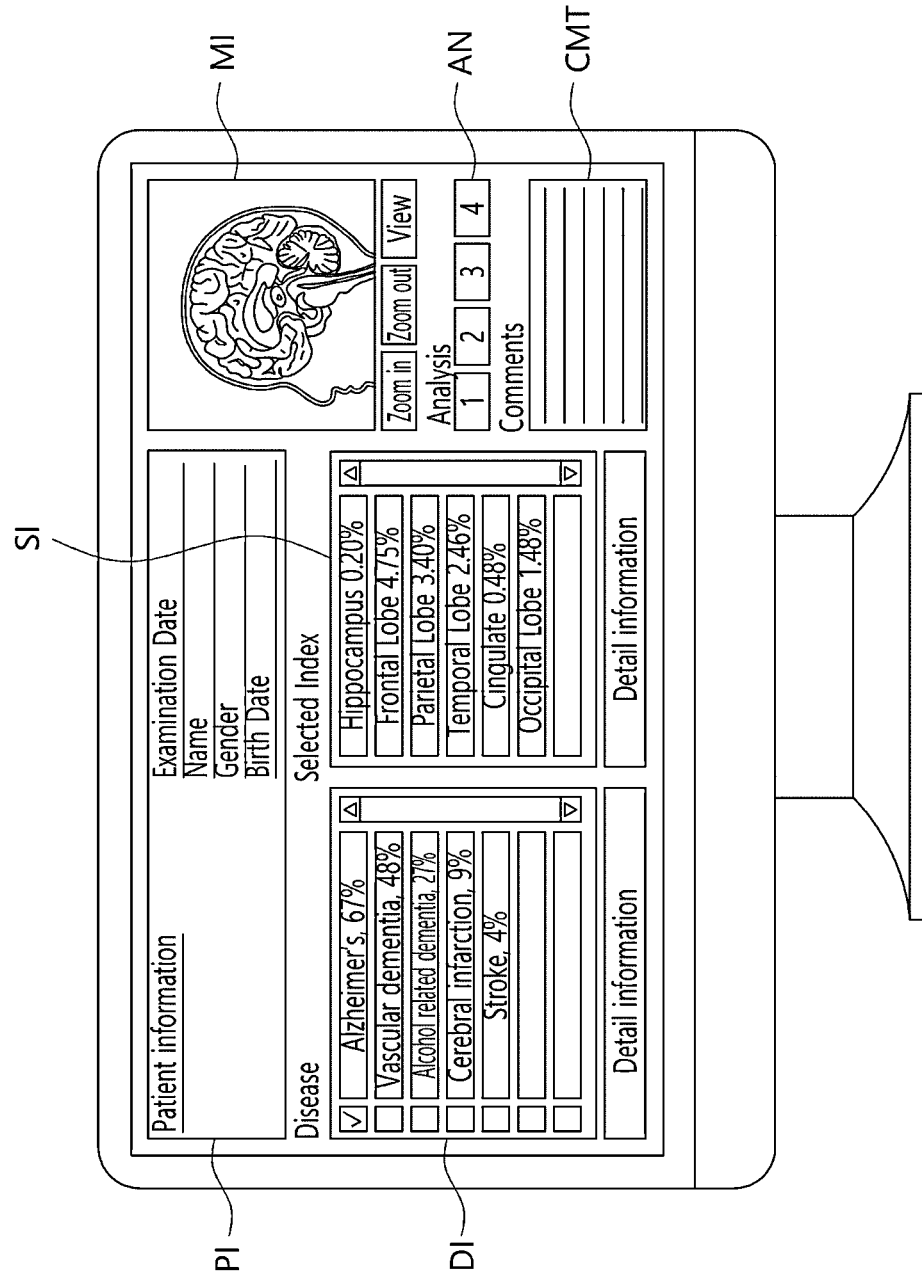
FIGS. 80 and 81 are diagrams illustrating a chosen information output screen.
Figure 81:
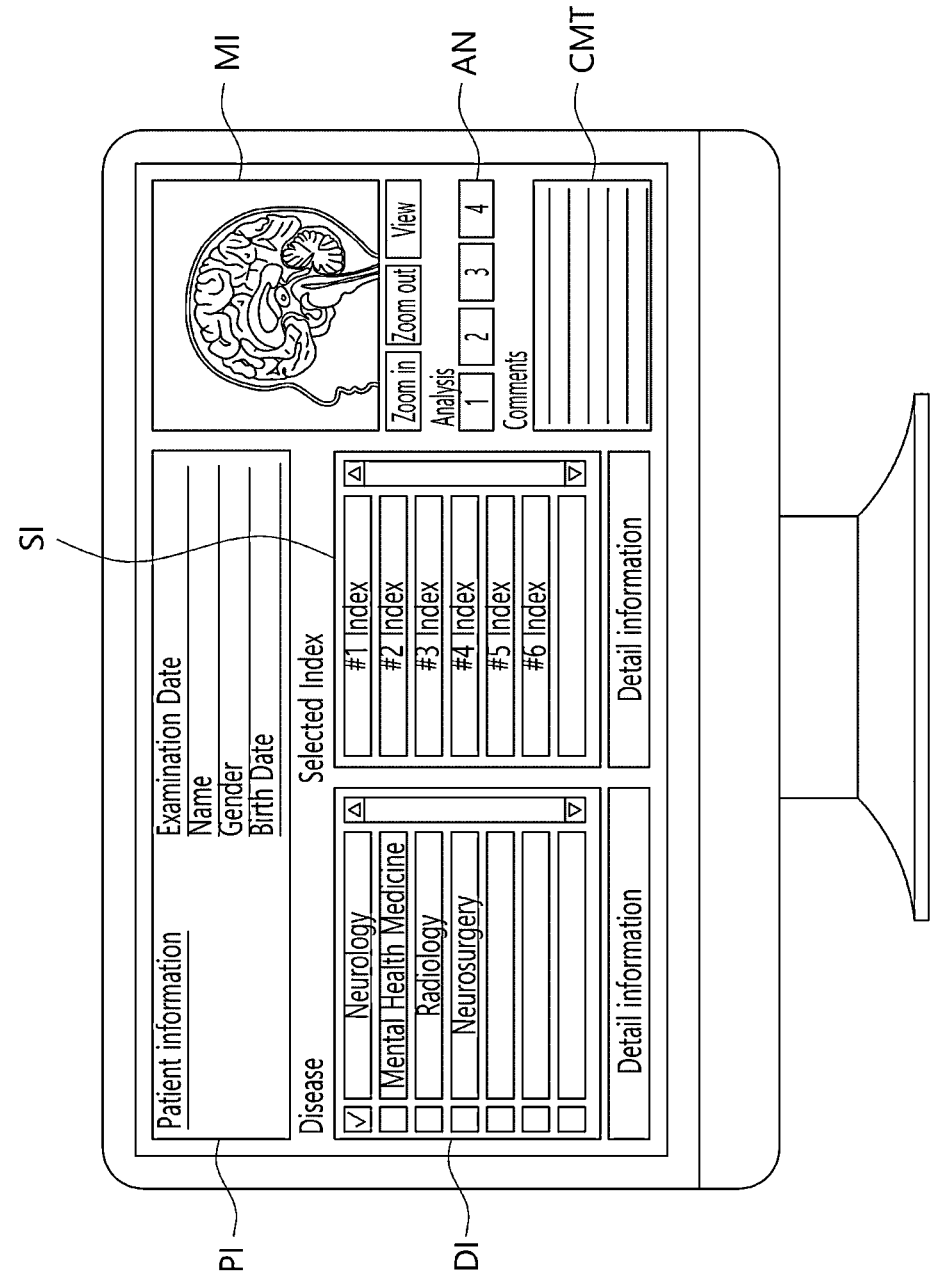

FIGS. 80 and 81 are diagrams illustrating a chosen information output screen.

Referring to FIG. 80, a chosen information output screen according to an embodiment may be an output screen based on information selected according to a choice criterion determined to select information related to patient information from among medical information.

The chosen information output screen according to an embodiment may include patient information PI, image information MI, disease information DI, chosen information SI, analysis information AN, or comment CMT.

Image information MI may include a medical image related to chosen information selected according to a choice criterion (e.g., a choice criterion corresponding to patient information).

Disease information DI may include disease information acquired based on chosen information selected according to a first choice criterion. In this case, disease information DI may include information on at least one disease that may occur in a target subject and information on a probability that a corresponding disease will occur in the target subject. Disease information DI may include information in which a plurality of diseases that may occur in the target subject are aligned according to a certain criterion.

Chosen information SI may include an anatomical index related to patient information among anatomical indices included in the medical information. Chosen information SI may include an anatomical index associated with disease information DI. For example, when a user selects first disease information from among a plurality of pieces of disease information, the chosen information output screen may provide first chosen information regarding an anatomical index related to a first disease. When a user selects first disease information and second disease information from among a plurality of pieces of disease information, the chosen information output screen may provide second chosen information regarding an anatomical index related to the first disease information and the second disease information.

Analysis information AN may include a comprehensive analysis result acquired based on medical information regarding a target subject, e.g., a comprehensive analysis result in a report format.

Comment CMT may include a comment generated based on chosen information. The above description herein is applicable to this comment. As the comment, a comment related to the first disease may be generated based on chosen information acquired based on the first disease among the medical information. For example, referring to FIG. 80, the comment may include first chosen information (e.g., the degree of hippocampal atrophy) related to Alzheimer's disease, second chosen information (e.g., the degree of frontal lobe atrophy), and information related to the Alzheimer's risk level of a target subject.

The comment may be changed in response to a user input of selecting one of the plurality of pieces of disease information. For example, as a user selects a vascular dementia disease information object in FIG. 80, the comment may be changed to include the vascular dementia risk level of a target subject and chosen information related to a target subject's vascular dementia.

Referring to FIG. 81, a chosen information output screen according to another embodiment may be an output screen based on information selected according to a choice criterion determined to select related information from among medical information according to a medical department.

The chosen information output screen according to another embodiment may include patient information PI, image information MI, medical department information CAT, chosen information SI, analysis information AN, or comment CMT.

Image information MI may include a medical image related to chosen information selected according to a choice criterion (e.g., a choice criterion corresponding to a medical department).

Medical department information CAT may include disease information acquired based on chosen information selected according to a second choice criterion. In this case, medical department information CAT may include a list of medical departments in which medical data related to a target subject is analyzed. The list of medical departments may include at least one medical department that requires analysis of medical data related to a target subject.

Chosen information SI may include an anatomical index related to selected medical department information CAT from among anatomical indices included in the medical information. Chosen information SI may include an anatomical index associated with selected medical department information CAT. For example, when a user selects a first medical department from among a plurality of medical departments, the chosen information output screen may provide third chosen information regarding an anatomical index related to the first medical department. When a user selects a first medical department and a second medical department from among a plurality of medical departments, the chosen information output screen may provide fourth chosen information regarding an anatomical index related to the first medical department and the second medical department.

Analysis information AN may include a comprehensive analysis result acquired based on medical information regarding a target subject, e.g., a comprehensive analysis result in a report format.

Comment CMT may include a comment generated based on chosen information. The above description herein is applicable to this comment. As the comment, a comment related to the first medical department may be generated based on chosen information acquired based on the first medical department. For example, referring to FIG. 81, the comment may include information regarding first chosen information and second chosen information which are related to a neurology department.

The comment may be changed in response to a user input of selecting one of the plurality of medical departments. For example, as a user selects a radiology department object in FIG. 81, the comment may be changed to include chosen information required by a radiology department.

The above-described image analysis methods of the image analysis device 2000 may be stored in the first memory 2020 of the image analysis device 2000, and the first controller 2030 of the image analysis device 2000 may be provided to perform the image analysis methods stored in the first memory 2020.

The brain image analysis method, the brain image analysis device, and the brain image analysis system disclosed in the present application may be used to analyze brain images.

In particular, the brain image analysis method, the brain image analysis device, and the brain image analysis system disclosed in the present application are applicable to all fields that provide brain disease-related information with high accuracy and reliability. For example, they are applicable to the field of healthy screening in which an auxiliary index for diagnosing brain diseases is computed or in which an auxiliary index related to a brain disease is provided.

However, the brain image analysis method, the brain image analysis device, and the brain image analysis system disclosed in the present application are applicable to any medical images as well as brain images. Therefore, they are applicable to all fields for acquiring and providing morphological indices related to the length, shape, volume, thickness, etc. of a specific portion to assist in diagnosing various diseases as well as an auxiliary index for diagnosing brain diseases.

The features, structures, and effects described in the above embodiments are incorporated into at least one embodiment of the present invention but are not necessarily limited to only one embodiment. Moreover, features, structures, and effects exemplified in one embodiment can easily be combined and modified for another embodiment and then be carried out by those skilled in the art. Therefore, these combinations and modifications should be construed as falling within the scope of the present invention.

While the present invention has been described with reference to embodiments, these are just examples and do not limit the present invention. It will be understood by those skilled in the art that various modifications and applications may be made therein without departing from the essential characteristics of the embodiments. That is, elements described in the embodiments above in detail may be modified. Furthermore, differences associated with such modifications and applications should be construed as being included in the scope of the present invention defined by the appended claims.

The invention claimed is:

1. A method for analyzing a medical image using a device which obtains the medical image and performs morphological analysis based on the medical image, the method comprising:
    obtaining a calibrating parameter calculated based on a correlation between a first morphological value related to a target element obtained from a first medical image acquired under a first scan condition and a second morphological value related to the target element obtained from a second medical image acquired under a second scan condition;
    obtaining a target medical image acquired under the second scan condition;
    obtaining a target area related to the target element from the target medical image by performing a segmentation of the target medical image into a plurality of areas corresponding a plurality of elements including the target element;
    obtaining a target morphological value related to the target element based on a voxel data corresponding to the target area;
    obtaining a calibrated morphological value based on the target morphological value and the calibrating parameter; and
    outputting a morphological index based on the calibrated morphological value.

2. The method of claim 1, wherein:
    the calibrating parameter includes a parameter calculating the first morphological value based on the second morphological value, and
    obtaining the calibrated morphological value includes, based on the target morphological value and the calibrating parameter, obtaining the calibrated morphological value which is an estimated morphological value of the target element under the first scan condition.

3. The method of claim 2, wherein:
    the calibrating parameter includes a parameter related to a linear function for calculating the first morphological value based on the second morphological value, and
    obtaining the calibrated morphological value includes obtaining the calibrated morphological value based on the target morphological value and the linear function including the parameter.

4. The method of claim 1, wherein each of the first scan condition and the second scan condition is related to at least one of a magnetic field strength related to a resolution of the medical image of a medical image device, a manufacturer of the medical image device, and a setting parameter related to a magnetic field generated by the medical image device.

5. The method of claim 1, wherein:
    the target medical image is obtained from a first object having a first feature,
    the calibrating parameter is obtained from the first medical image and the second medical image obtained from a second object having the first feature, and
    the first feature is related to an age or a sex of object.

6. The method of claim 1, wherein the segmentation is performed using a neural network for obtaining the plurality of areas corresponding to the plurality of elements based on the target medical image.

7. The method of claim 1, further comprising:
    converting the target medical image acquired under the second scan condition to medical image corresponding to image acquired under the first scan condition, wherein the segmentation is performed based on the converted medical image.

8. The method of claim 1, wherein:
    when the first scan condition and the second scan condition are related to the magnetic field strength, the calibrating parameter includes a parameter set for converting the second morphological value which is related to target element and is obtained from the second medical image acquired under the second magnetic field into the first morphological value which is related to target element and is obtained from the first medical image acquired under the first magnetic field, and
    when the target medical image is acquired under the second magnetic field, the calibrated morphological value is obtained based on the target morphological value and the parameter set.

9. A device for analyzing a medical image, the device comprising:
    an image acquisition unit for obtaining a target medical image; and a controller for providing analysis information of a medical image based on the target medical image, and wherein the controller is configured to:

obtain a calibrating parameter calculated based on a correlation between a first morphological value related to a target element obtained from a first medical image acquired under a first scan condition and a second morphological value related to the target element obtained from a second medical image acquired under a second scan condition;

obtain a target medical image acquired under the second scan condition;

obtain a target area related to the target element from the target medical image by performing a segmentation of the target medical image into a plurality of areas corresponding a plurality of elements including the target element;

obtain a target morphological value related to the target element based on a voxel data corresponding to the target area;

obtain a calibrated morphological value based on the target morphological value and the calibrating parameter; and output a morphological index based on the calibrated morphological value.

10. The device of claim 9, wherein the calibrating parameter includes a parameter calculating the first morphological value based on the second morphological value, and the controller configured to obtain the calibrated morphological value which is an estimated morphological value of the target element under the first scan condition based on the target morphological value and the calibrating parameter.

11. The device of claim 10, wherein:
the calibrating parameter includes a parameter related to a linear function for calculating the first morphological value based on the second morphological value, and
the controller is configured to obtain the calibrated morphological value based on the target morphological value and the linear function including the parameter.

12. The device of claim 9, wherein each of the first scan condition and the second scan condition is related to at least one of a magnetic field strength related to a resolution of the medical image of a medical image device, a manufacturer of the medical image device, and a setting parameter related to a magnetic field generated by the medical image device.

13. The device of claim 9, wherein:
the target medical image is obtained from a first object having a first feature,
the calibrating parameter is obtained from the first medical image and the second medical image obtained from a second object having the first feature, and
the first feature is related to an age or a sex of object.

14. The device of claim 9, wherein the segmentation is performed using a neural network for obtaining the plurality of areas corresponding to the plurality of elements based on the target medical image.

15. The device of claim 9, wherein:
the controller is configured to convert the target medical image acquired under the second scan condition to medical image corresponding to image acquired under the first scan condition, and
the segmentation is performed based on the converted medical image.

16. The device of claim 9, further comprising:
an output module for outputting a morphological information obtained based on the morphological index and a morphological index database, wherein:
the morphological information includes a percentile information on the morphological index database of the morphological index related to the object of the target medical image, and
the output module is configured to output the morphological information reflecting the percentile information.

17. The device of claim 9, wherein:
when the first scan condition and the second scan condition are related to the magnetic field strength, the calibrating parameter includes a parameter set for converting the second morphological value which is related to target element and is obtained from the second medical image acquired under the second magnetic field into the first morphological value which is related to target element and is obtained from the first medical image acquired under the first magnetic field, and
when the target medical image is acquired under the second magnetic field, the calibrated morphological value is obtained based on the target morphological value and the parameter set.

* * * * *